United States Patent
Ziv et al.

(10) Patent No.: US 10,195,286 B2
(45) Date of Patent: *Feb. 5, 2019

(54) COMPOUNDS AND METHODS FOR TRANS-MEMBRANE DELIVERY OF MOLECULES

(71) Applicant: Aposense LTD., Petach-Tikva (IL)

(72) Inventors: Ilan Ziv, Kfar Saba (IL); Hagit Grimberg, Herzliya (IL); Joseph Dubrovsky, Tel Aviv (IL)

(73) Assignee: Aposense Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,821

(22) Filed: Aug. 31, 2017

(65) Prior Publication Data

US 2019/0008976 A1   Jan. 10, 2019

Related U.S. Application Data

(63) Continuation-in-part of application No. 15/679,192, filed on Aug. 17, 2017, which is a continuation-in-part of application No. 15/662,665, filed on Jul. 28, 2017, which is a continuation-in-part of application No. 15/641,251, filed on Jul. 4, 2017.

(51) Int. Cl.
| | |
|---|---|
| *A61K 47/08* | (2006.01) |
| *A61K 47/18* | (2017.01) |
| *A61K 47/20* | (2006.01) |
| *A61K 47/22* | (2006.01) |
| *C12N 15/113* | (2010.01) |
| *A61K 47/54* | (2017.01) |
| *C07J 43/00* | (2006.01) |
| *C07J 41/00* | (2006.01) |
| *A61K 48/00* | (2006.01) |

(52) U.S. Cl.
CPC ........ *A61K 47/554* (2017.08); *A61K 48/0033* (2013.01); *C07J 41/0072* (2013.01); *C07J 43/003* (2013.01); *C12N 15/113* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 2012/0035362 A1 | 2/2012 | Barta et al. |
| 2013/0178512 A1 | 7/2013 | Manoharan et al. |
| 2017/0100486 A1 | 4/2017 | Ziv |

FOREIGN PATENT DOCUMENTS

WO   WO 2005/041859   5/2005

OTHER PUBLICATIONS

Yue-Ming, Dimpan Bhatia Li, and Krishna N. Ganesh. "Steroid—DNA conjugates: improved triplex formation with 5-amido-(7-deoxycholic acid)-dU incorporated oligonucleotides." *Bioorganic & medicinal chemistry letters*, vol. 9, No. 13 (1999): pp. 1789-1794.
International Search Report for PCT Application No. PCT/IL2018/50714 dated Nov. 20, 2018.

*Primary Examiner* — Richard A Schnizer
(74) *Attorney, Agent, or Firm* — Pearl Cohen Zedek Latzer Baratz LLP

(57) ABSTRACT

A conjugate for delivery of drugs, such as genetic drugs, [e.g., siRNA, dsiRNA, or antisense oligonucleotides (ASO)] across biological membranes is provided. The conjugates of the Invention are capable of delivering drugs in both presence and absence of plasma proteins.

Figure 1A:
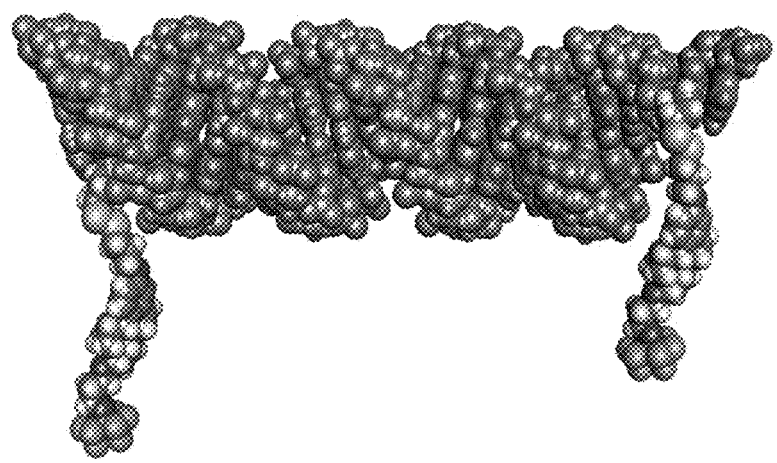

48 Claims, 9 Drawing Sheets
(2 of 9 Drawing Sheet(s) Filed in Color)
Specification includes a Sequence Listing.

Entry of the antisense strand into the RISC Complex for gene silencing

COMPOUNDS AND METHODS FOR TRANS-MEMBRANE DELIVERY OF MOLECULES

CROSS-REFERENCE TO RELATED APPLICATIONS

This application is a continuation-in-part of U.S. application Ser. No. 15/679,192, filed on Aug. 17, 2017, which is a continuation-in-part of U.S. application Ser. No. 15/662,665, filed on Jul. 28, 2017, which is a continuation-in-part of U.S. application Ser. No. 15/641,251 filed on Jul. 4, 2017 which are hereby incorporated by reference.

FIELD OF THE INVENTION

The invention relates to compounds and conjugates that comprise compounds and macromolecules, a delivery system, and methods for delivery of molecules and macromolecules across biological membranes into cells, destined for utilizations in vitro and in vivo.

BACKGROUND

"Oligonucleotide drugs" (OD), are macromolecule drugs that comprise sequences of nucleosides or nucleotides. OD may hold the promise for revolutionary medical treatments for numerous medical disorders. OD are single-stranded or double-stranded, natural or modified RNA or DNA molecules, or combinations thereof, as known in the art. Examples for OD are, among others, siRNA (small interfering RNA), siRNA substrates for the Dicer enzyme (dsiRNA), microRNA (miRNA), messenger RNA (mRNA) drugs, or DNA sequences designed to serve as antisense oligonucleotides (ASO), all of which are active in down-regulation of expression of target genes.

A major challenge in the implementation of OD in clinical practice, relates to optimization of their binding to plasma proteins, especially to albumin. Unmodified ("naked") oligonucleotides do not bind significantly to plasma proteins. By contrast, modification of an OD by adding lipophilic moieties, such as cholesterol, modifications that are often required for the trans-membrane delivery of the OD, leads to avid binding to plasma proteins, mainly to albumin. Strong binding of an OD to plasma proteins can prohibit drug availability for binding to the membranes of its target cells, with respective inhibition of effective OD uptake into the cells, potentially leading to lack of efficacy of the OD. Currently, many delivery systems for OD cannot overcome this challenge, and therefore require serum-free conditions, in order to preserve biological activity of the OD. While serum-free conditions can be applied in vitro, in tissue cultures, serum-free conditions are impracticable in vivo, where inevitably the OD is in close contact with plasma proteins. Therefore, there is an unmet need, for delivery systems for OD, that are capable of delivering the genetic drug across hydrophobic phospholipid membranes into cells, in both presence or absence of plasma proteins.

SUMMARY OF THE INVENTION

The invention is based on a molecular delivery system [(MDS), described in Formula (II)], that when conjugated to an OD, entails delivery of the OD across phospholipid membranes into cells, and respective activity in gene silencing, in both serum free [(S−) conditions], and in the presence of serum [(S+) conditions]. Chemical entities of similar structures, but devoid of the MDS, are either entirely biologically inactive (e.g., in gene silencing), or alternatively, are active in (S−) conditions, but less active or not active at all in (S+) conditions, as exemplified in Example 6.

In an embodiment of the invention, there are provided Conjugates, having the structure as set forth in Formula (I):

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes (i.e., a cargo drug), selected from a group consisting of a small-molecule drug, a peptide, a protein, and OD (i.e., a native or modified, single-stranded or double-stranded DNA or RNA, siRNA, dsiRNA, or ASO);

y, z and w are each an integer, independently selected from 0, 1, 2, 3 or 4, wherein if any of y, z or w or combination thereof is 0, it means that the respective E moiety (or moieties) is (are) null; at least one of y, z or w is different from 0;

E, E', or E" can be the same or different, each having independently a structure as set forth in general Formula (II):

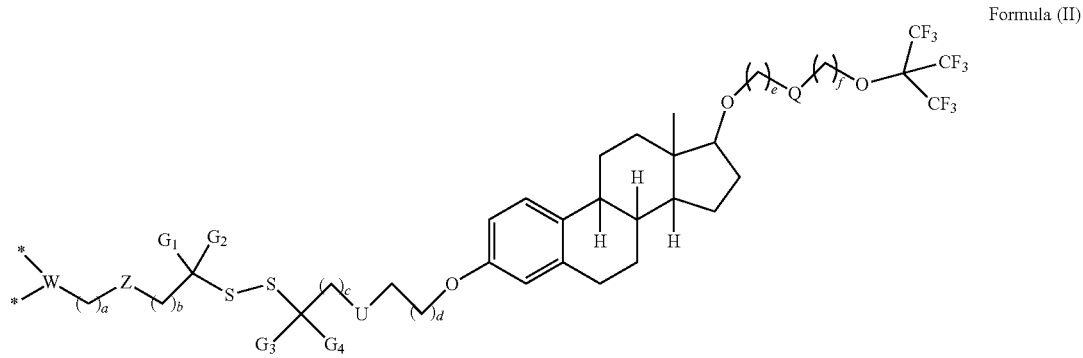

Formula (II)

including pharmaceutically acceptable salts, hydrates, solvates and metal chelates of the compound represented by the structure as set forth in Formula (II), and solvates and hydrates of the salts, wherein:

one of U or Q is independently null, and the other one is a selected from the group consisting of —NH—, —N(CH$_3$)—, —N(CH$_2$—CH$_3$)—, —NH—(CH$_2$)$_2$—NH—, or —N(CH$_3$)—(CH$_2$)$_2$—N(CH$_3$)—;

In another embodiment of the Invention, W is 2'-deoxyuridine.

In yet another embodiment of the Invention, W has the structure as set forth in Formula (II'), wherein J is —CH$_2$—.

In an embodiment of the Invention, it provides E, E', or E" according to Formula (II), having the structure as set forth in Formula (III):

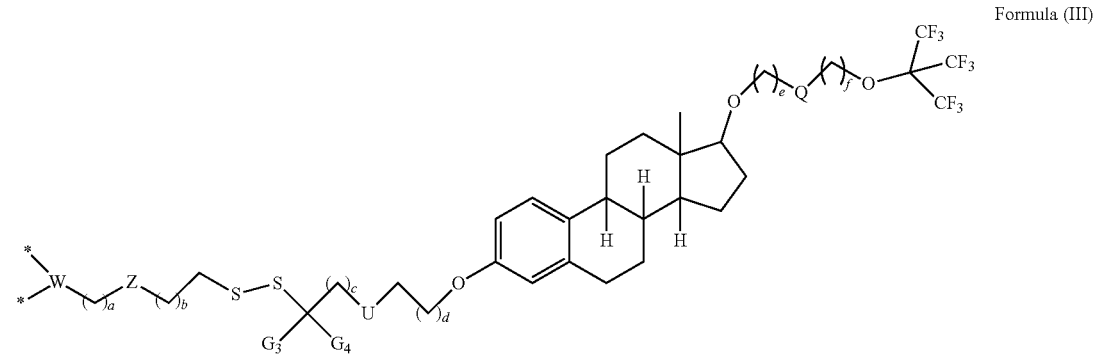

Formula (III)

$G_1$, $G_2$, $G_3$ and $G_4$ are each independently selected from the group consisting of hydrogen, methyl or ethyl; $G_1$, $G_2$, $G_3$ and $G_4$ moieties can be the same or different; at least two of $G_1$, $G_2$, $G_3$, and $G_4$ are hydrogen atoms;

is selected from the group consisting of null, ether, ester, amine, and amide;

a, b, c, d are integers, each being independently selected from the group consisting of 0, 1, 2, 3, 4, 5, 6 or 7, wherein 0=null; a, b, c, d can be the same or different;

e and f are integers, each being independently selected from the group consisting of 1, 2 and 3; e and f can be the same or different;

if any of each a or b is ≥2, then the respective hydrocarbon chain can be either saturated or non-saturated;

W is selected from a group comprising null, hydroxyl, di-hydroxyl, natural or modified nucleoside, and the structure as set forth in Formula (II'):

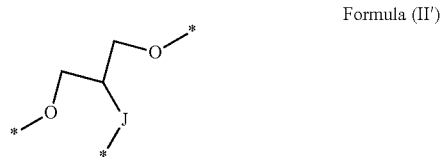

Formula (II')

wherein J is selected from null, —CH$_2$—, a secondary or tertiary amine, and oxygen;

* is selected from the group consisting of null; hydrogen; a linkage point to D; a linkage point to a protecting group, as defined herein (e.g., a protecting group for alcohol); a linkage point to a phosphate, sulfate or carboxyl group; and a linkage point to a solid support. In the context of the Invention, an E, E' or E" moiety may be linked to one D moiety via one or two points.

In an embodiment of the Invention, W is a nucleoside, selected from natural or modified adenine, cytosine, thymine and uracil; and the sugar moiety is ribose or 2'-deoxyribose.

including pharmaceutically acceptable salts, hydrates, solvates and metal chelates of the compound represented by the structure as set forth in Formula (III), and solvates and hydrates of the salts, wherein:

one of U or Q is independently null, and the other one is a selected from the group consisting of —NH—, —N(CH$_3$)—, —N(CH$_2$—CH$_3$)—, —NH—(CH$_2$)$_2$—NH—, or —N(CH$_3$)—(CH$_2$)$_2$—N(CH$_3$)—;

Z is selected from the group consisting of null, ether, ester, amine and amide;

$G_3$ and $G_4$ are each independently selected from the group consisting of hydrogen, methyl or ethyl; $G_3$ and $G_4$ moieties can be the same or different;

a, b, c, d are integers, each being independently selected from the group consisting of 0, 1, 2, 3, 4, 5, 6 or 7, wherein 0=null; a, b, c, d can be the same or different;

e and f are integers, each being independently selected from the group consisting of 1, 2 and 3; e and f can be the same or different;

if any of each a or b is ≥2, then the respective hydrocarbon chain can be either saturated or non-saturated;

W is selected from a group comprising null, hydroxyl, di-hydroxyl, natural or modified nucleoside, and the structure set forth in Formula (II'):

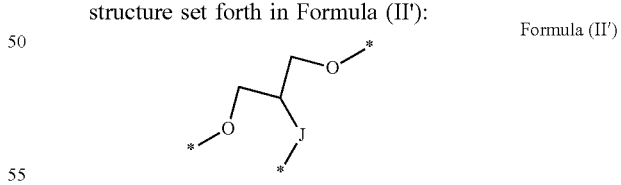

Formula (II')

wherein J is selected from null, —CH$_2$—, a secondary or tertiary amine, and oxygen;

* is selected from the group consisting of null; hydrogen; a linkage point to D; a linkage point to a protecting group, as defined herein (e.g., a protecting group for alcohol); a linkage point to a phosphate, sulfate or carboxyl group; and a linkage point to a solid support. In the context of the Invention, an E, E' or E" moiety may be linked to one D moiety via one or two points.

In an embodiment of the Invention, it provides E, E' or E" according to Formula (III), having the structure as set forth in Formula (IVb):

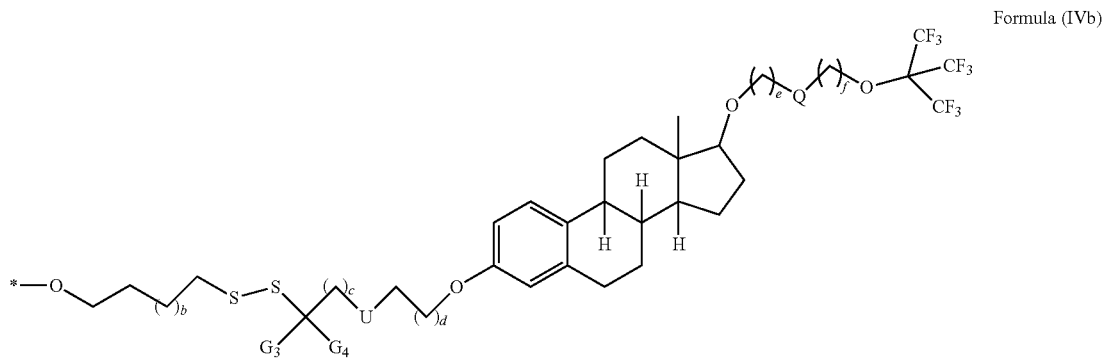

Formula (IVb)

including pharmaceutically acceptable salts, hydrates, solvates and metal chelates of the compound represented by the structure as set forth in Formula (IVb), and solvates and hydrates of the salts; wherein U, Q, G$_3$, G$_4$, b, c, d, e, f and *, each having the same meaning as in Formula (III).

The Invention also provides E, E' or E" according to Formula (IVb), having the structure as set forth in Formula (Vb'):

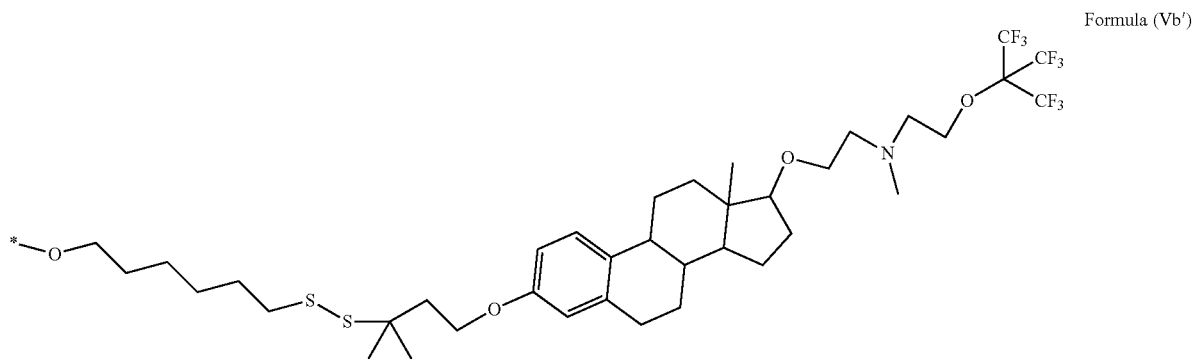 [SMILES: *OCCCCCCSSC(C)(C)CCOc1ccc2c(c1)CCC1C2CCC2(C)C(OCCN(C)CCOC(C(F)(F)F)(C(F)(F)F)C(F)(F)F)CCC12]

Formula (Vb')

including pharmaceutically acceptable salts, hydrates, solvates and metal chelates of the compound represented by the structure as set forth in Formula (Vb'); * has the same meaning as in Formula (IVb). This E, E', or E" moiety, as shown in Formula (Vb'), is designated Apo-Si-K-18. In the case that * is a linkage point to a phosphoramidite group, the compound is designated Apo-Si-K-18-Precursor.

The Invention also provides E, E' or E" according to Formula (IVb), having the structure as set forth in Formula (Vb"):

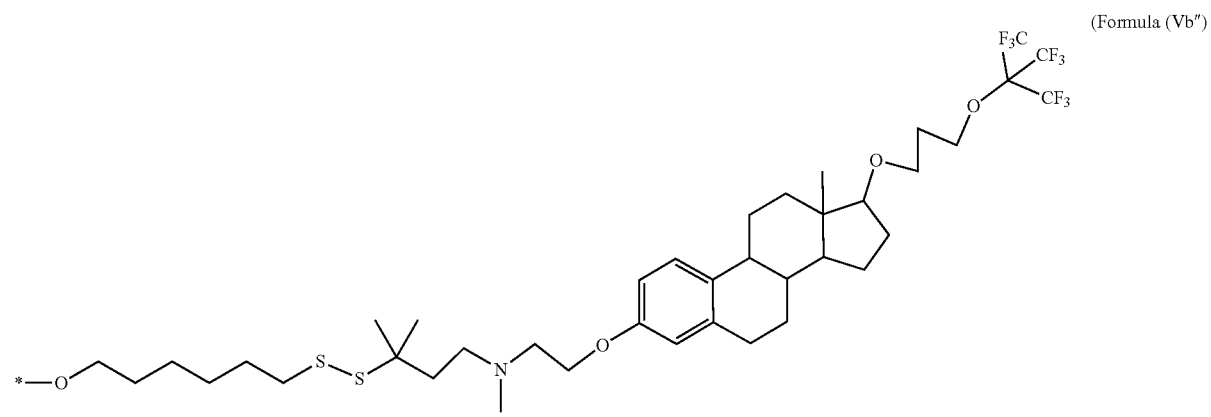 [SMILES: *OCCCCCCSSC(C)(C)CCN(C)CCOc1ccc2c(c1)CCC1C2CCC2(C)C(OCCCOC(C(F)(F)F)(C(F)(F)F)C(F)(F)F)CCC12]

(Formula (Vb"))

including pharmaceutically acceptable salts, hydrates, solvates and metal chelates of the compound represented by the structure as set forth in Formula (Vb"); * has the same meaning as in Formula (IVb). This E, E', or E" moiety, as shown in Formula (Vb"), is designated Apo-Si-K-13. In the case that * is a linkage point to a phosphoramidite group, the compound is designated Apo-Si-K-13-Precursor.

In an embodiment of the Invention, it provides E, E' or E" according to Formula (III), having the structure as set forth in Formula (IVc):

structure as set forth in Formula (Vc"); wherein * has the same meaning as in Formula (IVc). This E, E', or E" moiety, as shown in Formula (Vc"), is designated Apo-Si-K-43. In the case that one of * is a linkage point to a phosphoramidite group, and the second * is a linkage point to a DMT group, the compound is designated Apo-Si-K-43-Precursor.

In another embodiment of the invention, it provides E, E' or E" according to Formula (IVc), having the structure as set forth in Formula (Vc'''):

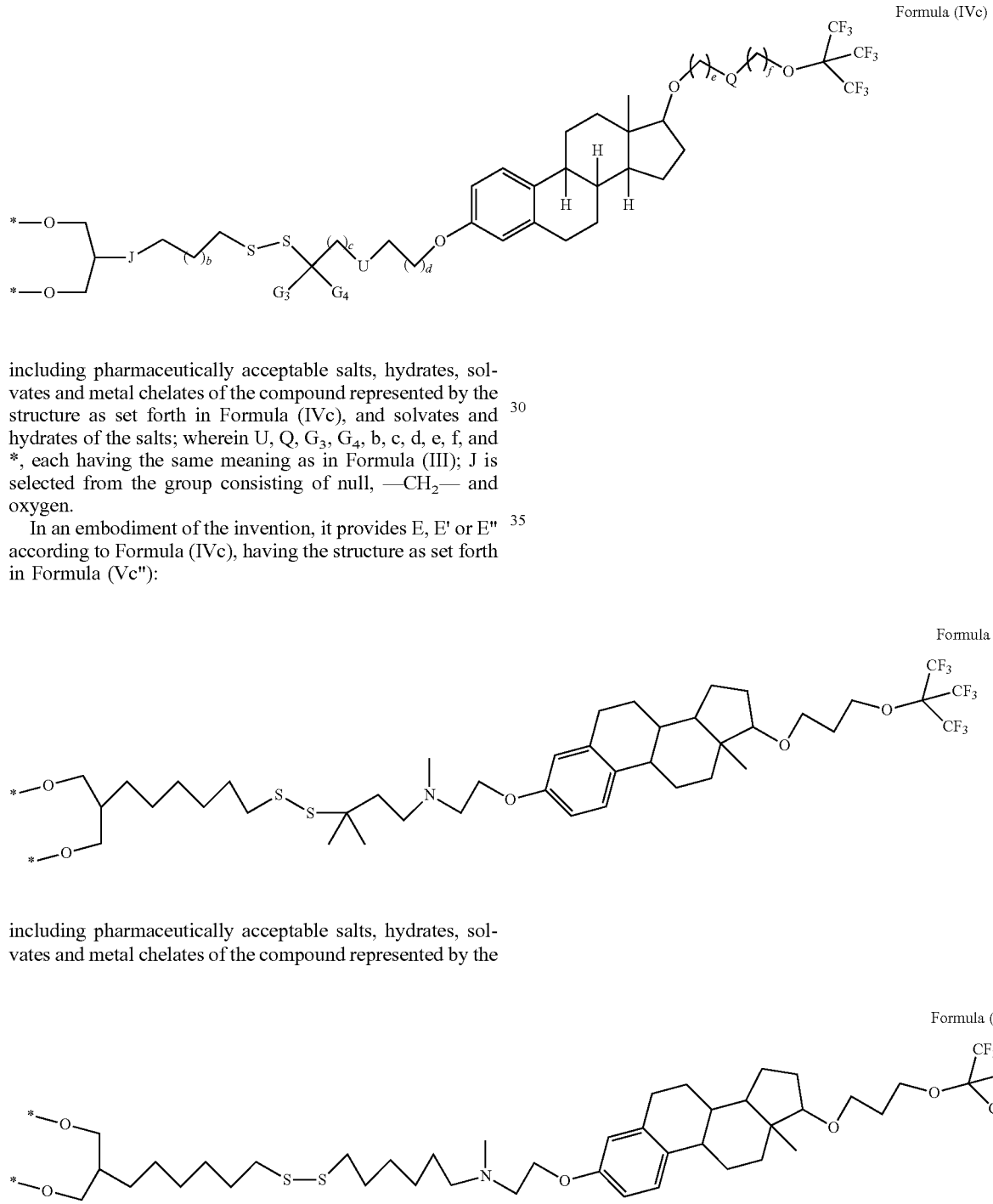

including pharmaceutically acceptable salts, hydrates, solvates and metal chelates of the compound represented by the structure as set forth in Formula (IVc), and solvates and hydrates of the salts; wherein U, Q, $G_3$, $G_4$, b, c, d, e, f, and *, each having the same meaning as in Formula (III); J is selected from the group consisting of null, —$CH_2$— and oxygen.

In an embodiment of the invention, it provides E, E' or E" according to Formula (IVc), having the structure as set forth in Formula (Vc"):

including pharmaceutically acceptable salts, hydrates, solvates and metal chelates of the compound represented by the including pharmaceutically acceptable salts, hydrates, solvates and metal chelates of the compound represented by the structure as set forth in Formula (Vc'''); wherein * has the same meaning as in Formula (IVc). This E, E', or E" moiety, as shown in Formula (Vc'''), is designated Apo-Si-K-63. In the case that one of * is a linkage point to a phosphoramidite group, and the second * is a linkage point to a DMT group, the compound is designated Apo-Si-K-63-Precursor.

In some embodiments, provided is a Precursor molecule, comprising an E, E' or E" moiety of the Invention, linked to one or more protecting groups for alcohol, as defined herein, wherein said group(s) is (are) destined to be removed or modified during conjugation of the E, E' or E" moiety to a cargo drug (e.g., a macromolecule drug).

In an embodiment, the Precursor molecule comprises E, E' or E" according to Formula (IVc), and has the following structure, as set forth in Formula (IVcP):

Formula (IVcP)

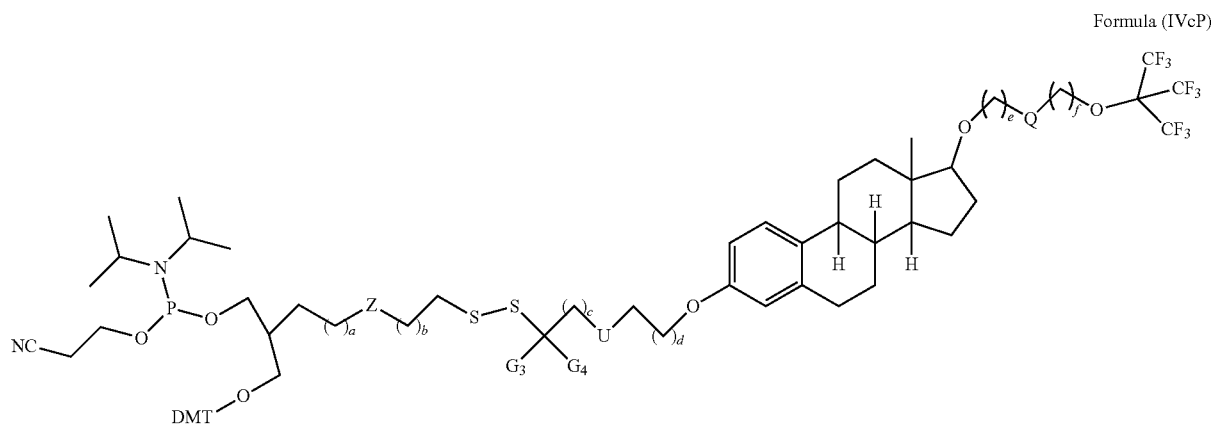

including pharmaceutically acceptable salts, hydrates, solvates and metal chelates of the compound represented by the structure as set forth in Formula (IVcP), and solvates and hydrates of the salts, wherein: Z, U, Q, $G_3$, $G_4$, a, b, c, d, e, f each having the same meaning as in Formula (IVc); DMT is a protecting group for alcohol [Dimethoxytrityl [bis-(4-methoxyphenyl) phenylmethyl]. This Precursor molecule may serve to attach the E, E', or E" moiety at either the 5'-end or the 3'-end, or at an internal position within the oligonucleotide chain.

In another embodiment, the Precursor molecule is according to Formula (IVcP), having the following structure, as set forth in Formula (PP-2):

Formula (PP-2)

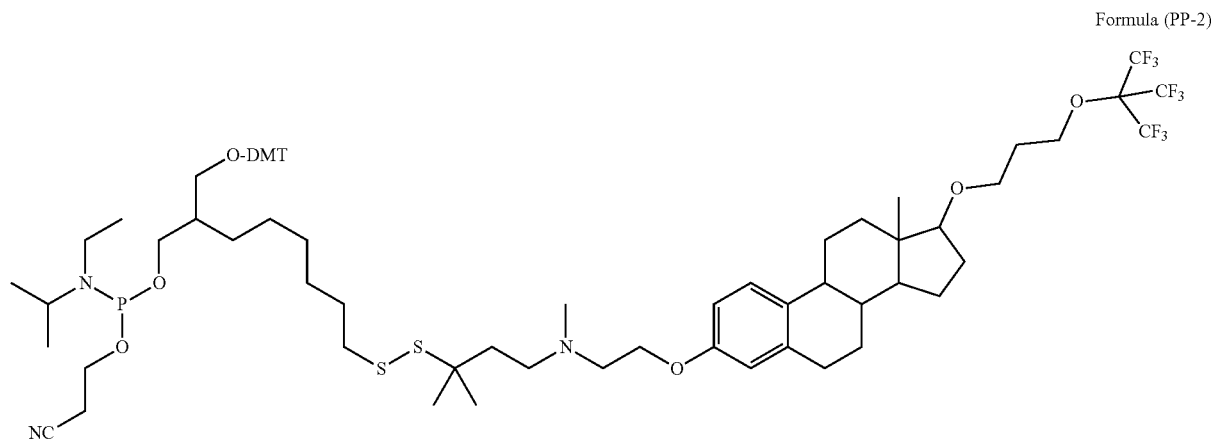

including pharmaceutically acceptable salts, hydrates, solvates and metal chelates of the compound represented by the structure as set forth in Formula (PP-2), and solvates and hydrates of the salts. This Precursor molecule may serve to attach the E, E', or E" moiety at either the 5'-end or the 3'-end, or at an internal position within the oligonucleotide chain. This Precursor molecule, as shown in Formula (PP-2), is designated Apo-Si-K-43-Precursor.

In another embodiment, the Precursor molecule is according to Formula (IVcP), having the following structure, as set forth in Formula (PP-3):

Formula (PP-3)

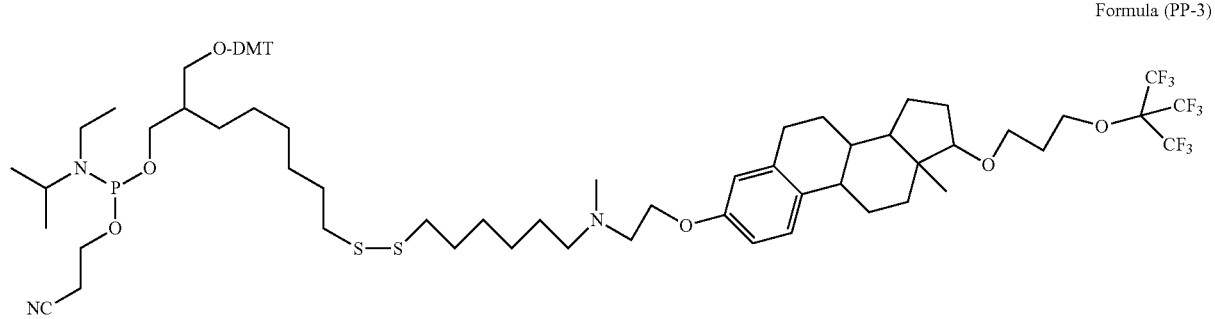

including pharmaceutically acceptable salts, hydrates, solvates and metal chelates of the compound represented by the structure as set forth in Formula (PP-3), and solvates and hydrates of the salts. This Precursor molecule, as shown in Formula (PP-3), is designated Apo-Si-K-63-Precursor.

In another embodiment of the Invention, it provides a Conjugate, that comprises linkage of D to E and E' moieties, each having a structure as set forth in Formula (Vc'''), and being linked to the 5'-ends of the RNA Duplex. This Conjugate has the following structure, as set forth in Formula (Cn-12):

Formula (Cn-12)

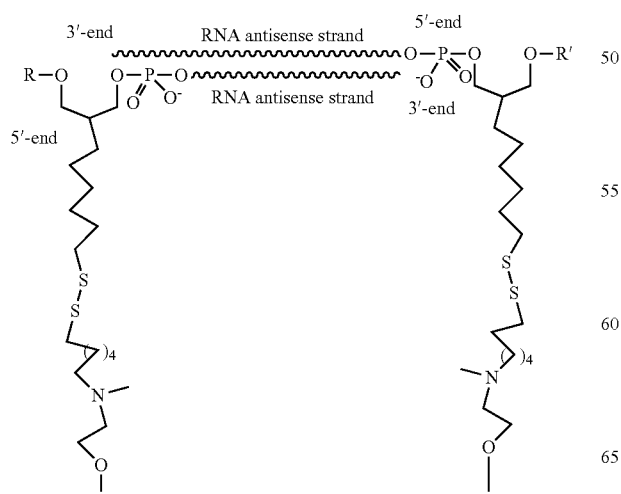

-continued

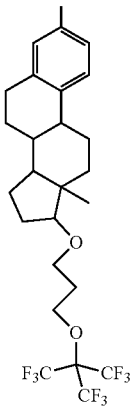 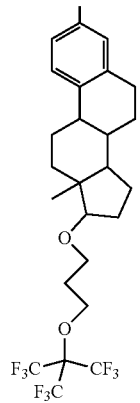

including pharmaceutically acceptable salts, hydrates, solvates and metal chelates of the compound represented by the structure as set forth in Formula (Cn-12), and solvates and hydrates of the salts, wherein R and R' are each selected independently from the group consisting of hydrogen, phosphate, sulfate and carboxyl group. This Conjugate, as shown in Formula (Cn-12), is designated Apo-Si-K-63-B.

In an embodiment of the Invention, it provides a Conjugate that comprises linkage of D to two E and E' moieties according to Formula (Vc'''), at the 5'-ends of the RNA Duplex, and in internal position at the sense (passenger) strand; this Conjugate having the following structure, as set forth in Formula (Cn-14):

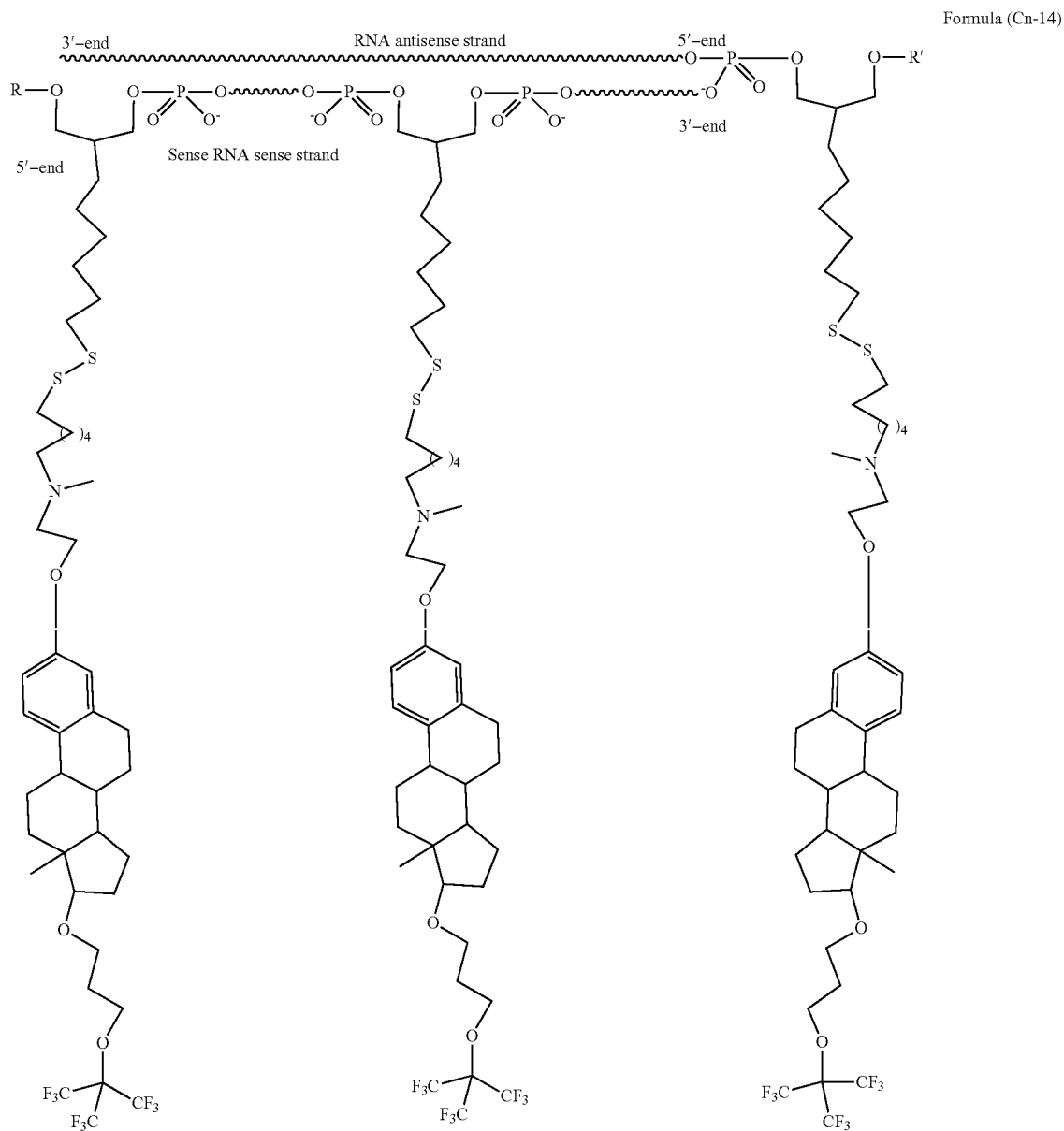

Formula (Cn-14)

including pharmaceutically acceptable salts, hydrates, solvates and metal chelates of the compound represented by the structure as set forth in Formula (Cn-14), and solvates and hydrates of the salts, wherein R and R' are each selected independently from the group consisting of hydrogen, phosphate, sulfate and carboxyl group. This Conjugate, as shown in Formula (Cn-14), is designated Apo-Si-K-63-C.

In an embodiment of the Invention, it provides a Conjugate, comprising an RNA Duplex, such as siRNA or a substrate for the Dicer enzyme (dsiRNA), wherein the RNA duplex has a length of 24-27 or 25-27 nucleotides, and is linked at two of its strand ends to an E, E' or E" moiety, each having the structure according to any of Formulae (II), (III), (IVa), (IVb), (IVc), (Va'), (Va"), (Va'''), (Vb'), (Vb"), (Vb'''), (Vc'), (Vc") or (Vc''').

In another embodiment of the Invention, it provides a Conjugate as described above, comprising E, E' or E" moieties according to one of the following options: (1). two E, E' or E" moieties, positioned at the ends of the RNA strands; or (2). three or more E, E' or E" moieties, positioned at the ends of the RNA strands, but also at an internal position(s) within the siRNA duplex; wherein each of E, E' or E" moiety(ies), has the structure according to any of Formulae (II), (III), (IVa), (IVb), (IVc), (Va'), (Va"), (Va'''), (Vb'), (Vb"), (Vb'''), (Vc'), (Vc") or (Vc''').

Some embodiments of the invention relate to a method for delivery of a drug across a biological membrane into cells, either in vitro or in vivo; the method comprising contacting the cells with a Conjugate as described herein.

Another embodiment relates to a method for treating a medical disorder in a patient in need; the method comprising administering to the patient a therapeutically-effective amount of a pharmaceutical composition, that comprises a Conjugate as described herein.

BRIEF DESCRIPTION OF THE FIGURES AND DRAWINGS

The patent or application file contains at least one drawing executed in color. Copies of this patent or patent application publication with color drawings will be provided by the Office upon request and payment of the necessary fee.

Figure 1B:
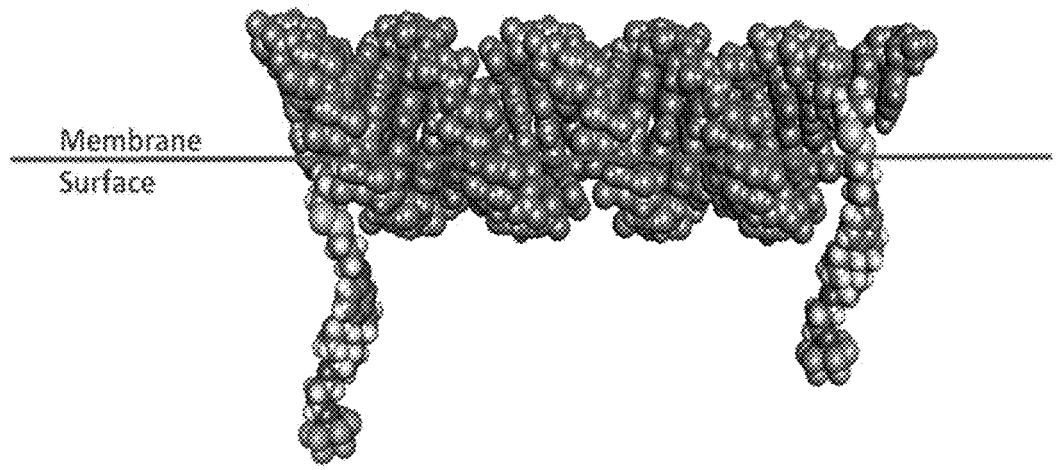

FIGS. 1a and 1b demonstrate a Conjugate of the Invention: FIG. 1a shows a Conjugate of the Invention, comprising two E moieties, each positioned at the 5'-end of a strand of an siRNA; and FIG. 1b shows the Conjugate upon its approaching the membrane, with the siRNA being parallel to the membrane surface, before the trans-membrane delivery process; wherein the blue and the brown colors indicate each an oligonucleotide strand of the RNA Duplex of the siRNA; yellow atoms are sulfur atoms of red-ox sensitive modules, designed to disengage in the reductive conditions within the cytoplasm, thus releasing the RNA from the MDS, to exert its gene silencing activity; grey and white atoms are carbon and hydrogen atoms, respectively; red and green atoms are atoms of oxygen and fluorine, respectively.

Figure 2A:
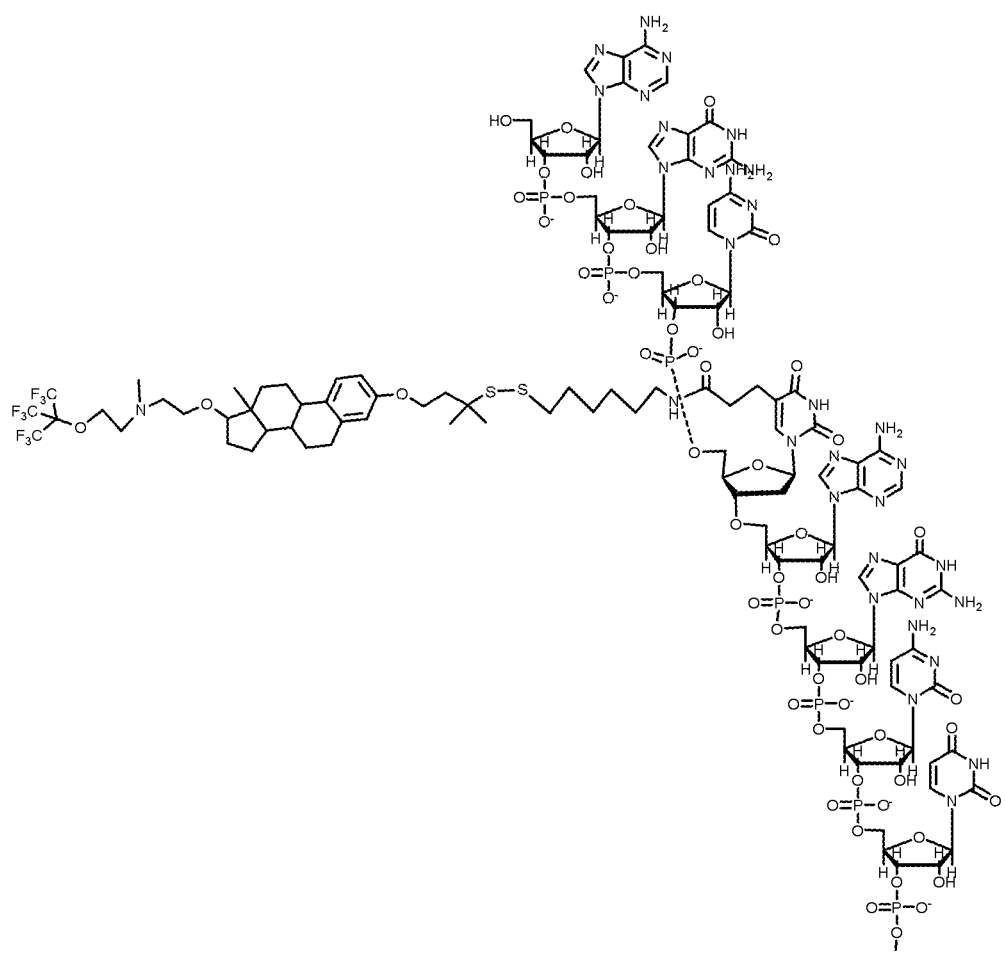
Figure 2B:
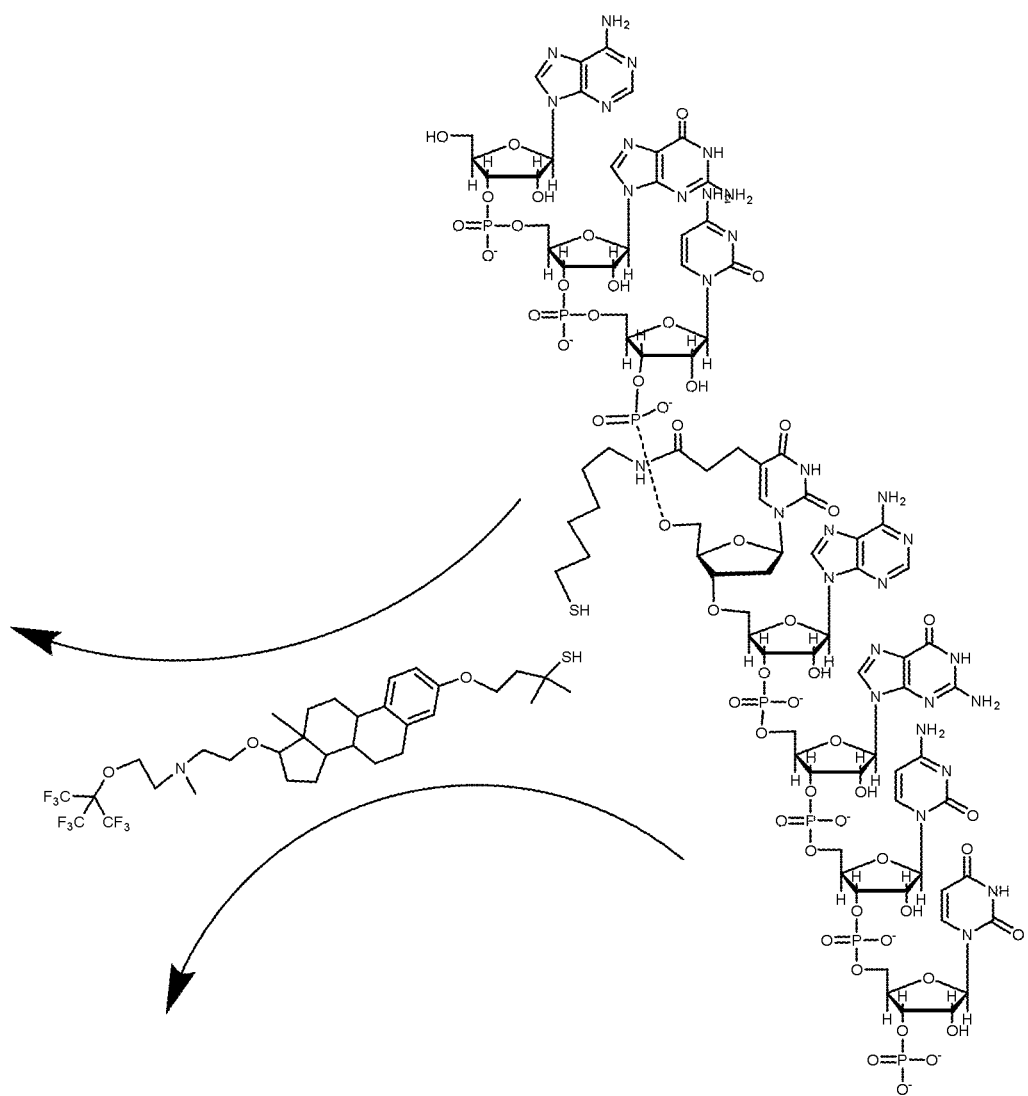

FIGS. 2a and 2b exemplify the mode of linkage of an E moiety of the Invention, according to Formula (Va'), and respective red-ox-mediated cleavage of an E moiety. FIG. 2a shows an RNA strand, wherein an E moiety according to Formula (Va'), is linked at an internal position; FIG. 2b exemplifies red-ox-mediated cleavage of the disulfide group of an E moiety according to Formula (Va') in reductive conditions, such as those prevailing within the cytoplasm, with consequent release of an RNA drug.

Figure 3A:
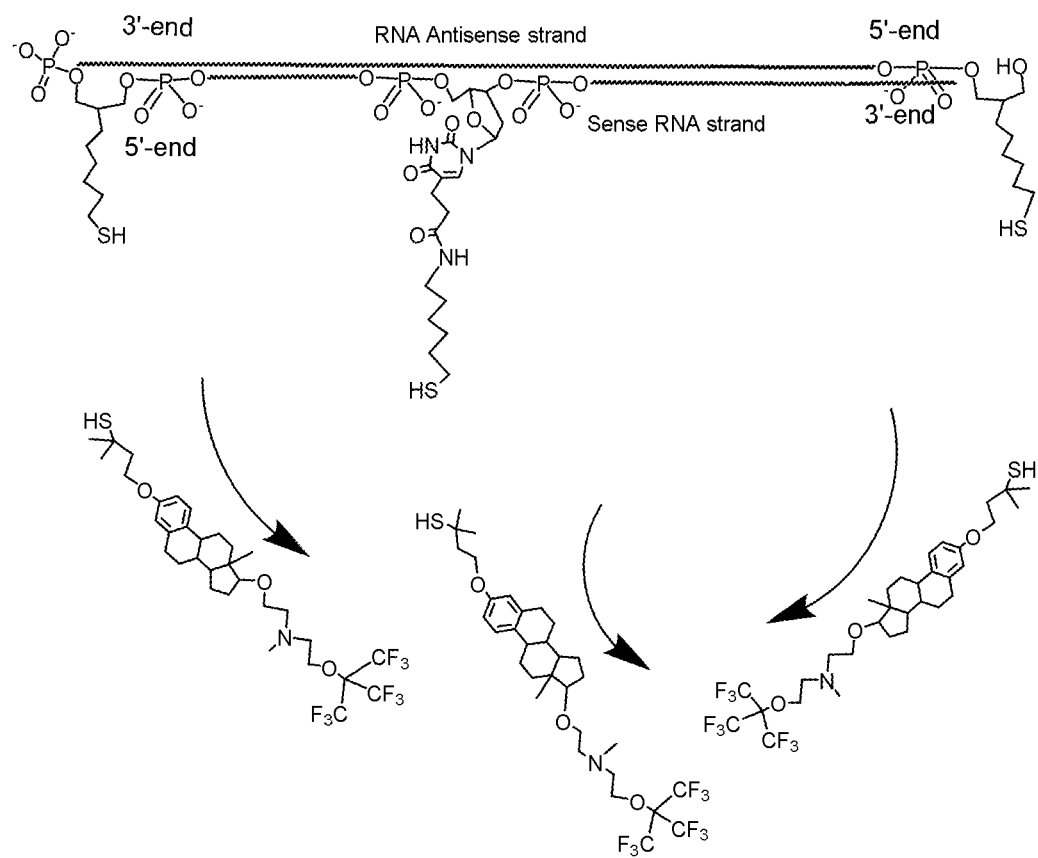
Figure 3B:
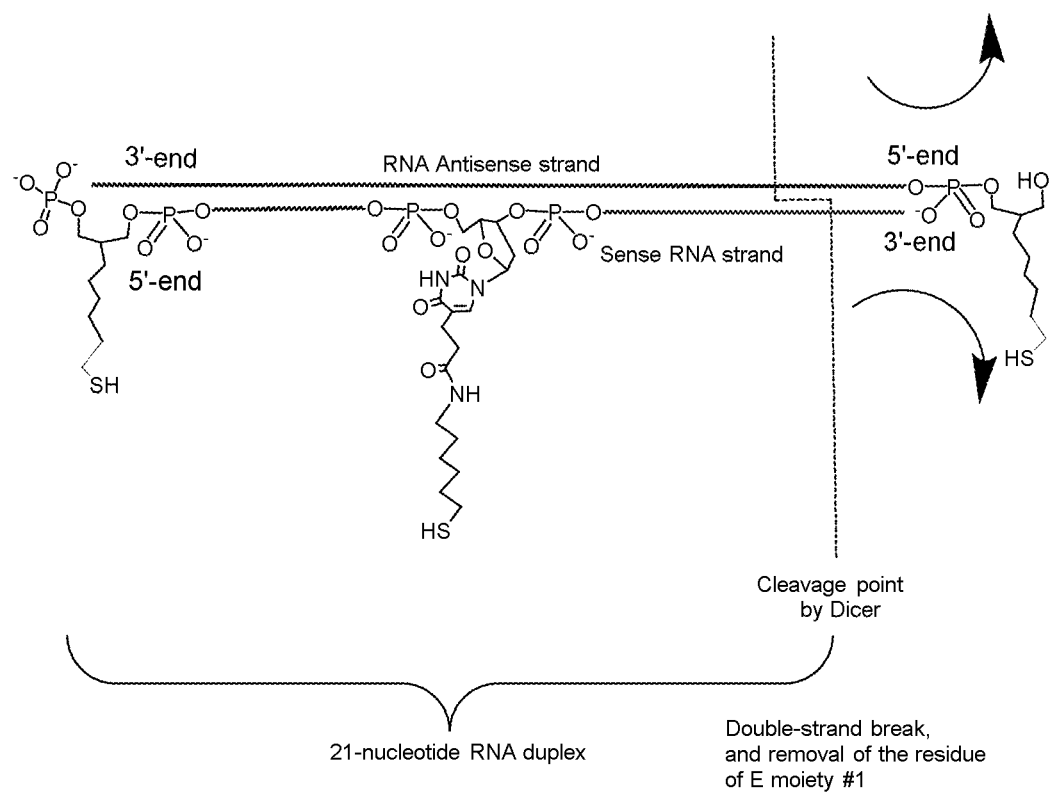
Figure 3C:
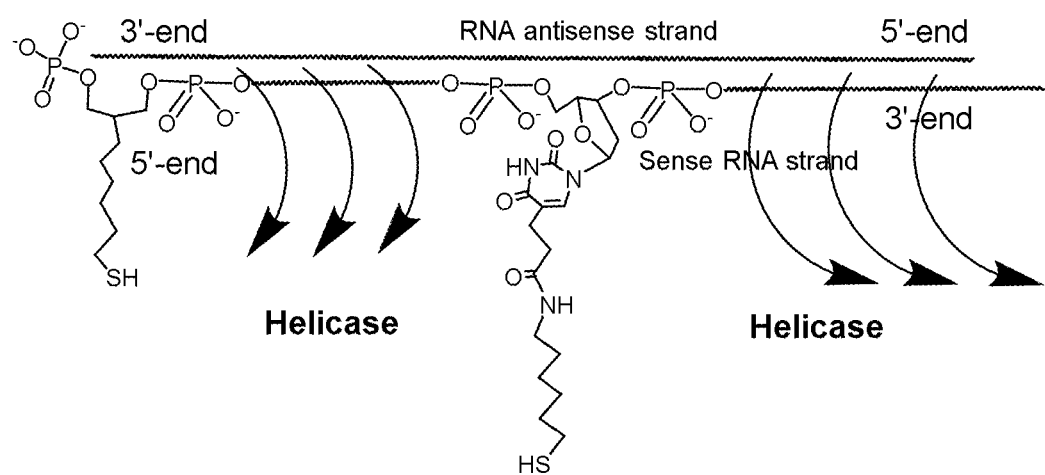
Figure 3D:
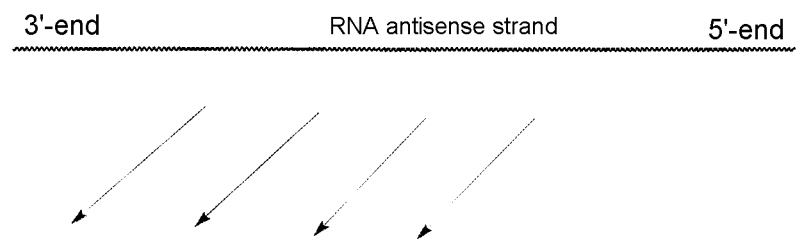

FIGS. 3a, 3b, 3c and 3d exemplify the Mechanism of Action (MOA) of a Conjugate of the Invention. Exemplified is a Conjugate according to Formula (Cn-3), wherein the RNA Duplex is a Dicer substrate of 25/27-nucleotide long, with a phosphate group linked at the 5'-end of the passenger strand: FIG. 3(a) demonstrates cleavage and removal of the E, E' and E" moieties in the reductive conditions that prevail in the cytoplasm; FIG. 3(b) demonstrates interaction of the RNA Duplex with the Dicer endonuclease, that induces a double-strand break, leaving a 21/21 RNA Duplex, with one remaining residue of E moiety, linked at the 5'-end of the passenger strand; FIG. 3(c) demonstrates the removal of the sense strand by the enzyme helicase (i.e., a cytoplasmatic enzyme, capable of separating RNA strands). This event leads to the removal of the residue of the stump of the second E moiety, thus releasing the intact antisense strand, to enter the RNA-induced silencing complex (RISC), in order to induce the desired gene silencing [FIG. 3(d)].

Figure 4A:
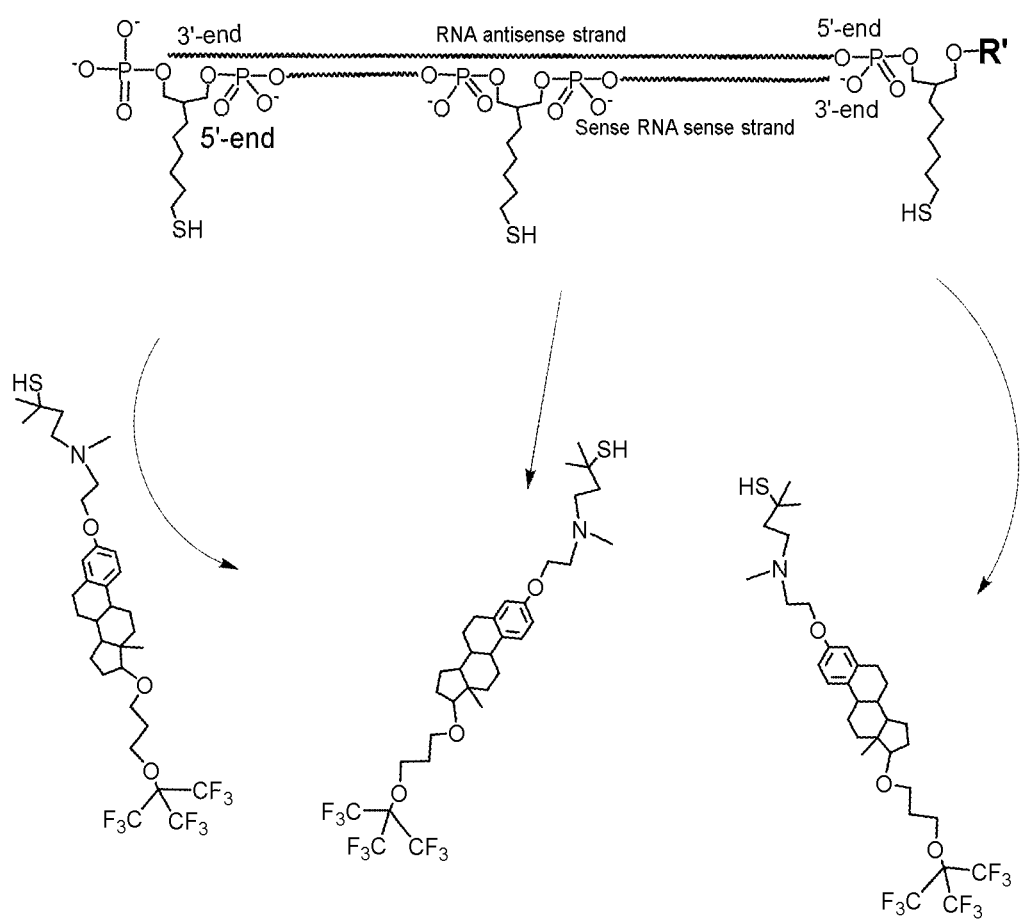
Figure 4B:
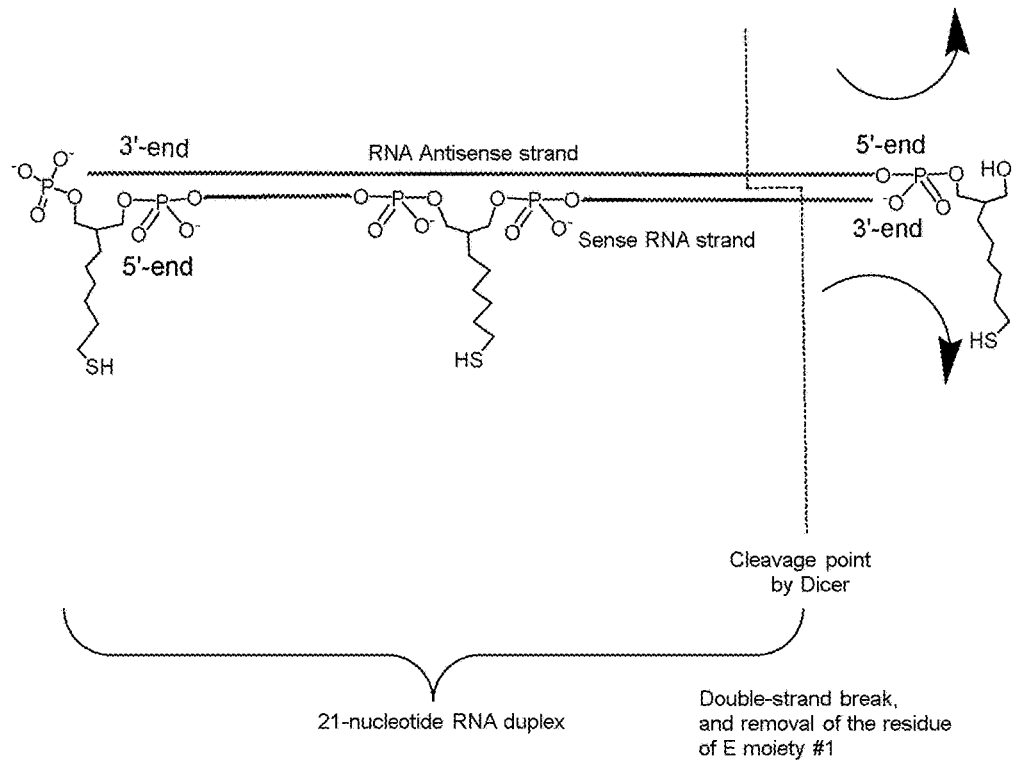
Figure 4C:
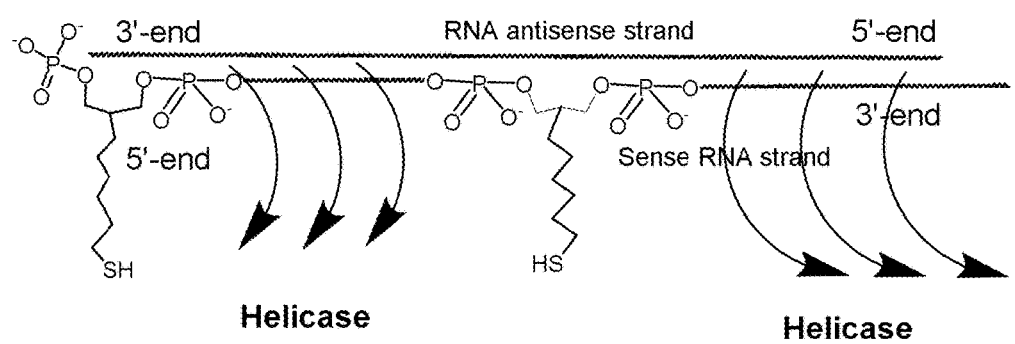
Figure 4D:
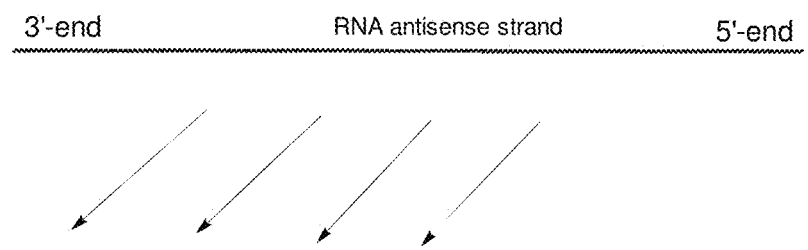

FIGS. 4a, 4b, 4c and 4d exemplify the Mechanism of Action (MOA) of a Conjugate of the Invention, wherein a Conjugate is according to Formula (Cn-8). The RNA Duplex is a Dicer substrate of 25/27-nucleotide long, with a phosphate group linked at the 5'-end of the passenger strand: FIG. 4(a) demonstrates cleavage and removal of the E, E' and E" moieties in the reductive conditions that prevail in the cytoplasm; FIG. 4(b) demonstrates interaction of the RNA Duplex with the Dicer endonuclease, that induces a double-strand break, leaving a 21/21 RNA Duplex, with one remaining residue of E moiety, linked at the 5'-end of the passenger strand; FIG. 4(c) demonstrates the removal of the sense strand by the enzyme helicase (i.e., a cytoplasmatic enzyme, capable of separating RNA strands). This event leads to the removal of the residue of the stump of the second E moiety, thus releasing the intact antisense strand, to enter the RNA-induced silencing complex (RISC), in order to induce the desired gene silencing [FIG. 4(d)].

Figure 5:
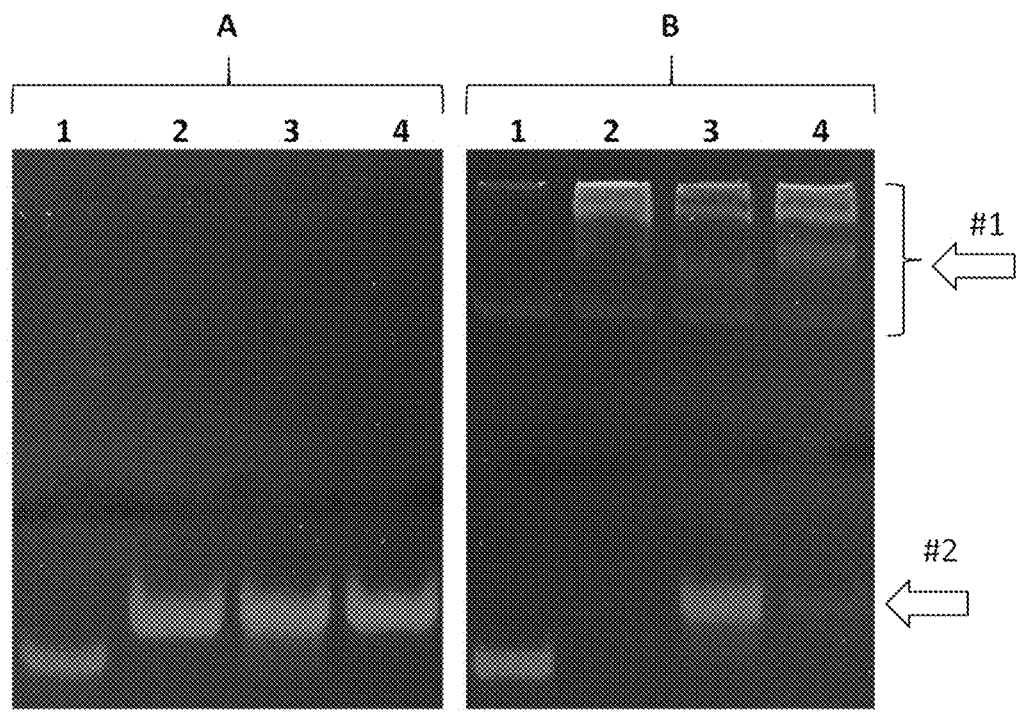

FIG. 5 presents gel electrophoresis of RNA Duplexes, each composed of one 25-nucleotide-long strand and one 27-nucleotide-long strand, specific for silencing the EGFP gene (as described in Example 6). Electrophoresis was performed with the Conjugates which were either dissolved in water (Lanes A), or in the presence of 10% bovine serum albumin (BSA) (Lanes B). These Duplexes were either non-conjugated (Lane 1); conjugated to two Control Apo-Si-S-1 E moieties (Lane 2); conjugated to two Apo-Si-K-13 E moieties of the Invention (Lane 3); or conjugated to two Apo-Si-K-18 E moieties of the Invention (Lane 4). As shown, during electrophoresis, while the Apo-Si-S-1 Conjugate manifested tight binding to albumin, and therefore did not have an albumin-free fraction, Apo-Si-K-13 and Apo-Si-K-18 Conjugates manifested both an albumin-bound fraction (Arrow #1), and an albumin-free fraction (Arrow #2).

DETAILED DESCRIPTION OF THE INVENTION

The invention relates to Conjugates and Precursors thereof, comprising macromolecule drugs such as OD, linked to a molecular delivery system (MDS) that can deliver the drug across phospholipid biological membranes into cells, to exert biological performance, in both serum-free conditions, and in the presence of plasma proteins. This delivery system enables the trans-membrane delivery of macromolecule drugs, such as genetic drugs, for example, siRNA or dsiRNA, antisense oligonucleotides (ASO), or therapeutic proteins. Activity in the presence of plasma proteins is specifically important for utilization of the Conjugates of the Invention in vivo, for local or systemic administration (e.g., via intravenous injection), to a living animal or a human subject.

In an embodiment of the invention, there are provided Conjugates, having the structure as set forth in Formula (I):

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes (i.e., a cargo drug), selected from a group consisting of a small-molecule drug, a peptide, a protein, and OD (i.e., a native or modified, single-stranded or double-stranded DNA or RNA, siRNA, dsiRNA, or ASO);

y, z and w are each an integer, independently selected from 0, 1, 2, 3 or 4, wherein if any of y, z or w or combination thereof is 0, it means that the respective E moiety (or moieties) is (are) null; at least one of y, z or w is different from 0;

E, E', or E" can be the same or different, each having independently a structure as set forth in general Formula (II):

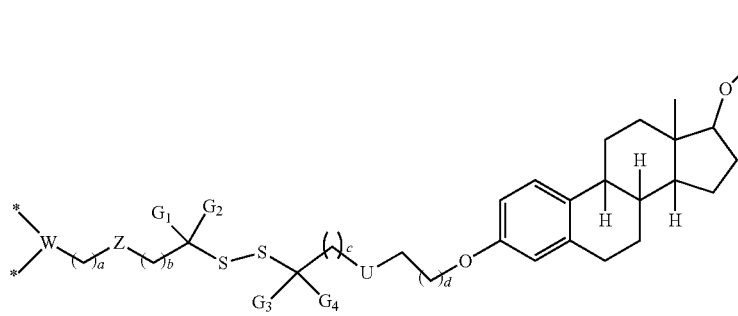

Formula (II)

including pharmaceutically acceptable salts, hydrates, solvates and metal chelates of the compound represented by the structure as set forth in Formula (II), and solvates and hydrates of the salts, wherein:

- one of U or Q is independently null, and the other one is a selected from the group consisting of —NH—, —N(CH$_3$)—, —N(CH$_2$—CH$_3$)—, —NH—(CH$_2$)$_2$—NH—, or —N(CH$_3$)—(CH$_2$)$_2$—N(CH$_3$)—;
- G$_1$, G$_2$, G$_3$ and G$_4$ are each independently selected from the group consisting of hydrogen, methyl or ethyl; G$_1$, G$_2$, G$_3$ and G$_4$ moieties can be the same or different; at least two of G$_1$, G$_2$, G$_3$, and G$_4$ are hydrogen atoms;
- Z is selected from the group consisting of null, ether, ester, amine and amide;
- a, b, c, d are integers, each being independently selected from the group consisting of 0, 1, 2, 3, 4, 5, 6 or 7, wherein 0=null; a, b, c, d can be the same or different;
- e and f are integers, each being independently selected from the group consisting of 1, 2 and 3; e and f can be the same or different;
- if any of each a or b is ≥2, then the respective hydrocarbon chain can be either saturated or non-saturated;
- W is selected from a group comprising null, hydroxyl, di-hydroxyl, natural or modified nucleoside, and the structure set forth in Formula (II'):

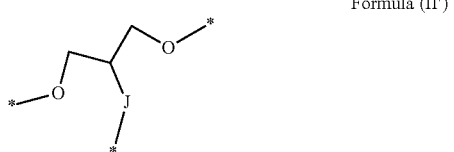

Formula (II')

wherein J is selected from null, —CH$_2$—, a secondary or tertiary amine, and oxygen;

* is selected from the group consisting of null; hydrogen; a linkage point to D; a linkage point to a protecting group, as defined herein (e.g., a protecting group for alcohol); a linkage point to a phosphate, sulfate or carboxyl group; and a linkage point to a solid support. In the context of the Invention, an E, E' or E'' moiety may be linked to one D moiety via one or two points.

In an embodiment of the Invention, W is a nucleoside, selected from natural or modified adenine, cytosine, thymine and uracil, and the sugar moiety is ribose or 2'-deoxyribose. In another embodiment of the Invention, W is 2'-deoxyuridine. In yet another embodiment of the Invention, W has the structure set forth in Formula (II'), wherein J is —CH$_2$—.

The role of chemical moieties according to Formula (II) in enabling trans-membrane delivery of the Conjugates of the Invention in both (S+) and (S−) conditions is exemplified in Example 6. This Example shows that E moieties that comply with the structure of Formula (II), manifest robust performance of the related Conjugates, in both delivery across cell membranes into cells, and in induction of a biological effect such as, for example, gene silencing. This performance is observed in both (S−) conditions and (S+) conditions. Example 6 describes two Conjugates of the Invention, both having E moieties that comply with Formula (II), linked to a Dicer substrate, which is a Duplex, designed to silence the expression of the gene for Enhanced fluorescent Green Protein (EGFP). One is the Apo-Si-K-18 Conjugate, having two E moieties of Apo-Si-K-18, according to Formula (Vb'), and the second is the Apo-Si-K-13 Conjugate, having two E moieties of Apo-Si-K-13, according to Formula (Vb''). The Example compares the performance of these Conjugates in gene silencing, to the performance of three structurally-related Control Conjugates, comprising Apo-Si-K-19, Apo-Si-W and Apo-Si-G moieties. These moieties, albeit being structurally-similar to the E moieties of the Invention, do not fully comply with Formula (II), and respectively fail to perform effectively in delivery into cells, and in gene silencing, in the presence of plasma proteins [S (+) conditions].

E moieties of all Conjugates, both Conjugates of the Invention and Control Conjugates, comprise a sterol backbone and a nona-fluorotert-butanol residue. Evidently, however, this is not sufficient to confer biological activity (e.g., in gene silencing), even in serum-free conditions. For example, as described in Example 6, Conjugate of Apo-Si-W was inactive, in either presence or absence of plasma proteins. Adding a disulfide group per E moiety entailed activity (e.g., in gene silencing) in serum-free conditions, as reflected in the performance of the Conjugates of the Invention, as well as the performance of the Control Conjugate Apo-Si-G, which manifested activity without serum. However, installment of a disulfide moiety per se, was not sufficient to enable performance in the presence of plasma proteins. By contrast, adding for each E moiety one Q or U moiety that is not null did confer activity in the presence of plasma proteins, reflected by effective performance in gene silencing in Serum (+) conditions, exerted by the Conjugates that comprise Apo-Si-K-18 or Apo-Si-K-13 moieties.

Taken together, these data support the notion, that Formula (II) indeed represents a unique, novel and unpredictable balance, between various determinants required for the trans-membrane delivery of an Oligonucleotide Drug, and for exerting respective favorable biological performance (e.g., in gene silencing).

"Drug" or "Cargo Drug" (i.e., moiety D) in the context of the present Invention, refers to a molecule(s) to be delivered by the Conjugates of the Invention, being either small-molecule drugs, or macromolecules, such as peptides, proteins or oligonucleotide drugs.

A "drug" or "medicament" in the context of the present invention, relate to a chemical substance, that when administered to a patient suffering from a disease, is capable of exerting beneficial effects on the patient. The beneficial effects can be amelioration of symptoms, or counteracting the effects of an agent or substance, that play(s) a role in the disease process. The drug may comprise a small molecule, or a macromolecule, such as a protein, or single- or double-stranded RNA or DNA, administered to inhibit gene expression. Among others, the drug may comprise siRNA or ASO. In some embodiments, the drug is aimed at treating degenerative disorders, cancer, ischemic, infectious, toxic insults, metabolic disease or immune-mediated disorders.

The term "Oligonucleotide drug", hereinafter also designated "OD", in the context of the Invention, refers to a drug that comprises nucleosides or nucleotides. Examples for Oligonucleotide drugs (OD) are single-stranded or double-stranded, natural or modified RNA or DNA. Examples for OD are siRNA (small interfering RNA), a substrate for the Dicer enzyme (dsiRNA), microRNA (miRNA), messenger RNA (mRNA), or DNA sequences designed to serve as antisense oligonucleotides (ASO). Linkage between the nucleotide building blocks of the OD can be, among others, via phosphate-triester, or phosphorothioate bonds.

In more specific embodiments among OD, the Invention discloses:

"siRNA", being an RNA duplex, wherein each RNA strand is 19-21-nucleotide long, aimed at silencing gene expression via the RISC (RNA-induced silencing complex) protein complex;

siRNA substrate for Dicer, ("dsiRNA"), being an RNA duplex, wherein each RNA strand is 24-30-nucleotide long. In an embodiment, the dsiRNA Duplex consists of one strand of 25 nucleotides, while the second strand consists of 27 nucleotides. In another embodiment, the dsiRNA Duplex consists of one strand of 24 nucleotides, while the second strand consists of 27 nucleotides;

"Antisense Oligonucleotide" (ASO), being a synthetic, single stranded, natural or modified DNA or RNA oligo-nucleotide, usually 15-20 nucleotide long. The sequence of the ASO is antisense, i.e., it is complementary to the sense sequence of a specific mRNA of a protein, which synthesis is sought to be inhibited. Binding of the ASO to said complementary sequence blocks the ability of ribosomes to move along the mRNA, thus preventing synthesis of the protein, or hastens the rate of degradation of the mRNA.

A "nucleoside" in the context of the present invention, is defined as a chemical moiety, that comprises a nitrogenous base (nucleobase), and a sugar of five- or six-carbon atoms (e.g., ribose or deoxyribose). The nucleobases are selected from natural or modified purines (e.g., adenine, guanine) and natural or modified pyrimidines (e.g., thymine, cytosine, uracil). The nucleobase can be modified by various modifications, as known in the art (e.g., methylation, acetylation). In addition, the sugar moiety of the nucleoside can also be modified, as known in the art [e.g., 2'-deoxy derivative, methylation at the 2' position of the ribose, installment of a 2'-fluoro atom, or having a bridge connecting the 2' oxygen and 4' carbon atoms, thus generating locked nucleic acid (LNA)]. The use of such modified nucleosides is therefore also within the scope of the invention. In an embodiment, the nucleoside comprises a pyrimidine derivative, selected from natural or modified cytosine, thymine and uracil, and the sugar moiety is either ribose or deoxyribose.

A "nucleotide", in the context of the Invention, is a nucleoside as defined above, linked to a phosphate group. Nucleotides are the building blocks of the oligonucleotides.

A "Precursor molecule" in the context of the invention, is defined as an E, E' or E" moiety, having the structure as set forth in any of Formulae (II), (III), (IVa), (IVb), (IVc), (Va'), (Va"), (Va'''), (Vb'), (Vb"), (Vb'''), (Vc'), (Vc") or (Vc'''), of the invention, that is attached via linkage point * to a protecting group, as defined below.

A "protecting group" in the context of the invention, is defined as a chemical group that is destined to be removed or modified during the synthesis of the Conjugate. Such removal or modification may occur at various stages of the synthesis; for example without limitation, during the attachment of E, E' or E" moieties to D, in the case that D is a macromolecule drug, such as an oligonucleotide drug. In a preferred embodiment of the Invention, the protecting group is a protecting group for alcohol, as defined below.

A "protecting group for alcohol" in the context of the Invention, refers to a chemical group attached to a hydroxyl group, in order to "mask" it during certain chemical reactions, and which is potentially removed thereafter, as known in the art. Examples for such protecting groups are Acetyl (Ac), Benzoyl (Bz), Benzyl (Bn), 3-Methoxyethoxymethyl ether (MEM), Dimethoxytrityl [bis-(4-methoxyphenyl) phenylmethyl] (DMT), Methoxymethyl ether (MOM), Methoxytrityl [(4-methoxyphenyl)diphenylmethyl] (MMT), p-Methoxy-benzyl ether (PMB), Pivaloyl (Piv), Tetrahydropyranyl (THP), Tetrahydrofuran (THF), Trityl (triphenylmethyl, Tr), Silyl ether [e.g., trimethylsilyl (TMS), tert-butyldimethylsilyl (TBDMS), tri-iso-propylsilyloxymethyl (TOM), and triisopropylsilyl (TIPS) ethers], Ethoxyethyl ethers (EE), phosphoramidite, N-hydroxysuccinimide (NHS). Frequently used protecting groups for alcohol are Dimethoxytrityl [bis-(4-methoxyphenyl) phenylmethyl] (DMT), and phosphoramidite.

The term "linkage point to a solid support" in the context of the Invention means a point of attachment of an E, E' or E" moiety to a solid support during chemical synthesis. For example, Controlled Pore Glass (CPG) may be used as a solid support, for attachment at the 3'-end of the oligonucleotide during the synthesis of the conjugate of the invention.

The term "biological membrane" according to the invention, refers to any phospholipid membrane related to a biological system. Examples for such phospholipid membranes are the plasma membrane of cells, intracellular membranes, or phospholipid membranes associated with biological barriers, such as the blood-brain-barrier (BBB), the blood-ocular-barrier (BOB), or the blood-placenta barrier.

In an embodiment of the Invention, is provides E, E', or E" according to Formula (II), having the structure as set forth in Formula (III):

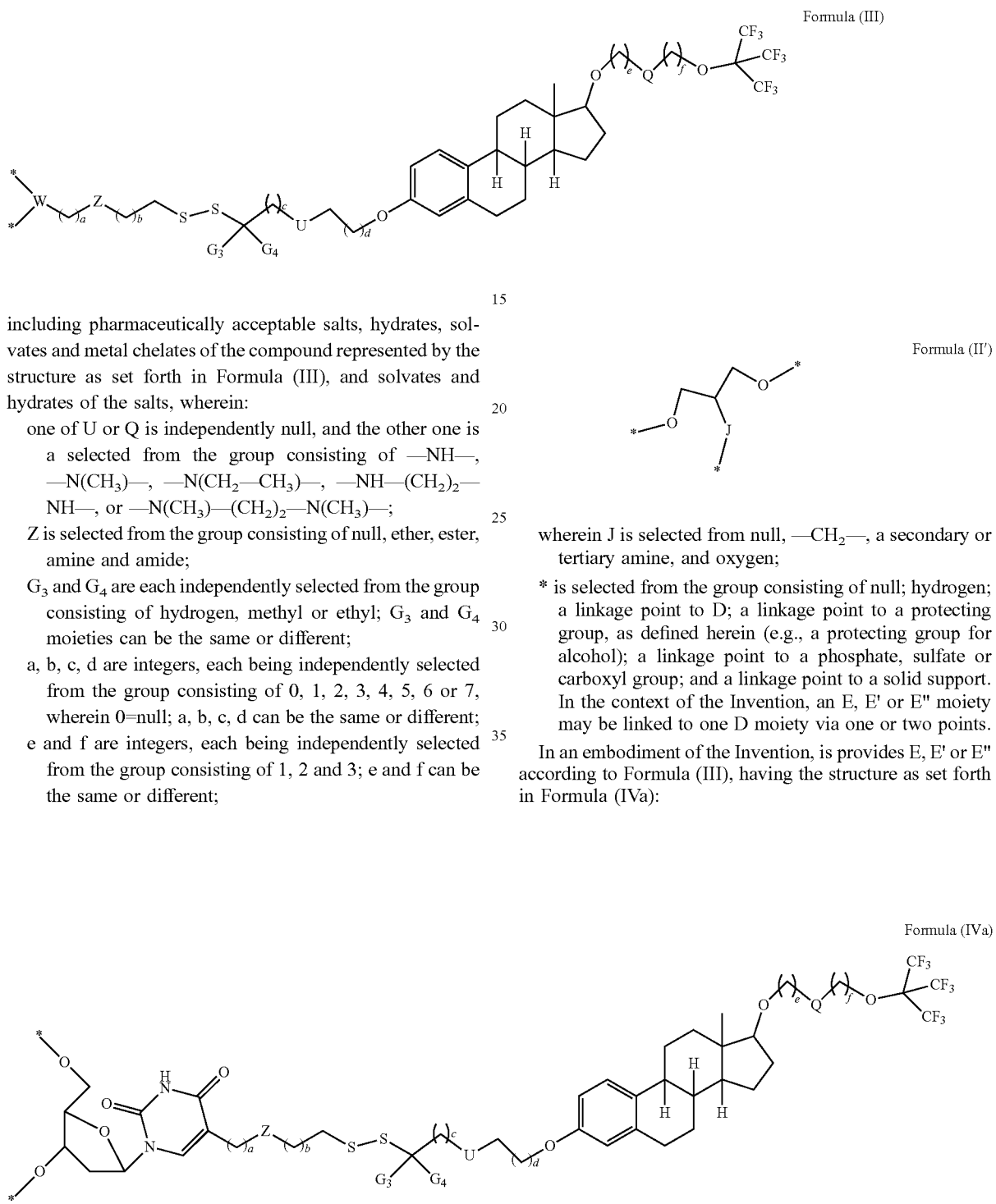

Formula (III)

Formula (II')

including pharmaceutically acceptable salts, hydrates, solvates and metal chelates of the compound represented by the structure as set forth in Formula (III), and solvates and hydrates of the salts, wherein:
- one of U or Q is independently null, and the other one is a selected from the group consisting of —NH—, —N(CH$_3$)—, —N(CH$_2$—CH$_3$)—, —NH—(CH$_2$)$_2$—NH—, or —N(CH$_3$)—(CH$_2$)$_2$—N(CH$_3$)—;
- Z is selected from the group consisting of null, ether, ester, amine and amide;
- G$_3$ and G$_4$ are each independently selected from the group consisting of hydrogen, methyl or ethyl; G$_3$ and G$_4$ moieties can be the same or different;
- a, b, c, d are integers, each being independently selected from the group consisting of 0, 1, 2, 3, 4, 5, 6 or 7, wherein 0=null; a, b, c, d can be the same or different;
- e and f are integers, each being independently selected from the group consisting of 1, 2 and 3; e and f can be the same or different;
- if any of a, b is ≥2, then the respective hydrocarbon chain can be either saturated or non-saturated;

W is selected from a group comprising null, hydroxyl, di-hydroxyl, natural or modified nucleoside, and the structure set forth in Formula (II'):

wherein J is selected from null, —CH$_2$—, a secondary or tertiary amine, and oxygen;
* is selected from the group consisting of null; hydrogen; a linkage point to D; a linkage point to a protecting group, as defined herein (e.g., a protecting group for alcohol); a linkage point to a phosphate, sulfate or carboxyl group; and a linkage point to a solid support. In the context of the Invention, an E, E' or E" moiety may be linked to one D moiety via one or two points.

In an embodiment of the Invention, is provides E, E' or E" according to Formula (III), having the structure as set forth in Formula (IVa):

including pharmaceutically acceptable salts, hydrates, solvates and metal chelates of the compound represented by the structure as set forth in Formula (IVa), and solvates and hydrates of the salts; wherein: Z, U, Q, G$_3$, G$_4$, a, b, c, d, e, f and *, each having the same meaning as in Formula (III).

In an embodiment of the Invention, is provides E, E' or E" according to Formula (III), having the structure as set forth in Formula (IVb):

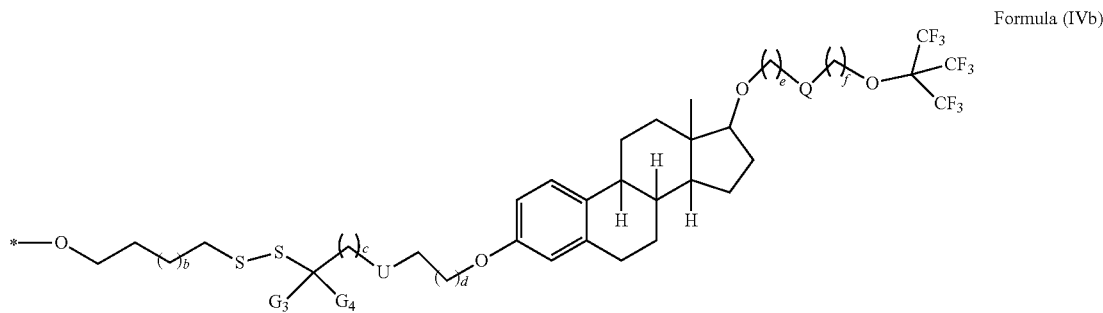

Formula (IVb)

including pharmaceutically acceptable salts, hydrates, solvates and metal chelates of the compound represented by the structure as set forth in Formula (IVb), and solvates and hydrates of the salts; wherein U, Q, $G_3$, $G_4$, b, c, d, e, f and *, each having the same meaning as in Formula (III).

In an embodiment of the Invention, is provides E, E' or E" according to Formula (III), having the structure as set forth in Formula (IVc):

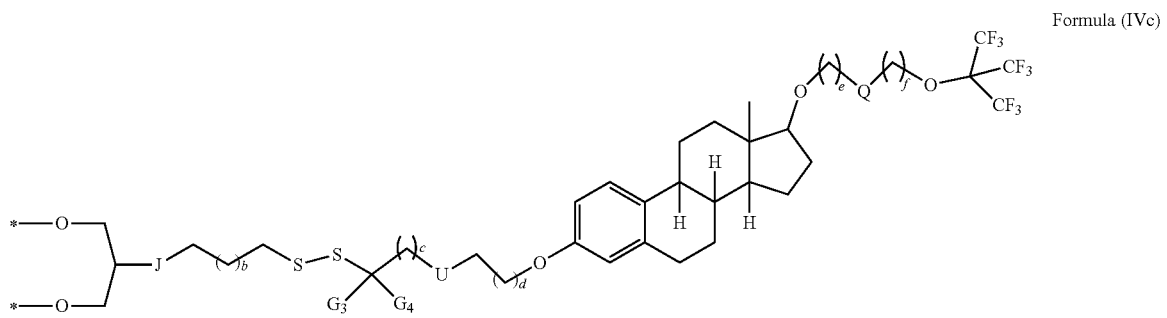

Formula (IVc)

including pharmaceutically acceptable salts, hydrates, solvates and metal chelates of the compound represented by the structure as set forth in Formula (IVc), and solvates and hydrates of the salts; wherein U, Q, $G_3$, $G_4$, b, c, d, e, f, and *, each having the same meaning as in Formula (III); J is selected from the group consisting of null, —$CH_2$—, and oxygen.

The Invention also provides E, E' or E" according to Formula (IVa), having the structure as set forth in Formula (Va'):

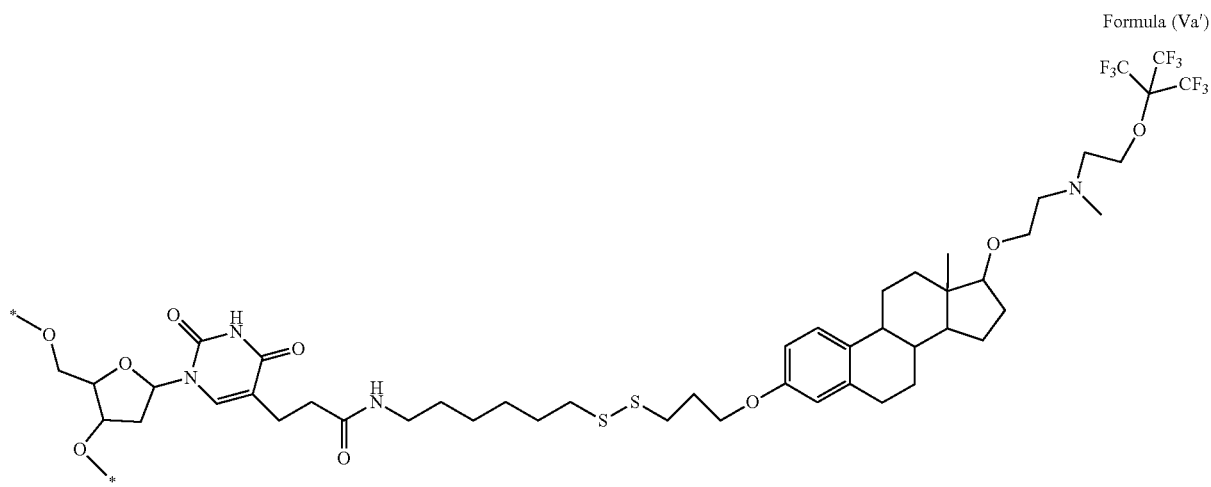 [SMILES: COCC1OC(n2cc(CCC(=O)NCCCCCCSSCCCOc3ccc4c(c3)CCC3C4CCC4(C)C(OCCN(C)CCOC(C(F)(F)F)(C(F)(F)F)C(F)(F)F)CCC34)c(=O)[nH]c2=O)CC1OC]

Formula (Va')

including pharmaceutically acceptable salts, hydrates, solvates and metal chelates of the compound represented by the structure as set forth in Formula (Va'); wherein * has the same meaning as in Formula (IVa).

The Invention also provides E, E' or E" according to Formula (IVa), having the structure as set forth in Formula (Va"):

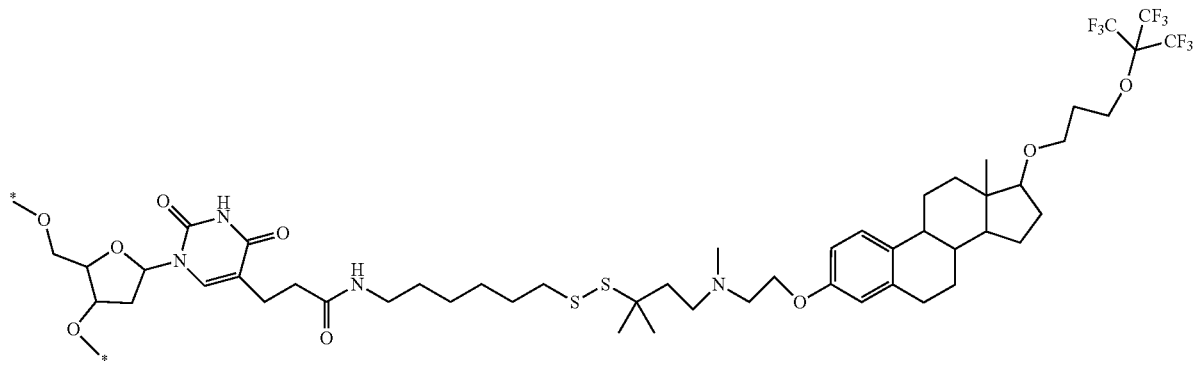

Formula (Va")

including pharmaceutically acceptable salts, hydrates, solvates and metal chelates of the compound represented by the structure as set forth in Formula (Va"); wherein * has the same meaning as in Formula (IVa). In the case that one of * is a linkage point to a phosphoramidite group, and the second * is a linkage point to a DMT group, the compound is designated Apo-Si-K-29D-Precursor.

The Invention also provides E, E' or E" according to Formula (IVa), having the structure as set forth in Formula (Va'''):

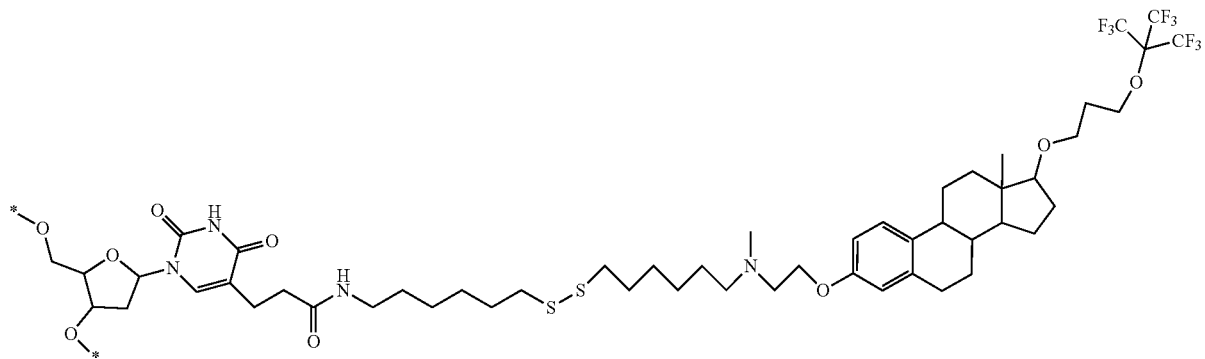

Formula (Va''')

including pharmaceutically acceptable salts, hydrates, solvates and metal chelates of the compound represented by the structure as set forth in Formula (Va'''); wherein * has the same meaning as in Formula (IVa).

The Invention also provides E, E' or E" according to Formula (IVb), having the structure as set forth in Formula (Vb'):

Formula (Vb')

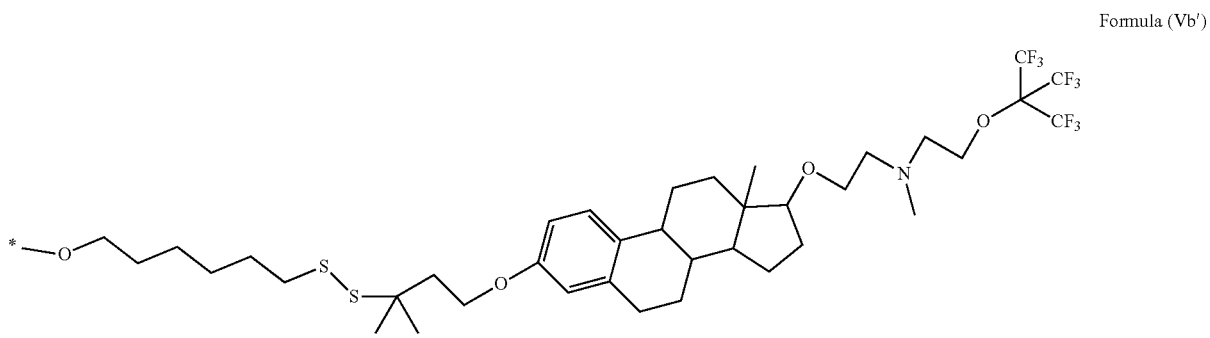 [SMILES: COCCCCCCSSC(C)(C)CCOc1ccc2c(c1)CCC1C2CCC2(C)C(OCCN(C)CCOC(C(F)(F)F)(C(F)(F)F)C(F)(F)F)CCC12]

including pharmaceutically acceptable salts, hydrates, solvates and metal chelates of the compound represented by the structure as set forth in Formula (Vb'); * has the same meaning as in Formula (IVb). This E, E', or E" moiety, as shown in Formula (Vb'), is designated Apo-Si-K-18. In the case that * is a phosphoramidite group, the compound is designated Apo-Si-K-18-Precursor.

The Invention also provides E, E' or E" according to Formula (IVb), having the structure as set forth in Formula (Vb"):

Formula (Vb")

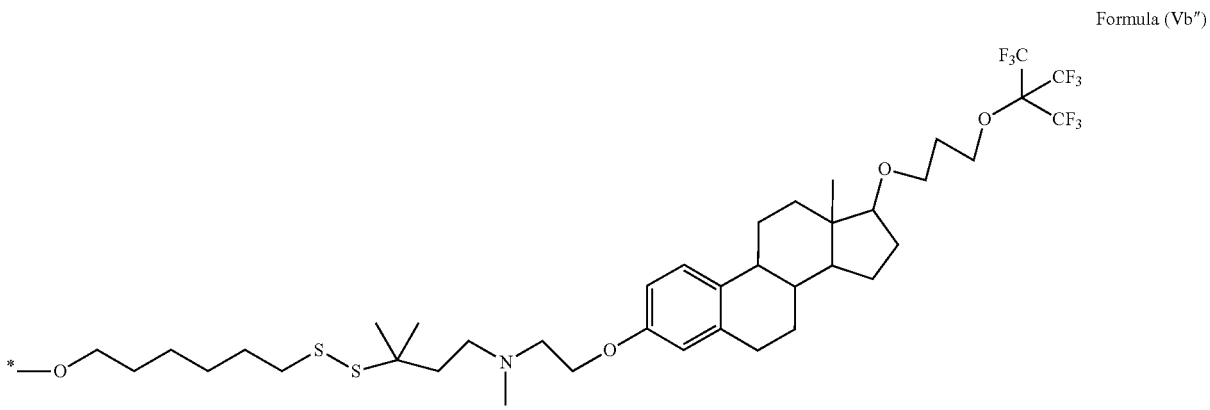 [SMILES: COCCCCCCSSC(C)(C)CCN(C)CCOc1ccc2c(c1)CCC1C2CCC2(C)C(OCCCOC(C(F)(F)F)(C(F)(F)F)C(F)(F)F)CCC12]

including pharmaceutically acceptable salts, hydrates, solvates and metal chelates of the compound represented by the structure as set forth in Formula (Vb"); * has the same meaning as in Formula (IVb). This E, E', or E" moiety, as shown in Formula (Vb"), is designated Apo-Si-K-13. In the case that * is a phosphoramidite group, the compound is designated Apo-Si-K-13-Precursor.

The Invention also provides E, E' or E" according to Formula (IVb), having the structure as set forth in Formula (Vb'''):

Formula (Vb''')

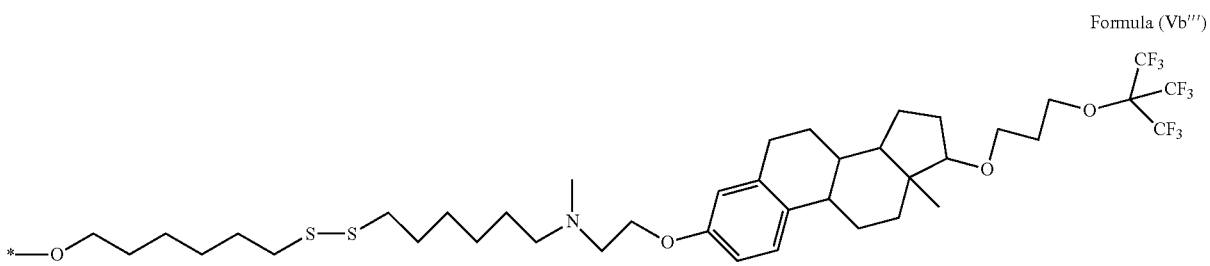 [SMILES: COCCCCCCSSCCCCCCN(C)CCOc1ccc2c(c1)CCC1C2CCC2(C)C(OCCCOC(C(F)(F)F)(C(F)(F)F)C(F)(F)F)CCC12]

including pharmaceutically acceptable salts, hydrates, solvates and metal chelates of the compound represented by the structure as set forth in Formula (Vb'''); * has the same meaning as in Formula (IVb). This E, E', or E" moiety, as shown in Formula (Vb'''), is designated Apo-Si-K-11. In the case that * is a phosphoramidite group, the compound is designated Apo-Si-K-11-Precursor.

In an embodiment, the Invention provides E, E' or E" according to Formula (IVc), having the structure as set forth in Formula (Vc'):

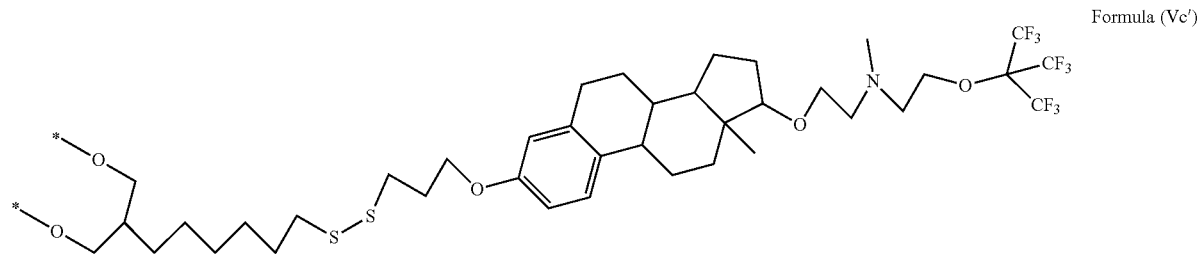 [SMILES: COCC(CCCCCCSSCCCOc1ccc2c(c1)CCC1C2CCC2(C)C(OCCN(C)CCOC(C(F)(F)F)(C(F)(F)F)C(F)(F)F)CCC12)COC]

Formula (Vc')

including pharmaceutically acceptable salts, hydrates, solvates and metal chelates of the compound represented by the structure as set forth in Formula (Vc'); wherein * has the same meaning as in Formula (IVc). This E, E', or E" moiety, as shown in Formula (Vc'), is designated Apo-Si-K-40. In the case that one of * is a linkage point to a phosphoramidite group, and the second * is a linkage point to a DMT group, the compound is designated Apo-Si-K-40-Precursor.

In an embodiment, the Invention provides E, E' or E" according to Formula (IVc), having the structure as set forth in Formula (Vc"):

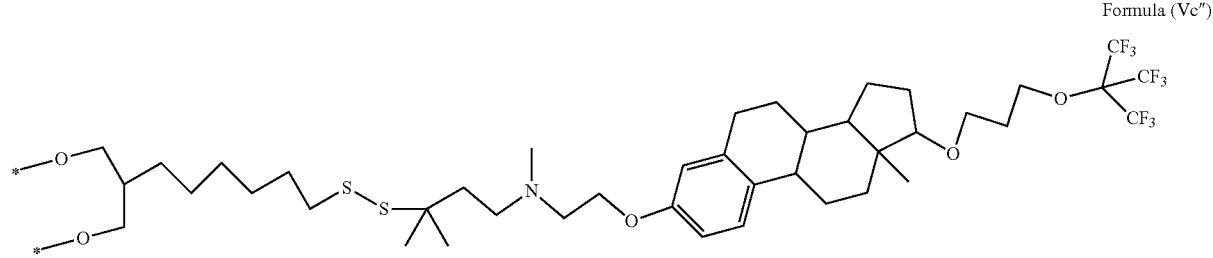 [SMILES: COCC(CCCCCCSSC(C)(C)CCN(C)CCOc1ccc2c(c1)CCC1C2CCC2(C)C(OCCCOC(C(F)(F)F)(C(F)(F)F)C(F)(F)F)CCC12)COC]

Formula (Vc")

including pharmaceutically acceptable salts, hydrates, solvates and metal chelates of the compound represented by the structure as set forth in Formula (Vc"); wherein * has the same meaning as in Formula (IVc). This E, E', or E" moiety, as shown in Formula (Vc"), is designated Apo-Si-K-43. In the case that one of * is a linkage point to a phosphoramidite group, and the second * is a linkage point to a DMT group, the compound is designated Apo-Si-K-43-Precursor.

In another embodiment of the invention, it provides E, E' or E" according to Formula (IVc), having the structure as set forth in Formula (Vc'''):

including pharmaceutically acceptable salts, hydrates, solvates and metal chelates of the compound represented by the structure as set forth in Formula (Vc'''); wherein * has the same meaning as in Formula (IVc). This E, E', or E" moiety, as shown in Formula (Vc'''), is designated Apo-Si-K-63. In the case that one of * is a linkage point to a phosphoramidite group, and the second * is a linkage point to a DMT group, the compound is designated Apo-Si-K-63-Precursor.

In an embodiment, the Invention provides a Precursor molecule, that comprises E, E' or E" according to Formula (IVa), and has the following structure, as set forth in Formula (IVaP):

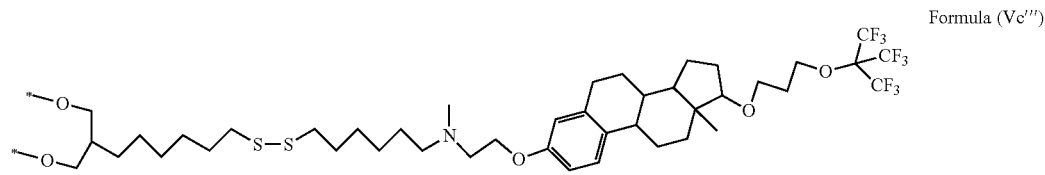 [SMILES: COCC(CCCCCCSSCCCCCCN(C)CCOc1ccc2c(c1)CCC1C2CCC2(C)C(OCCCOC(C(F)(F)F)(C(F)(F)F)C(F)(F)F)CCC12)COC]

Formula (Vc''')

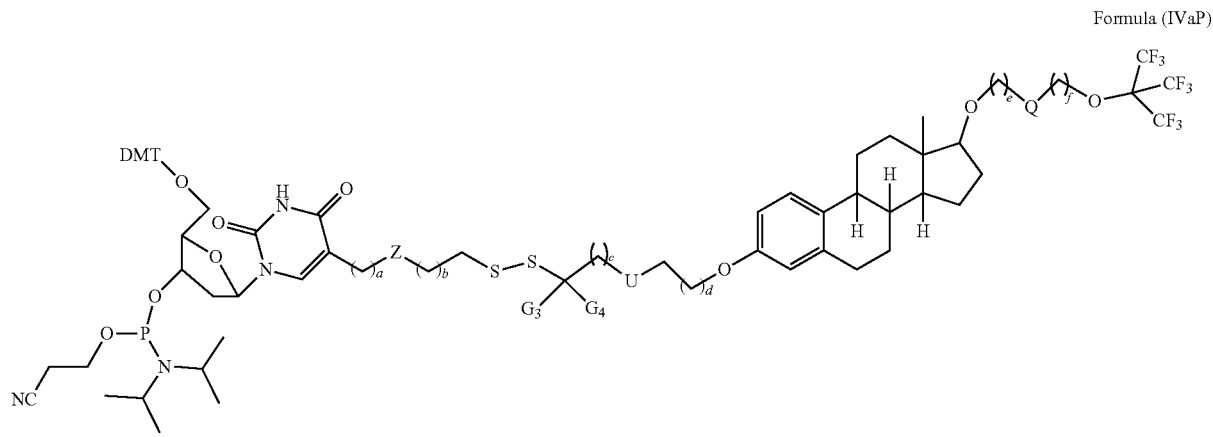

Formula (IVaP)

including pharmaceutically acceptable salts, hydrates, solvates and metal chelates of the compound represented by the structure as set forth in Formula (IVaP), and solvates and hydrates of the salts, wherein: Z, U, Q, $G_3$, $G_4$, a, b, c, d, e, f, each having the same meaning as in Formula (IVa). This Precursor molecule may serve to attach the E, E', or E" moiety at either the 5'-end or the 3'-end, or at an internal position within an oligonucleotide chain.

In another embodiment, the Invention provides a Precursor molecule, that comprises E, E' or E" according to Formula (IVb), and has the following structure, as set forth in Formula (IVbP):

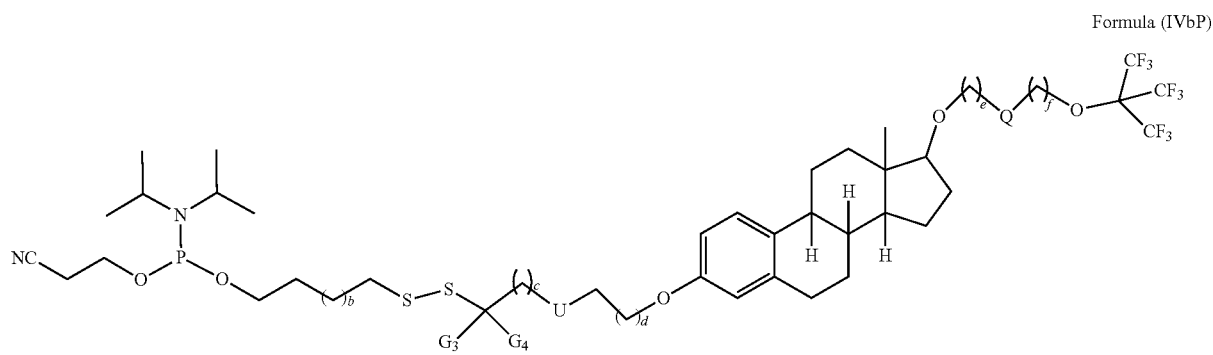

Formula (IVbP)

including pharmaceutically acceptable salts, hydrates, solvates and metal chelates of the compound represented by the structure as set forth in Formula (IVbP), and solvates and hydrates of the salts, wherein U, Q, $G_3$, $G_4$, b, c, d, e, f, each having the same meaning as in Formula (IVb).

In still another embodiment, the Invention provides a Precursor molecule, that comprises E, E' or E" according to Formula (IVc), and has the following structure, as set forth in Formula (IVcP):

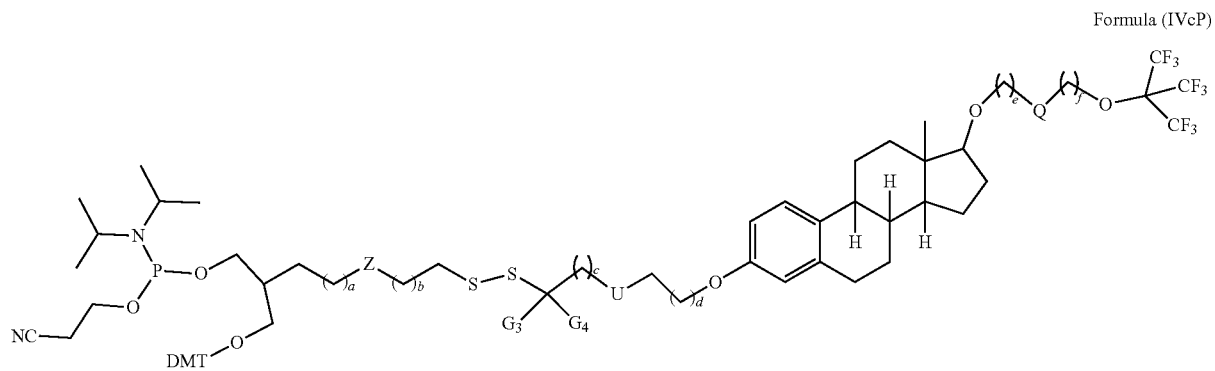

Formula (IVcP)

including pharmaceutically acceptable salts, hydrates, solvates and metal chelates of the compound represented by the structure as set forth in Formula (IVcP), and solvates and hydrates of the salts, wherein: Z, U, Q, $G_3$, $G_4$, a, b, c, d, e, f each having the same meaning as in Formula (IVc); This Precursor molecule may serve to attach the E, E', or E" moiety at either the 5'-end or the 3'-end, or at an internal position within the oligonucleotide chain.

In a specific embodiment, the Precursor molecule is according to Formula (IVcP), having the following structure, as set forth in Formula (PP-1):

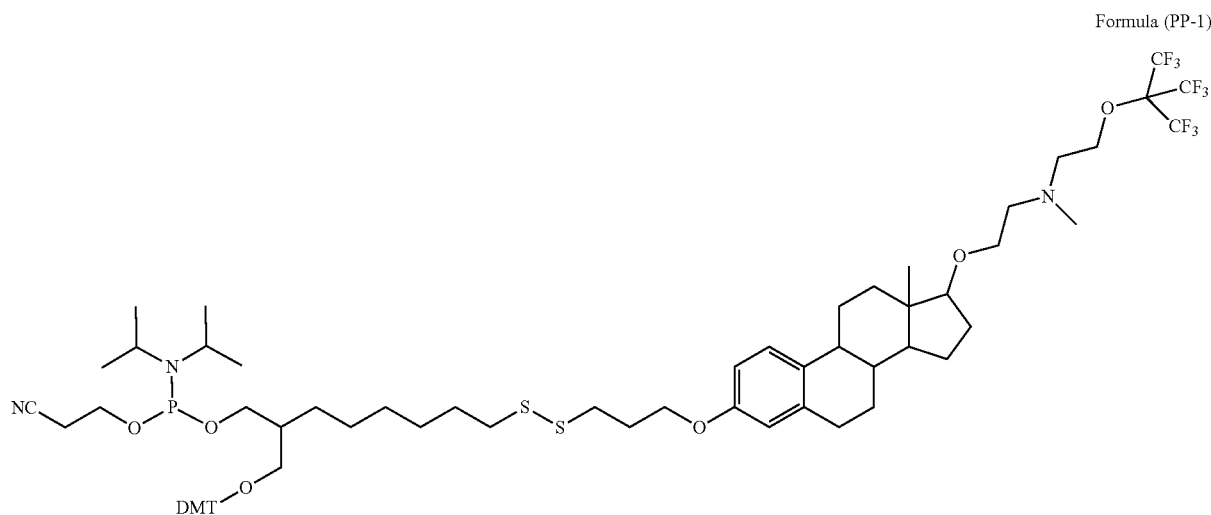

Formula (PP-1)

including pharmaceutically acceptable salts, hydrates, solvates and metal chelates of the compound represented by the structure as set forth in Formula (PP-1), and solvates and hydrates of the salts. This Precursor molecule may serve to attach the E, E', or E" moiety at either the 5'-end or the 3'-end, or at an internal position within the oligonucleotide chain. This Precursor molecule, as shown in Formula (PP-1), is designated Apo-Si-K-40-Precursor.

In another specific embodiment, the Precursor molecule is according to Formula (IVcP), having the following structure, as set forth in Formula (PP-2):

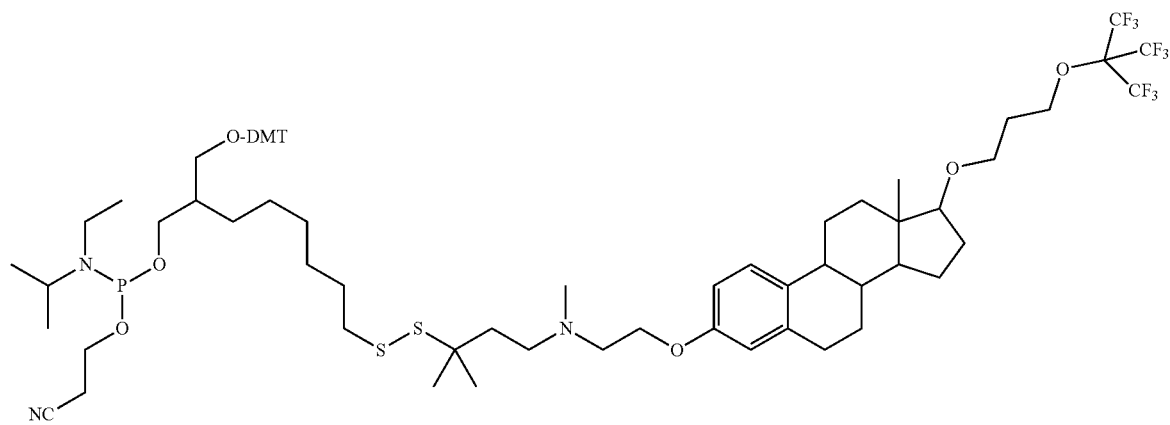

Formula (PP-2)

including pharmaceutically acceptable salts, hydrates, solvates and metal chelates of the compound represented by the structure as set forth in Formula (PP-2), and solvates and hydrates of the salts. This Precursor molecule may serve to attach the E, E', or E" moiety at either the 5'-end or the 3'-end, or at an internal position within the oligonucleotide chain. This Precursor molecule, as shown in Formula (PP-2), is designated Apo-Si-K-43-Precursor.

In another embodiment, the Precursor molecule is according to Formula (IVcP), having the following structure, as set forth in Formula (PP-3):

delivery into cells. In the case that D is an Oligonucleotide Drug (OD), Conjugates can be according to any one of the following options:

(i). D is linked to a single E, E', or E" moiety.

(ii). D is linked to two E and E' moieties, being the same or different; optionally at one end (e.g., the 5'-end) of each oligonucleotide chain.

(iii). D is linked to E, E' and E" moieties, being the same or different; E and E' moieties are linked at the end (e.g., at the 5-end) of each oligonucleotide chain, while E" is linked at an internal position within the oligonucleotide chain.

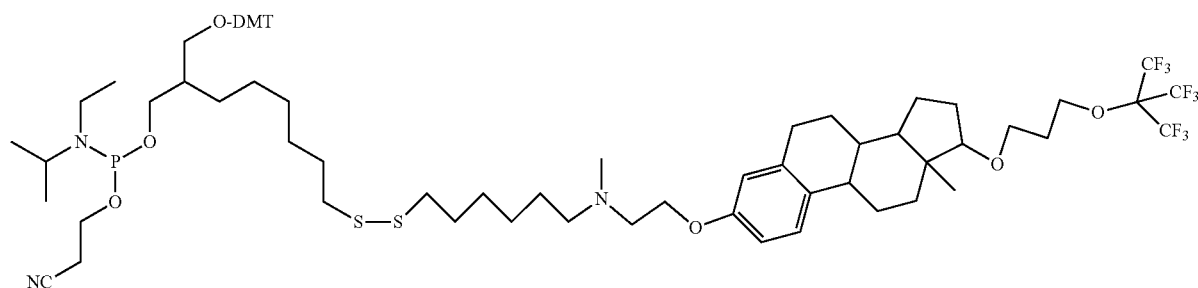

Formula (PP-3)

including pharmaceutically acceptable salts, hydrates, solvates and metal chelates of the compound represented by the structure as set forth in Formula (PP-3), and solvates and hydrates of the salts. This Precursor molecule, as shown in Formula (PP-3), is designated Apo-Si-K-63-Precursor.

Compound(s) according to any of Formulae (II), (III), (IVa), (IVb), (IVc), (Va'), (Va"), (Va'"), (Vb'), (Vb"), (Vb'"), (Vc'), (Vc") or (Vc'"), can serve as E, E', or E" moieties, for linkage to D, thus forming a desired Conjugate of the Invention, for biological performance in the trans-membrane (iv). D is linked to several (n>3) E moieties, being the same or different; E moieties are linked at the end (e.g., at the 5-end) of each oligonucleotide chain, while several other E moieties are linked at several internal positions along the oligonucleotide chain.

In an embodiment of the Invention, it provides a Conjugate, that comprises linkage of D to E and E' moieties according to Formula (Va'), at the 5'-ends of an RNA Duplex; said Conjugate having the following structure, as set forth in Formula (Cn-1):

Formula (Cn-1)

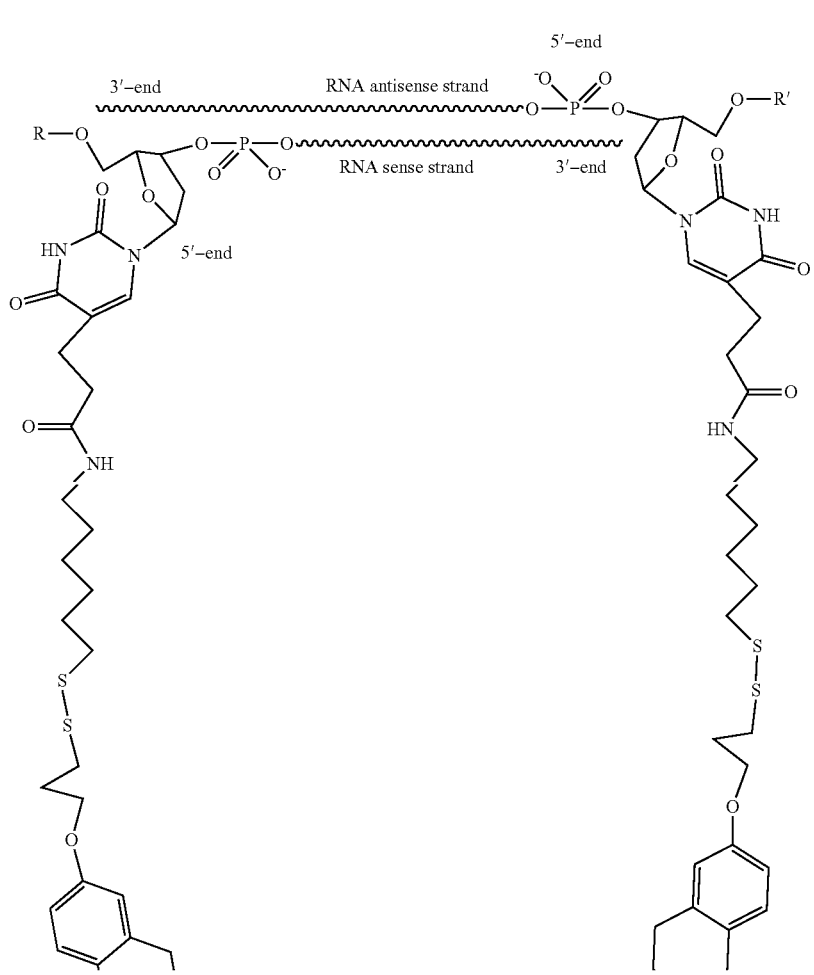

including pharmaceutically acceptable salts, hydrates, solvates and metal chelates of the compound represented by the structure as set forth in Formula (Cn-1), and solvates and hydrates of the salts, wherein R and R' are each selected independently from the group consisting of hydrogen, phosphate, sulfate or carboxyl group.

In another embodiment of the Invention, it provides a Conjugate that comprises linkage of D to two E and E' moieties according to Formula (Vc'), at the 5'-ends of the RNA Duplex; said Conjugate having the following structure, as set forth in Formula (Cn-2):

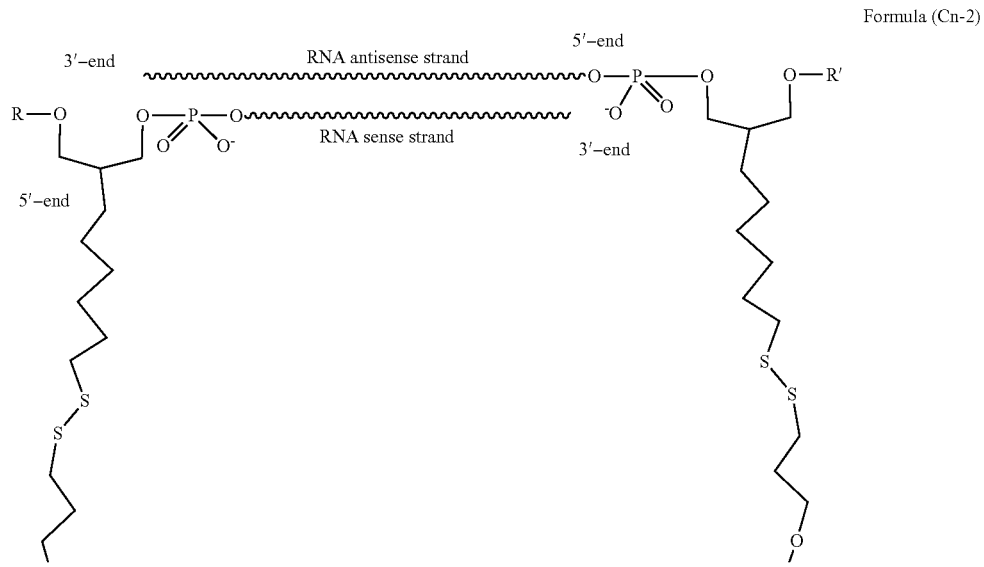

Formula (Cn-2)

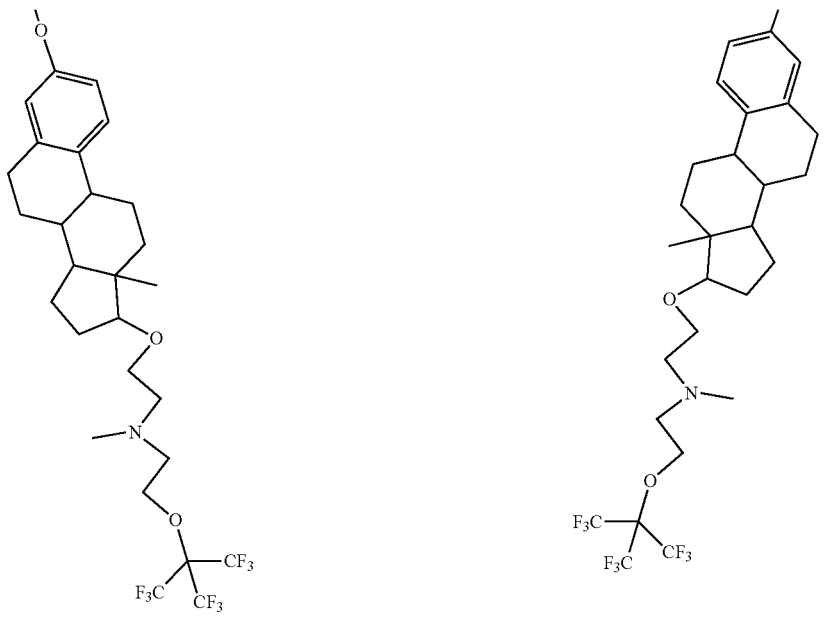

including pharmaceutically acceptable salts, hydrates, solvates and metal chelates of the compound represented by the structure as set forth in Formula (Cn-2), and solvates and hydrates of the salts, wherein R and R' are each selected independently from the group consisting of hydrogen, phosphate, sulfate or carboxyl group.

In another embodiment of the Invention, it provides a Conjugate, that comprises linkage of D to E and E' moieties, each having a structure as set forth in Formula (Vc'), being linked to the 5'-ends of the RNA Duplex; and an E" moiety, having the structure as set forth in Formula (Va'), being linked at an internal position along the oligonucleotide chain; this Conjugate has the following structure, as set forth in Formula (Cn-3):

Formula (Cn-3)

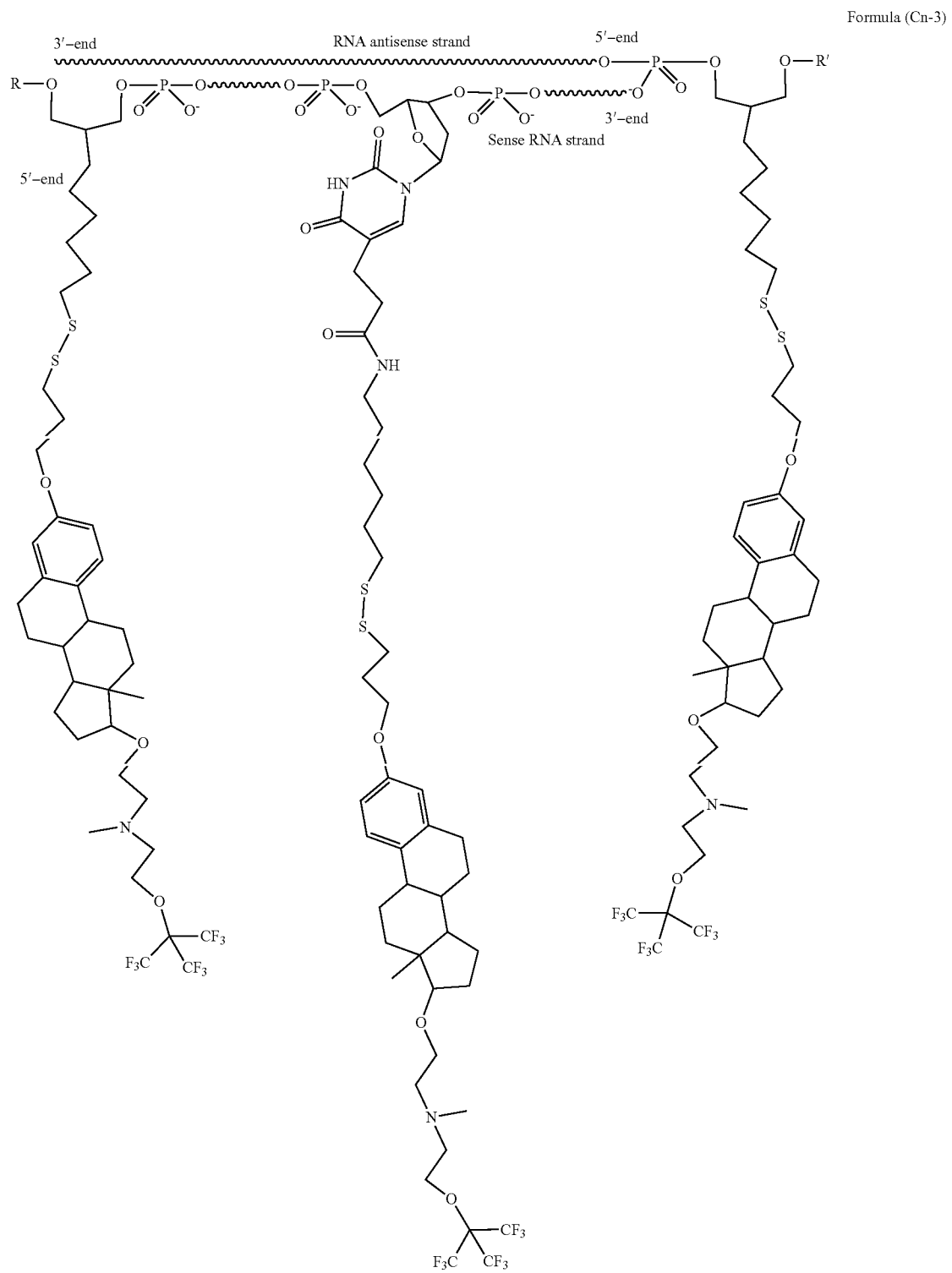

including pharmaceutically acceptable salts, hydrates, solvates and metal chelates of the compound represented by the structure as set forth in Formula (Cn-3), and solvates and hydrates of the salts, wherein R and R' are each selected independently from the group consisting of hydrogen, phosphate, sulfate or carboxyl group.

In another embodiment of the Invention, it provides a Conjugate, that comprises linkage of D to E and E' moieties according to Formula (Vc'), at the 5'-ends of the RNA Duplex; and an E" moiety according to Formula (Vc'), linked at an internal position along the oligonucleotide chain; said Conjugate having the following structure, as set forth in Formula (Cn-4):

Formula (Cn-4)

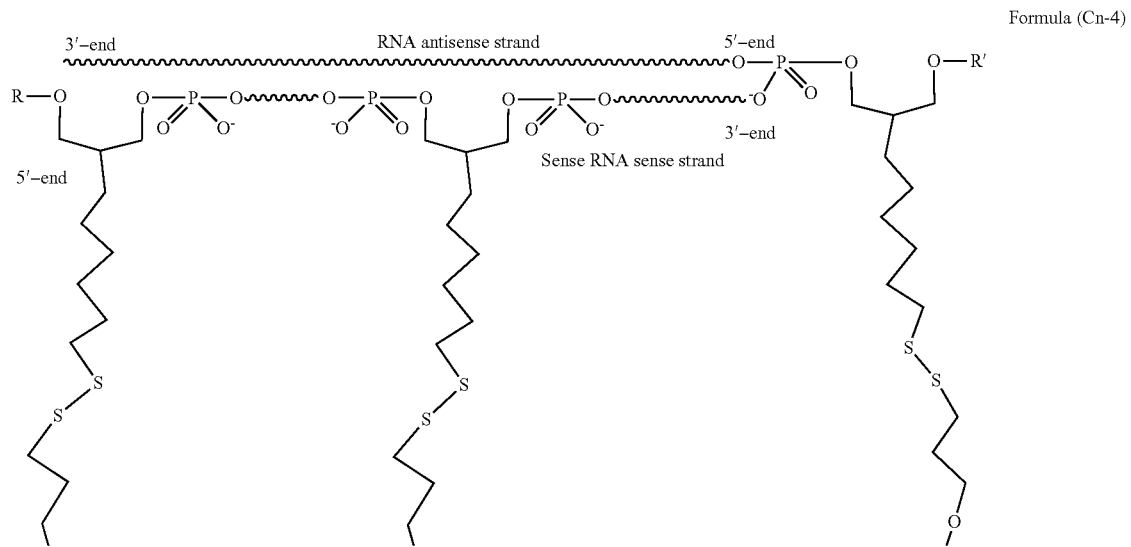

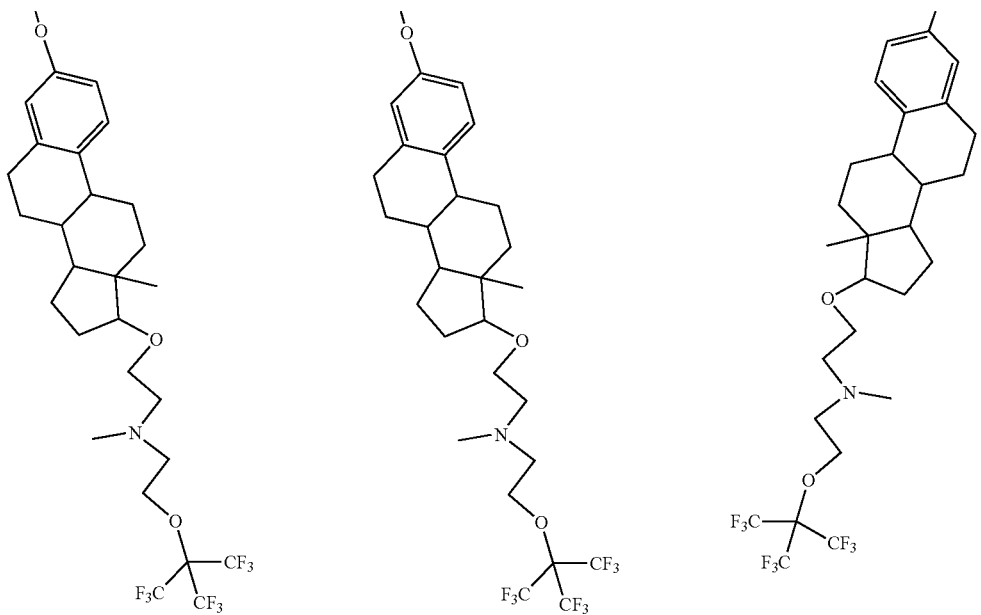

including pharmaceutically acceptable salts, hydrates, solvates and metal chelates of the compound represented by the structure as set forth in Formula (Cn-4), and solvates and hydrates of the salts, wherein R and R' are each selected independently from the group consisting of hydrogen, phosphate, sulfate or carboxyl group.

In another embodiment of the Invention, it provides a Conjugate, that comprises D that is an antisense oligonucleotide (ASO) as defined above, comprising a single-stranded oligonucleotide of 15-25 nucleotide long, selected from the group consisting of natural or modified DNA, RNA, locked nucleic acid nucleotides (LNA), phosphorothioate nucleotides, or combinations thereof. This Conjugate is having the following structure, as set forth in Formula (Cn-5):

Formula (Cn-5)

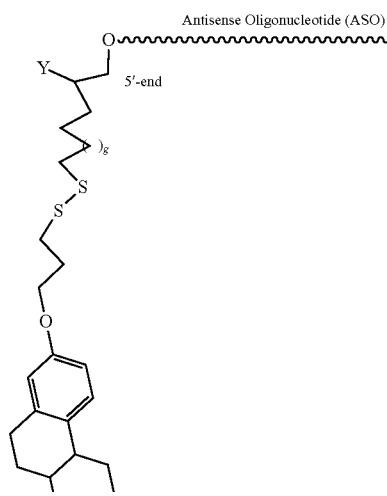
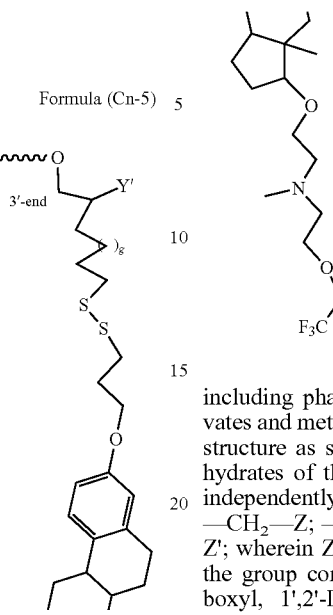
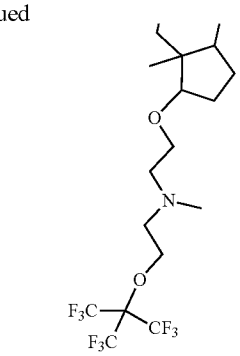

including pharmaceutically acceptable salts, hydrates, solvates and metal chelates of the compound represented by the structure as set forth in Formula (Cn-5), and solvates and hydrates of the salts; wherein Y and Y' are each selected independently from the group consisting of hydrogen, —CH$_2$—Z; —CH$_2$—Z'; —CH$_2$—O—Z; and —CH$_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

In another embodiment of the Invention, it provides a Conjugate, that comprises linkage of D to E and E' moieties according to Formula (Va") at the 5'-ends of an RNA Duplex. This Conjugate has the following structure, as set forth in Formula (Cn-6):

Formula (Cn-6)

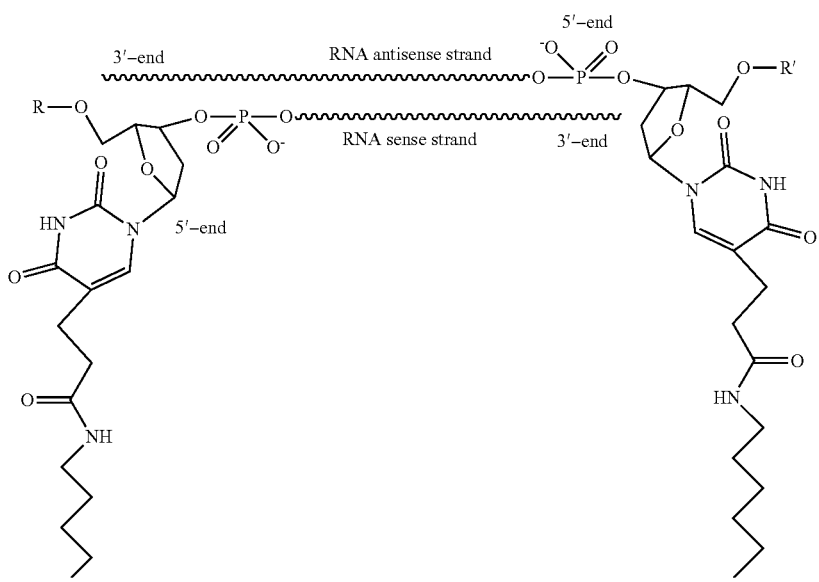

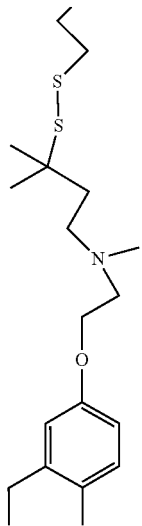
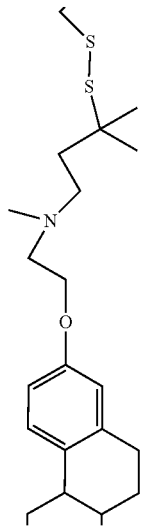
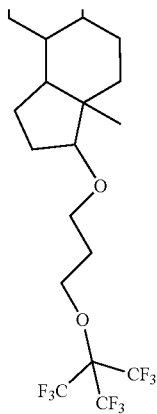
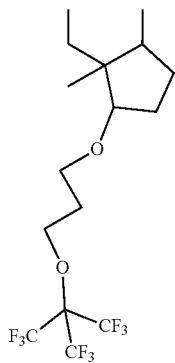

including pharmaceutically acceptable salts, hydrates, solvates and metal chelates of the compound represented by the structure as set forth in Formula (Cn-6), and solvates and hydrates of the salts, wherein R and R' are each selected independently from the group consisting of hydrogen, phosphate, sulfate and carboxyl group.

In another embodiment of the Invention, it provides a Conjugate that comprises linkage of D to two E and E' moieties according to Formula (Vc''), at the 5'-ends of the RNA Duplex; this Conjugate having the following structure, as set forth in Formula (Cn-7):

Formula (Cn-7)

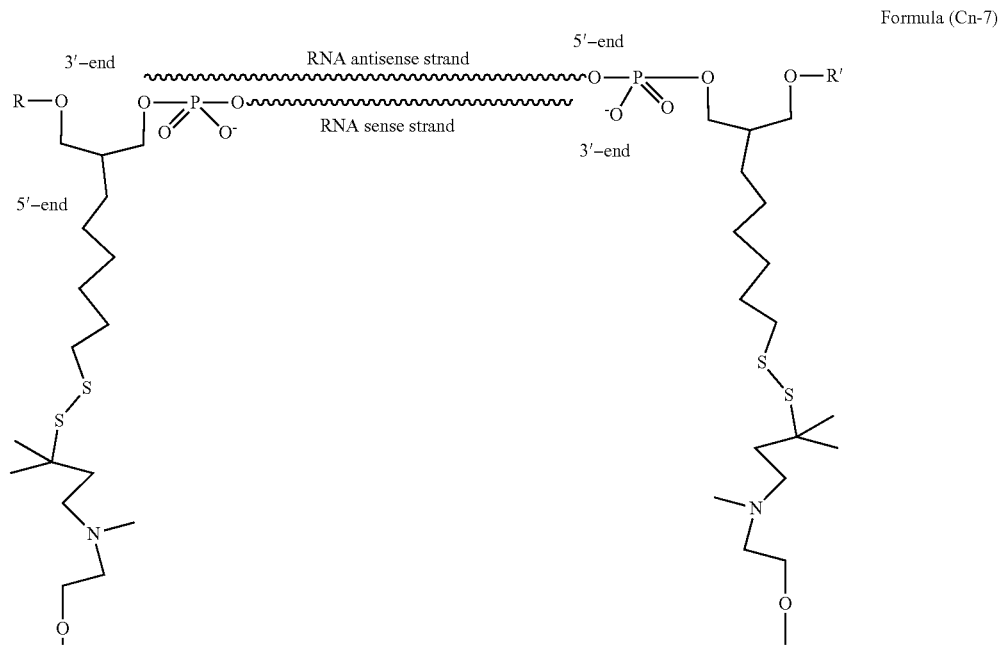

including pharmaceutically acceptable salts, hydrates, solvates and metal chelates of the compound represented by the structure as set forth in Formula (Cn-7), and solvates and hydrates of the salts, wherein R and R' are each selected independently from the group consisting of hydrogen, phosphate, sulfate or carboxyl group.

In another embodiment of the Invention, it provides a Conjugate, that comprises linkage of D to E and E' moieties, each having a structure as set forth in Formula (Vc"), and being linked to the 5'-ends of the RNA Duplex; and an E" moiety according to Formula (Va"), being linked at an internal position along the oligonucleotide chain; this Conjugate has the following structure, as set forth in Formula (Cn-8):

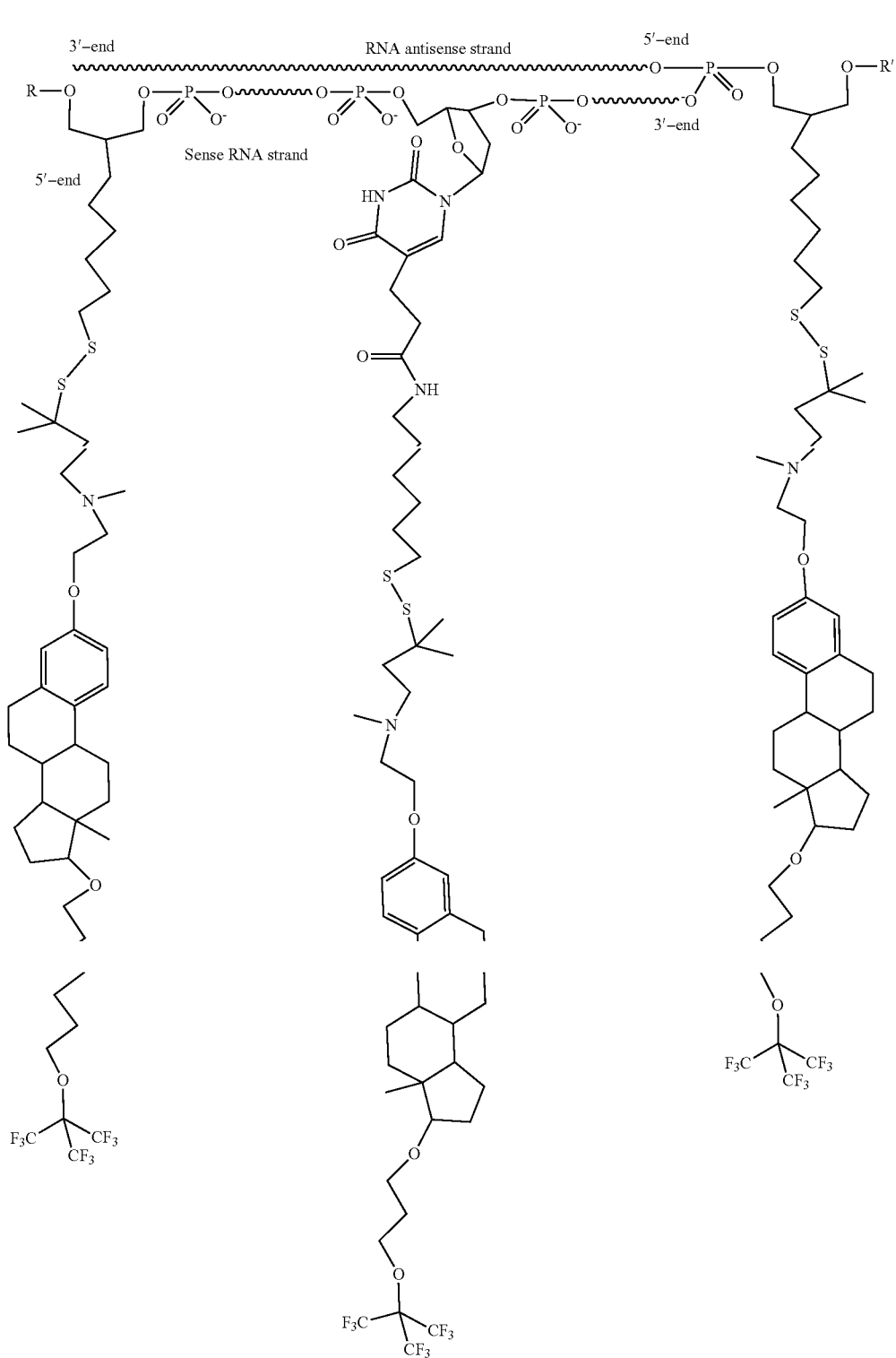

Formula (Cn-8)

including pharmaceutically acceptable salts, hydrates, solvates and metal chelates of the compound represented by the structure as set forth in Formula (Cn-8), and solvates and hydrates of the salts, wherein R and R' are each selected independently from the group consisting of hydrogen, phosphate, sulfate or carboxyl group.

In another embodiment of the Invention, it provides a Conjugate that comprises linkage of D to E and E' moieties according to Formula (Vc"), at the 5'-ends of the RNA Duplex; and an E" moiety according to Formula (Vc"), being linked at an internal position along the oligonucleotide chain; said Conjugate having the following structure, as set forth in Formula (Cn-9):

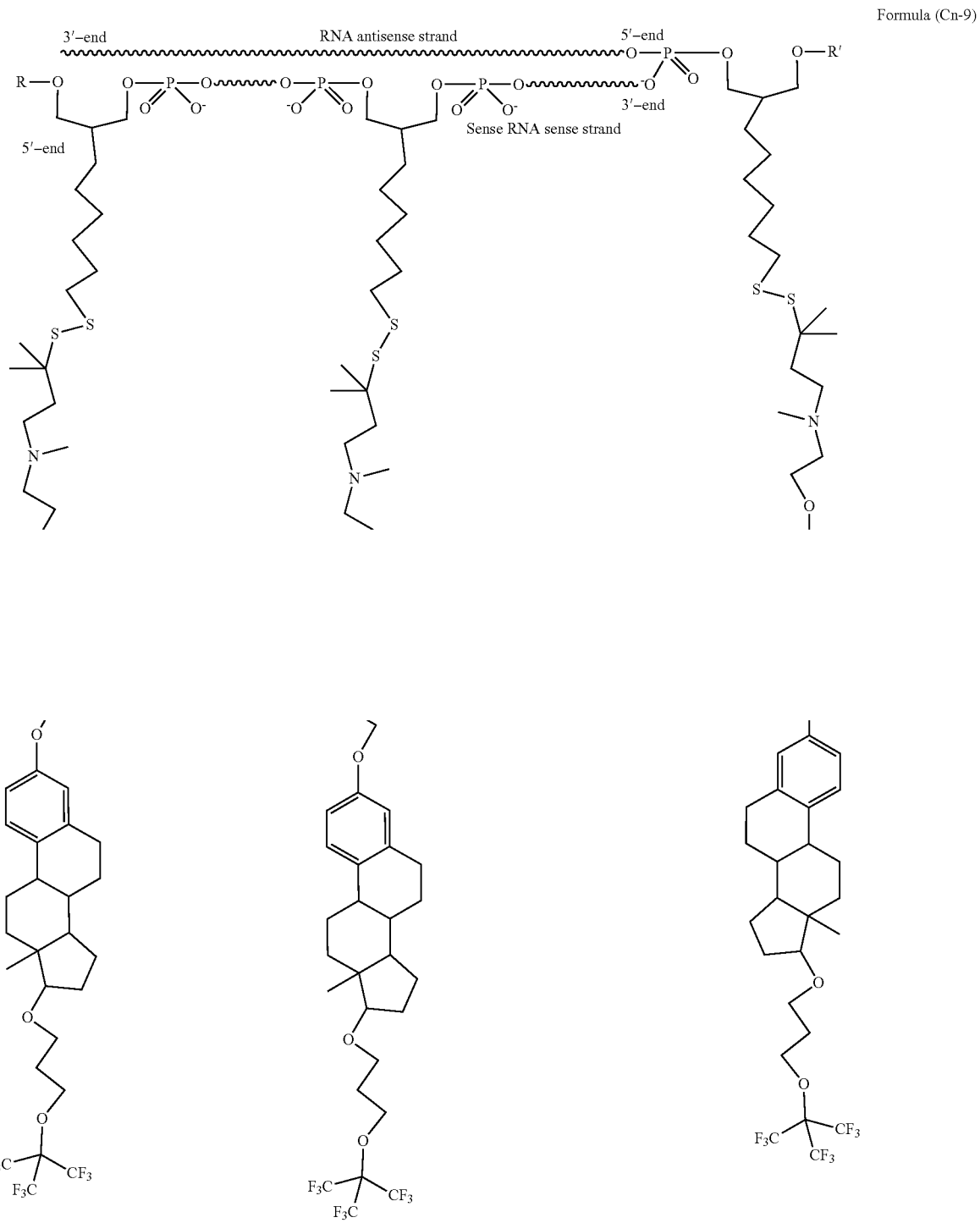

Formula (Cn-9)

including pharmaceutically acceptable salts, hydrates, solvates and metal chelates of the compound represented by the structure as set forth in Formula (Cn-9), and solvates and hydrates of the salts, wherein R and R' are each selected independently from the group consisting of hydrogen, phosphate, sulfate or carboxyl group.

In another embodiment of the Invention, it provides a Conjugate, that comprises D that is an antisense oligonucleotide (ASO) as defined above, comprising a single-stranded oligonucleotide of 15-25 nucleotide long, selected from the group consisting of natural or modified DNA, RNA, locked nucleic acid (LNA) nucleotides, phosphorothioate nucleotides, or combinations thereof. This Conjugate having the following structure, as set forth in Formula (Cn-10):

Formula (Cn-10)

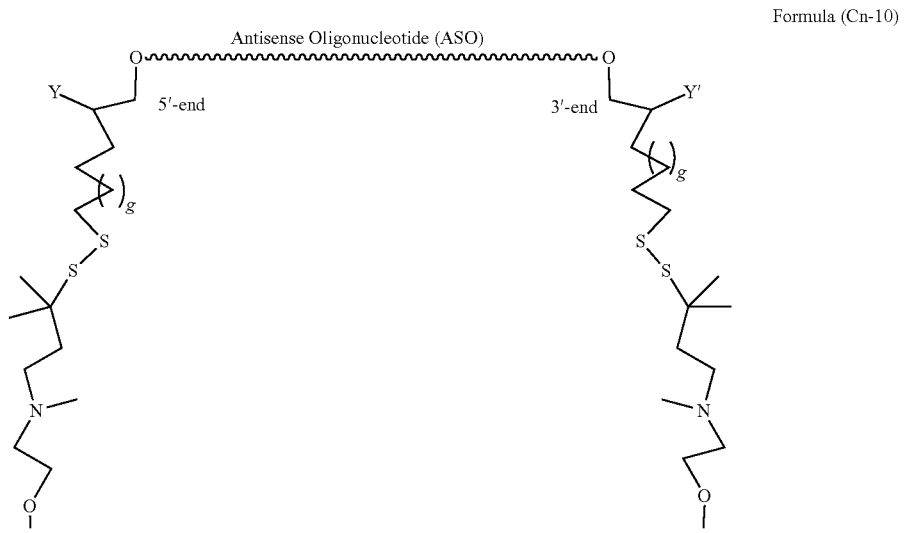

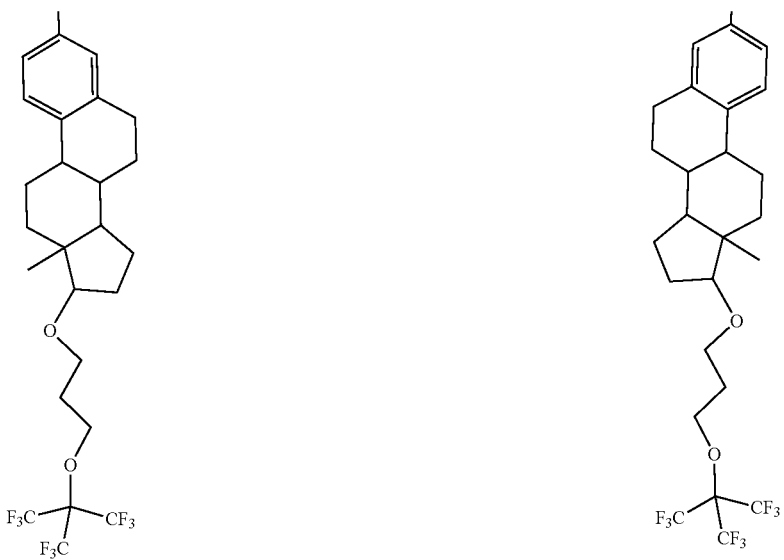

including pharmaceutically acceptable salts, hydrates, solvates and metal chelates of the compound represented by the structure as set forth in Formula (Cn-10), and solvates and hydrates of the salts; wherein Y and Y' are each selected independently from the group consisting of hydrogen, —$CH_2$—Z; —$CH_2$—Z'; —$CH_2$—O—Z; and —$CH_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

In another embodiment of the Invention, it provides a Conjugate that comprises linkage of D to E and E' moieties, each having a structure as set forth in Formula (Va'''), and being linked to the 5'-ends of the RNA Duplex; this Conjugate has the following structure, as set forth in Formula (Cn-11):

Formula Cn-11)

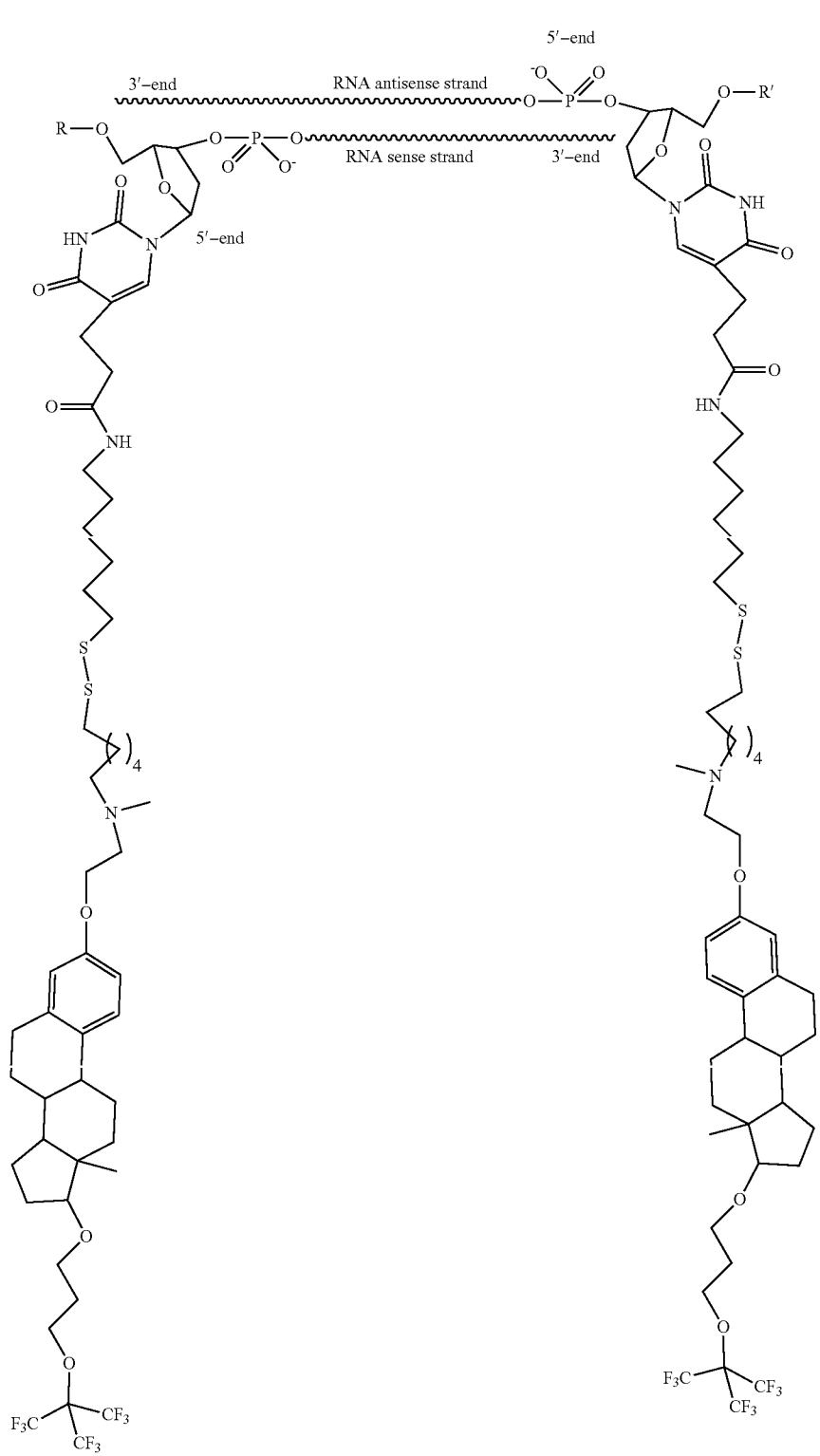

including pharmaceutically acceptable salts, hydrates, solvates and metal chelates of the compound represented by the structure as set forth in Formula (Cn-11), and solvates and hydrates of the salts, wherein R and R' are each selected independently from the group consisting of hydrogen, phosphate, sulfate and carboxyl group.

In another embodiment of the Invention, it provides a Conjugate, that comprises linkage of D to E and E' moieties, each having a structure as set forth in Formula (Vc'''), and being linked to the 5'-ends of the RNA Duplex. This Conjugate has the following structure, as set forth in Formula (Cn-12):

Formula (Cn-12)

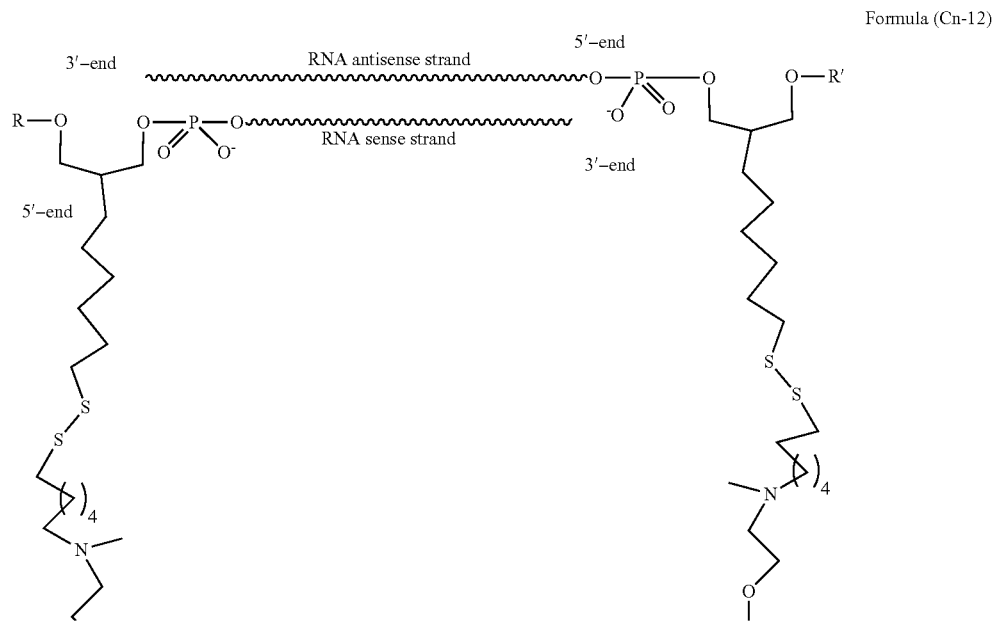

including pharmaceutically acceptable salts, hydrates, solvates and metal chelates of the compound represented by the structure as set forth in Formula (Cn-12), and solvates and hydrates of the salts, wherein R and R' are each selected independently from the group consisting of hydrogen, phosphate, sulfate and carboxyl group. This Conjugate, as shown in Formula (Cn-12), is designated Apo-Si-K-63-B.

In another embodiment of the Invention, it provides a Conjugate, that comprises linkage of D to E and E' moieties, each having a structure as set forth in Formula (Vc'''), and being linked to the 5'-ends of the RNA Duplex; and an E'' moiety according to Formula (Va''') being linked at an internal position along the oligonucleotide chain; this Conjugate has the following structure, as set forth in Formula (Cn-13):

Formula (Cn-13)

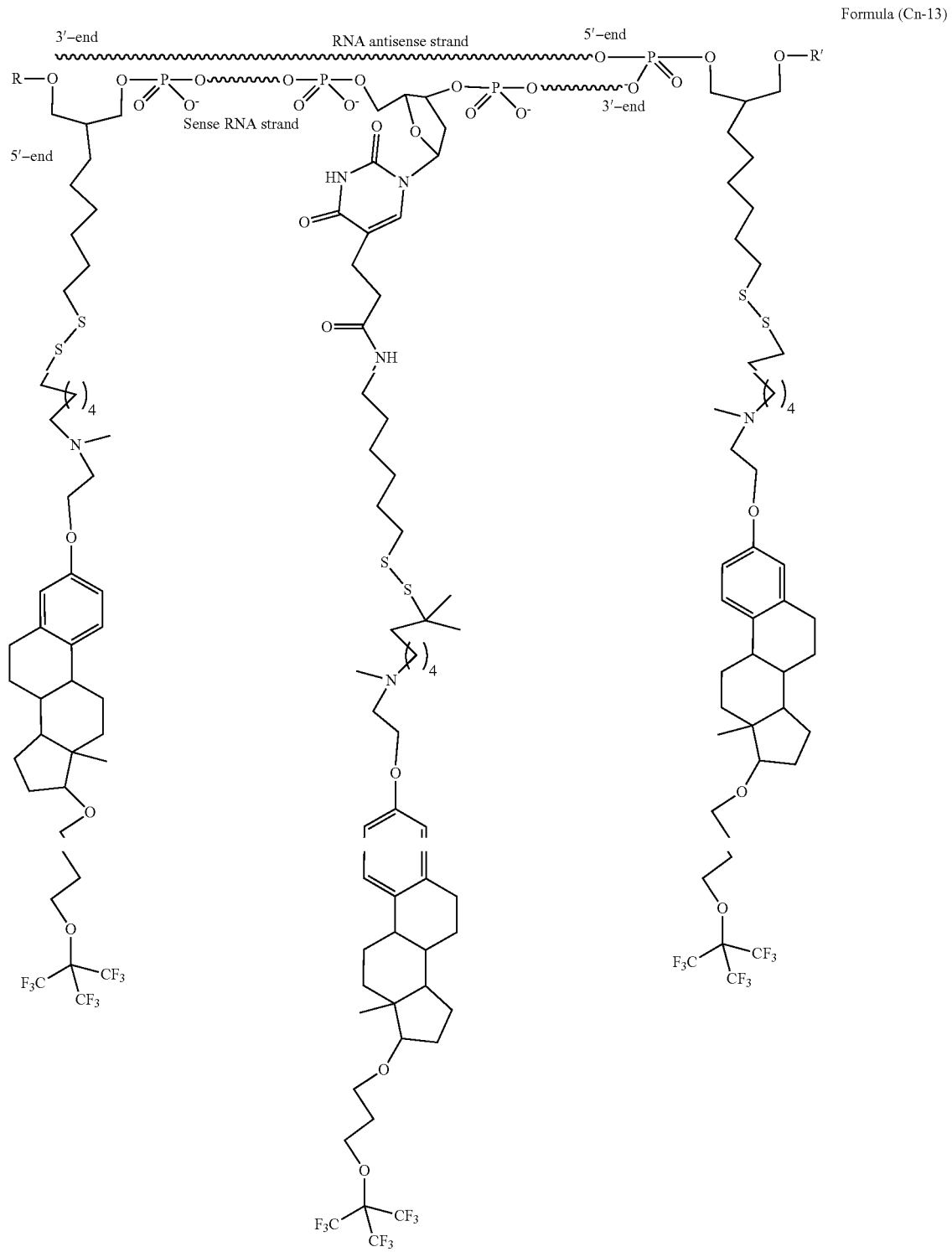

including pharmaceutically acceptable salts, hydrates, solvates and metal chelates of the compound represented by the structure as set forth in Formula (Cn-13), and solvates and hydrates of the salts, wherein R and R' are each selected independently from the group consisting of hydrogen, phosphate, sulfate and carboxyl group.

In another embodiment of the Invention, it provides a Conjugate, that comprises linkage of D to E and E' moieties, each having a structure as set forth in Formula (Vc'''), and being linked to the 5'-ends of the RNA Duplex; and an E'' moiety according to Formula (Vc'''), being linked at an internal position along the oligonucleotide chain; this Conjugate has the following structure, as set forth in Formula (Cn-14):

Formula (Cn-14)

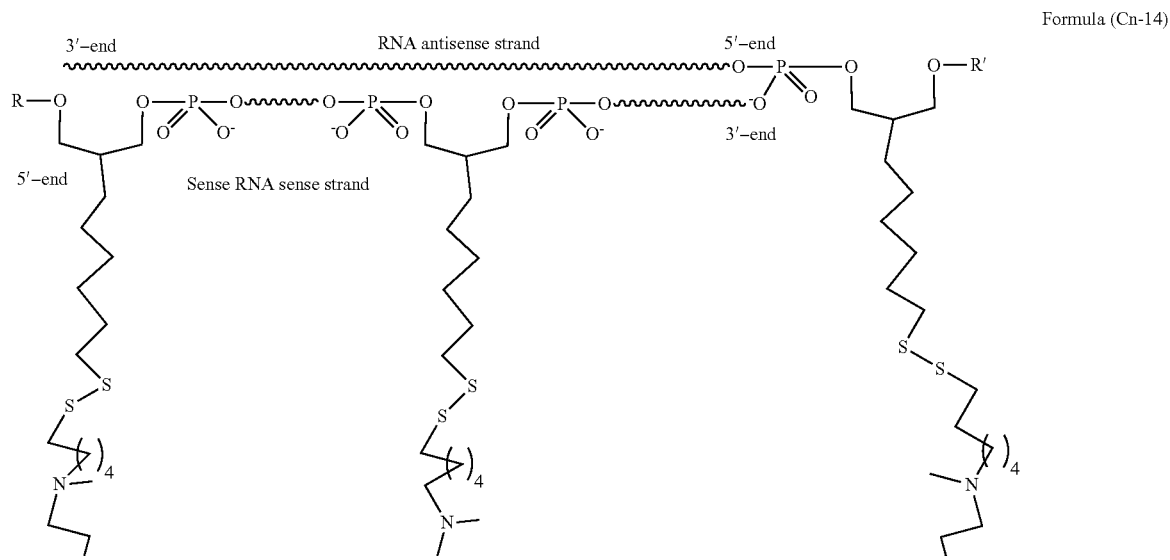

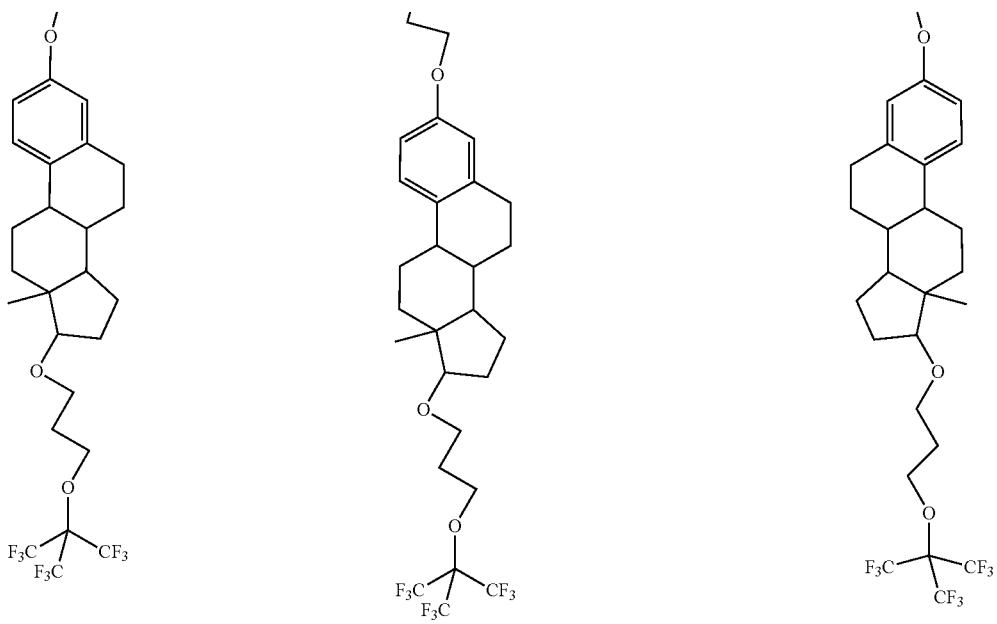

including pharmaceutically acceptable salts, hydrates, solvates and metal chelates of the compound represented by the structure as set forth in Formula (Cn-14), and solvates and hydrates of the salts, wherein R and R' are each selected independently from the group consisting of hydrogen, phosphate, sulfate and carboxyl group. This Conjugate, as shown in Formula (Cn-14), is designated Apo-Si-K-63-C.

Another embodiment of the Invention, it provides a Conjugate, that comprises D that is an antisense oligonucleotide (ASO) as defined above, comprising a single-stranded oligonucleotide of 15-25 nucleotide long, selected from the group consisting of natural or modified DNA, RNA, locked nucleic acid (LNA) nucleotides, phosphorothioate nucleotides, or combinations thereof. This Conjugate having the following structure, as set forth in Formula (Cn-15):

Formula (Cn-15)

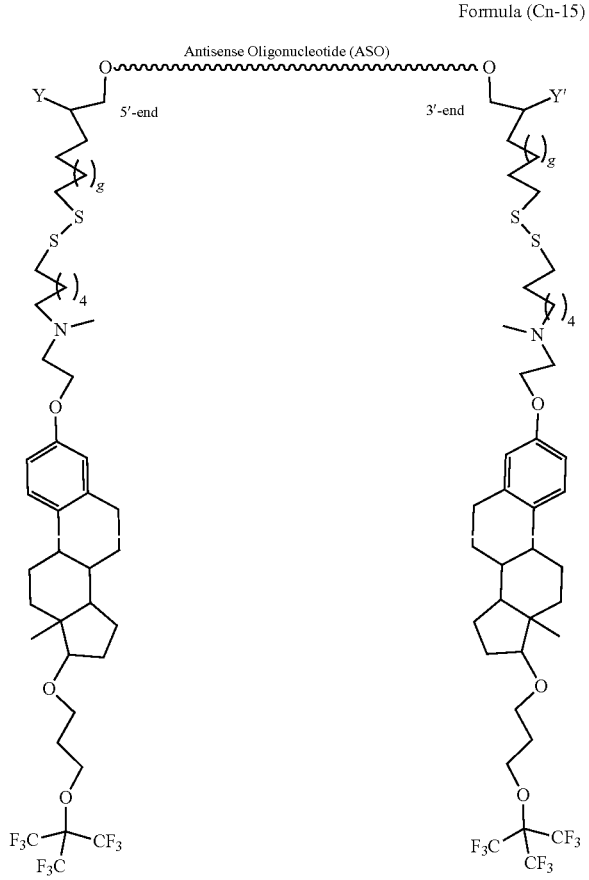

including pharmaceutically acceptable salts, hydrates, solvates and metal chelates of the compound represented by the structure as set forth in Formula (Cn-15), and solvates and hydrates of the salts; wherein Y and Y' are each selected independently from the group consisting of hydrogen, —CH$_2$—Z; —CH$_2$—Z'; —CH$_2$—O—Z; and —CH$_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

In an embodiment of the Invention, it provides a Conjugate, or a pharmaceutical composition that includes the Conjugate, comprising an RNA Duplex, such as siRNA, or a substrate for the Dicer enzyme (dsiRNA), wherein said RNA duplex is a 27-25 or 27-24 nucleotide long, linked at two of its ends to an E, E' or E" moiety, each having the structure according to any of Formulae (II), (III), (IVa), (IVb), (IVc), (Va'), (Va"), (Va'"), (Vb'), (Vb"), (Vb'"), (Vc'), (Vc") or (Vc'"), with potential additional linkage of a phosphate, sulfate or carboxyl group at the 5'-end of the Passenger (Sense) strand, and/or at the 5'-end of the Guide (Antisense) strand.

In another embodiment of the Invention, it provides the Conjugate as described above, being also linked at two of its ends, and also at one or more internal position(s) within the siRNA duplex, to an E, E' or E" moiety, each having the structure according to any Formulae (II), (III), (IVa), (IVb), (IVc), (Va'), (Va"), (Va'"), (Vb'), (Vb"), (Vb'"), (Vc'), (Vc") or (Vc'"), with potential additional linkage of a phosphate, sulfate or carboxyl group at the 5'-end of the Passenger (Sense) strand, and/or at the 5'-end of the Guide (Antisense) strand.

Embodiments of the invention further relate to the use of Conjugates according to the invention, comprising therapeutically-useful drugs, such as proteins or OD (e.g., siRNA, dsiRNA or ASO), for the treatment of medical disorders in a subject in need thereof. The medical disorders may be, without limitation, degenerative disorders, cancer, vascular disorders, metabolic disorders, traumatic, toxic or ischemic insults, infections (e.g., viral or bacterial) or immune-mediated disorders, in which specific protein(s) play(s) a role in either disease etiology or pathogenesis. For such medical disorders, modulation of expression of the respective gene(s) through siRNA or antisense mechanisms, or modulation of the activity of the respective protein by a therapeutic protein, such as by an antibody, or by a protein that functions in signal transduction, or by protein replacement therapy, may have beneficial effects in inhibiting disease-related processes, or in treating an underlying cause of the disease.

For example, Conjugates according to embodiments of the invention, may be used as antisense, siRNA or dsiRNA therapy, which is a form of medical treatment, that comprises the administration of a single-stranded or a double-stranded nucleic acid sequences (DNA, RNA or chemical analogues), that bind either to a DNA sequence that encodes for a specific protein, or to a messenger RNA (mRNA) that translates it into a protein. This treatment may act to inhibit the expression of disease-related genes, thereby preventing the production of disease-related proteins, that may play a role in disease etiology or pathogenesis. Alternatively, the Conjugates of the invention may comprise therapeutic proteins, or protein/nucleic acid complexes, such as the Cas9-RNA complex, capable of performing gene editing.

Embodiments of the invention provide pharmaceutical compositions, comprising the Conjugates described herein, and pharmaceutically-acceptable carrier(s) or salt(s). According to some embodiments, the Conjugates and pharmaceutical compositions of the invention may be used in vivo, in the living subject, including in the clinical setting.

Other embodiments of the invention include Conjugates of the invention, or pharmaceutical compositions comprising Conjugates of the invention, for use for the treatment of medical disorders, in a patient in need thereof. Further embodiments of the invention include the use of Conjugates of the invention, in the preparation of pharmaceutical compositions for the treatment of medical disorders, in a patient in need thereof. In some embodiments, the medical disorder is cancer, metabolic disease, infectious disease, degenerative disease, vascular disease, or an immune mediated disease.

A Conjugate according to embodiments of the invention may be advantageous in improving the delivery of siRNA, dsiRNA, ASO, or a therapeutic protein such as an antibody, through cell membranes, or through biological barriers, such as the Blood-Brain-Barrier (BBB), in comparison to the performance of the same therapeutic agents, without the E, E' or E" moieties of the Invention. Thus, the Conjugates of the Invention may improve the performance of the macromolecule drug in one or more aspects, such as, for example, efficacy, toxicity, or pharmacokinetics.

Conjugates of the Invention, wherein D moieties are oligonucleotides can be synthesized, in a non-limiting manner, according to the following method: initially, a gene to be silenced is chosen, based on its role in disease etiology or pathogenesis. Then, based on bioinformatic methodologies, as known in the art, the nucleotide sequences to be incorporated in the Conjugate are designed and determined [typically 19-21 base-pairs double-stranded siRNA for a RISC substrate, or 24-29 base-pairs double-stranded RNA for a Dicer substrate (dsiRNA)]. Synthesis is carried-out in the 3' to 5' direction of the oligonucleotide. Solid phase synthesis is applied, using protected building blocks, derived from protected 2'-deoxynucleosides (dA, dC, dG, and dT), ribonucleosides (A, C, G, and U), or chemically modified nucleosides, e.g. [LNA (locked nucleic acids), or BNA (bridged-nucleic-acids)]. The building blocks are provided as nucleoside precursors, wherein the 5'- and the 3'-hydroxyl groups are protected by DMT and phosphoramidite, respectively. These groups are sequentially removed during the reactions of coupling the nucleotide to the growing oligonucleotide chain, in an order as determined by the desired nucleotide sequence.

For the purpose of synthesis of the Conjugates of the Invention, the E groups are provided as Precursor molecules, each being an E, E' or E" moiety of the Invention, linked to protecting group, as described above. While the protecting group can be any protecting group for hydroxyl known in the art, phosphoramidite and DMT [Dimethoxytrityl bis-(4-methoxyphenyl) phenyl methyl] are customarily used in oligonucleotide synthesis. A major advantage of Conjugates of the current Invention, is that they provide, as described for Formulae (IVa) and (IVc) above, the option of linking E, E', or E" moieties to either the 5'-end of an oligonucleotide strand, to the 3'-end of an oligonucleotide strand, or at internal position along the oligonucleotide. Thereby, the E moieties of the Invention can become integrated within the oligonucleotide chain, similar to any inherent, natural oligonucleotide building block. Upon completion of the assembly of the chain, the product is released from the solid support into solution, de-protected, and collected. The desired Conjugate is then isolated by high-performance liquid chromatography (HPLC), to obtain the desired Conjugate of the Invention in high purity. In the case of siRNA or dsiRNA, each of a complementary RNA strands is synthesized separately, and then annealing of the two strands is performed in standard conditions, as known in the art, to yield the desired double-stranded siRNA or dsiRNA, which is then subjected to purification and aliquoting.

In an embodiment of the invention, it provides a method for delivery of drugs across phospholipid biological membranes, selected from a group consisting of cell membranes, and biological barriers, wherein said biological barriers are selected from the blood-brain-barrier, the blood-ocular-barrier or the blood-fetal-barrier; the method comprising contacting the cells with a Conjugate of the invention.

In an embodiment of the invention, it provides a method for delivery of a drug into biological cells, wherein said cells are in culture, or in a living animal, or in a human subject; the method comprising contacting the cells with a Conjugate or with a pharmaceutical composition that comprises the Conjugate of the invention.

In an embodiment of the invention, it provides a Conjugate of the Invention, or a pharmaceutical composition that includes a Conjugate according to Formula (I), wherein E, E' or E" each having independently the structure as set forth in any of Formulae (II), (III), (IVa), (IVb), (IVc), (Va'), (Va"), (Va'''), (Vb'), (Vb"), (Vb'''), (Vc'), (Vc") or (Vc''').

The invention also comprises methods for specific inhibition of gene expression, in vitro or in vivo. In one embodiment of the Invention, the method may include utilization of a Conjugate according to any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15), or a pharmaceutical composition that includes said Conjugate, wherein D is siRNA, dsiRNA or an ASO, designed to silence the expression of a specific gene. In some embodiments, the gene encodes for a pathogenic protein that has a role in the etiology or pathogenesis of a disease. In some embodiments, D is a therapeutic protein.

In yet another embodiment of the Invention, it provides, in a non-limiting manner, a method for induction of endocytosis or flip-flop within a biological membrane; said method comprising contacting a Conjugate of the Invention, or a pharmaceutical composition that includes said Conjugate, with the biological membrane, wherein the Conjugate comprises an siRNA or dsiRNA Duplex, linked in at two of its two ends, and potentially also at an internal position within the siRNA duplex, to E, E' or E" moieties, wherein each having the structure as set forth in any of Formulae (II), (III), (IVa), (IVb), (IVc), (Va'), (Va"), (Va'''), (Vb'), (Vb"), (Vb'''), (Vc'), (Vc") or (Vc'''). Due to the structure of the Conjugate of the Invention, the siRNA approaches the membrane parallel to its surface, with the E, E' or E" moieties oriented towards the membrane core, perpendicular to the membrane surface (demonstrated in FIG. 1). The resultant forced proximity of the highly negatively-charged RNA to the membrane surface, can induce formation of membrane vesicles within the cell (endosomes, generated by endocytosis), and also movement of the Conjugate from one membrane leaflet to the other (flip-flop). Both processes can be highly-useful for the initiation and/or propagation of trans-membrane delivery of siRNA or other macromolecule drugs of the Invention, into the cell.

Conjugates according to embodiments of the invention, may be used for the treatment of a medical disorder. Embodiments of the invention include methods for medical treatment, comprising the administration to a patient in need, therapeutically effective amounts of a pharmaceutical composition, comprising a Conjugate according to any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15); wherein D is a drug useful for treatment of the respective medical disorder.

In one embodiment, the method is for genetic medical treatment with siRNA, dsiRNA or ASO; said method comprising the administration to a patient in need, therapeutically effective amounts of a pharmaceutical composition, comprising a Conjugate of the invention, according to any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15); wherein D is siRNA, dsiRNA, ASO or a therapeutic protein, useful in inhibition of the expression of a gene, or blocking activity of a protein which plays a role in the disease of the specific patient.

In another embodiment of the invention, the invention includes a method for medical treatment of a disease by a Conjugate of the invention, according to any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15); wherein D is siRNA, dsiRNA, ASO or a therapeutic protein, that has to be delivered across biological phospholipid membranes into cells, or through biological barriers, such as the blood-brain barrier. Said cells are either cells in culture in vitro, or cells in a living animal or a human subject in vivo. In some embodiments, the cell is a neoplastic cell. In some embodiments, the neoplastic cell is a tumor cell. In some embodiments, the neoplastic cell is a cell within a metastasis. The cell may be a eukaryotic cell, a eukaryotic cell transfected by an oncogenic agent, a human cell, a cell that is a pre-cancerous cell, or any combination thereof. The cell may be in vitro, i.e., within a cell culture, ex vivo, namely taken-out from a living subject, or in vivo, namely within a living animal or a human subject.

In yet another embodiment of the invention, D is a protein, administered as a replacement therapy, e.g., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes). In one embodiment, said protein may be a member of the CRISPRs (clustered regularly interspaced short palindromic repeats)-related proteins. Specifically, said protein can be the Cas9 protein (CRISPR associated protein 9), an RNA-guided DNA nuclease enzyme, or an analogue thereof, potentially loaded with its guide oligonucloetide sequence.

In one of the embodiments of the invention, it describes a method for genetic treatment of a medical disorder, wherein said method comprises administration to a patient in need, therapeutically effective amounts of a pharmaceutical composition, comprising a Conjugate according to any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15), wherein D is a CRISPR protein, such as Cas9, administered together with an appropriate guide oligonucleotide, thus achieving delivery of the protein, loaded with a respective guide oligonucleotide into the cells, where the CRISPR protein can exert its genome editing activity. A guide oligonucleotide in this context, is a sequence of RNA or DNA, that guides the Cas9 protein to a specific locus (place) on the genomic DNA, in order to induce a double-strand DNA cleavage at that site, thus enabling repair of the local defect in the genetic material. In the case of Cas9, the guide oligonucleotide is a short segment of RNA, the sequence of which is complementary to the sequence of the target DNA locus.

Therefore, Conjugates according to embodiments of the invention and the respective pharmaceutical compositions, as well as the respective methods, may be beneficial, among others, in the treatment of medical disorders, selected, among others, from cancer, toxic insults, metabolic disease, ischemic disease, infectious disease, vascular disorders, protein storage disease, trauma, immune-mediated disease, or degenerative diseases.

Therefore, in an embodiment of the Invention, it provides a method for treatment of a medical disorder, said method comprising administration to a patient in need, therapeutically effective amounts of a pharmaceutical composition, that comprises an Conjugate according to any of any of Formulae (I), (II), (III), (IVa), (IVb), (IVc),), (Va'), (Va"), (Va'''), (Vb'), (Vb"), (Vb'''), (Vc'), (Vc") or (Vc'''), (Cn-1), (Cn-2), (Cn-3), (Cn-4), (Cn-5), (Cn-6), (Cn-7), (Cn-8), (Cn-9), (Cn-10), (Cn-11), (Cn-12), (Cn-13), (Cn-14) or (Cn-15); wherein D is drug useful for the treatment of this medical disorder.

According to some embodiments, the medical disorder is cancer. As used herein, the term "cancer" refers to the presence of cells that manifest characteristics that are typical of cancer-causing cells, such as uncontrolled proliferation, loss of specialized functions, immortality, significant metastatic potential, significant increase in anti-apoptotic activity, rapid growth and proliferation rate, or certain characteristic morphology and cellular markers known to be associated with cancer. Typically, cancer cells are in the form of a tumor, existing either locally within an animal, or circulating in the bloodstream as independent cells, as are, for example, leukemic cells.

In the field of neurological disorders, Conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

In the field of infectious disorders, Conjugates according to embodiments of the invention may be useful, among others, for the delivery of antibiotics to combat bacterial, fungal, or other parasitic infections; or delivery of antiviral agents to combat viral infractions. Accordingly, the Conjugates of the invention may have anti-infective properties, thus being useful for the treatment of infectious diseases, such as bacterial or viral infections. Examples for viral infections, for which the Conjugates of the invention can be useful, are, without limitation, human immunodeficiency virus (HIV); hepatotropic viruses such as hepatitis C virus (HCV), or hepatitis B virus (HBV); infection by orthomyxoviridae, such as influenza virus A, influenza virus B, or influenza virus C; or infections by parainfluenza viruses. Accordingly, an embodiment of the Invention, is a Conjugate of E, E' or E" moiety (or moieties), linked to an antiviral or antibacterial drug. Such drug can be, among others, a genetic sequence(s), aimed at interacting with the genetic material of the infective agent, thus interfering with genetic processes that have a role in replication, metabolism, infectiveness, or survival of said pathogen. Such genetic sequences can be siRNA or dsiRNA, specifically-designed to silence the expression of the viral genes.

The utility of the Conjugates of the Invention in combating infection can be in at least one of the following utilizations: either in the delivery of therapeutically-useful agents across biological membranes into cells of the host (e.g., a human patient); or across biological membranes into cells of the pathogen (e.g., bacteria or virus).

In the field of metabolic disorders, Conjugates according to embodiments of the invention may be useful, among others, for the delivery genetic treatments, aimed at down-regulation the expression of a gene or genes responsible for said metabolic disorder, or for administration of a protein, to replace a defective mutated protein, that has a role in the disease etiology or pathogenesis.

In other embodiments, the Invention relates to utilization of the Compounds of the Invention to enhance delivery of chemical compounds across phospholipid membranes into cells of plants, thus being beneficial for utilizations in agriculture. Depending on the attached chemical compound, and the desired indication, such delivery can have various useful utilizations in agriculture. For example, such delivery in plants can assist in improving crop quality and quantity, among others, by improving plant's genetics, or by eradication of various insects, bacteria or fungi.

EXAMPLES

Some examples will now be described, in order to further illustrate the invention, and in order to demonstrate how embodiments of the invention may be carried-out in practice.

Example 1: A General Method for Synthesis of Conjugates According to Embodiments of the Invention, Wherein D Moieties are Oligonucleotides Initially, a gene to be silenced is chosen, based on its role in disease etiology or pathogenesis. Then, based on bioinformatic methodologies known in the art, the nucleotide sequences to be incorporated in the Conjugate are designed and determined [typically 19-21 base-pairs double-stranded siRNA for a RISC substrate, or 24-29 base-pairs double-stranded RNA for a Dicer substrate (dsiRNA)].

Synthesis is carried-out in the 3' to 5' direction of the oligonucleotide. Solid phase synthesis is applied, using protected building blocks, derived from protected 2'-deoxynucleosides (dA, dC, dG, and dT), ribonucleosides (A, C, G, and U), or chemically modified nucleosides, e.g. [LNA (locked nucleic acids), or BNA (bridged-nucleic-acids)]. The building blocks are provided as nucleoside precursors, wherein the 5'- and the 3'-hydroxyl groups are protected by DMT and phosphoramidite, respectively. These groups are sequentially removed during the reactions of coupling the nucleotide to the growing oligonucleotide chain, in an order as determined by the desired nucleotide sequence.

For the purpose of synthesis of the Conjugates of the Invention, the E groups are provided as Precursor molecules, each being an E, E' or E" moiety of the Invention, linked to protecting group, as described above. While the protecting group can be any protecting group for hydroxyl known in the art, phosphoramidite and DMT [Dimethoxytrityl bis-(4-methoxyphenyl) phenyl methyl] are customarily used in oligonucleotide synthesis. A major advantage of Conjugates of the current Invention, is that they provide, as described for Formulae (IVa) and (IVc) above, the option of linking E, E', or E" moieties to either the 5'-end of an oligonucleotide strand, to the 3'-end of an oligonucleotide strand, or at internal position along the oligonucleotide. Thereby, the E moieties of the Invention can become integrated within the oligonucleotide chain, similar to any inherent, natural oligonucleotide building block. Upon completion of the assembly of the chain, the product is released from the solid support into solution, de-protected, and collected. The desired Conjugate is then isolated by high-performance liquid chromatography (HPLC), to obtain the desired Conjugate of the Invention in high purity. In the case of siRNA or dsiRNA, each of a complementary RNA strands is synthesized separately, and then annealing of the two strands is performed in standard conditions, as known in the art, to yield the desired double-stranded siRNA or dsiRNA, which is then subjected to purification and aliquoting.

Examples 2: Methods for Chemical Synthesis of Precursor Molecules, Comprising E, E' or E" Moiety of the Invention Example 2a: Synthesis of Apo-Si-K-29E-Precursor

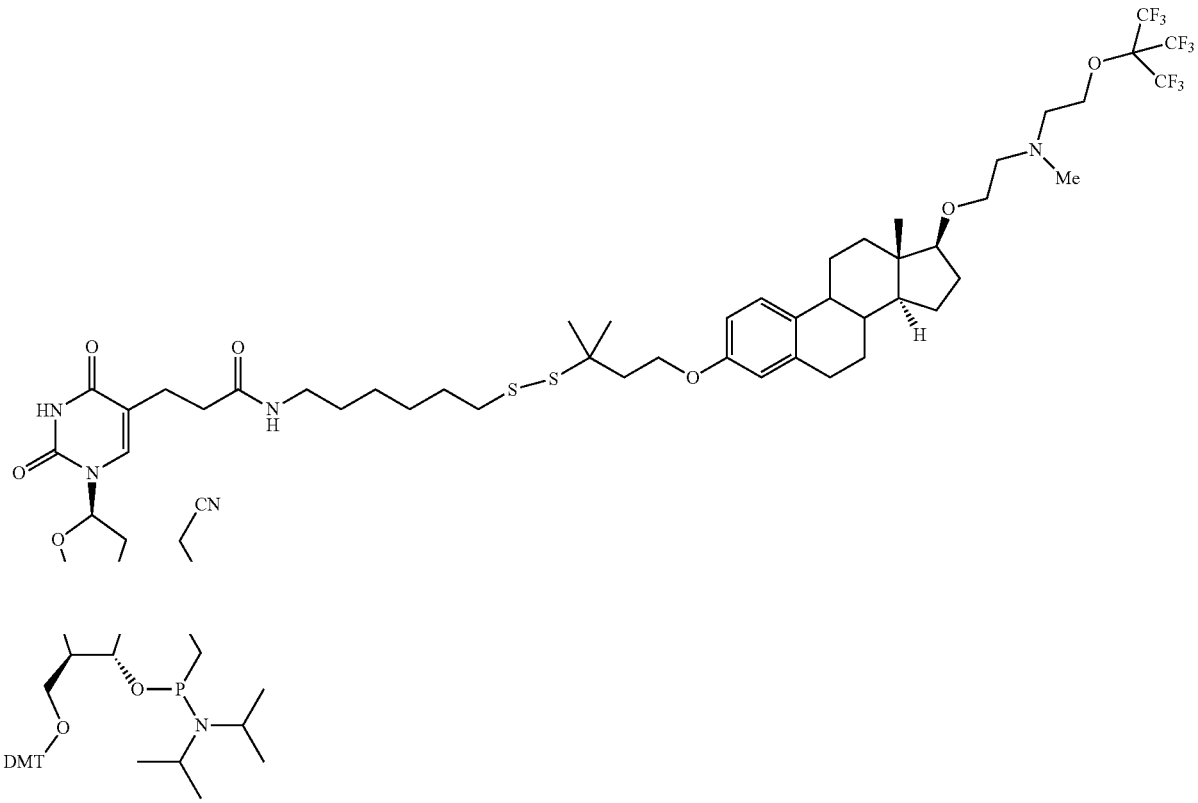

Apo-Si-K-29E-Precursor

2aA. Synthesis of Phenol 2
Estradiol was treated with benzyl bromide and potassium carbonate in a mixture of acetonitrile and methanol. Methanol was employed as co-solvent to facilitate solubility leading to full and clean conversion. After filtration and concentrated of the filtrate, the crude product (2) was used in the next step.
Scheme 1. Synthesis of phenol 2
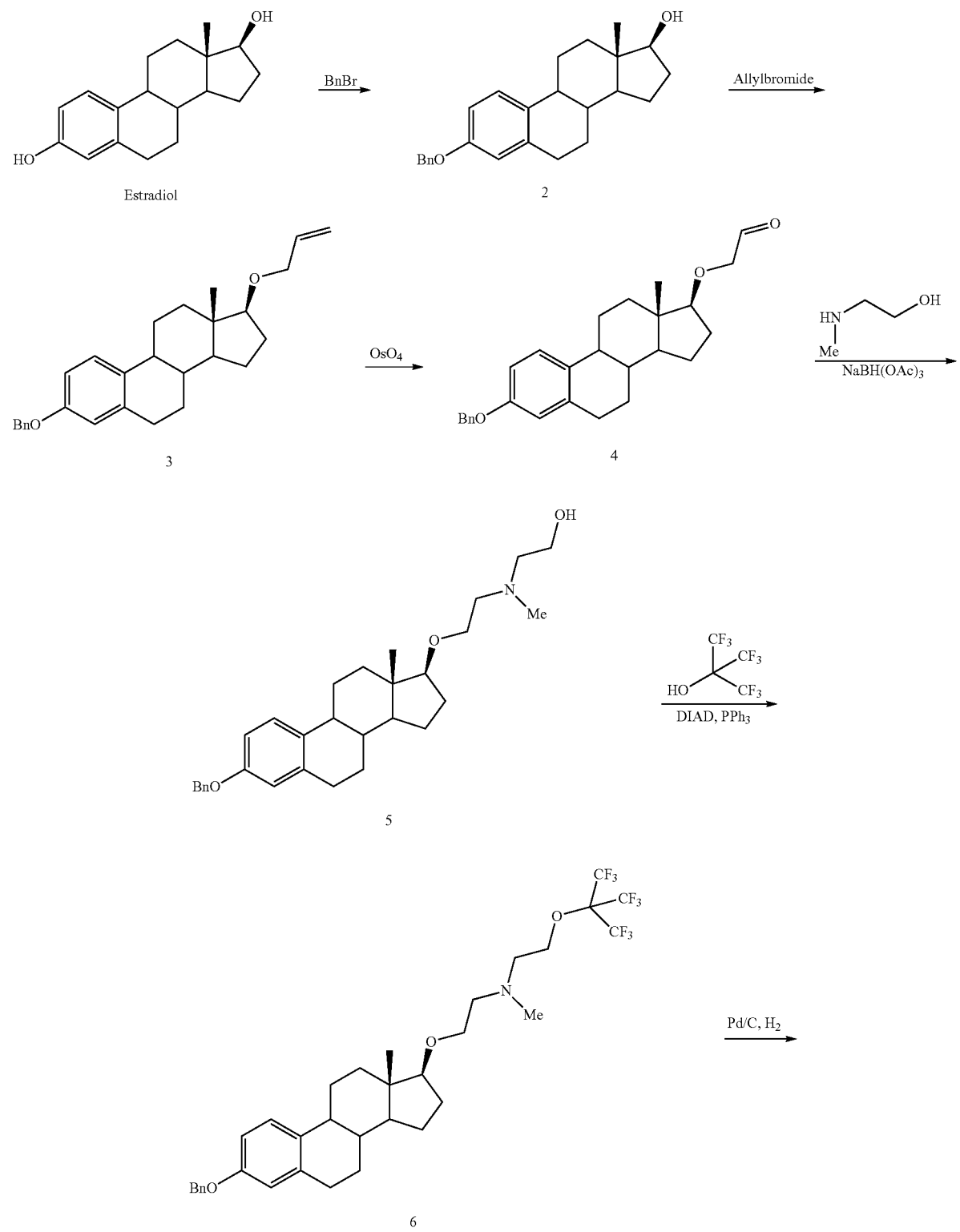

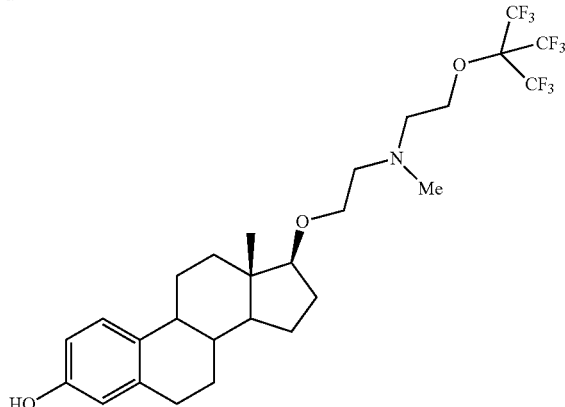

Phenol 2

Compound 2 was treated with excess of sodium hydride, followed by the addition of allylbromide, which resulted in clean conversion towards compound 3. Treatment of allyl-derivative 2 with $OsO_4$ and $NaIO_4$ provided aldehyde 4. Reductive amination between aldehyde 4 and N-methyl aminoethanol provided alcohol 5, which was subsequently reacted under Mitsunobu conditions with perfluoro-t-BuOH, resulted in compound 6. Finally, the benzyl protecting group was removed by hydrogenation to provide phenol 2.

2aA1. (8R,9S,13S,14S,17S)-3-Benzyloxy-17-hydroxyestra-1,3,5(10)-triene (2)

A mixture of estradiol (2, 300 g, 1.1 mol), benzyl bromide (200 mL, 1.68 mol) and potassium carbonate (304 g, 2.2 mol) in acetone (2 L) and MeOH (0.5 L) was heated at reflux for 18 h. After cooling at room temperature, the reaction mixture was filtered and concentrated in vacuo. The concentrate was dissolved in hot toluene and concentrated under reduced pressure. The crude material (compound 2, 508 g) was used as such in the next reaction.

2aA2. (8R,9S,13S,14S,17S)-17-Allyloxy-3-benzyloxyestra-1,3,5(10)-triene (3)

Sodium hydride (110 g, 60% dispersion in mineral oil, 2.7 mol) was added portionwise to a solution of the crude alcohol 3 (508 g, ca 1.1 mol) in anhydrous THF (4 L). After ca. 30 min, allyl bromide (240 mL, 2.7 mol) and tetrabutylammonium iodide (40 g, 108 mmol) were added and the resulting mixture was heated at reflux for ca. 18 hours. The reaction mixture was allowed to cool to room temperature and carefully quenched with water (1 L) the mixture was partially concentrated. The mixture was dissolved in EtOAc (1.5 L) and washed with water (3×500 mL). The organic phase was washed with brine, dried over $Na_2SO_4$ and concentrated to afford crude compound 3 (550 g, 1.36 mol) in sufficient purity for the next step.

2aA3. 2-(((13S,17S)-3-(Benzyloxy)-13-methyl-7,8,9,11,12,13,14,15,16,17-decahydro-6H-cyclopenta[a]phenanthren-17-yl)oxy)acetaldehyde (4)

To a solution of compound 3 (2.0 g, 5.0 mmol) in diethyl ether (30 mL) and water (30 mL) were added 2,6-lutidine (1.33 g, 12.4 mmol), sodium periodate (4.26 g, 20 mmol) and a 2.5% solution of $OsO_4$ in tBuOH (2 mL). The mixture was stirred for 16 hours at room temperature. The phases were separated and the aqueous layer was extracted twice with diethyl ether. The combined organic layers were washed with aqueous saturated sodium thiosulfate and brine, dried over $Na_2SO_4$ and concentrated. Further purification provided aldehyde 4 (1.51 g, 3.7 mmol as a clear oil in 75% yield.

2aA4. 2-((2-(((13S,17S)-3-(benzyloxy)-13-methyl-7,8,9,11,12,13,14,15,16,17-decahydro-6H-cyclopenta[a]phenanthren-17-yl)oxy)ethyl)(methyl) amino) ethan-1-ol To a solution of compound 4 (2.0 g, 4.9 mmol) in dichloroethane (100 mL) was added 2-(methylamino)ethan-1-ol (0.79 mL, 9.8 mmol, 2 eq.) and the resulting mixture was stirred for 15 minutes. Then AcOH (0.56 mL, 9.8 mmol, 2 eq.) was added and the mixture was stirred for another 10 minutes. $NaBH(OAc)_3$ (4.2 g, 19.6 mmol, 4 eq.) was added and the resulting mixture was stirred overnight. NaOH (1 M, 400 mL) was added, the mixture was shaken and the layers were separated. The aqueous layer was extracted with EtOAc (2×, 300 mL). The combined organic layers were washed with brine, dried over $Na_2SO_4$, and concentrated to provide compound 5 (2.4 g, 4.9 mmol, in a quantitative yield).

2aA5. 2-(((13S,17S)-3-(benzyloxy)-13-methyl-7,8,9,11,12,13,14,15,16,17-decahydro-6H-cyclopenta[a]phenanthren-17-yl)oxy)-N-(2-((1,1,1,3,3,3-hexafluoro-2-(trifluoromethyl)propan-2-yl)oxy)ethyl)-N-methylethan-1-amine (6)

To a solution of alcohol 5 (2.4 g, 5 mmol) in Tetrahydrofuran (THF) (100 mL) were added perfluoro-t-butanol (0.93 mL, 6.5 mmol, 1.3 eq.), $PPh_3$ (2.1 g, 8.0 mmol, 1.6 eq.) and Diisopropyl azodicarboxylate (DIAD) (1.3 mL, 6.5 mmol, 1.3 eq.) and the resulting mixture was stirred overnight at room temperature. The mixture was concentrated and the crude material was purified by column chromatography (20% EtOAc/heptane+1% $NEt_3$) to provide compound 6 as a colorless oil, that slowly solidified (2.1 g, 3.1 mmol, 62%).

2aA6. (13S,17S)-17-(2-((2-((1,1,1,3,3,3-Hexafluoro-2-(trifluoromethyl)propan-2-yl)oxy)ethyl)(methyl)amino)ethoxy)-13-methyl-7,8,9,11,12,13,14,15,16,17-decahydro-6H-cyclopenta[a]phenanthren-3-ol (phenol 2)

Compound 6 (7.5 g, 11.0 mmol) was dissolved in Ethylacetate (EtOAc, 150 mL) and 10% Pd/C (900 mg ABCR+ 900 mg Merck) was added. The mixture was stirred for 16 hours under a 5 bar hydrogen atmosphere. The suspension was filtered over a short path of Celite and concentrated. Phenol 2 (5.7 g, 9.6 mmol) was isolated as a colorless oil.

2aB. Synthesis of K-1-7

Further derivatization of phenol 2 required building block K-1-7. This compound was prepared by attachment of the fluorenyl group using 9-Fluorenylmethyl N-succinimidyl carbonate (FmocOSu), with the thiol using basic conditions.

Scheme 2. Synthesis of K-1-7

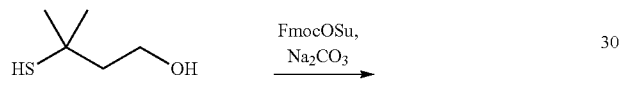

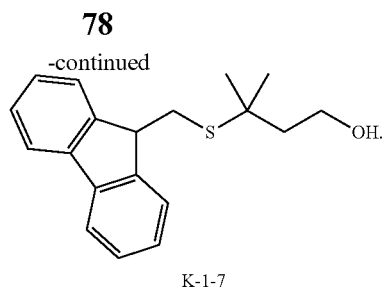

(((9H-Fluoren-9-yl)methyl)thio)-3-methylbutan-1-ol (K-1-7)

To a suspension of 3-methyl-3-thiobutanol (13.6 g, 113 mmol) and sodium carbonate (24 g, 340 mmol) in N,N-Dimethylformamide (DMF) (300 mL) was added FmocOSu (25.2 g, 75.4 mmol). The mixture was stirred for 2 hours at 40° C., then cooled to room temperature. Ethyl acetate (200 mL) and heptane (400 mL) was added and the mixture was washed with water (3×200 mL), dried over sodium sulfate and concentrated. Further purification using flash chromatography (30% ethyl acetate (EtOAc in heptane) provided compound K-1-7 (17.0 g, 57.2 mmol) as a sticky oil in 76% yield.

2aC. Synthesis of K-29U

The synthesis of building block K-29U was performed as shown in scheme 3:

Scheme 3. Synthesis of K-29U

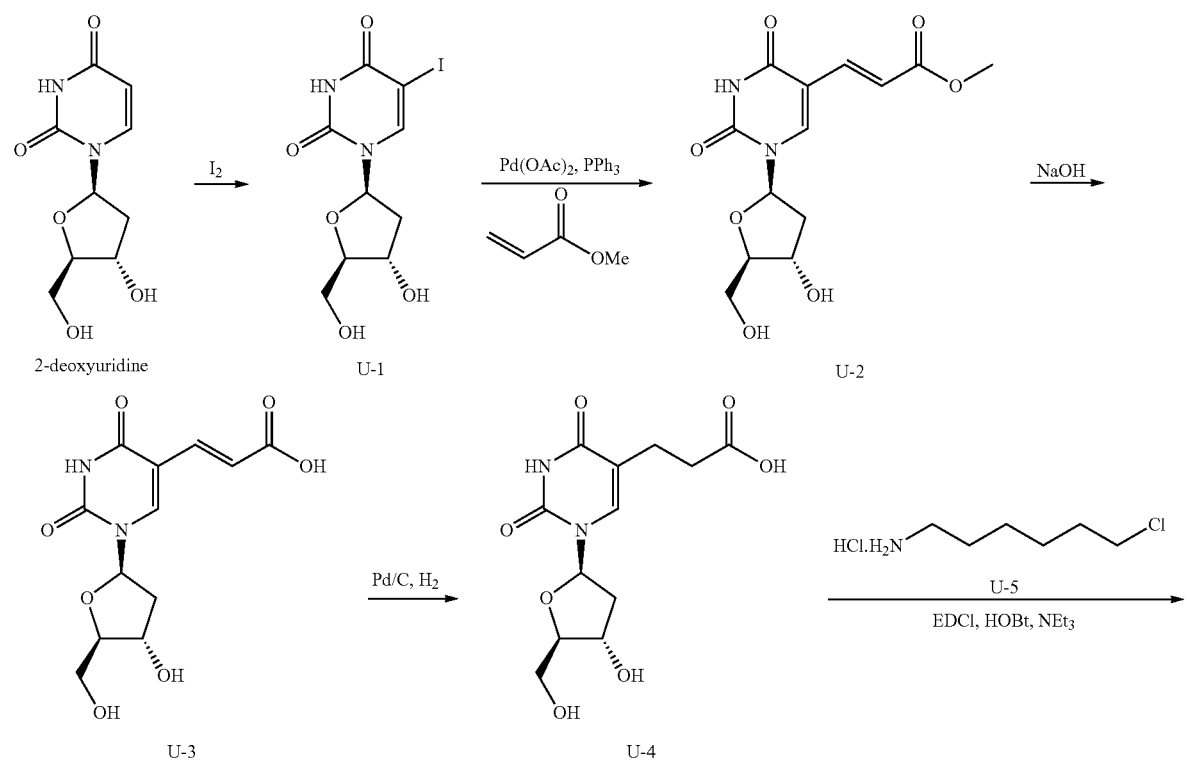

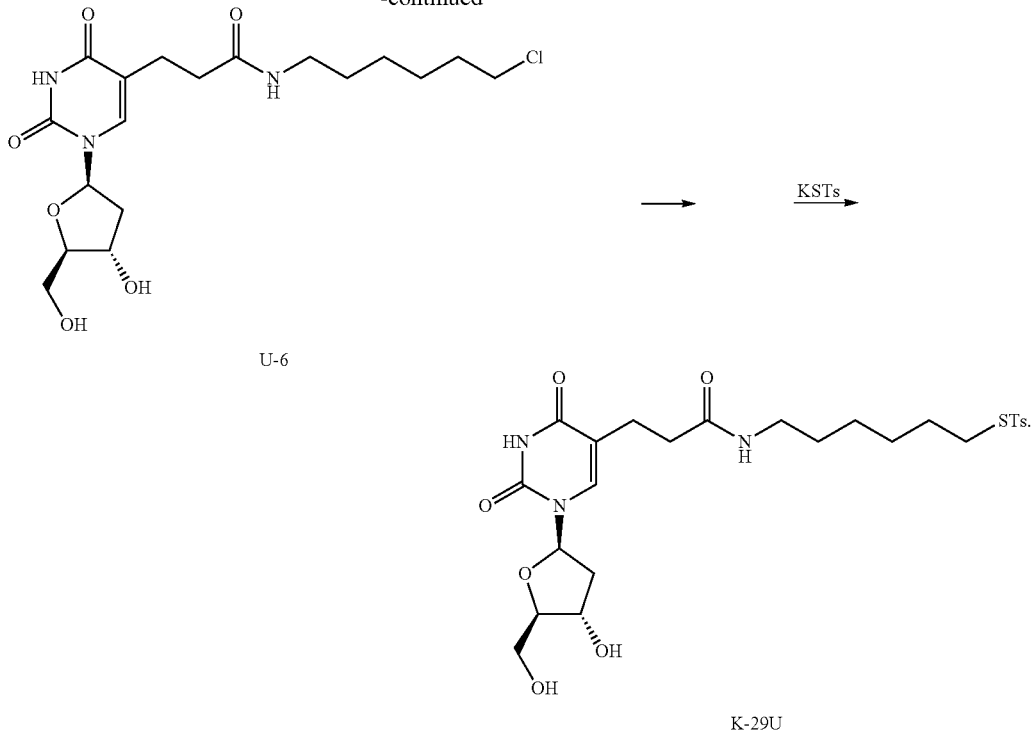

U-6

K-29U

2-Deoxyuridine was treated with $I_2$ in the presence of $HNO_3$, to provide iodo-derivative of deoxyuridine U-1. Iodide U-1 was coupled to methylacrylate using a Heck reaction to provide methyl ester U-2 after purification by column chromatography. The methyl ester of U-2 was hydrolyzed with NaOH, and the resulting compound U-3 was hydrogenated using Pd/C and $H_2$ to provide intermediate U-4. Intermediates U-4 and U-5 (commercially-available) were coupled using 1-Ethyl-3-(3-dimethylaminopropyl) carbodiimide (ED(CI) as a coupling reagent to afford chloride U-6. Chloride U-6 was treated with potassium thiotosylate at elevated temperatures to provide building block K-29U.

2aC1. 1-((2R,4S,5R)-4-Hydroxy-5-(hydroxymethyl) tetrahydrofuran-2-yl)-5-iodopyrimidine-2,4(1H,3H)-dione (U-1)

2-Deoxyuridine (15 g, 66 mmol) and $I_2$ (19 g, 73 mmol, 1.1 eq.) were dissolved in a mixture of $CHCl_3$ (750 mL) and $HNO_3$ (aq., 1M, 150 mL) and the resulting purple mixture was stirred at reflux for 5 hours, after which a precipitate had formed. The mixture was cooled, first by air, then by an ice bath. The cooled mixture was filtered and the residue was washed with cold $CHCl_3$. The solids were collected and dried in vacuo to provide iodide U-1 as an off-white solid (20 g, 57 mmol, 86%).

2aC2. Methyl (E)-3-(1-((2R,4S,5R)-4-hydroxy-5-(hydroxymethyl)tetrahydrofuran-2-yl)-2,4-dioxo-1,2,3,4-tetrahydropyrimidin-5-yl)acrylate (U-2)

Iodide U-1 (5.2 g, 15 mmol) was dissolved in DMF (100 mL) and TEA (4.1 mL, 29.4 mmol, 2 eq.), methyl acrylate (8.0 mL, 88.2 mmol, 6 eq.), $PPh_3$ (0.77 g, 2.9 mmol, 0.2 eq.), and palladium acetate (0.33 g, 1.5 mmol, 0.1 eq.) were added to the mixture. The resulting mixture was stirred at 100° C. for 4 hours. The reaction mixture was filtered over Celite and the filtrate was concentrated. The crude material was purified by column chromatography (10% MeOH in $CH_2Cl_2$) to provide acrylate U-2 (4.0 g, 13 mmol, 87%) as an orange oil that slowly crystallized.

2aC3. (E)-3-(1-((2R,4S,5R)-4-Hydroxy-5-(hydroxymethyl)tetrahydrofuran-2-yl)-2,4-dioxo-1,2,3,4-tetrahydropyrimidin-5-yl)acrylic acid (U-3)

Acrylate U-2 (5.0 g, 16 mmol) was dissolved in NaOH (aq., 2M, 60 mL) and the resulting mixture was stirred at room temperature for 2 hours. The mixture was cooled to 0° C. and HCl (37%) was added until the mixture was around pH 1 (as measured by pH paper). The mixture was stirred at 0° C. for 1 hour, after which a precipitation had formed. The solids where collected by filtration and were transferred to a flask. The crude material was coevaporated with toluene twice to provide the crude product U-3 (a lot of water present) an off-white slightly brown solid (3.3 g, 11 mmol, 69%)

2aC4. 3-(1-((2R,4S,5R)-4-Hydroxy-5-(hydroxymethyl)tetrahydrofuran-2-yl)-2,4-dioxo-1,2,3,4-tetrahydropyrimidin-5-yl)propanoic acid (U-4)

Crude carboxylic acid U-3 (28.6 g, 96 mmol) was dissolved in $H_2O$ (500 mL). NaOH (10 mL, 10 M) was added until all had dissolved. Pd/C (10%, 3 g) was added and the mixture was stirred under 5 bar of $H_2$ overnight. The mixture was filtered over celite and concentrated to provide a yellow oil (50 g). Since the mixture contained salts, it was dissolved in a minimal amount of $H_2O$ (total volume of 130 mL) and acidified to approximately pH ~2 (pH paper). The crude mixture was desalted using reverse phase chromatography. The product-containing fractions were pooled, concentrated, and lyophilized to provide carboxylic acid U-4 (10 g, 33 mmol, 35%) as a fluffy white solid.

2aC5. N-(2-(3-Chloropropoxy)ethyl)-3-(1-((2R,4S, 5R)-4-hydroxy-5-(hydroxyl-methyl)tetrahydrofuran-2-yl)-2,4-dioxo-1,2,3,4-tetrahydropyrimidin-5-yl) propanamide (U-6)

To a solution of uridine carboxylic acid derivative U-4 (5.5 g, 18.4 mmol) and amine U-5 (3.2 g, 18.4 mmol) in 350 mL DMF were added TEA (10.3 mL, 73.5 mmol, 4 eq.), HOBt (3.1 g, 20.2 mmol, 1.1 eq.), and 1-Ethyl-3-(3-dimethylaminopropyl) carbodiimide (EDCI, 3.9 g, 20.2 mmol, 1.1 eq.). The resulting suspension was stirred for 5 days at room temperature, after which most material had dissolved. The mixture was concentrated in vacuo. The crude mixture was purified by column chromatography [7-8% MeOH in dichloromethane (DCM) to provide amide U-6 (7.2 g, 17 mmol, 93%) as a yellow/orange oil that slowly solidified.

2aC8. S-(3-(2-(3-(1-(((2R,4S,5R)-4-Hydroxy-5-(hydroxymethyl)tetrahydrofuran-2-yl)-2,4-dioxo-1,2,3, 4-tetrahydropyrimidin-5-yl)propanamido) ethoxy) propyl) 4-methylbenzenesulfonothioate (K-29U)

Chloride U-6 (3.6 g, 8.6 mmol) was dissolved in DMF (100 mL) and TBAI (0.32 g, 0.86 mmol) and potassium toluenethiosulfonate (2.9 g, 12.9 mmol) were added. The resulting mixture was stirred for 40 hours at 80° C. The mixture was concentrated in vacuo. EtOAc (500 mL) and $H_2O$ (300 mL) were added and the layers were separated. The organic layer washed with brine. The combined aqueous layers were extracted with EtOAc (4×250 mL). The combined organic layers were dried over $Na_2SO_4$ and concentrated. The crude mixture was purified using column chromatography (3-7% MeOH in dichloromethane (DCM) to provide thiotosylate K-29U (1.75 g, 3.1 mmol, 36%) as a sticky solid.

2aD. Completion of the Synthesis of Apo-Si-K-29E-Precursor

Phenol 2 and building block K-1-7 were coupled under Mitsunobu conditions to provide protected thiol K-29E-1. The fluorenyl group can be removed in situ by NaOMe in the presence of K-29U to afford disulfide K-29E-2. DMT group was attached using standard phosphoramidate moiety were attached using standard procedures, as known in the art.

Scheme 4. Synthesis of Apo-Si-K-29E-Precursor

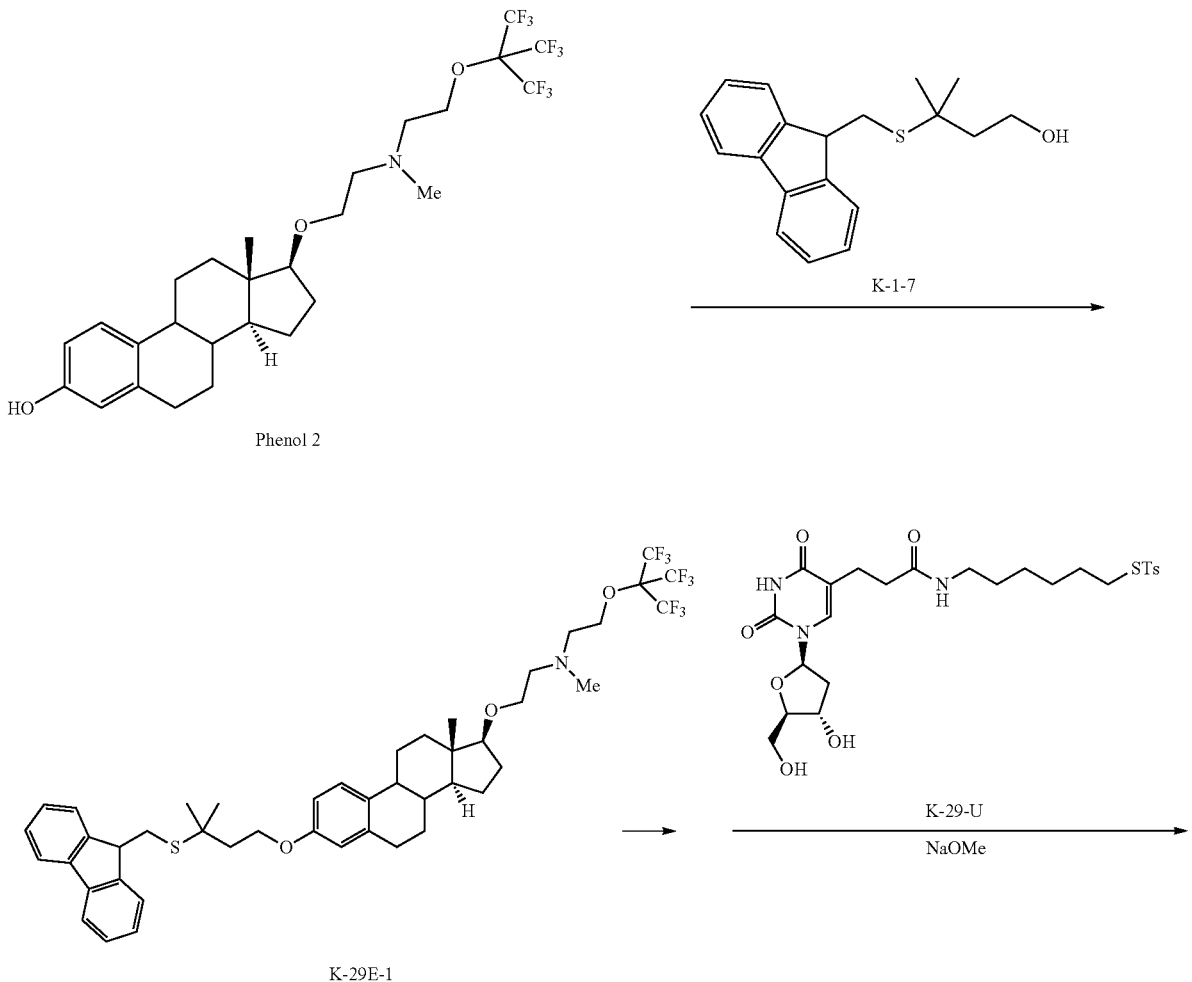

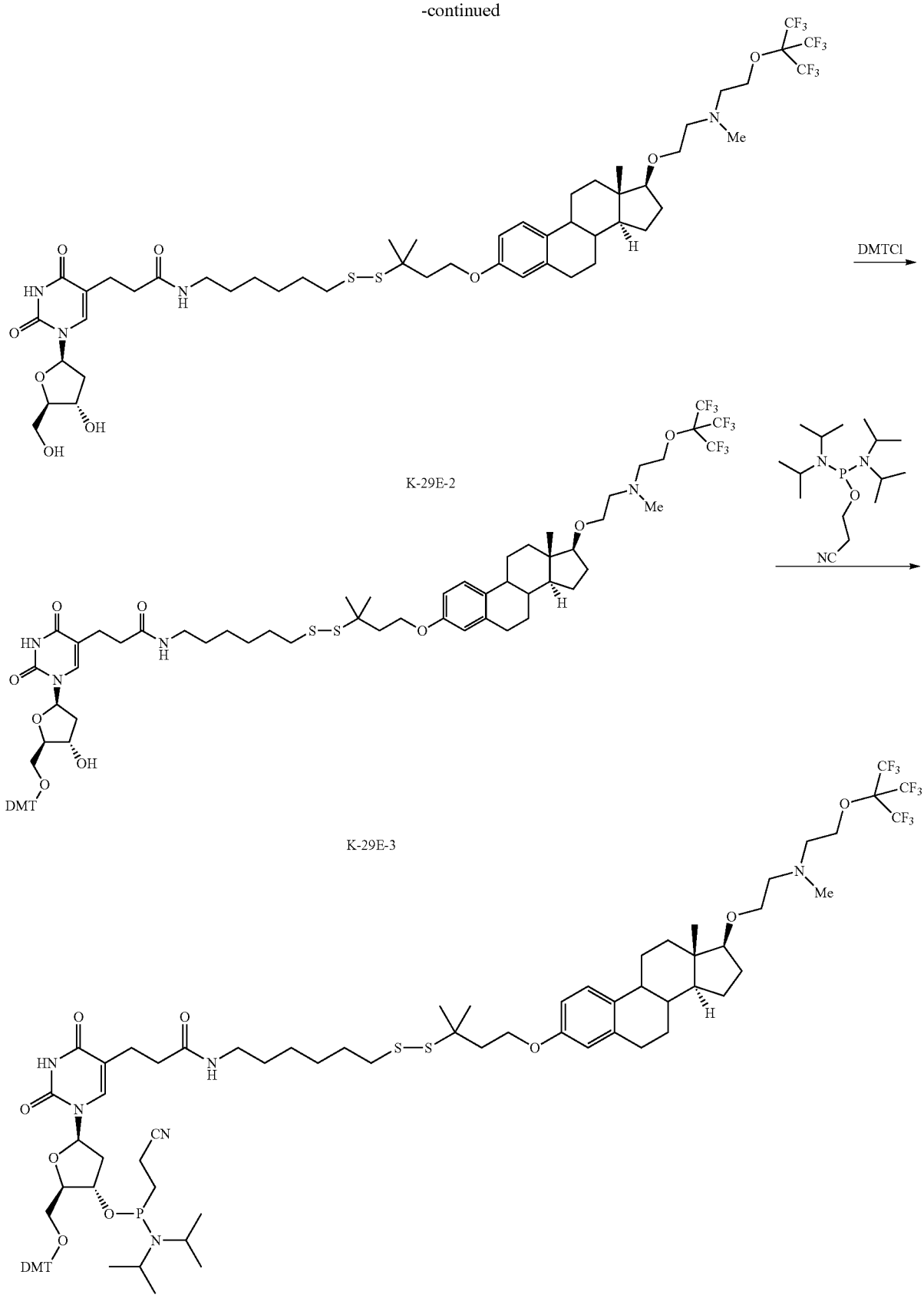

2aD1. 2-(((13S,14S,17S)-3-(3-(((9H-Fluoren-9-yl)methyl)thio)-3-methylbutoxy)-13-methyl-7,8,9,11,12,13,14,15,16,17-decahydro-6H-cyclopenta[a]phenanthren-17-yl)oxy)-N-(2-((1,1,1,3,3,3-hexafluoro-2-(trifluoromethyl)propan-2-yl)oxy)ethyl)-N-methylethan-1-amine (K-29E-1)

To a solution of phenol 2 (1.47 g, 2.5 mmol) in THF (40 mL) were added alcohol K-1-7 (1.48 g, 5.0 mmol), triphenyl phosphine (0.91 g, 3.5 mmol) and diisopropyl azodicarboxylate (0.6 mL, 2.9 mmol). The mixture was stirred for 16 hours at room temperature. After concentration, the mixture was further purified using flash chromatography (20% EtOAc and 1% Et$_3$N in heptanes) to provide K-29E-1 (1.5 g, 1.7 mmol) as a clear oil in 67% yield.

2aD2. N-(6-((4-(((13S,14S,17S)-17-(2-((2-((1,1,1,3,3,3-hexafluoro-2-(trifluoromethyl)propan-2-yl)oxy)ethyl)(methyl)amino)ethoxy)-13-methyl-7,8,9,11,12, 13, 14,15, 16,17-decahydro-6H-cyclopenta[a]phenanthren-3-yl)oxy)-2-methylbutan-2-yl)disulfanyl)hexyl)-3-(1-((2R,4S,5R)-4-hydroxy-5-(hydroxymethyl)tetrahydrofuran-2-yl)-2,4-dioxo-1,2,3,4-tetrahydropyrimidin-5-yl)propanamide (K-29E-2)

A solution of compound K-29E-1 (1 eq.) and tosylate K-29U (1.5 eq.) in dichloromethane was treated with 2M NaOMe in MeOH (4 eq.) The mixture was stirred for 16 hours at room temperature. The cloudy suspension was washed with brine, dried over sodium sulfate and concentrated. Further purification using flash provided compound K-29E-2.

2aD3. 3-(1-((2R,4S,5R)-5-((bis(4-methoxyphenyl)(phenyl)methoxy)methyl)-4-hydro xytetrahydrofuran-2-yl)-2,4-dioxo-1,2,3,4-tetrahydropyrimidin-5-yl)-N-(6-((4-(((13S,14S,17S)-17-(2-((2-((1,1,1,3,3,3-hexafluoro-2-(trifluoromethyl)propan-2-yl)oxy)ethyl)(methyl)amino)ethoxy)-13-methyl-7,8,9,11,12,13,14,15,16,17-decahydro-6H-cyclopenta[a]phenanthren-3-yl)oxy)-2-methylbutan-2-yl)disulfanyl) hexyl)propanamide (K-29E-3)

To a solution of K-29E-2 (1 eq.) in pyridine were added DMT-Cl (2 eq.) and DMAP (0.1 eq.) and the resulting mixture was stirred overnight at room temperature, after which the mixture was concentrated. The residue was purified using column chromatography to provide compound K-29E-3.

2aD4. 3-(1-((2R,4S,5R)-5-((bis(4-methoxyphenyl)(phenyl)methoxy)methyl)-4-(((2-cyano ethyl)(diisopropylamino)phosphanyl)oxy)tetrahydrofuran-2-yl)-2,4-dioxo-1,2,3,4-tetrahydropyrimidin-5-yl)-N-(6-((4-(((13S,14S,17S)-17-(2-((2-((1,1,1,3,3,3-hexafluoro-2-(trifluoromethyl)propan-2-yl)oxy)ethyl)(methyl) amino)ethoxy)-13-methyl-7,8,9,11,12,13,14,15,16,17-decahydro-6H-cyclopenta[a]phenanthren-3-yl)oxy)-2-methylbutan-2-yl)disulfanyl)hexyl)propanamide Apo-Si-K29E-Precursor)

To a solution of compound K-29E-3 (1 eq.) in dichloromethane was added 2-Cyanoethyl N,N,N',N-tetraisopropylphosphorodiamidite (1.3 eq.), followed by dropwise addition of a 0.5 M solution of N-methylmorpholine and 0.25 M trifluoroacetic acid in dichloromethane (1.3 equivalent of N-methylmorpholine to the phosphorodiamidite-agent). The resulting mixture was stirred for 2 hours at room temperature, then quenched with aqueous saturated sodium bicarbonate and stirring continued for an additional 10 minutes. The organic layer was separated, dried over sodium sulfate and concentrated. Further purification using flash chromatography provided compound Apo-Si-K-29E-Precursor.

Example 2b: Synthesis of Apo-Si-K-29D-Precursor

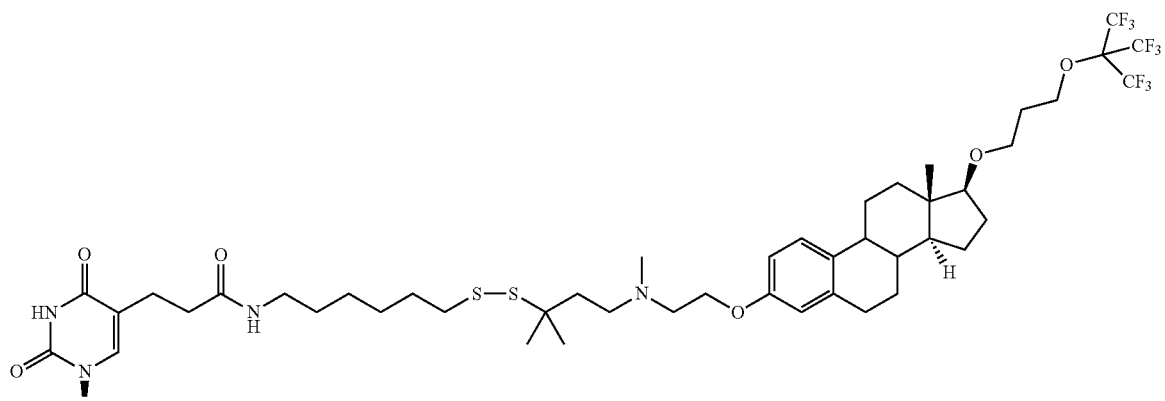

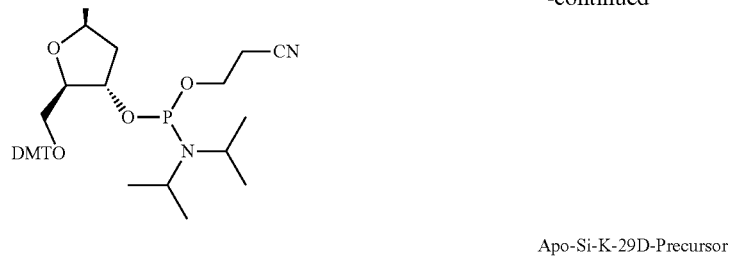

Apo-Si-K-29D-Precursor

2bA. Synthesis of Phenol 1

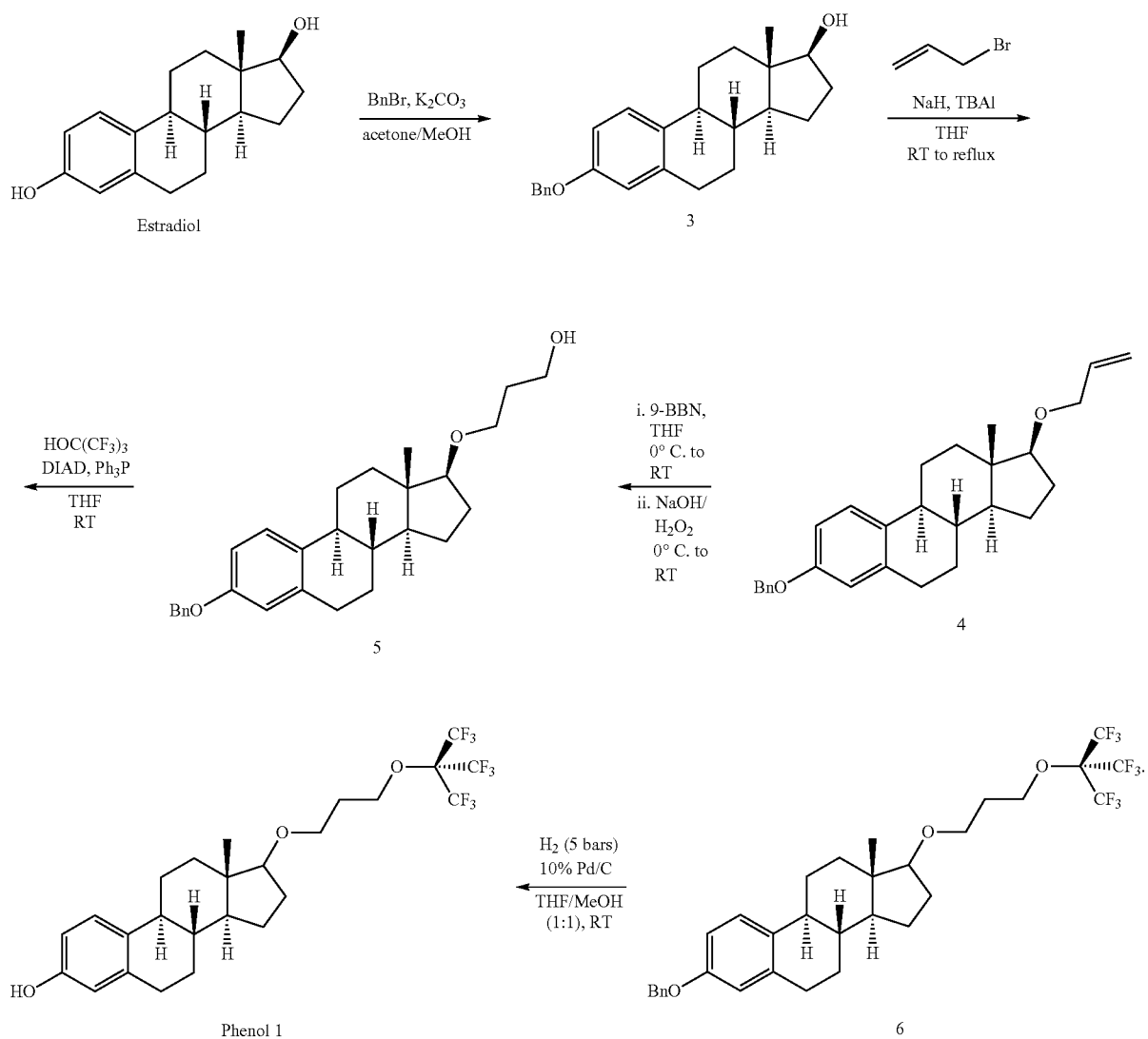

Scheme 1. Synthesis of phenol 1

Estradiol was treated with excess of sodium hydride, followed by addition of allylbromide, which resulted in clean conversion towards compound 3. Subsequent hydroboration with 1.5 equivalents of 9-BBN solely resulted in the terminal hydroxy group, while hydroboration with $BH_3$ is much less selective and provided a mixture of adducts. Alcohol 5 was submitted to Mitsunobu-reaction conditions, to couple it with perfluorinated tert-butanol to receive compound 6. Hydrogenolysis of the benzyl group of compound 8 furnished phenol 1. In conclusion, phenol 1 was prepared from estradiol via 5 synthetic steps in 45% overall yield.

2bA1. (8R,9S,13S,14S,17S)-3-Benzyloxy-17-hydroxyestra-1,3,5(10)-triene (2)

The synthesis of (8R,9S,13S,14S,17S)-3-Benzyloxy-17-hydroxyestra-1,3,5(10)-triene (2) is disclosed herein above in section 2aA1.

2bA2. (8R,9S,13S,14S,17S)-17-Allyloxy-3-benzyloxyestra-1,3,5(10)-triene (3)

The synthesis of (8R,9S,13S,14S,17S)-17-Allyloxy-3-benzyloxyestra-1,3,5(10)-triene (3) is disclosed herein above in section 2aA2.

2bA3. (8R,9S,13S,14S,17S)-3-Benzyloxy-17-(3-hydroxypropoxy)estra-1,3,5(10)-triene (7)

9-Borabicyclo[3.3.1]nonane (800 mL, 0.5 M solution in THF, stabilized, 400 mmol) was added dropwise to a solution of the crude alkene 3 (101.2 g, 251 mmol) in THF (1 L) at 0° C. and upon complete addition the mixture was stirred at room temperature overnight. The solution was cooled to 0° C. and slowly aqueous 30% NaOH (150 mL, 1.3 mol) and 35% aqueous (120 mL, 1.3 mol) were added dropwise simultaneously and the resulting heterogeneous mixture was vigorously stirred at room temperature for ca. 1 h. The reaction mixture was then partitioned between EtOAc (2 L) and brine (500 mL). The organic phase was washed with an additional 500 mL brine, dried over $Na_2SO_4$ and concentrated in vacuo. This procedure was repeated in a similar fashion and both portions were combined. Further purification of the concentrate by flash chromatography (silica gel, gradient 25% to 35% EtOAc in heptanes) afforded the alcohol 5 (130 g, 310 mmol) as a white solid in 61% yield (3 steps).

2bA4. (8R,9S,13S,14S,17S)-3-Benzyloxy-17-[3-(perfluoro-tert-butyloxy) propoxy]estra-1,3,5(10)-triene (8)

Diisopropyl azodicarboxylate (80 mL, 407 mmol) was added dropwise to a stirred mixture of alcohol 7 (130 g, 301 mmol), triphenylphosphine (162 g, 618 mmol), perfluoro-tert-butanol (70 mL, 497 mmol) and in dry THF (2 L) under a nitrogen atmosphere. The mixture was stirred at room temperature for ca. 18 h. The reaction mixture partially concentrated and heptane (1 L) was added. After full removal of the THF, precipitation started. The solids were removed using filtration and the filtrate was concentrated. Acetonitrile (1.5 L) was added and the mixture was stirred for 30 minutes while precipitation started. The solids were collected via filtration and dried in vacuo. Compound 8 (160 g, 251 mmol) was isolated as a white solid in 81% yield.

2bA5. (8R,9S,13S,14S,17S)-3-Hydroxy-17-[3-(perfluoro-tert-butyloxy) propoxy]estra-1,3,5(10)-triene (Phenol 1)

A Parr vessel was charged with benzyl ether 8 (160 g, 251 mmol) in EtOAc (1 L) to which 10% Palladium on carbon (4 g) was added. The mixture was stirred under hydrogen pressure (5 bars) at room temperature. The reaction was monitored with $^1H$ NMR. After ca. 72 h, the reaction mixture was filtered through a pad of Celite (flushed with EtOAc) and resubmitted with fresh 10% Palladium on charcoal (4 g) to a hydrogen atmosphere (5 bars). After ca. 16 h, the reaction mixture was filtered through a pad of Celite (flushed with EtOAc) and concentrated to provide phenol 1 (125 g, 228 mmol) as a greyish solid in 91% yield.

2bB. Synthesis of K-29U

The synthesis of building block K-29U was described herein above in section 2aC (2aC1-2aC8).

2bC. Completion of the Synthesis of Apo-Si-K-29D-Precursor

The synthesis commenced by Mitsunobu-coupling between Boc-protected methylaminoethanol and phenol 1. The coupling provided about 50% conversion. However, using column chromatography the product (K-29C-1) was isolated and the starting material can be recovered. Removal of the Boc-group using TFA allowed for the subsequent reductive amination using $NaBH(OAc)_3$, a method that allows for the presence of acid-protection of the amine. Formation of the disulfide using in situ deprotection of the thioacetate was then performed, followed by attachment of the DMT group and the phosphoramidate moiety, using standard procedures as known in the art.

Scheme 5. Synthesis of Apo-Si-K-29D-Precursor

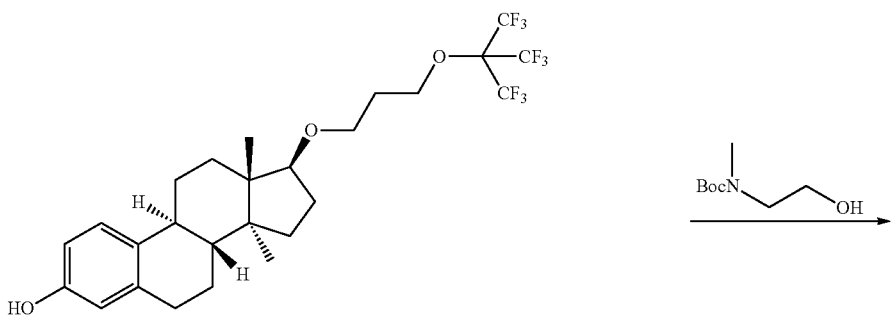

Phenol 1

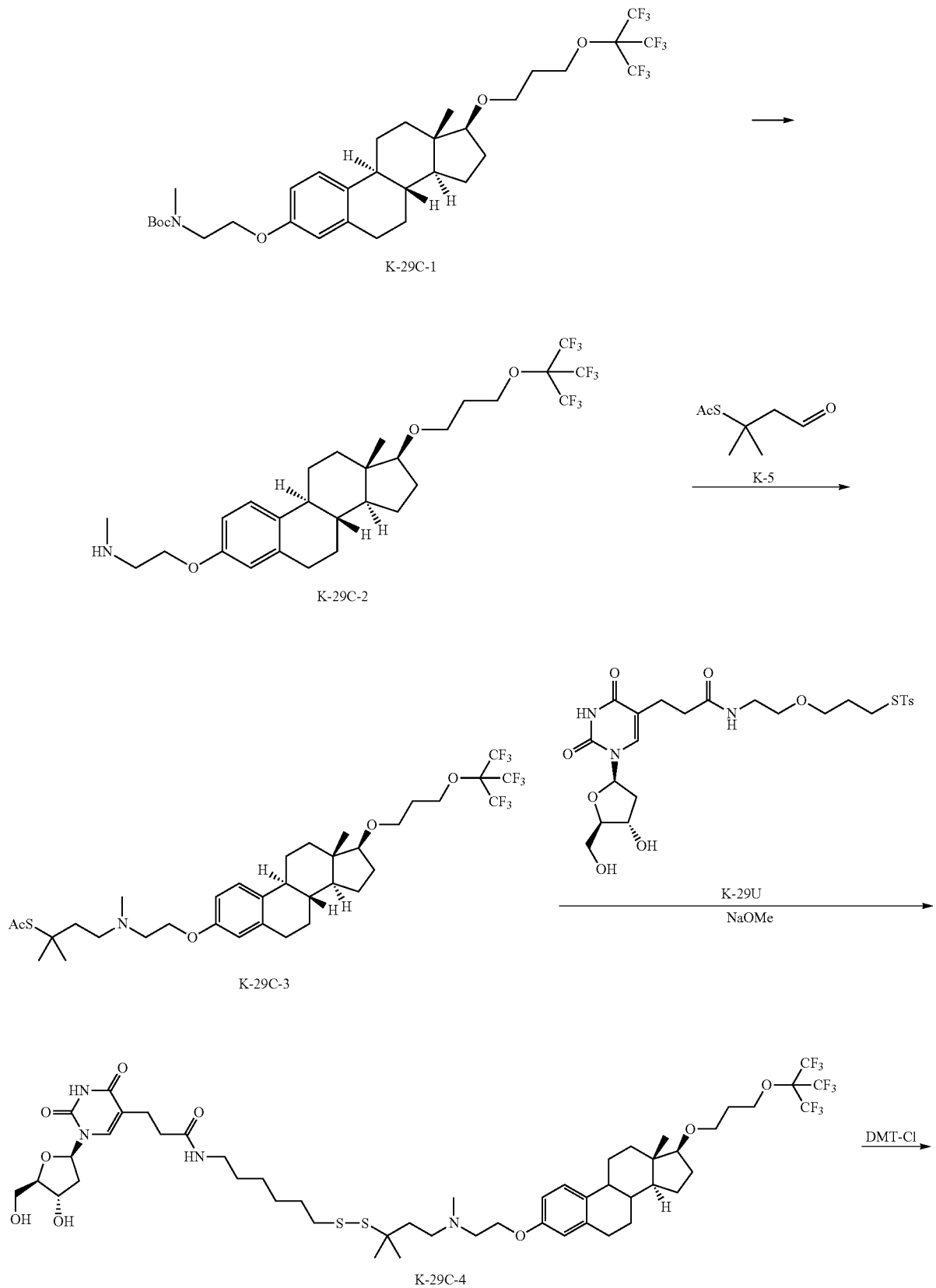

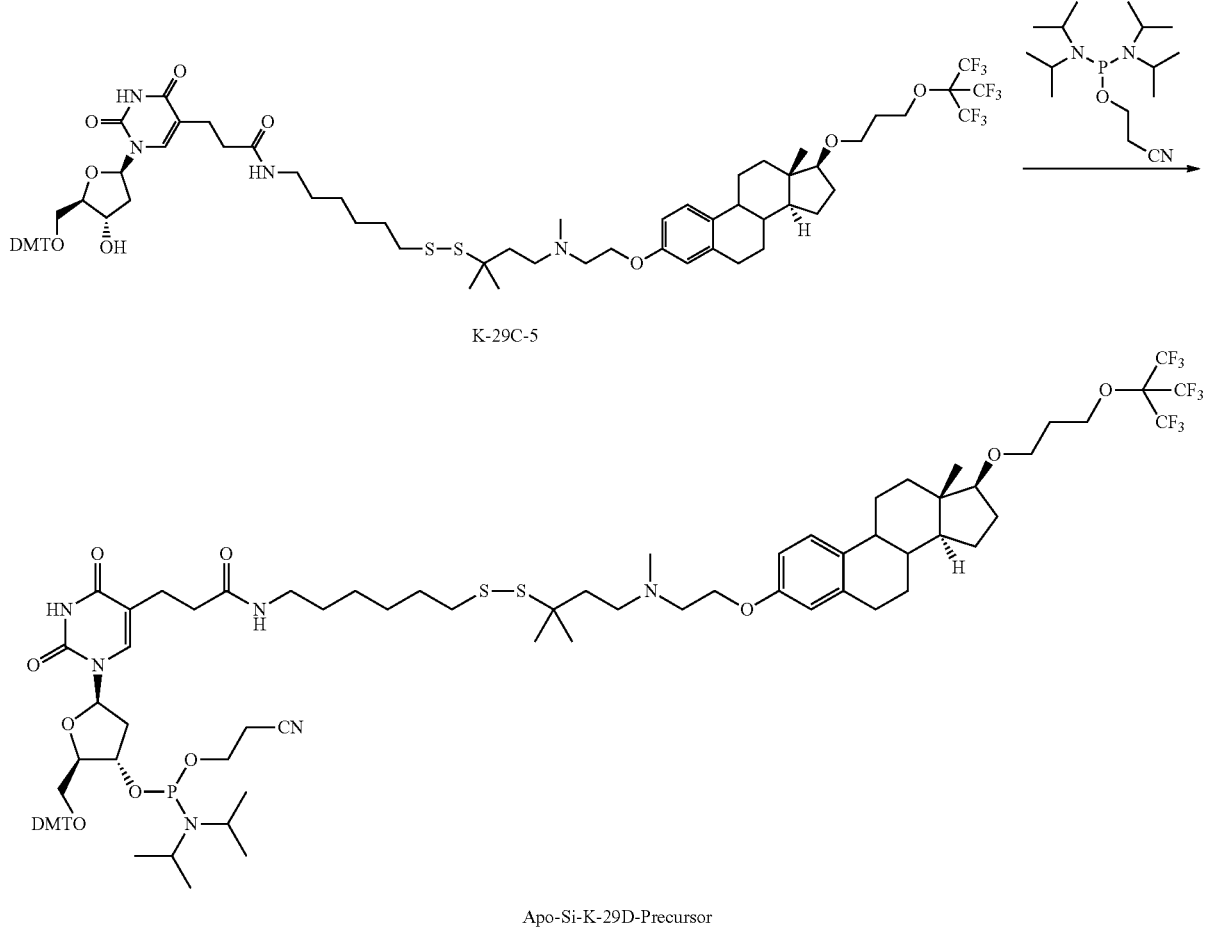

Apo-Si-K-29D-Precursor

2bC1. tert-Butyl (2-((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl) carbamate (K-29C-1)

To a solution of Phenol 1 (50 g, 91 mmol) and Boc N-methyl glycinol (32 g, 182 mmol) was added PPh₃ (38 g, 146 mmol) and the resulting mixture was stirred until all had dissolved. DIAD (23 mL, 118 mmol) was added and the resulting mixture was stirred 64 h. The mixture was concentrated and heptane was was added. The resulting precipitation was filtered off and the filtrate was concentrated. The crude material was purified using column chromatography (10% EtOAc/heptane with 0.1% TEA) (three times). The pure fractions were pooled and concentrated and provided compound K-29C-1 (51 g, 73 mmol, 80%) as well as recovered Phenol 1 (5 g, 9.5 mmol, 10%).

2bC2. 2-(((8R,9S,13S,14S,17S)-17-(3-((1,1,1,3,3,3-Hexafluoro-2-(trifluoro methyl) propan-2-yl)oxy) propoxy)-13-methyl-7,8,9,11,12,13,14,15,16,17-deca hydro-6H-cyclopenta[a]phenanthren-3-yl)oxy)-N-methylethan-1-amine (K-29C-2)

Compound K-29C-1 (5.6 g, 7.9 mmol) was dissolved in 2M HCl in EtOAc (100 mL) and the resulting solution was stirred overnight. Aqueous NaOH (2M, 150 mL) was added and stirred vigorously until all had dissolved. Layers were separated and the organic layer was washed with brine, dried over Na₂SO₄, and concentrated to provide K-29C-2 (4.5 g, 7.4 mmol, 94%) as a pink oily substance.

2bC3. S-(2-methyl-4-oxobutan-2-yl) ethanethioate (K-5)

To a mixture of dimethyl acrolein (25 mL, 435 mmol) and thioacetic acid (44 mL, 608 mmol, 1.4 eq.) at 0° C., TEA (31 mL, 435 mmol) was added dropwise. The resulting mixture was stirred overnight at room temperature. EtOAc and NaOH (1M) were added. The layers were separated and the organic layer was washed with brine, dried over Na₂SO₄, and concentrated. The crude material was purified by column chromatography (10% EtOAc in heptane) to provide K-5 as a yellow oil (22 g, 137 mmol, 32%)

2bC4. S-(4-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) ethanethioate (K-29C-3)

To a solution of K-29C-2 (2.0 g, 3.3 mmol) in dichloroethane (100 mL) were added Z-8-1 (1.1 g, 6.6 mmol, 2 eq.), acetic acid (0.57 mL, 9.9 mmol, 3 eq.), and NaBH (OAc)₃ (2.1 g, 9.9 mmol, 3 eq.) and the resulting mixture was stirred for 4 h. NaHCO₃ (sat., 500 mL) was added and the mixture was extracted with CH₂Cl₂ (3×, 200 mL). The combined organic layers were washed with brine, dried over Na₂SO₄ and concentrated. The crude material was purified using column chromatography (30% EtOAc in heptane+ 0.1% NEt₃) to provide K-29C-3 (1.1 g, 1.5 mmol, 44%).

2bC4. N-(6-((4-((2-(((13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) disulfanyl)hexyl)-3-(1-((2R,4S,5R)-4-hydroxy-5-(hydroxymethyl)tetrahydrofuran-2-yl)-2,4-dioxo-1,2,3,4-tetrahydropyrimidin-5-yl)propanamide (K-29C-4)

A solution of compound K-29C-3 (1 eq.) and tosylate K-29U (1.5 eq.) in dichloromethane was treated with 2M NaOMe in MeOH (4 eq.) The mixture was stirred for 16 hours at room temperature. The cloudy suspension was washed with brine, dried over sodium sulfate and concentrated. Further purification using flash provided compound K-29C-4.

2bC5. 3-(1-((2R,4S,5R)-5-((bis(4-methoxyphenyl)(phenyl)methoxy)methyl)-4-hydroxy tetrahydrofuran-2-yl)-2,4-dioxo-1,2,3,4-tetrahydropyrimidin-5-yl)-N-(6-((4-((2-(((13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) disulfanyl) hexyl)propanamide (K-29C-5)

To a solution of K-29C-4 (1 eq.) in pyridine were added DMT-Cl (2 eq.) and DMAP (0.1 eq.) and the resulting mixture was stirred overnight at room temperature, after which the mixture was concentrated. The crude material was purified using column chromatography to provide compound K-29C-5.

2bC6. (2R,3S,5R)-2-((bis(4-methoxyphenyl)(phenyl)methoxy)methyl)-5-(5-(3-((6-((4-((2-(((13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) disulfanyl)hexyl)amino)-3-oxoprop-2,4-dioxo-24-dioxo-3,4-dihydropyrimidin-1(2H)-yl)tetrahydrofuran-3-yl (2-cyanoethyl) diisopropylphosphoramidite (Apo-Si-K29D-Precursor)

To a solution of compound K-29C-5 (1 eq.) in dichloromethane was added 2-Cyanoethyl N,N,N',N-tetraisopropylphosphorodiamidite (1.3 eq.), followed by dropwise addition of a 0.5 M solution of N-methylmorpholine and 0.25 M trifluoroacetic acid in dichloromethane (1 equivalent of N-methylmorpholine to the phosphorodiamidite-agent). The resulting mixture was stirred for 2 hours at room temperature, then quenched with aqueous saturated sodium bicarbonate and stirring continued for an additional 10 minutes. The organic layer was separated, dried over sodium sulfate and concentrated. Further purification using flash chromatography provided compound Apo-Si-K-29D-Precursor.

Example 2c: Synthesis of Apo-Si-K-18-Precursor

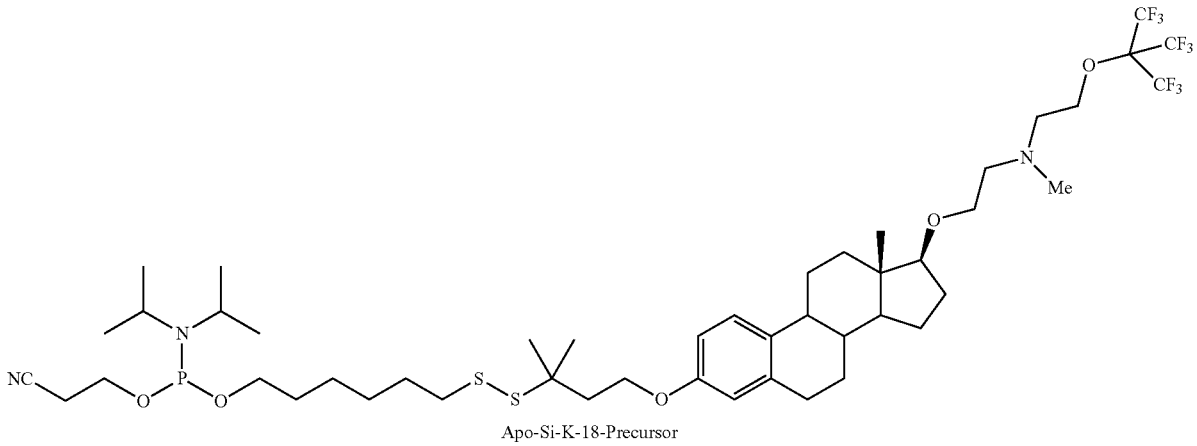 [SMILES: CC(C)N(C(C)C)P(OCCC#N)OCCCCCCSSC(C)(C)CCOc1ccc2c(c1)CCC1C2CC[C@@]2(C)C1CC[C@@H]2OCCN(C)CCOC(C(F)(F)F)(C(F)(F)F)C(F)(F)F]

Apo-Si-K-18-Precursor

2cA. Synthesis of Phenol 2

The synthesis of Phenol 2 was described herein above in section 2aA (2aA1-2aA6).

2cB. Synthesis of K-1-7

The synthesis of the building block K-1-7 was described herein above in section 2aB (2aA1-2aA6).

2cC. Synthesis of K-6

The last building block K-6, was prepared by substitution reaction of potassium thiotosylate to chlorohexanol.

Scheme 3. Synthesis of K-6

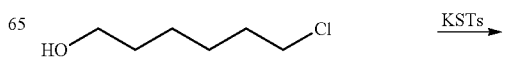

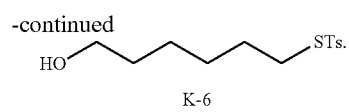

S-(6-hydroxyhexyl) 4-methylbenzenesulfonothioate (K-6)

3-Chlorohexan-1-ol (5.0 mL, 36.6 mmol) was dissolved in dimethylformamide (DMF, 150 mL) and Potassium p-toluenethiosulfonate (KSTs, 12.4 g, 54.9 mmol, 1.5 eq.) and tetrabutylammonium iodide (TBAI, 1.35 g, 3.66 mmol, 0.1 eq.) were added. The resulting mixture was stirred at 80° C. overnight. H$_2$O (500 mL) and EtOAc/heptane (800 mL, 1/1, v/v) were added. The layers were separated and the organic layer was washed with H$_2$O (300 mL) and brine (300 mL), dried over Na$_2$SO$_4$, and concentrated to provide K-6 (9.0 g, 31.2 mmol, 85%) as a clear oil.

2cD. Completion of the Synthesis of Apo-Si-K-18-Precursor

The completion of the synthesis of Apo-Si-K-18 starting from phenol 2 is shown in scheme 4. Building block K-1-7 was coupled to Phenol 2 using Mitsunobu conditions. After some initial tests to deprotect the fluorenyl protective group on the sulfur, it was found that K-18-1 could be deprotected in situ in the presence of K-6 to form the disulfide K-18-2.

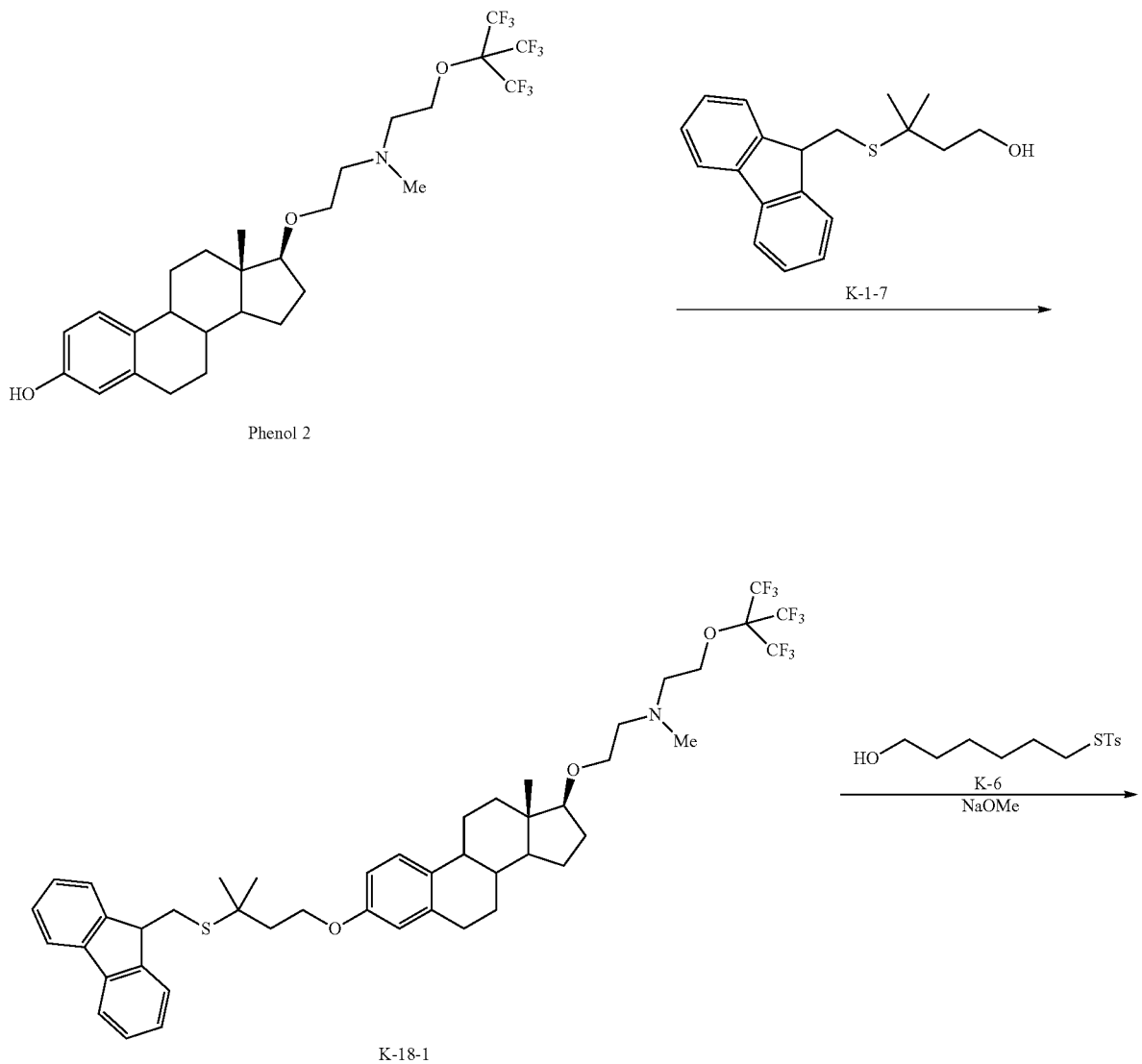

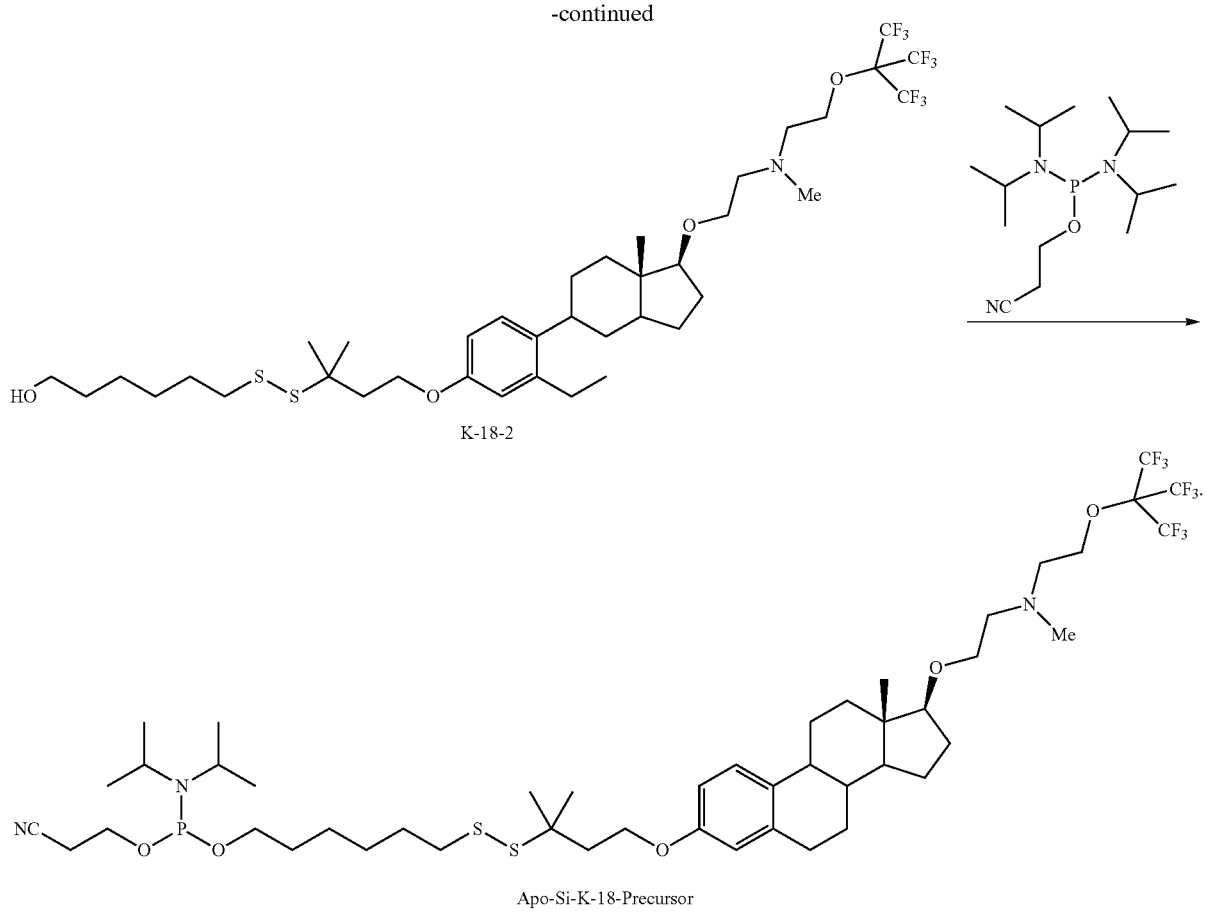

Final attachment of the phosphoramidate using the suitable phosphorodiamidate-agent gave straightforward access to Apo-Si-K-18. Purification of this material using flash chromatography was achieved, following deactivation with Et$_3$N prior to the exposure to the acid-labile phosphoramidate.

In conclusion, Compound Apo-Si-K-18 (2×350 mg) was prepared from estradiol in 11 steps in reasonable overall yield from phenol 2.

2cD1. 2-(((13S,14S,17S)-3-(3-(((9H-Fluoren-9-yl) methyl)thio)-3-methyl butoxy)-13-methyl-7,8,9,11, 12,13,14,15,16,17-decahydro-6H-cyclopenta [a]phenanthren-17-yl)oxy)-N-(2-((1,1,1,3,3,3-hexafluoro-2-(trifluoromethyl)propan-2-yl)oxy) ethyl)-N-methylethan-1-amine (K-18-1)

To a solution of phenol 2 (1.47 g, 2.5 mmol) in THF (40 mL) were added alcohol K-1-7 (1.48 g, 5.0 mmol), triphenyl phosphine (0.91 g, 3.5 mmol) and diisopropyl azodicarboxylate (0.6 mL, 2.9 mmol). The mixture was stirred for 16 hours at room temperature. After concentration, the mixture was further purified using flash chromatography (20% EtOAc and 1% Et$_3$N in heptanes) to provide K-18-1 (1.5 g, 1.7 mmol) as a clear oil in 67% yield.

2cD2. 6-((4-(((13S,14S,17S)-17-(2-((2-((1,1,1,3,3,3-Hexafluoro-2-(trifluoromethyl)propan-2-yl)oxy) ethyl)(methyl)amino)ethoxy)-13-methyl-7,8,9,11,12, 13, 14,15,16,17-decahydro-6H-cyclopenta[a] phenanthren-3-yl)oxy)-2-methylbutan-2-yl) disulfanyl)hexan-1-ol (K-18-2)

A solution of compound K-18-1 (400 mg, 0.45 mmol) and tosylate K-6 (388 mg, 1.34 mmol) in dichloromethane (15 mL) was treated with 2M NaOMe in MeOH (0.9 mL, 1.8 mmol). The mixture was stirred for 16 hours at room temperature. The cloudy suspension was washed with brine, dried over sodium sulfate and concentrated. Further purification using flash chromatography (30% to 40% EtOAc+1% Et$_3$N in heptanes) provided compound K-18-2 (220 mg, 0.27 mmol) as colorless oil in 59% yield.

2cD3. 2-Cyanoethyl (6-((4-(((8R,9S,13S,14S,17S)-17-(2-((2-((1,1,1,3,3,3-hexa fluoro-2-(trifluoromethyl)propan-2-yl)oxy)ethyl)(methyl)amino)ethoxy)-13-methyl-7,8,9,11,12,13,14,15,16,17-decahydro-6H-cyclopenta[a] phenanthren-3-yl)oxy)-2-methylbutan-2-yl)disulfanyl)hexyl)diisopropyl phosphoramidite (Apo-Si-K-18-Precursor)

To a solution of compound K-18-2 (656 mg, 0.79 mmol) in dichloromethane (25 mL) was added 2-Cyanoethyl N,N, N',N-tetraisopropylphosphorodiamidite (0.31 mL, 1 mmol), followed by dropwise addition of a 0.5 M solution of N-methylmorpholine and 0.25 M trifluoroacetic acid in dichloromethane (2.1 mL, 1 equivalent of N-methylmorpholine to the phosphorodiamidite-agent). The yellowish solution was stirred for 2 hours at room temperature, then quenched with aqueous saturated sodium bicarbonate and stirring continued for an additional 10 minutes. The organic layer was separated, dried over sodium sulfate and concentrated. Further purification using flash chromatography (30% EtOAc and 1% Et$_3$N in heptane) provided compound Apo-Si-K-18-Precursor (480 mg, 0.47 mmol) as a clear oil in 59% yield. Also, starting material K-18-2 (193 mg, 0.23 mmol) was recovered in 29% yield.

Example 2d: Synthesis of Apo-Si-K-13-Precursor

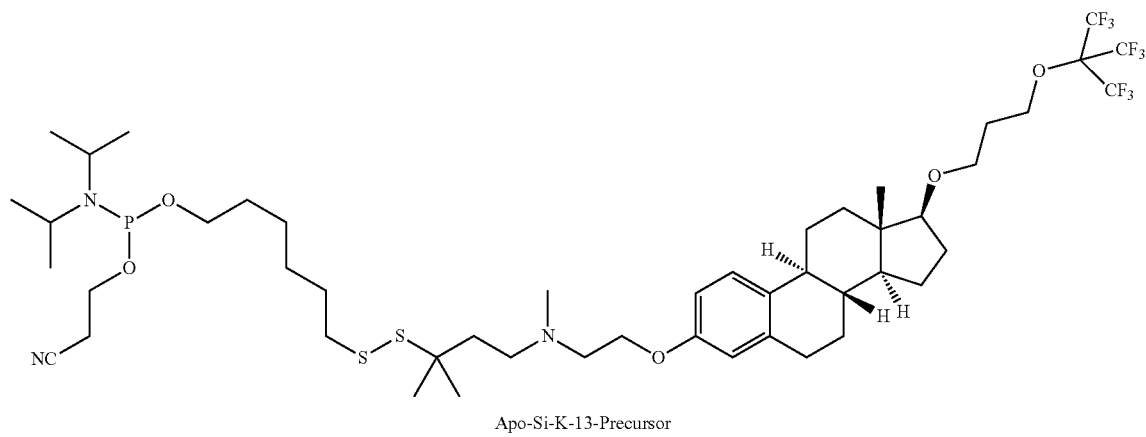 [SMILES: CC(C)N(C(C)C)P(OCCC#N)OCCCCCCSSC(C)(C)CCN(C)CCOc1ccc2c(c1)CC[C@@H]1[C@@H]2CC[C@]2(C)[C@@H](OCCCOC(C(F)(F)F)(C(F)(F)F)C(F)(F)F)CC[C@@H]12]

Apo-Si-K-13-Precursor

2dA. Synthesis of Phenol 1

The synthesis of Phenol 1 was described herein above in section 2bA (2bA1-2bA5).

2 dB. Completion of the Synthesis of Apo-Si-K-13-Precursor

Phenol 1 was coupled to Boc-protected methylaminoethanol using Mitsunobu-reaction conditions to compound K-13-1 in moderate yield (43%). Removal of the Boc-group using trufluoroacetuc acid (TFA) gave K-13-2 as TFA-salt, which was used in the subsequent reductive amination with K-5 using sodium triacetoxyborohydride as reducing agent. The yield of the pure product was rather low due to acetate transfer from the thiol to the amine, blocking part of the substrate to react further to the desired product.

Sodium methoxide in methanol was added to a solution of K-13-3 and K-6, which removed the acetate from K-13-3, allowing the resulting thiol to react with K-6 to form the desired Sulphur-bridge. Compound K-13-4 was reacted with the suitable phosphoramidite-agent to afford Apo-Si-K-13-Precursor. Purification of the acid-labile phosphoramidite product was done using flash chromatography with silica that had been pretreated with Et$_3$N.

In conclusion, Compound Apo-Si-K-13-Precursor (622 mg) was prepared from phenol 1 in five steps. Phenol 1 was prepared from estradiol via 5 synthetic steps in 45% overall yield.

Scheme 2. Synthesis of Apo-Si-K-13-Precursor

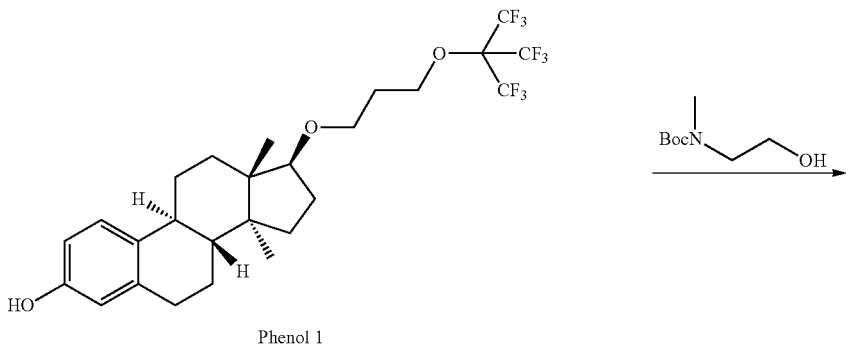

Phenol 1

-continued
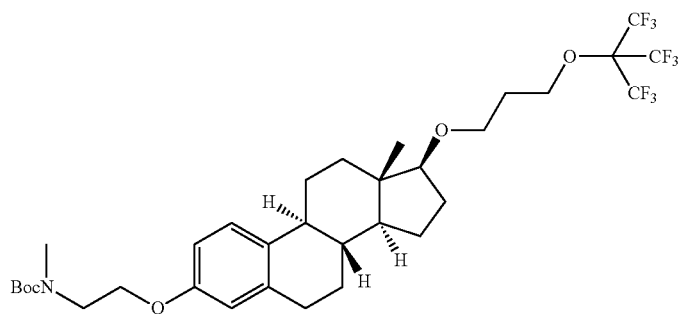
K-13-1
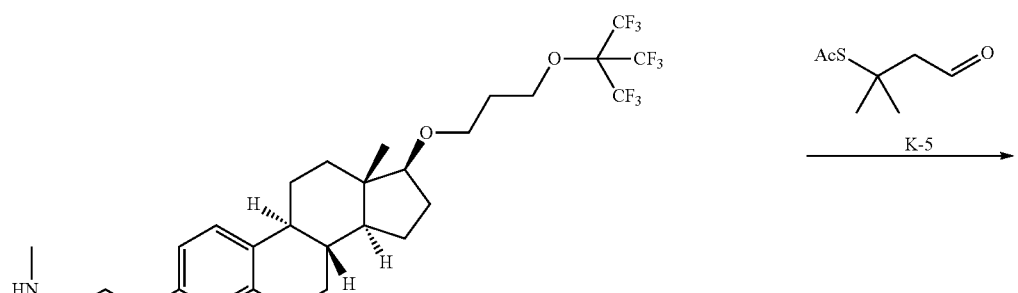
K-13-2
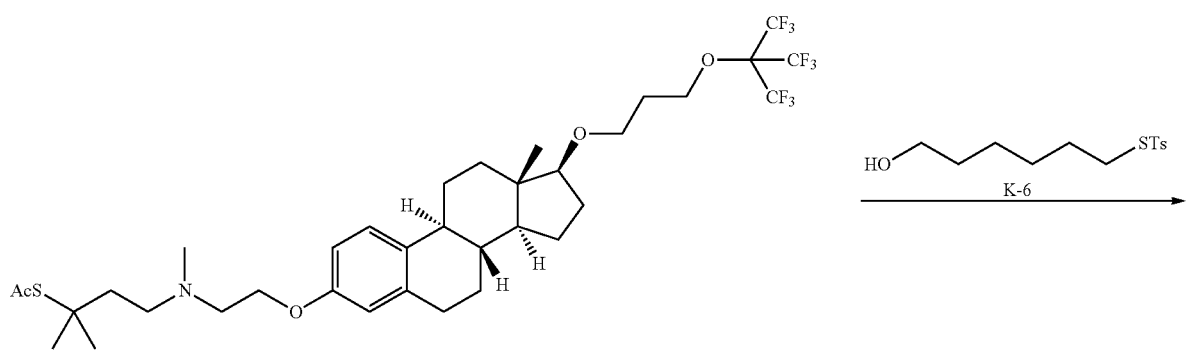
K-13-3
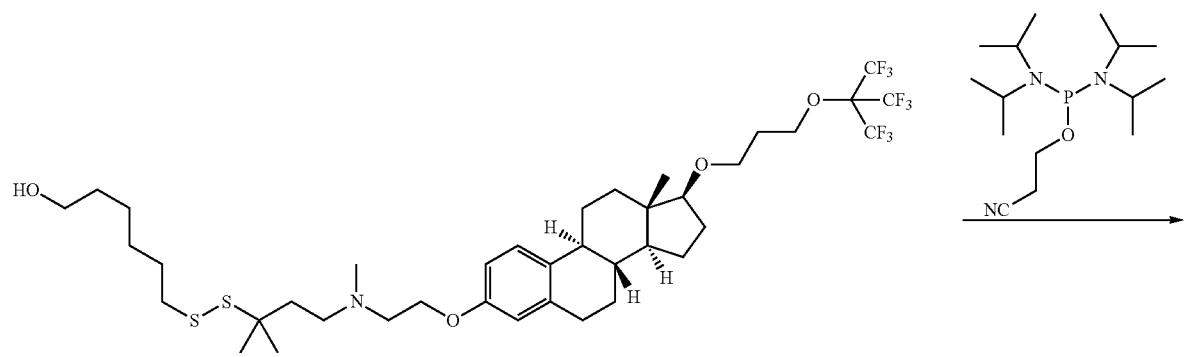
K-13-4

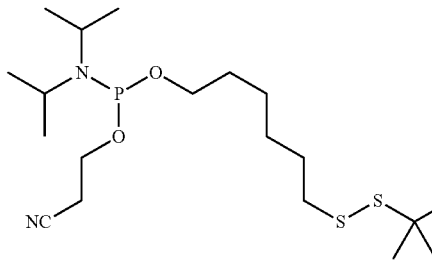
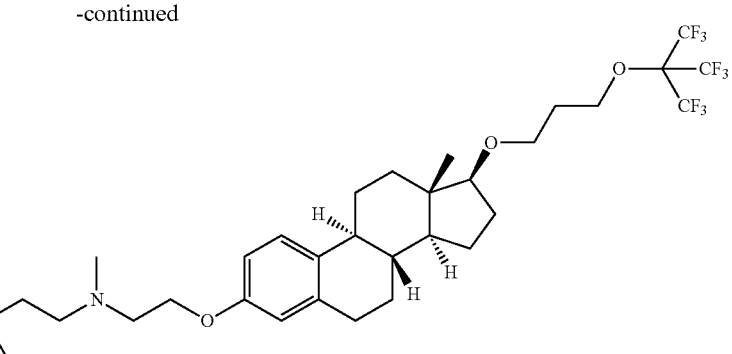

Apo-Si-K-13-Precursor

2dB1. tert-Butyl (2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl) (methyl)carbamate (K-13-1)

To a solution of phenol 1 (23.4 g, 42.7 mmol) in THF (600 mL) were added triphenylphosphine (26 g, 100 mmol), tert-butyl (2-hydroxyethyl)(methyl)carbamate (9.8 g, 61 mmol) and dropwise DIAD (12 mL, 61 mmol). The mixture was stirred for 16 at room temperature. The yellowish solution was partially concentrated, heptane was added and the solution was further concentrated to remove all traces of THF. The resulting precipitate was filtered off and the filtrate was concentrated. Further purification using flash chromatography (gradient 5% to 7% EtOAc in heptane) provided compound K-13-1 (13.05 g, 18.5 mmol) in 43% yield as yellowish oil.

2dB2. S-(4-((2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) ethanethioate (K-13-3)

A solution of compound K-13-1 (13.05 g, 18.5 mmol) was dissolved in dichloromethane (65 mL) and trifluoroacetic acid (40 mL) was added. After the mixture was stirred for 2 hours, the bubbling ceased. The mixture was concentrated and used as such. The residue was dissolved in 1,2-dichloroethane (400 mL) and acetic acid (5 mL, 75 mmol), aldehyde K-5 (6 g, 37 mmol) were added and stirring continued for 5 minutes. Then, sodium triacetoxyborohydride (16 g, 75 mmol) was added and the mixture was stirred for 16 hours at room temperature. The mixture was washed with 1 M NaOH and brine, dried over Na$_2$SO$_4$ and concentrated. Further purification provided compound K-13-3 (3.0 g, 4 mmol) as a clear yellowish oil in 22% yield.

2dB3. S-(6-hydroxyhexyl) 4-methylbenzenesulfonothioate (K-6)

3-Chlorohexan-1-ol (5.0 mL, 36.6 mmol) was dissolved in DMF (150 mL) and KSTs (12.4 g, 54.9 mmol, 1.5 eq.) and TBAI (1.35 g, 3.66 mmol, 0.1 eq.) were added. The resulting mixture was stirred at 80° C. overnight. H$_2$O (500 mL) and EtOAc/heptane (800 mL, 1/1, v/v) were added. The layers were separated and the organic layer was washed with H$_2$O (300 mL) and brine (300 mL), dried over Na$_2$SO$_4$, and concentrated to provide K-6 (9.0 g, 31.2 mmol, 85%) as a clear oil.

2dB4. 6-((4-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl)disulfanyl)hexan-1-ol (K-13-4)

A solution of compound K-13-3 (1 g, 1.34 mmol) and tosylate K-6 (770 mg, 2.7 mmol) in dichloromethane (30 mL) was treated with 2M NaOMe in MeOH (2 mL, 4 mmol). The mixture was stirred for 16 hours at room temperature. The cloudy suspension was washed with brine, dried over sodium sulfate and concentrated. Further purification using flash chromatography (30% EtOAc+1% Et$_3$N in heptanes) provided compound K-13-4 (650 mg, 0.77 mmol) as colorless oil in 58% yield.

2dB5. 2-Cyanoethyl (6-((4-((2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14, 15,16,17-decahydro-6H-cyclopenta[a]phenanthren-3-yl) oxy)ethyl)(methyl) amino)-2-methylbutan-2-yl)disulfanyl)hexyl) diisopropylphosphoramidite (Apo-Si-K-13-Precursor)

To a solution of compound K-13-4 (650 mg, 0.77 mmol) in dichloromethane (25 mL) was added 2-Cyanoethyl N,N,N',N'-tetraisopropylphosphorodiamidite (0.3 mL, 1 mmol) and dropwise a 0.5 M solution of N-methylmorpholine and 0.25 M trifluoroacetic acid in dichloromethane (2 mL, 1 equivalent of N-methylmorpholine to the phosphoramidite-agent). The yellowish solution was stirred for 2 hours at room temperature. Then, the reaction mixture was quenched with aqueous saturated sodium bicarbonate and stirring continued for an additional 10 minutes. The organic layer was separated, dried over sodium sulfate and concentrated. Further purification using flash chromatography (30% EtOAc and 1% Et$_3$N in heptane) provided compound Apo-Si-K-13 (622 mg, 0.60 mmol) as a clear oil in 78% yield.

Example 2e: Synthesis of Apo-Si-K-40-Precursor

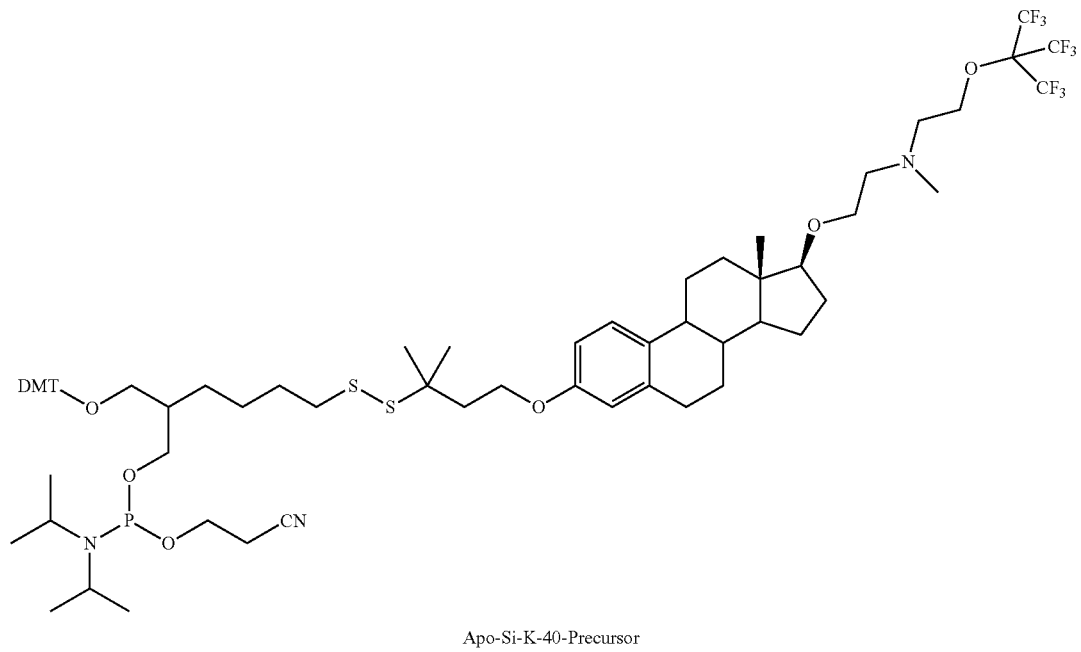

Apo-Si-K-40-Precursor

2eA. Synthesis of Phenol 2

The synthesis of Phenol 2 was described herein above in section 2aA (2aA1-2aA6).

2eB. Synthesis of K-1-7

The synthesis of the building block K-1-7 was described herein above in section 2aB (2aA1-2aA6).

2eC. Synthesis of K-40-2

Scheme 3: The synthesis of K-40-2

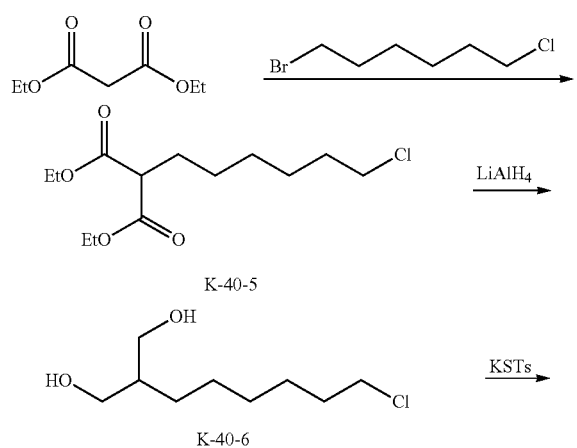

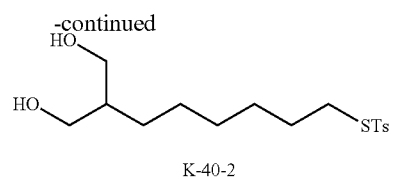

K-40-2

2eC1. Diethyl 2-(6-chlorohexyl)malonate (K-40-5)

To an ice-cooled suspension of NaH (2.6 g, 66 mmol, 1 eq.) in DMF (300 mL) was added dropwise diethyl malonate (20 mL, 131 mmol, 2 eq.). After the addition was complete, the ice-bath was removed and the mixture was stirred for 1 hour while warming to room temperature. The mixture had become a clear solution. The mixture cooled to 0° C. and 1-bromo-6-chlorohexane (9.8 mL, 66 mmol, 1 eq.) was added dropwise. The resulting mixture was stirred for 1 hour at 0° C. and for another 3 hours at room temperature. The reaction was quenched with concentrated HCl (3 mL) and $H_2O$ (500 mL). The reaction mixture was extracted with EtOAc/heptane (1/1, v/v, 3×400 mL). The combined organics were washed with brine, dried over $Na_2SO_4$, and concentrated. The crude material was purified using column chromatography (5% EtOAc in heptane) to provide K-40-5 (9.7 g, 35 mmol, 53%) as a clear oil.

2eC2. 2-(6-chlorohexyl)propane-1,3-diol (K-40-6)

To an ice-cooled suspension of $LiAlH_4$ (2.6 g, 70 mmol) in $Et_2O$ (250 mL) was added a solution of K-40-5 (9.7 g, 35 mmol) dropwise over 30 minutes, while keeping the temperature below 10° C. After the addition was complete the reaction mixture was stirred for 2 hours at 0° C. The reaction was quenched with $H_2O$ (5 mL), NaOH (aqueous., 30%, 2.5 mL), and H₂O (12 mL) in that order. The resulting mixture was stirred at room temperature for 1 hour, after which an insoluble white precipitate had formed. The precipitate was filtered off and the filtrate was concentrated to provide K-40-6 (6.1 g, 31 mmol, 90%) as a colorless oil.

2eC3. S-(8-hydroxy-7-(hydroxymethyl)octyl) 4-methylbenzenesulfonothioate (K-40-2)

Chloride K-40-6 (6.1 g, 31 mmol) was dissolved in DMF (200 mL) and potassium thiotosylate (10.7 g, 47 mmol, 2 eq.) and TBAI (1.2 g, 3.1 mmol, 0.1 eq.) were added. The resulting mixture was stirred for 24 hours at 80° C., after which it was concentrated in vacuo. The crude material was purified using column chromatography (7:3 EtOAc:heptane) to provide one fraction containing mainly the product (5.6 g) and a second fraction containing both the product and the starting material (3.3 g). The latter fraction was dissolved in DMF (100 mL) and potassium thiotosylate (4.5 g, 20 mmol) and TBAI (0.37 g, 1.0 mmol) were added. The resulting mixture was stirred for 24 hours at 80° C. and EtOAc (350 mL) and heptane (350 mL) were added. The organics were washed with H₂O (500 mL) and brine (250 mL), dried over Na₂SO₄, and concentrated. The crude material was combined with the product-containing fraction from the first column and the crude material was purified using column chromatography (7:3 EtOAc:heptane) to provide K-40-2 (8.2 g, 24 mmol, 75%) as a pinkish oil.

2eD. Completion of the Synthesis of Apo-Si-K-40-Precursor

Phenol 2 and building block K-1-7 were coupled before under Mitsunobu conditions to provide protected thiol K-40-1. The fluorenyl group was removed in situ, by NaOMe in the presence of K-40-2, to afford disulfide K-40-3. Finally, the DMT protecting group and the phosphoramidite groups were attached to provide the final compound Apo-Si-K-40-Precursor:

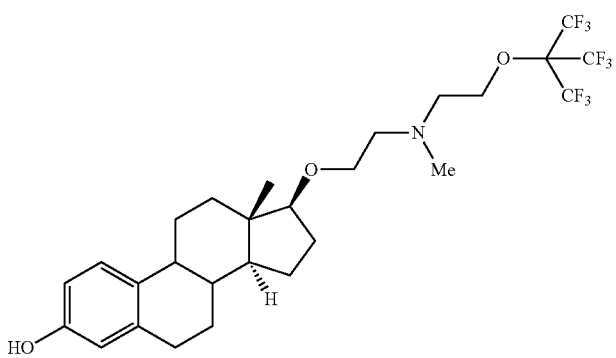

Phenol 2

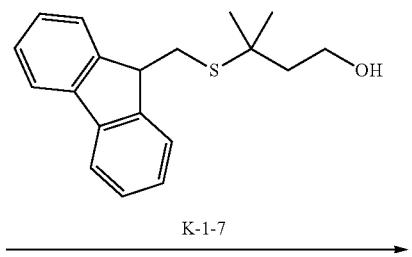

K-1-7

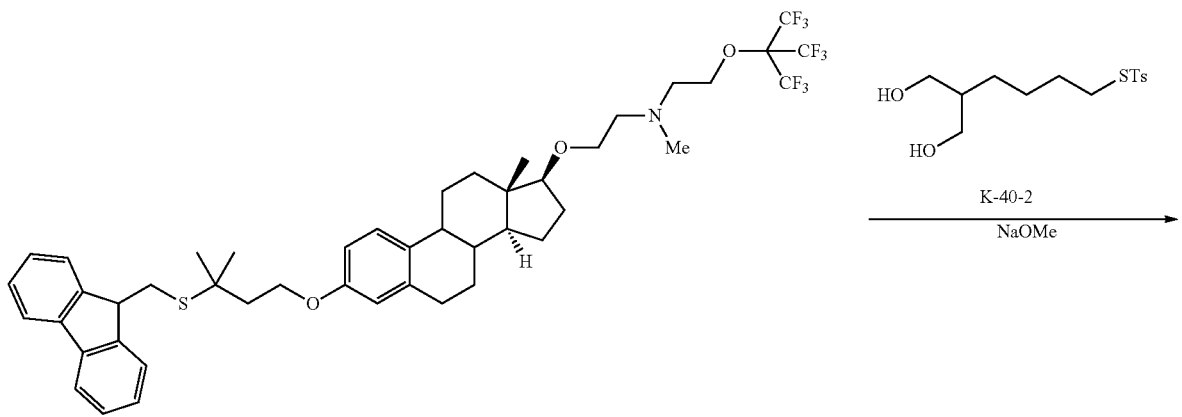

K-40-1

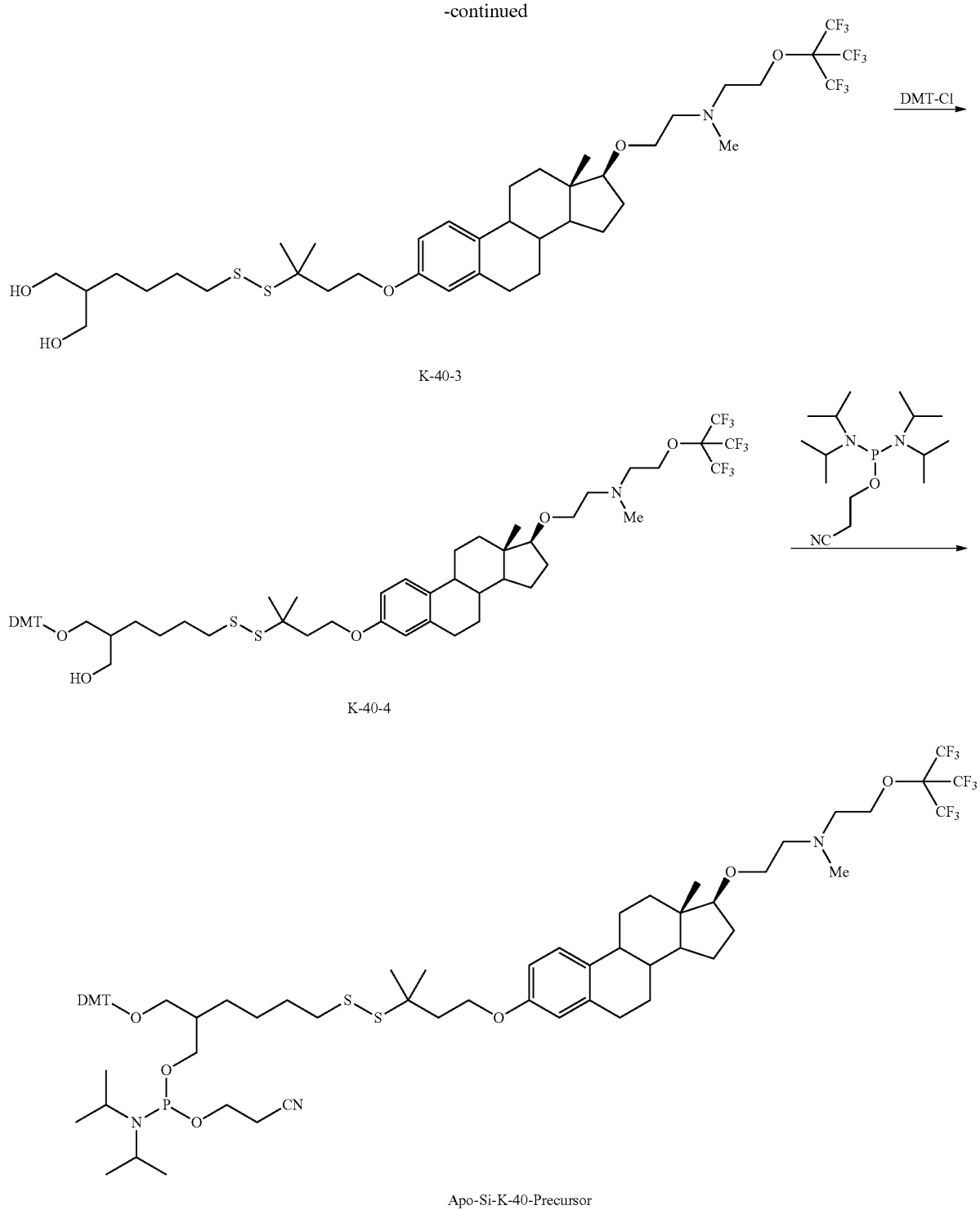

2eD1. 2-(((13S,14S,17S)-3-(3-(((9H-Fluoren-9-yl)methyl)thio)-3-methylbutoxy)-13-methyl-7,8,9,11,12,13,14,15,16,17-decahydro-6H-cyclopenta[a]phenanthren-17-yl)oxy)-N-(2-((1,1,1,3,3,3-hexafluoro-2-(trifluoromethyl)propan-2-yl)oxy)ethyl)-N-methylethan-1-amine (K-40-1)

To a solution of phenol 2 (1.47 g, 2.5 mmol) in THF (40 mL) were added alcohol K-1-7 (1.48 g, 5.0 mmol), triphenyl phosphine (0.91 g, 3.5 mmol) and diisopropyl azodicarboxylate (0.6 mL, 2.9 mmol). The mixture was stirred for 16 hours at room temperature. After concentration, the mixture was further purified using flash chromatography (20% EtOAc and 1% Et$_3$N in heptanes) to provide K-40-1 (1.5 g, 1.7 mmol) as a clear oil in 67% yield.

2eD2. 2-(6-((4-(((13S,17S)-17-(2-((2-((1,1,1,3,3,3-hexafluoro-2-(trifluoromethyl) propan-2-yl)oxy) ethyl)(methyl)amino)ethoxy)-13-methyl-7,8,9,11,12, 13,14,15,16, 17-decahydro-6H-cyclopenta[a] phenanthren-3-yl)oxy)-2-methylbutan-2-yl) disulfanyl) hexyl)propane-1,3-diol (K-40-3)

A solution of compound K-40-1 (1 eq.) and tosylate K-40-2 (1.5 eq.) in dichloromethane was treated with 2M NaOMe in MeOH (4 eq.) The mixture was stirred for 16 hours at room temperature. The cloudy suspension was washed with brine, dried over sodium sulfate and concentrated. Further purification using flash provided compound K-40-3.

2eD3. 2-((bis(4-methoxyphenyl)(phenyl)methoxy) methyl)-8-((4-(((13S,17S)-17-(2-((2-((1,1,1,3,3,3-hexafluoro-2-(trifluoromethyl)propan-2-yl)oxy) ethyl)(methyl) amino)ethoxy)-13-methyl-7,8,9,11, 12,13,14,15,16,17-decahydro-6H-cyclopenta [a]phenanthren-3-yl)oxy)-2-methylbutan-2-yl)disulfanyl)octan-1-ol (K-40-4)

To a solution of K-40-3 (1 eq.) in pyridine were added DMT-Cl (2 eq.) and DMAP (0.1 eq.) and the resulting mixture was stirred overnight at room temperature, after which the mixture was concentrated. The residue was purified using column chromatography to provide compound K-40-4.

2eD4. 2-((bis(4-methoxyphenyl)(phenyl)methoxy) methyl)-8-((4-(((13S,17S)-17-(2-((2-((1,1,1,3,3,3-hexafluoro-2-(trifluoromethyl)propan-2-yl)oxy) ethyl)(methyl) amino)ethoxy)-13-methyl-7,8,9,11, 12,13,14,15,16,17-decahydro-6H-cyclopenta [a]phenanthren-3-yl)oxy)-2-methylbutan-2-yl)disulfanyl)octyl(2-cyanoethyl) diisopropylphosphoramidite (Apo-Si-K40-Precursor)

To a solution of compound K-40-4 (1 eq.) in dichloromethane was added 2-Cyanoethyl N,N,N',N-tetraisopropylphosphorodiamidite (1.3 eq.), followed by dropwise addition of a 0.5 M solution of N-methylmorpholine and 0.25 M trifluoroacetic acid in dichloromethane (1.3 equivalent of N-methylmorpholine to the phosphorodiamidite-agent). The resulting mixture was stirred for 2 hours at room temperature, then quenched with aqueous saturated sodium bicarbonate and stirring continued for an additional 10 minutes. The organic layer was separated, dried over sodium sulfate and concentrated. Further purification using flash chromatography provided compound Apo-Si-K-40-Precursor.

Example 2f: Synthesis of Apo-Si-K-43-Precursor

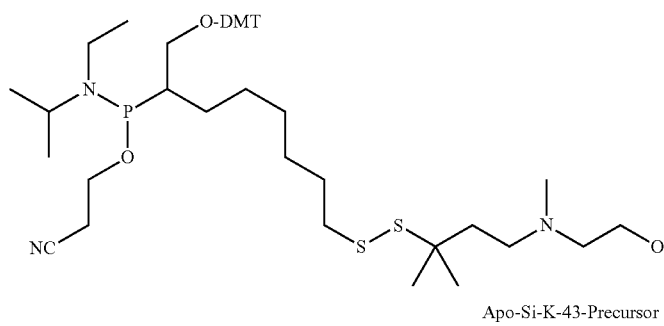

Apo-Si-K-43-Precursor

2fA. Synthesis of Phenol 1

The synthesis of Phenol 1 was described herein above in section 2aA (2aA1-2aA6).

2fB. Synthesis of Building Block K-43-4

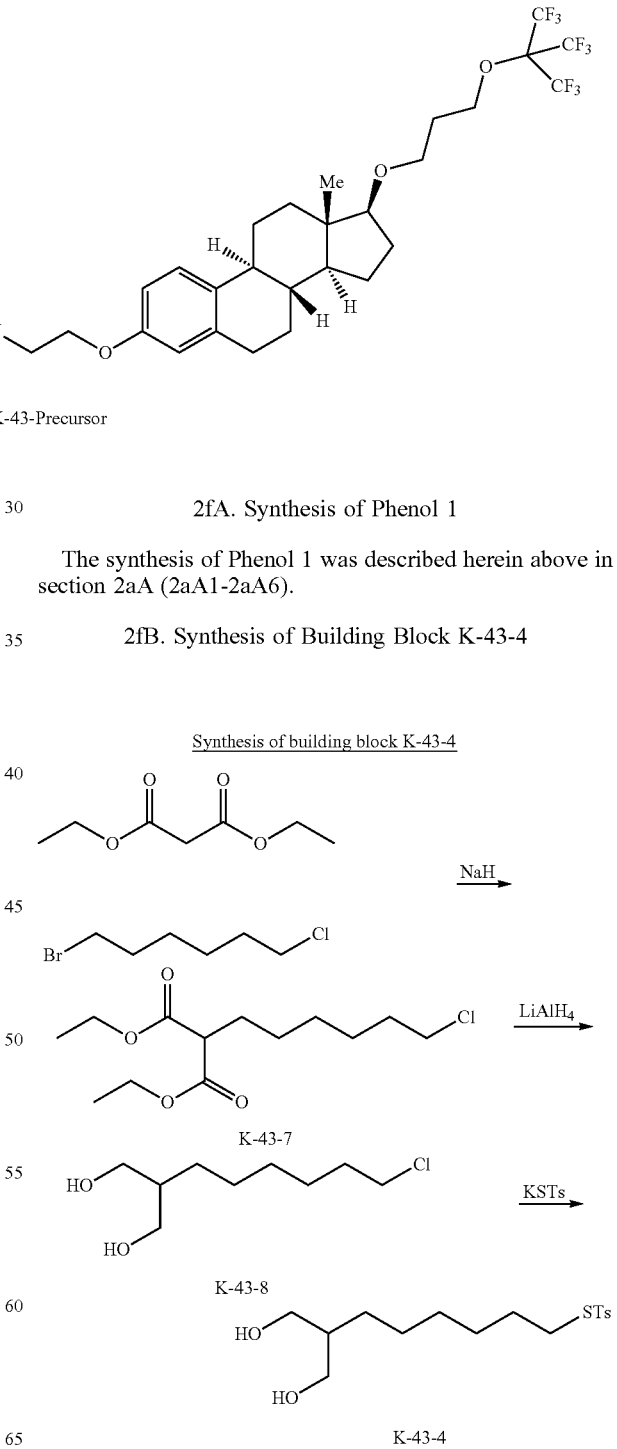

K-43-4

Diethylmalonate was reacted with sodium hydride and bromochlorohexane to provide alkylated product K-43-7. Treatment with lithium aluminum hydride reduced the diester to diol K-43-8. Compound K-43-8 was reacted with potassium thiotosylate to provide the desired building block K-43-4.

2fB1. Diethyl 2-(6-chlorohexyl)malonate (K-43-7)

To an ice-cooled suspension of NaH (2.6 g, 66 mmol, 1 eq.) in DMF (300 mL) was added diethyl malonate (20 mL, 131 mmol, 2 eq.) dropwise. The resulting mixture was stirred for 1 hour while warming up to room temperature. The mixture was cooled to 0° C. and 1,6-bromochlorohexane (9.8 mL, 66 mmol, 1 eq.) was added slowly. The resulting mixture was stirred at 0° C. for 1 hour and at room temperature for 3 hours. The reaction was quenched with HCl (2 M, 3 mL) and water (500 mL) was added. The mixture was extracted with EtOAc/heptane (1/1, v/v, 3×400 mL) and the combined organic layers were washed with brine, dried over $Na_2SO_4$ and concentrated. Further purification by column chromatography (5% EtOAc in heptane) provided compound K-43-7 (9.7 g, 34.8 mmol, 53%) as a clear oil.

2fB2. 2-(6-Chlorohexyl)propane-1,3-diol (K-43-8)

To an ice-cooled suspension of $LiAlH_4$ (2.6 g, 70 mmol, 2 eq.) in diethylether (200 mL) was added a solution of K-43-7 (9.7 g, 35 mmol, 1 eq.) in diethyl ether (50 mL) slowly while keeping the temperature of the mixture below 10° C. The resulting mixture was stirred at 0° C. for 2 hours, after which the reaction was quenched by the addition of water (5 mL), NaOH (30% aq., 2.5 mL), and water (12 mL), in that order. The resulting mixture was stirred for 1 hour at room temperature, after which the formed solids were filtered off. The filtrate was concentrated in vacuo to provide compound K-43-8 (6.1 g, 31 mmol, 90%) as a colorless oil.

2fB3. S-(8-Hydroxy-7-(hydroxymethyl)octyl) 4-methylbenzenesulfonothioate (K-43-4)

To a solution of K-43-8 (6.1 g, 31 mmol) in DMF (200 mL) were added potassium thiotosylate (11 g, 47 mmol, 1.5 eq.) and TBAI (1.2 g, 3.1 mmol). The resulting mixture was stirred at 80° C. overnight, after which the mixture was concentrated. Purification by column chromatography provided K-43-4 (5.6 g, 16 mmol, 52%) as a pinkish oil.

2fC. Completion of the Synthesis of Apo-Si-K-43-Precursor

Phenol 1 was coupled to Boc-protected methylaminoethanol using Mitsunobu-reaction conditions to compound K-13-1 in moderate yield (43%). Removal of the Boc-group using TFA gave K-13-2 as TFA-salt, which was used in the subsequent reductive amination with K-5 using sodium triacetoxyborohydride as reducing agent.

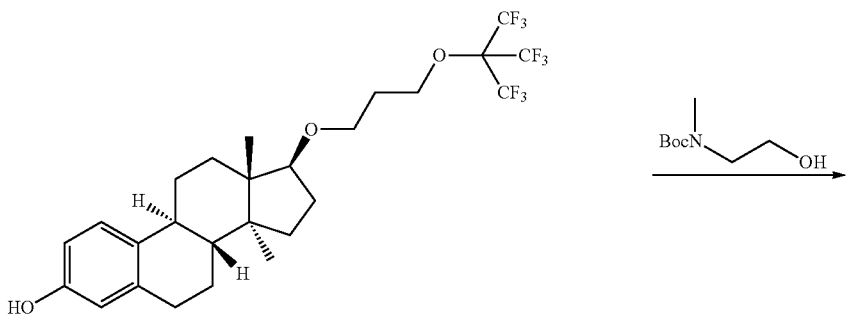

Phenol 1

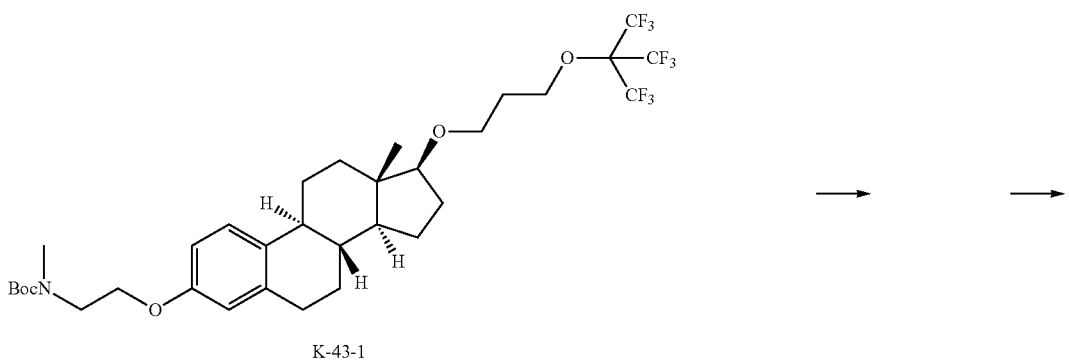

K-43-1

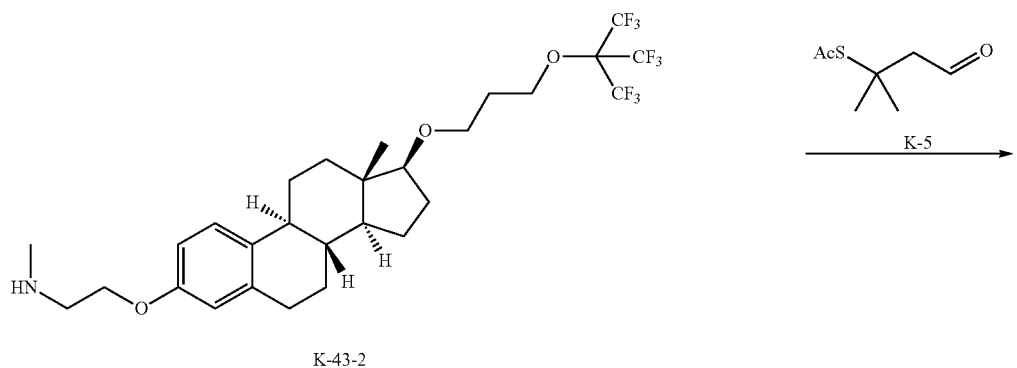
K-43-2
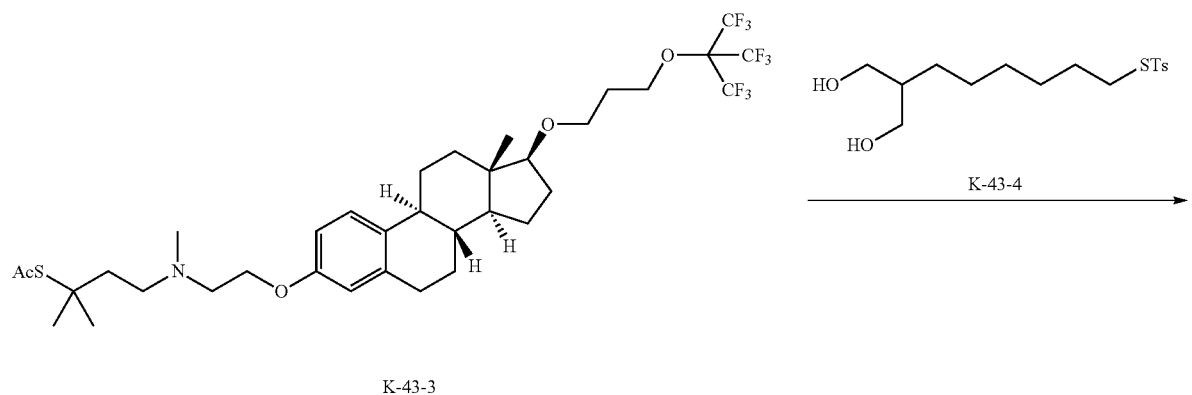
K-43-3
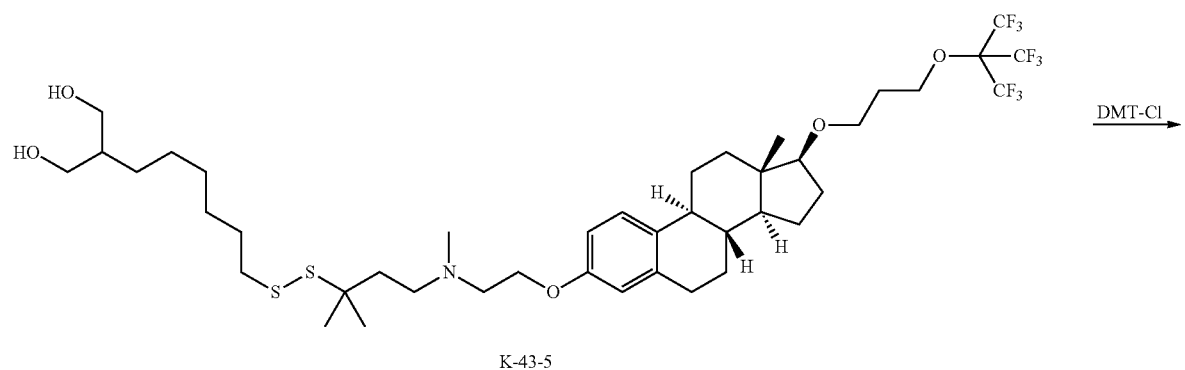
K-43-5
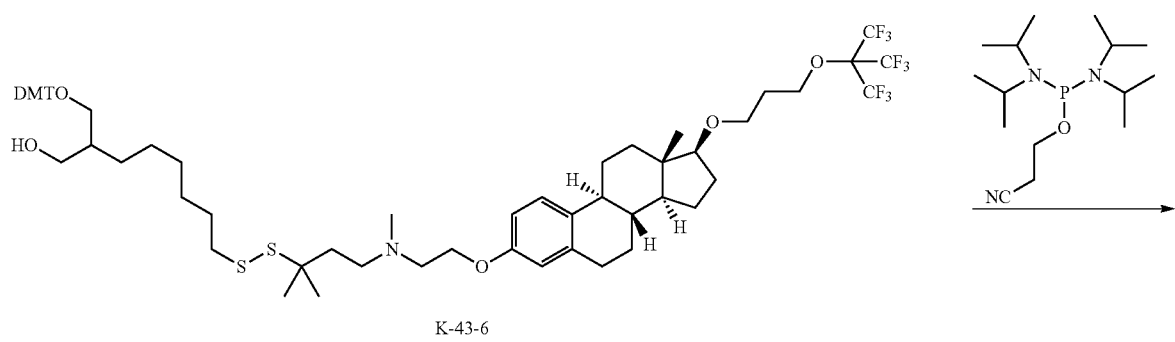
K-43-6

-continued

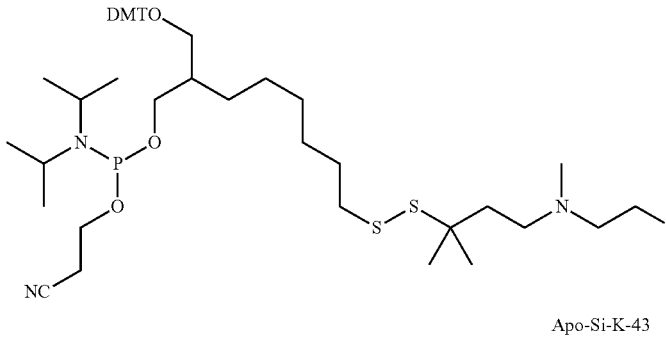

Apo-Si-K-43

Sodium methoxide in methanol was added to a solution of K-43-3 and K-43-4, which removed the acetate from K-43-3 allowing the resulting thiol to react with K-43-4 to form the desired Sulphur-bridge. Compound K-43-5 was reacted with DMT-Cl to provide mono-protected diol K-43-6. Reaction with the suitable phosphoramidite-agent afforded Apo-Si-K-43 Precursor (1.6 g). Purification of the acid-labile phosphoramidite product was done using flash chromatography with silica that had been pretreated with Et₃N.

2fC1. tert-Butyl (2-(((8R,9S,13S,14S,17S)-17-(3-((1,1,1,3,3,3-hexafluoro-2-(trifluoromethyl) propan-2-yl)oxy)propoxy)-13-methyl-7,8,9,11,12,13,14,15,16,17-decahydro-6H-cyclopenta[a]phenanthren-3-yl)oxy)ethyl)(methyl)carbamate (K-43-1)

To a solution of phenol 1 (23.4 g, 42.7 mmol) in THF (600 mL) were added triphenylphosphine (26 g, 100 mmol), tert-butyl (2-hydroxyethyl)(methyl)carbamate (9.8 g, 61 mmol) and dropwise DIAD (12 mL, 61 mmol). The mixture was stirred for 16 at room temperature. The yellowish solution was partially concentrated, heptane was added and the solution was further concentrated to remove all traces of THF. The resulting precipitate was filtered off and the filtrate was concentrated. Further purification using flash chromatography (gradient 5% to 7% EtOAc in heptane) provided compound K-43-1 (13.05 g, 18.5 mmol) in 43% yield as yellowish oil.

2fC2. SS-(4-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)-2-methylbutan-2-yl) ethanethioate (K-43-3)

A solution of compound K-43-1 (13.05 g, 18.5 mmol) was dissolved in dichloromethane (65 mL) and trifluoroacetic acid (40 mL) was added. After the mixture was stirred for 2 h bubbling ceased. The mixture was concentrated and used as such. The residue was dissolved in 1,2-dichloroethane (400 mL) and acetic acid (5 mL, 75 mmol), aldehyde K-5 (6 g, 37 mmol) were added and stirring continued for 5 min. Then, sodium triacetoxyborohydride (16 g, 75 mmol) was added and the mixture was stirred for 16 h at room temperature. The mixture was washed with 1 M NaOH and brine, dried over Na₂SO₄ and concentrated. Further purification provided compound K-43-3 (3.0 g, 4 mmol) as a clear yellowish oil in 22% yield.

2fC3. 2-(6-((4-((2-(((8R,9S,13S,14S,17S)-17-(3-((1,1,1,3,3,3-Hexafluoro-2-(trifluoromethyl) propan-2-yl)oxy)propoxy)-13-methyl-7,8,9,11,12,13,14,15,16,17-decahydro-6H-cyclopenta[a]phenanthren-3-yl) oxy)ethyl)(methyl)amino)-2-methylbutan-2-yl) disulfaneyl)hexyl)propane-1,3-diol (K-43-5)

A solution of compound K-43-3 (2.2 g, 2.9 mmol) and tosylate K-43-4 (1.5 g, 4.4 mmol) in methanol (100 mL) was treated with 5.4 M NaOMe in MeOH (1.6 mL, 8.7 mmol). The mixture was stirred for 2 h at room temperature. The mixture was washed with NaHCO₃ and brine, dried over sodium sulfate, and concentrated. Further purification using flash chromatography (20-30% acetone+1% Et₃N in heptanes) provided compound K-43-5 (1.3 g, 1.5 mmol) as colorless oil in 50% yield.

2fC4. 2-((bis(4-Methoxyphenyl)(phenyl)methoxy) methyl)-8-((4-((2-(((8R,9S,13S,14S,17S)-17-(3-((1,1,1,3,3,3-hexafluoro-2-(trifluoromethyl)propan-2-yl) oxy)propoxy)-13-methyl-7,8,9,11,12,13,14,15,16,17-decahydro-6H-cyclopenta[a]phenanthren-3-yl)oxy) ethyl)(methyl)amino)-2-methylbutan-2-yl) disulfaneyl)octan-1-ol (K-43-6)

To a solution of K-43-5 (1.3 g, 1.5 mmol, 1 eq.) were added Et₃N (0.2 mL, 1.5 mmol, 1 eq.) and DMAP (17 mg, 0.15 mmol, 0.1 eq.). To the resulting mixture DMT-Cl (0.49 g, 1.5 mmol, 1 eq.) was added. The resulting orange mixture was stirred overnight at room temperature, after which it had turned yellow. Methanol (30 mL) was added and the mixture was stirred for 1 hour, after which it was concentrated. Purification by column chromatography (20% acetone and 1% Et₃N in heptane) provided compound K-43-6 (1.5 g, 1.3 mmol, 86%) as a yellow oil.

2fC5. 2-((bis(4-Methoxyphenyl)(phenyl)methoxy) methyl)-8-((4-((2-(((8R,9S,13S,14S,17S)-17-(3-((1,1,1,3,3,3-hexafluoro-2-(trifluoromethyl)propan-2-yl) oxy)propoxy)-13-methyl-7,8,9,11,12,13,14,15,16,17-decahydro-6H-cyclopenta[a]phenanthren-3-yl)oxy) ethyl)(methyl)amino)-2-methylbutan-2-yl) disulfaneyl)octyl (2-cyanoethyl) diisopropylphosphoramidite (Apo-Si-K-43-Precursor)

To a solution of K-43-6 (1.5 g, 1.25 mmol) in dichloromethane (25 mL) was added 2-Cyanoethyl N,N,N', N'-tetraisopropylphosphorodiamidite (0.51 mL, 1.6 mmol, 1.3 eq.) and a 0.5 M solution of N-methylmorpholine and 0.25 M trifluoroacetic acid in dichloromethane (3.3 mL, 1 equivalent of N-methylmorpholine to the phosphoramidite-agent). The yellowish solution was stirred for 2 h at room temperature. TLC (20% acetone in heptane and 1% Et$_3$N) showed incomplete conversion, so an additional 0.5 eq. of 2-Cyanoethyl N,N,N',N'-tetraisopropylphosphorodiamidite was added. The resulting mixture was stirred for 1 hour at room temperature. Then, the reaction mixture was quenched with aqueous saturated sodium bicarbonate. The organic layer was separated, dried over sodium sulfate and concentrated. Further purification using flash chromatography (10% acetone and 1% Et$_3$N in heptane) provided compound Apo-Si-K-43-Precursor (1.6 g, 1.1 mmol) as a slightly yellow oil in 91% yield.

Example 2g: Synthesis of Apo-Si-K-63-Precursor; Formula (PP-3)

Formula (PP-3)

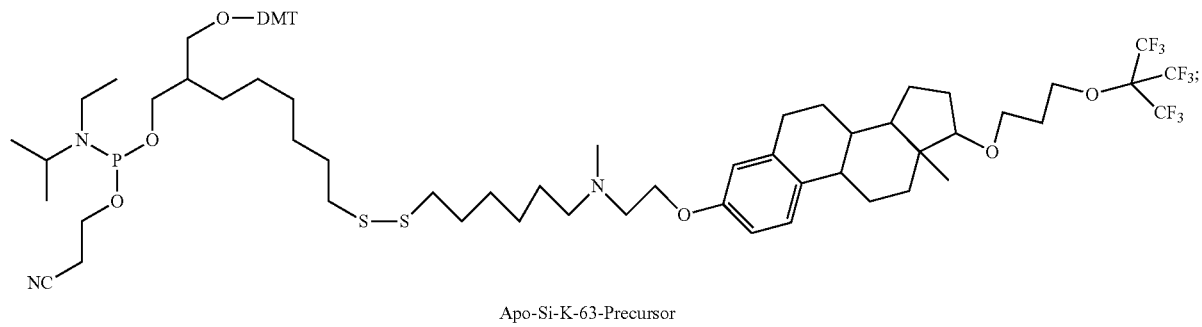

Apo-Si-K-63-Precursor

Structure of Apo-Si-K-63-Precursor is very similar to that of Apo-Si-K-43-Precursor, with the only difference is a fragment of 6 carbon atom, linear hydrocarbon. Synthesis is therefore very similar to the synthesis of Apo-Si-K-43-Precursor described in Example 2f.

2gA. Synthesis of Phenol 1

The synthesis of Phenol 1 was described herein above in section 2aA (2aA1-2aA6).

2gB. Synthesis of Building Block K-43-4

The synthesis of building block K-43-4 was described herein above in section 2fB (2fB1-2fB3).

2gC. Linear Hydrocarbon Fragment 1,6-dibromohexane is commercially-available.

2gD. Completion of the Synthesis of Apo-Si-K-63-Precursor; Formula (PP-3)

Completion of synthesis was performed according to the following synthetic scheme:

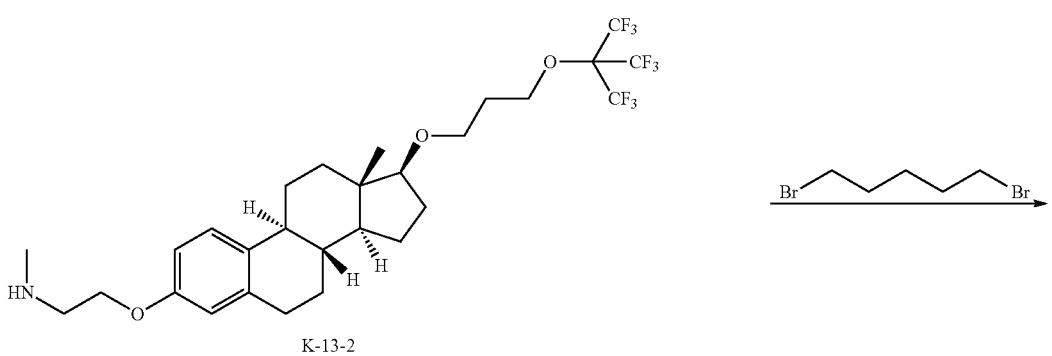

K-13-2

-continued
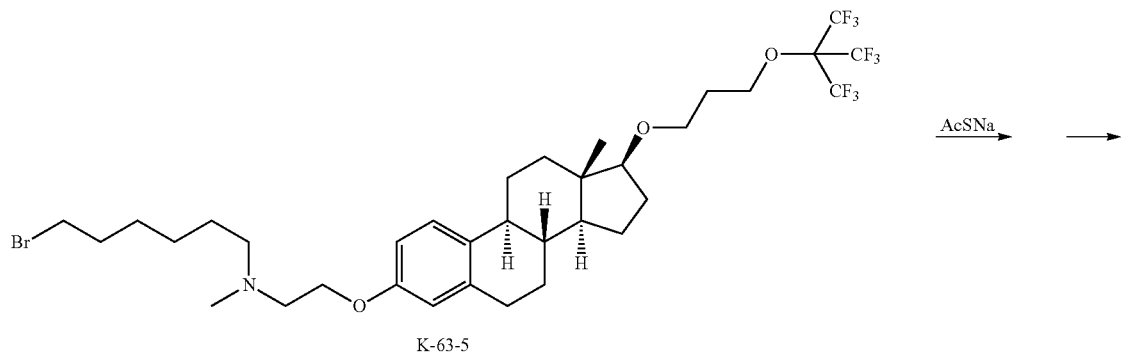
K-63-5
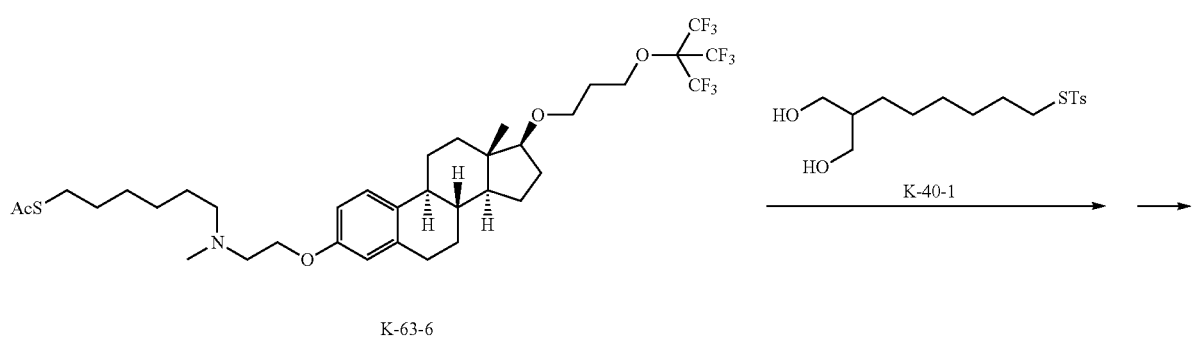
K-63-6
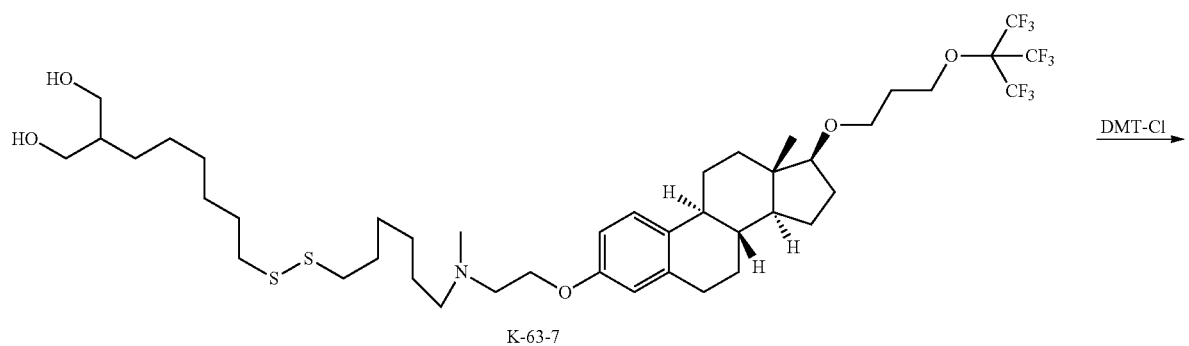
K-63-7
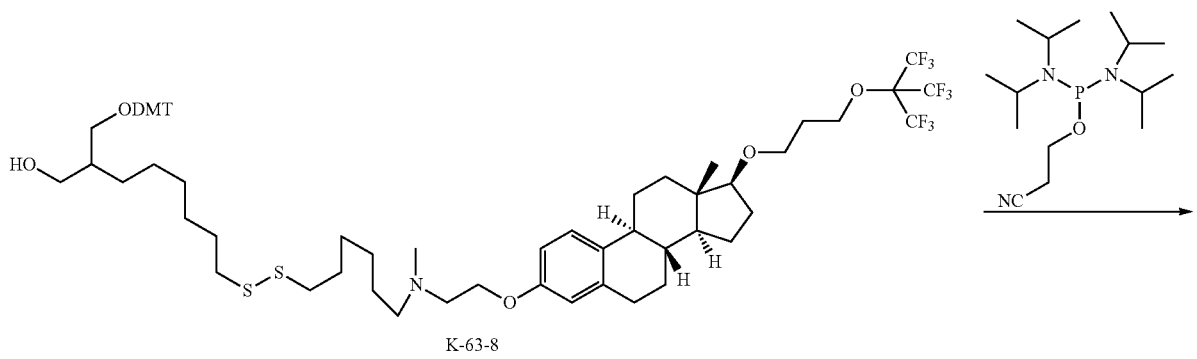
K-63-8

-continued

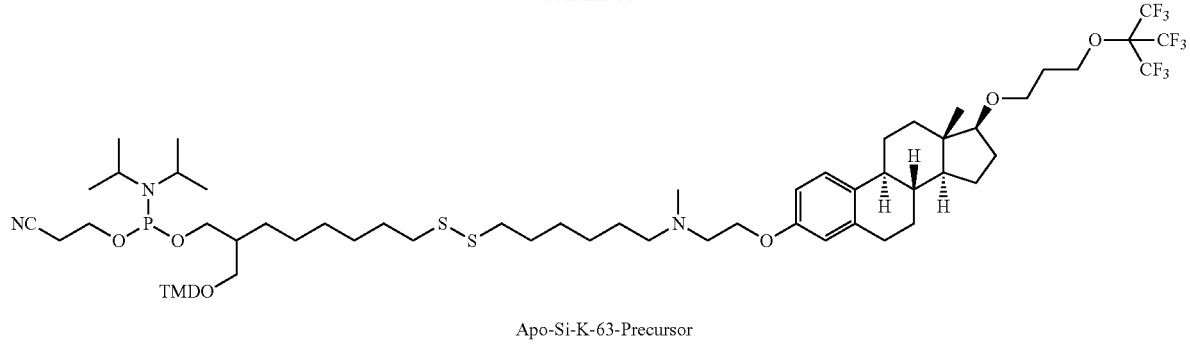

Apo-Si-K-63-Precursor

Example 3: Mode of Linkage of an E Moiety of the Invention, at an Internal Position within an Oligonucleotide Chain Exemplified is a Precursor for an E moiety, having the structure as set forth in Formula (Va'P). Initially, the E moiety is at its protected form, with 4,4'-Dimethoxytrityl (DMT) and phosphoramidie groups at 3'- and 5'-positions of deoxyribose moiety, respectively:

Formula (Va'P)

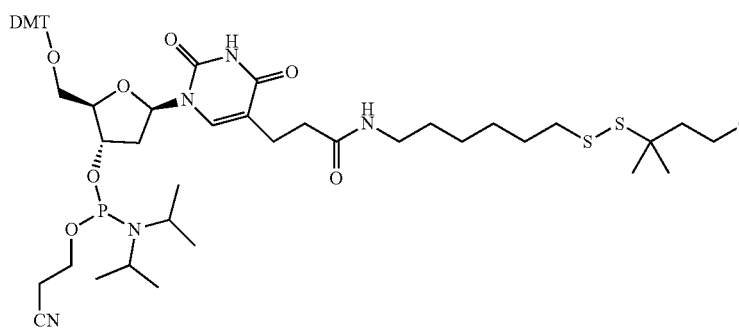

Integration within the oligonucleotide chain is performed similar to incorporation of any nucleoside building block in customary oligonucleotide synthesis, leading to the resultant configuration, as described in FIGS. 2a and 2b.

Example 4: Red-Ox-Mediated Detachment and Removal of the E Moiety within the Cytoplasm, to Release the Cargo Drug. (e.g, siRNA)

While at least one E, E' or E" moiety, as described above, is required for the trans-membrane passage of siRNA or dsiRNA Conjugates, it is desirable to remove these moieties once the Conjugate reaches the cytoplasm, and excrete them from the body. In the case that the cargo drug is siRNA, or dsiRNA, this cleavage is beneficial for avoiding steric issues in the interaction of the siRNA or dsiRNA with the gene silencing protein complexes (Dicer and RISC). In addition, such detachment of the cargo drug from the E moieties would minimize burden of Conjugates on cellular phospholipid membranes, which is advantageous from the safety perspective. For this purpose, the E moieties of the Invention comprise a disulfide moiety. Under oxidative conditions, such as those that prevail in the extracellular environment, the disulfide is stable, and therefore enabling the Conjugate, upon its systemic administration in vivo, to distribute in the body, and cross cellular phospholipid membranes into cells. By contrast, the cytoplasm is a highly reductive environment, mainly due to its high concentrations of reduced glutathione, being continuously generated within the cytoplasm of any living cell, reaching a concentration gradient of about four-orders of magnitude between the cytoplasm and the extracellular space. Due to these remarkable reductive conditions within the cytoplasm, disulfide groups of E moieties undergo robust reduction in the cytoplasmatic milieu. Consequently, there is release of the Cargo drug (e.g., dsiRNA), to exert its pharmacological actions at its target sites in the cytoplasm (e.g., at the Dicer or RISC protein complexes for gene silencing). Concurrently, the E moieties of the Invention are excreted from the body via the bile and/or the urine, similar to other sterol-based molecules (e.g., estrogens), either directly or following metabolism (e.g., cytochrome-P-450-mediated hydroxylation in the liver). This redox-mediated cleavage is exemplified in FIGS. 2a and 2b, FIGS. 3a, 3b, 3c and 3d, and FIGS. 4a, 4b, 4c and 4d. The Figures demonstrate RNA duplexes, harboring E moieties according to Formula (Va'), Formula (Vc'), or Formula (Vc"). While the Conjugate is intact in oxidative conditions, as those present in the extracellular space (FIG. 2a), entry into the cytoplasm, due to its characteristic reductive conditions, leads to cleavage of the disulfide bond (FIGS. 3a, 3b, 3c, 3d, 4a, 4b, 4c and 4d): the cargo drug is released to exert its pharmacological activity at its cytoplasmatic target sites (e.g., RISC), while the E moiety is excreted form the body, similar to other sterol-based compounds. The steric hindrance, provided, by the gem-dimethyl moiety at the sulfhydryl group, further acts to confer stability in the blood at the oxidized disulfide form, and to stabilize the free sulfhydryl form after cleavage.

Example 5: An Example of the Structure of a Conjugate of the Invention

Exemplified is a Conjugate according to Formula (Cn-14). The Conjugate comprises linkage of D (dsiRNA) to E, E' and E" moieties according to Formula (Vc'''), located at the 5'-ends of the RNA Duplex, and at an internal position along the oligonucleotide chain:

Formula (Cn-14)

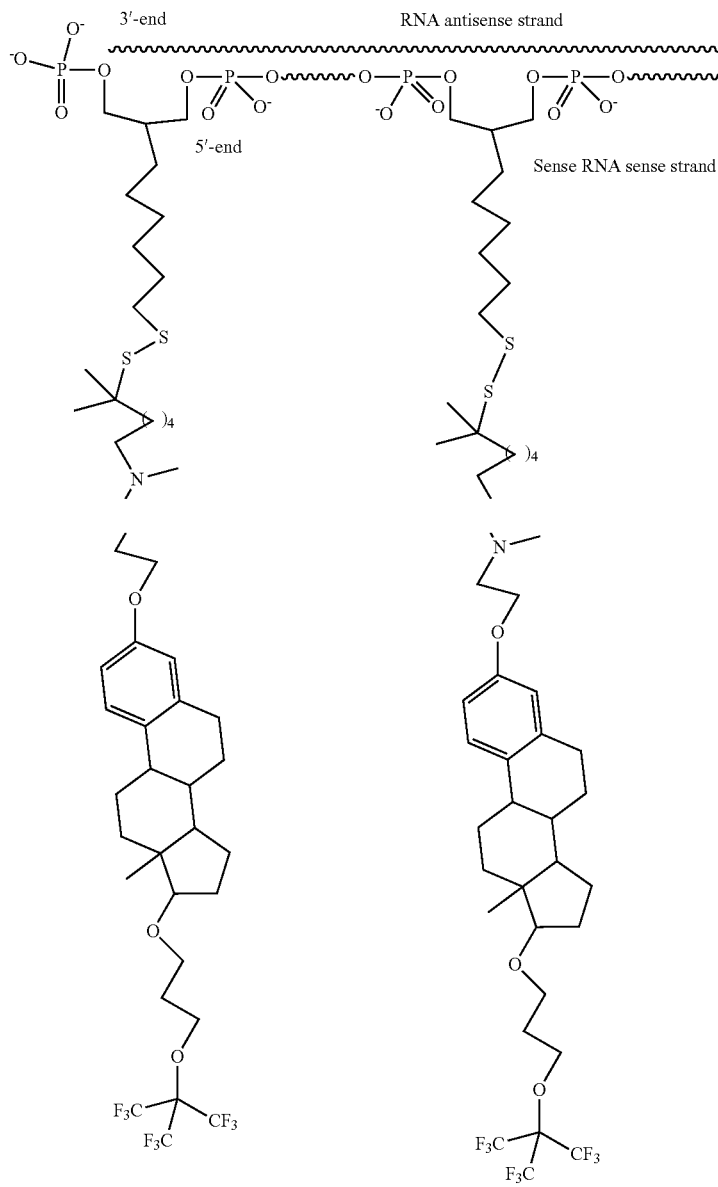
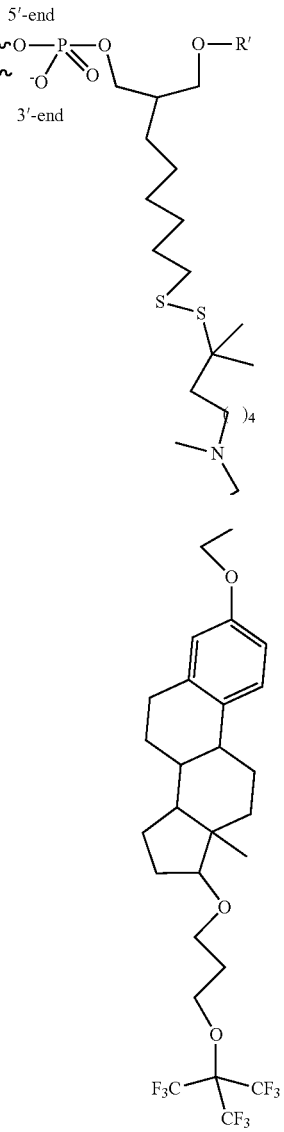

In this example, R is a phosphate group, while R' is hydrogen. As shown, a phosphate group at the 5'-end of the passenger (sense) strand of the Dicer's substrate RNA Duplex (dsiRNA), may interact with a positively-charged pocket in the Dicer's RNA binding site, thus facilitating its activity, and the consequent overall gene silencing, mediated by this enzyme (see Example 7).

Example 6: Performance of the Conjugates of the Invention in Serum-Free (S−) Conditions, and in the Presence of Plasma Proteins [(S+) Conditions]

Objectives:

This Example aims at demonstrating that Conjugates, comprising key chemical moiety according to Formula (II), linked to a macromolecule drug such as OD, can perform delivery across phospholipid membranes into cells, and respectively exert gene silencing, in both (S−) conditions and in (S+) conditions. By contrast, similar compounds, which structure is not according to Formula (II), should be either totally inactive in trans-membrane delivery, or should induce gene silencing only in serum-free conditions.

Methods:

E Moieties:

E, E' or E" moieties of the Invention: Apo-Si-K-18, according to Formula (Vb'), and Apo-Si-K-13, according to Formula (Vb"), comply with all structural features as set forth in Formula (II). Their structures are as follows:

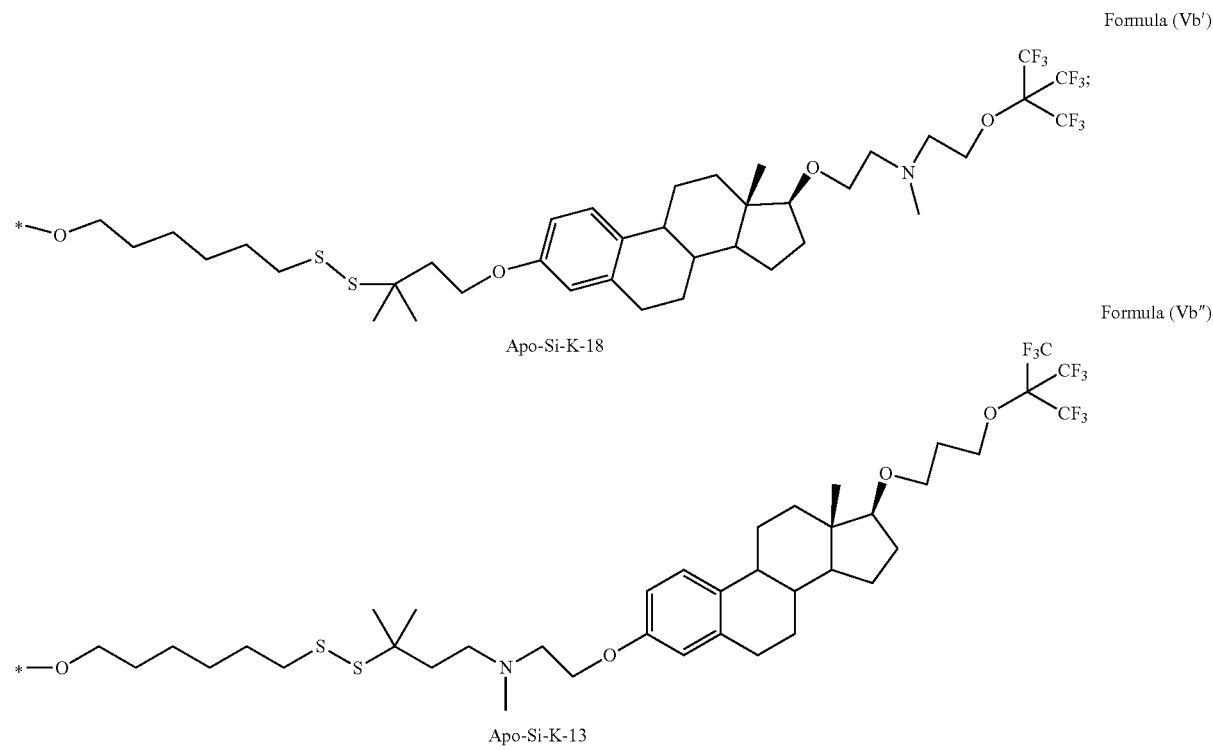

Formula (Vb')

Apo-Si-K-18

Formula (Vb")

Apo-Si-K-13 wherein * is a linkage point of each E moiety, to the 5'-end of an oligonucleotide strand of a dsiRNA Duplex. Apo-Si-K-18 and Apo-Si-K-13 were synthesized according to the previous Examples.

In addition, the following structurally-related moieties (Apo-Si-K-19, Apo-Si-W, and Apo-Si-G) served as Controls, since albeit their sharing substantial structural similarity to Apo-Si-K-18 and Apo-Si-K-13, these moieties do not fully comply with all structural features of Formula (II), as follows: (i). In Apo-Si-K-19, both U and Q are not null, while Formula (II) implies that one of U or Q should be null; (ii). Apo-Si-W does not comprise a disulfide moiety, which is an integral part of Formula (II); (iii). In Apo-Si-G, both U and Q are null, while Formula (II) implies that one of Q or U should be other than null.

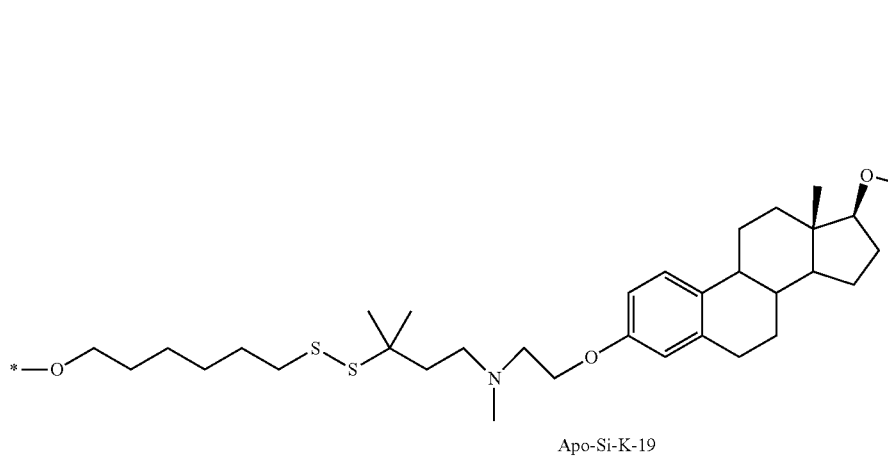

Apo-Si-K-19

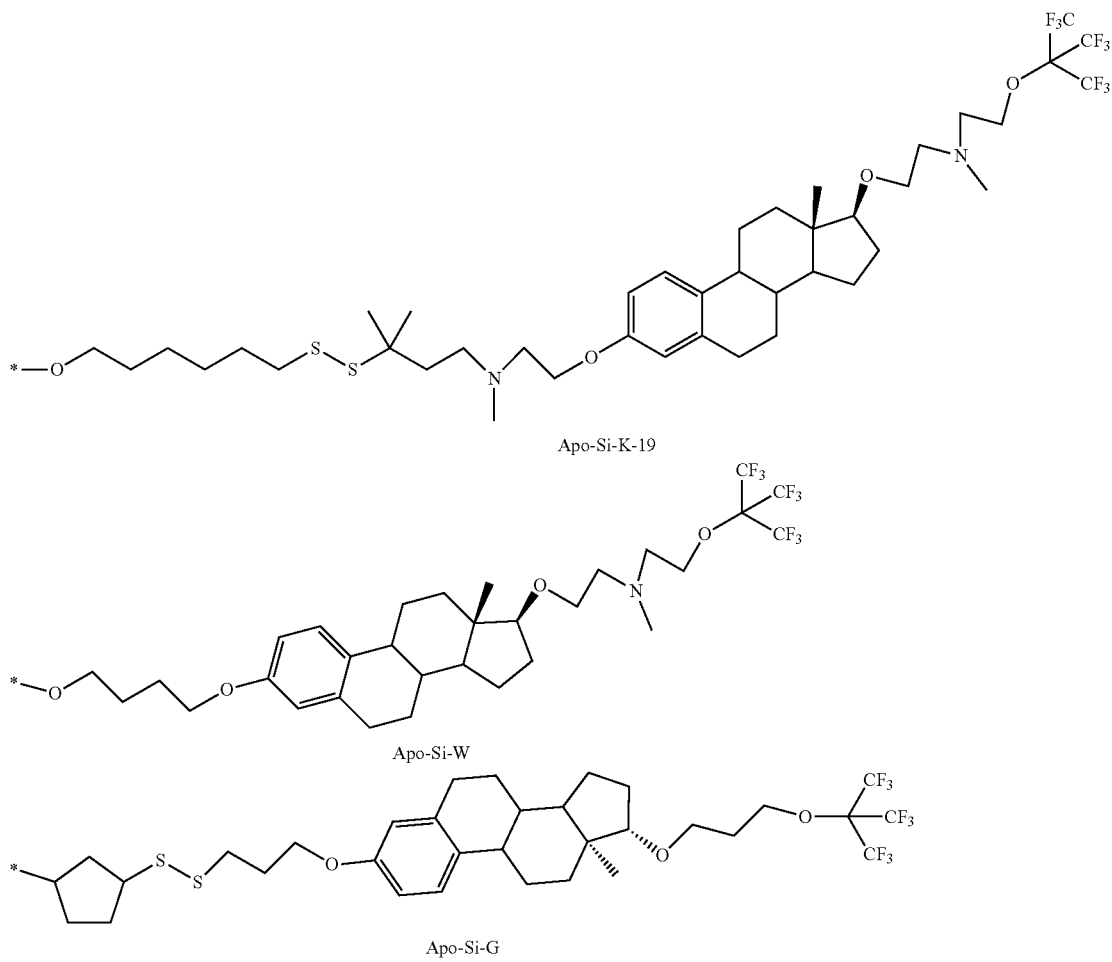

Apo-Si-W

Apo-Si-G

Conjugates:

RNA Duplexes, each composed of one 25-nucleotide long strand and one 27-nucleotide long strand were designed as Dicer's Substrates (dsiRNA), aimed at silencing expression of the gene encoding for EGFP (Enhanced Green Fluorescent Protein). Oligonucleotide sequences were as follows:

Antisense Strand Sequence:

5'-E-CGGUGGUGCAGAUGAACUUCAGGGUCA-3' (SEQ ID NO. 1);

Sense RNA Sequence:

5'-E-ACCCUGAAGUUCAUCUGCACCACCG-3' (SEQ ID NO. 2); wherein E means an E, E' or E" of the Invention, or a respective Control; r=ribose and m (for example mG)=methylation at the 2'-hydroxyl of the ribose moiety. Each Duplex was attached to two identical E moieties, being either E moieties of the Invention (Apo-Si-K-18 or Apo-Si-K-13); or the respective control moieties (Apo-Si-K-19, Apo-Si-W, or Apo-Si-G).

Taken together, 5 Conjugates were therefore synthesized, each comprising dsiRNA for silencing the EGFP gene, and each is attached to two E moieties. Two were Conjugates of the Invention, comprising either Apo-Si-K-13 or Apo-Si-K-18 moieties, while three Conjugates were Control Conjugates, wherein the dsiRNA duplex was attached to either Apo-Si-G, Apo-Si-K-19, or Apo-Si-W moieties. Each Conjugate was named as according to its E moiety.

Cell Culture:

HeLa-EGFP cell line was obtained from Cell Biolabs. Cells were grown in Dulbecco's modified Eagle's medium (Gibco) supplemented with 10% FBS (Gibco), 100 U/ml penicillin, 100 mg/ml streptomycin (Biological Industries, Israel), and blasticidin 10 μg/ml. Cells were maintained in a 37° C. incubator, with 5% $CO_2$ humidified air.

One day before transfection, cells were plated (40,000 cells/well) on 24-well black-plate with glass bottom. The following day, cells were incubated with either the Apo-Si-K-18 Conjugate, or with the Apo-Si-K-13 Conjugate (Conjugates of the Invention), or with the respective Controls, in the presence of 10% Fetal bovine serum [FBS, serum (+) conditions]. For incubation in serum-free conditions, medium was aspirated, cells were washed with Hank's Balanced Salt Solution (HBSS), and medium was then replaced with serum-free Opti-MEM medium (Thermo Fisher Scientific). After 24 hours, the medium was replaced by 10% FCS medium. Incubation period for all cells was 72 hours. Various concentrations of the Conjugates were evaluated, at the dose range of 40-300 nM.

Down-Regulation of Gene Expression:

Down-regulation of gene expression was measured 72 hours post transfection. For this purpose, medium was aspirated, and cells were washed with HBSS. Protein expression was measured via measurement of the intensity of the EGFP fluorescence, which was quantified by the infinite M200-Pro Multimode Reader (Tecan); excitation wavelength 488 nm, emission wavelength 535 nm. Experiments were performed in triplicates, and EGFP fluorescence results were compared to the fluorescence intensity of untreated cells, (i.e., not treated by the Conjugates). Results are presented as the percentage of the fluorescence intensity, as compared to the Controls. Significance of inter-group differences was evaluated by two-tail t-test, with $p<0.05$ defined as significant.

Results:

Conjugates of the Invention: Apo-Si-K-13 and Apo-Si-K-18:

Serum-Free Conditions:

Both Apo-Si-K-13 and Apo-Si-K-18 Conjugates manifested robust uptake by the cells, and respective effective gene silencing. Apo-Si-K-13 Conjugate manifested 75.5±2.0% silencing at 40 nM of the Conjugate (mean±SD). Silencing was increased to 86.6±0.5% at 150 nM of the Conjugate. Apo-Si-K-18 Conjugate manifested a similar silencing efficacy of 68.4±0.5% at 40 nM of the Conjugate (mean±SD), which was increased to 84.7±0.2% silencing at 150 nM of the Conjugate; [$p<0.001$, t-test as compared to Control, untreated cells].

In the Presence of Serum:

In the presence of serum, both Apo-Si-K-13 and Apo-Si-K-18 Conjugates provided significant gene silencing. Apo-Si-K-13 Conjugate provided 15.5±3.2% gene silencing at 300 nM, increasing to 44±1.5% at 600 nM, while Apo-Si-K-18 Conjugate provided 65.4±0.6% gene silencing at 300 nM (mean±SD); ($p<0.001$ t-test as compared to Control, untreated cells).

Control Conjugates: Apo-Si-G, Apo-Si-K-19, Apo-Si-W:

Serum-Free Conditions:

In serum-free conditions, Apo-Si-G Conjugate manifested robust uptake by the cells, and respective effective gene silencing. Apo-Si-G Conjugate manifested 40.7±2.2% silencing at 40 nM (mean±SD), which was increased to 70.9±1.1% at 150 nM. Apo-Si-K-19 manifested gene silencing of 37.7±0.8% at 150 nM (mean±SD); ($p<0.001$ as compared to Control, untreated cells).

In the Presence of Serum:

None of the Control Conjugates Apo-Si-G, Apo-Si-K-19, and Apo-Si-W, albeit their structural similarities to the Conjugates of the Invention, manifested any gene silencing in the presence of serum. Apo-Si-W Conjugate did not manifest any gene silencing, even in the serum-free conditions.

Summary of the Results:

Both Apo-Si-K-13 and Apo-Si-K-18 Conjugates manifested robust uptake and gene silencing when incubated with cells in vitro. Gene silencing activity exerted by both Conjugates was evident in either presence or absence of plasma proteins in the culture medium, i.e., in both (S+) conditions and in (S−) conditions, respectively. This performance of the Conjugates of the Invention was in clear contrast to the performance of the Control Conjugates. Apo-Si-G and Apo-Si-K-19 Conjugates, but not Apo-Si-W Conjugate were active in gene silencing in serum-free (S−) conditions; None of the Control Conjugates was active in gene silencing in the presence of plasma proteins [(S+) conditions].

Discussion:

As shown in this Example, the key chemical moiety of the Invention, having the structure as set forth in Formula (II), indeed entails robust performance of the related Conjugates, in delivery across cell membranes into cells, and in inducing biological effect: gene silencing. This performance was observed in both (S−) conditions and in (S+) conditions. Importantly, the Conjugates of the Invention and the Panel of Control Conjugates, provide important structure/function perspectives on the key chemical moiety of the Invention according to Formula (II): E moieties of all Conjugates, both Conjugates of the Invention, and the Control Conjugates, comprise a sterol backbone and a nona-fluorotert-butanol residue. Evidently, however, this is not sufficient to confer activity, even in the serum-free conditions (reflected, for example, in the results of Conjugate Apo-Si-W, which showed no activity). Adding a disulfide group per E moiety entails activity in serum-free conditions (for example, the performance of the Conjugates of the Invention Apo-Si-K-13 and Apo-Si-K-18, as well as the performance of the Control Conjugate Apo-Si-G in the serum-free conditions). However, this was not sufficient to enable performance in the presence of plasma proteins.

By contrast, adding for each E moiety one U or Q moiety that is not null, did confer activity of the Conjugate in the presence of plasma proteins, shown by the effective gene silencing observed with Apo-Si-K-18 or Apo-Si-K-13 Conjugates. An unexpected observation was provided by Apo-Si-K-19, showing that the case of both U and Q are not null per E moiety is deleterious to the biological performance of the respective Conjugate.

Taken together, these data support the notion, that Formula (II) indeed represents a unique, novel and unpredictable balance between various determinants, that cumulatively and interactively entail desired performance of the respective Conjugates in trans-membrane delivery and consequent gene silencing.

Example 7: Positive Impact of 5'-Phosphate on the Performance of a Dicer Substrate of the Invention Objective:

Dicer substrates, having the structures as set forth in any of Formulae Cn-1, Cn-2, Cn-3, Cn-4, Cn-6, Cn-7, Cn-8, or Cn-9 may also comprise a phosphate, sulfate or a carboxyl group at the 5'-end of the Passenger (Sense) RNA strand, aimed to interact with a binding pocket, lined with positively-charged amino acid residues, that resides at the RNA anchoring site on the Dicer Enzyme. The experiment was performed in order to demonstrate, the beneficial impact on performance of a Dicer substrates of the Invention, exerted by such negatively-charged moiety.

Methods:

Two Dicer substrates were used in the experiment, each having the specific sequence to silence the expression of the EGFP gene, as described in Example 6. One of the dsiRNA had, in addition, a phosphate group attached to the 5'-end of the Passenger (Sense) strand [designated (P+) dsiRNA], while the other dsiRNA, the 5'-end of the Passenger (Sense) strand was the 5'-hydroxyl of the terminal nucleotide [designated (P−) dsiRNA]. HeLa-GFP cell lines, obtained from Cell Biolabs, were grown in Dulbecco's modified Eagle's medium (Gibco), supplemented with 10% FBS (Gibco), 100 U/ml penicillin, 100 mg/ml streptomycin (Biological Industries, Israel) and blasticidin 10 μg/ml. Cells were maintained in a 37° C. incubator with 5% $CO_2$ humidified air. One day before transfection, cells (40,000 cells/well) were plated on 24-well black-glass bottom plate, with complete medium, without the supplement of antibiotics. The following day, cells were transfected with RNAiMAX (Lipofectamine, Invitrogen), according to manufacture instructions, in sub-optimal conditions using 0.1 nM dsiRNA and 1 ul transfection reagent. Cells were then incubated with transfection mix for 24 hours, followed by addition of complete medium without antibiotics (1 ml/well). Protein down-regulation was measured at 72 hours post transfection: for this purpose, medium was aspirated, and the cells were washed with HBSS. EGFP fluorescence intensity was quantified by the infinite M200-Pro Multimode Reader (Tecan), at excitation wavelength of 488 nm, emission wavelength 535 nm.

Results:

At the low, suboptimal doses employed (0.1 nM dsiRNA), the (P−) dsiRNA down-regulated EGFP levels by 20±2%, (mean±SD). By contrast, (P+) dsiRNA silenced the gene expression by 67±2% (p<0.0001; t-test).

Conclusion:

Dicer substrate that comprises a phosphate group at the 5'-end of the passenger (sense) strand, manifests advantageous performance in gene silencing, as compared to dsiRNA devoid of this group.

Example 8: The Mechanism of Action of a Conjugate of the Invention, being a Dicer Substrate FIGS. 3a, 3b, 3c and 3d and FIGS. 4a, 4b, 4c and 4d exemplify the Mechanism of Action (MOA) of a Conjugate of the Invention. Exemplified are Conjugates according to Formulae (Cn-3) and (Cn-9), respectively, wherein the RNA Duplex is a Dicer substrate of 25/27-nucleotide long, with a phosphate group linked to the 5'-end of the passenger strand: Upon reaching the cytoplasm, due to the markedly reductive ambient conditions, cleavage and removal of the E, E' and E" moieties take place, leaving a short stump per each E moiety, comprising a thiol group, linked to a 6-carbon hydrocarbon chain (FIGS. 3a and 4a). The RNA Duplex then interacts with the Dicer endonuclease. This interaction is initiated by binding of the 3'-end of the Guide (Antisense) strand Duplex, which consists of a 2-nucleotide overhang, to a hydrophobic pocket of the protein, and interaction of the phosphate group of the Passenger (Sense) strand with a respective positively charged pocket on the protein surface. This anchoring positions the RNA on the protein, enabling it to perform an accurate double-strand break of the RNA Duplex, leaving a 21/21-nucleotide double-helix, linked to one remaining E stump [FIGS. 3b and 4b]. FIGS. 3c and 4c demonstrate the removal of the sense strand by the enzyme helicase (a cytoplasmatic enzyme, capable of separating RNA strands). This action removes the second E residue stump, thus releasing the intact antisense strand, to enter the RNA-induced silencing complex (RISC), in order to induce the desired gene silencing [FIGS. 3d and 4d].

Example 9: Both Albumin-Bound and Albumin-Free Fractions are Observed Upon Incubation of the Compounds of the Invention with the Plasma Proteins Objective:

The experiment was conducted in order to evaluate whether Compounds of the Invention, when incubated with albumin, manifest both albumin-bound and albumin-free fractions, thus supporting a potential mechanism of action, for their observed activity in serum (+) conditions.

Rationale:

A major advantage of the Conjugates of the Invention is their ability to manifest biological activity in both absence and presence of plasma proteins. Binding of a drug to plasma proteins can be advantageous in various aspects, such as prolongation of the drug's half-life in the circulation and protection from degradation. However, binding affinity to albumin that is too high, can untowardly limit the availability of the drug to interact with its target cells. It is therefore desirable for the Conjugates of the Invention, to have, upon their interaction with albumin, both a fraction that is bound to the plasma protein (albumin-bound fraction), and a fraction that is free to diffuse in extracellular fluids, to reach and interact with the target cells (albumin-fee fraction). The present Example was performed in order to demonstrate these features of the Conjugates of the Invention.

Methods:

Gel electrophoresis was used to examine to what extent are the Conjugates of Invention bound to bovine serum Albumin (BSA). For free fraction detection, RNA samples were diluted in Tris buffer, pH=8 and BSA (10%) was added to a final concentration of 2 mg/ml (lanes B). Control samples were diluted in water (lanes A).

For Each Group (A or B), Lanes were Designated According to the Following Table:

| | Lane number | | | |
|---|---|---|---|---|
| | 1 | 2 | 3 | 4 |
| Conjugate | 25/27 nucleotide "naked RNA" | Apo-Si-G Conjugate | Apo-Si-K-13 Conjugate | Apo-Si-18 Conjugate |

All samples were incubated overnight at 25° C. RNA Samples of all lanes were then loaded (19 pmol per lane) on 12% native poly-acryl-amide gel, and induced to migrate in an electric field 5V/cm for 1 hour (Bio-Rad mini-protean instrument, Israel).

Results:

As shown in FIG. 5, incubation of the Conjugates of the Invention, comprising E moieties Apo-Si-K-13 or Apo-Si-K-18, resulted in generation of two fractions: one that was albumin-bound (Arrow #1), and one that was albumin-free (Arrow #2). By contrast, the Control Conjugate that comprised E moieties of Apo-Si-G had only one fraction: only the albumin-bound fraction was observed.

Conclusions:

These findings demonstrate that the Conjugates of the Invention, comprising Apo-Si-K18 or Apo-Si-K-13 moieties, manifest two fractions upon contact with albumin: an albumin-bound, and an albumin-free fraction. This can explain their biological performance (e.g., in gene silencing) observed in both presence (S+) and absence (S−) of plasma proteins, since even in the presence of plasma proteins, this Conjugates manifest a non-bound fraction, that is free to diffuse and interact with the target cells. By contrast, Control Conjugates such as the Apo-Si-G Conjugate have very large affinity to albumin, and therefore manifest only an albumin-bound fraction. These Control Conjugates, upon interaction with albumin, do not have the free fraction required for diffusion through the extracellular space for interaction with the target cells, and are therefore active only in the serum-free conditions.

Example 10: Conjugates of the Invention that Comprise Three E Moieties are Superior Over Conjugates that Comprise Only Two E Moieties; in Both Serum-Free [(S−) Conditions], and in the Presence of Plasma Proteins [(S+) Conditions]

Methods:

The E moiety used in these experiments was Apo-Si-K-43, having the following structure, as set forth in Formula (Vc"):

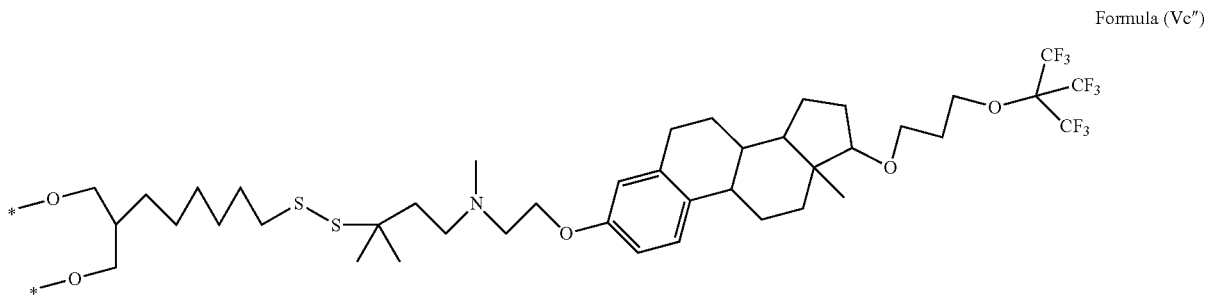

Formula (Vc″)

Two Conjugates comprising said E moiety were examined: one comprising two E moieties, and one comprising three E moieties, wherein in each case, * was a linkage point of the E moiety to the oligonucleotide or to a phosphate group. Each Conjugate comprised a Dicer's substrate RNA Duplex (dsiRNA), comprising one 25-nucleotide-long strand and one 27-nucleotide-long strand, aimed at silencing the expression of the gene encoding for EGFP (Enhanced Green Fluorescent Protein). Thus, silencing of the expression of the EGFP gene was chosen as the biological function to be evaluated following the trans-membrane delivery in vitro, enabled by the E moieties of the invention. The nucleotide sequence of said dsiRNA was as described above in Example 6.

One of the Conjugates was Conjugate (Cn-7), having the following structure (i.e., having two E moieties):

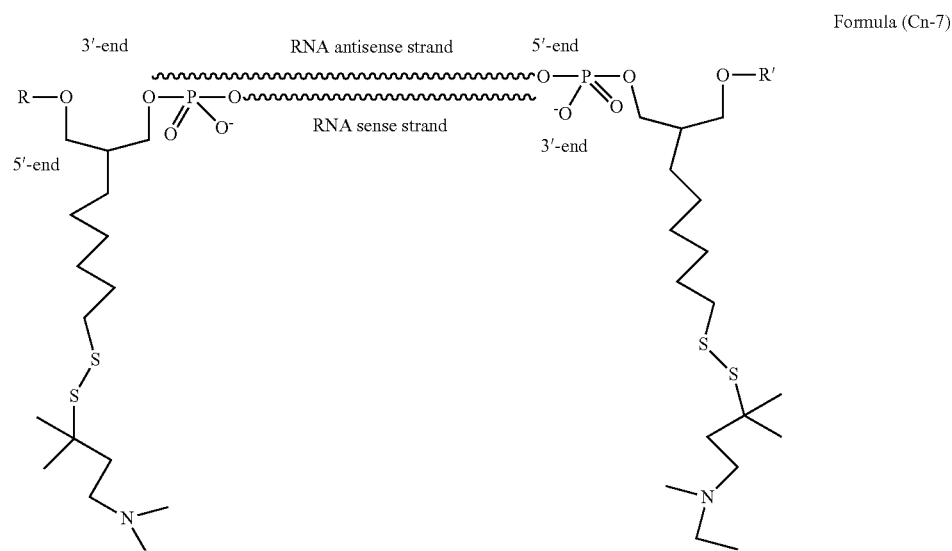

Formula (Cn-7)

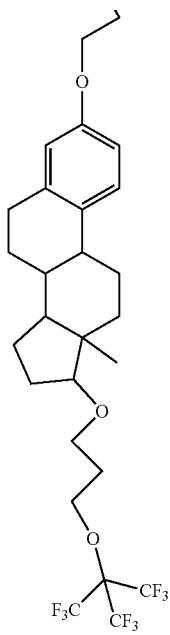
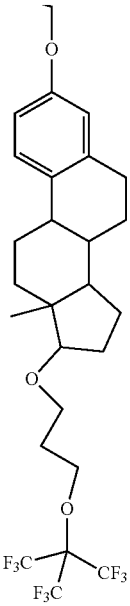
The second Conjugate was Conjugate (Cn-9), having the following structure (i.e., having three E moieties):
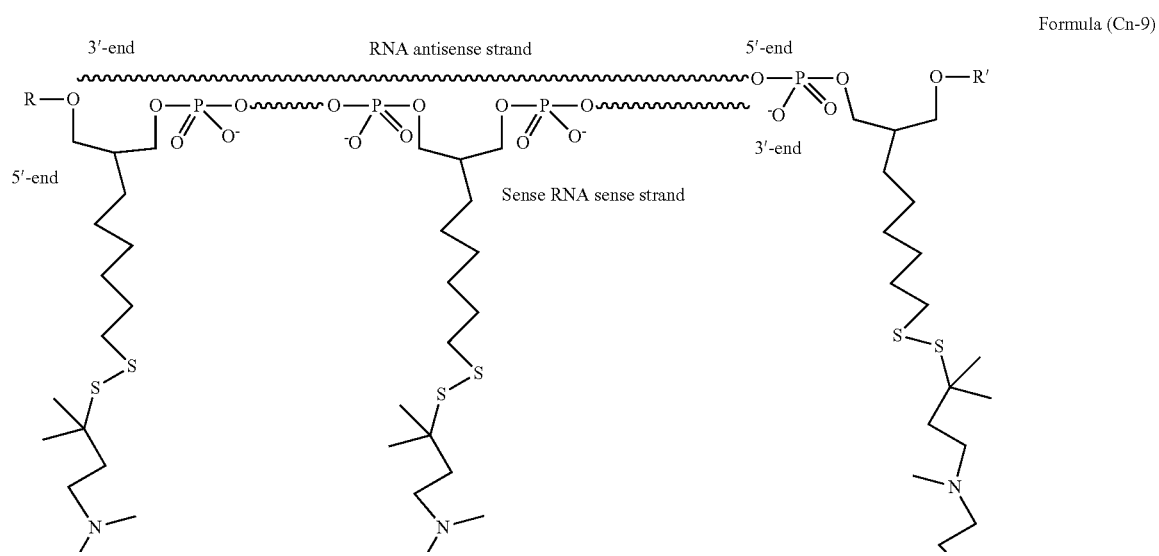
Formula (Cn-9)

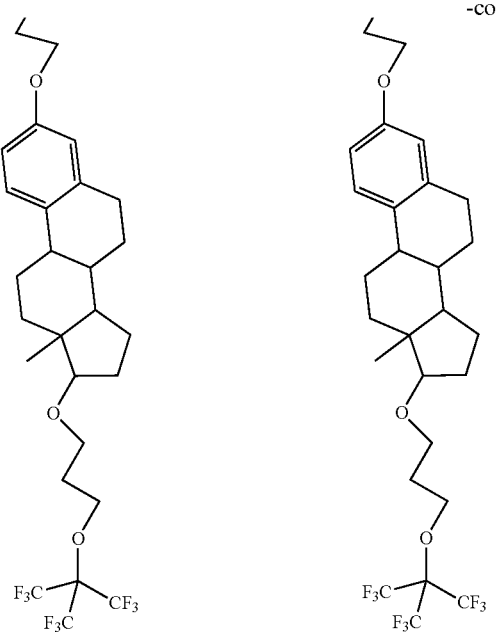
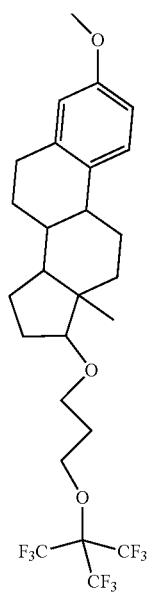

In both Conjugates, all R and R' moieties were phosphate groups.

Cell Culture:

HeLa-EGFP cell line was obtained from Cell Biolabs. Cells were grown in Dulbecco's modified Eagle's medium (Gibco), supplemented with 10% FBS (Gibco), 100 U/ml penicillin, 100 mg/ml streptomycin (Biological Industries, Israel), and blasticidin 10 µg/ml. Cells were maintained in a 37° C. incubator, with 5% $CO_2$ humidified air.

One day before transfection, cells were plated (40,000 cells/well) on 24-well black-plate with a glass bottom. The following day, cells were incubated with either Conjugate (Cn-7), or Conjugate (Cn-9) in the presence of 10% Fetal bovine serum [FBS, serum (+) conditions]. For incubation in serum-free conditions [serum (−) conditions], medium was aspirated, cells were washed with Hank's Balanced Salt Solution (HBSS), and medium was then replaced by serum-free Opti-MEM medium (Thermo Fisher Scientific). After 24 hours, medium was replaced by 10% FCS medium, for the rest of the incubation period (72 hours in total). Cells were incubated with either Conjugate (Cn-7) or Conjugate (Cn-9): a dose of 150 nM in conditions without serum [(S−) conditions] and a dose of 600 nM in the presence of plasma proteins [(S+) conditions].

Down-Regulation of Gene Expression:

Down-regulation of gene expression was measured 72 hours post transfection. For this purpose, medium was aspirated, and cells were washed with HBSS. Protein expression was measured via measurement of the intensity of the EGFP fluorescence, which was quantified by the infinite M200-Pro Multimode Reader (Tecan); excitation wavelength 488 nm, emission wavelength 535 nm. Experiments were performed in triplicates, and EGFP fluorescence results were compared to the fluorescence intensity of untreated cells, (i.e., not treated by the Conjugates). Results were presented as percentage of fluorescence intensity, as compared to that of the other Conjugate. Significance of differences between Conjugates was evaluated by a two-tail t-test, with $p<0.05$ defined as significant.

Results:

Serum-Free Conditions:

Both Conjugates Cn-7 and Cn-9 manifested significant uptake by the cells, and respective effective gene silencing. Conjugate Cn-7 manifested 41.4±1.0% gene silencing at 150 nM of the Conjugate (mean±SD). Conjugate Cn-9 manifested higher silencing efficacy, of 61.0±0.5% at 150 nM of the Conjugate. The difference between Conjugates was statistically significant [$p<0.001$, t-test of comparison between the Cn-7 and Cn-9 Conjugates].

In the Presence of Serum:

Both Conjugates Cn-7 and Cn-9 manifested significant uptake by the cells, and respective effective gene silencing. Conjugate Cn-7 provided 12.3±1.6% gene silencing at concentration of 600 nM of the Conjugate, while Cn-9 provided stronger gene silencing, of 25.4±1.0% at that concentration (mean±SD); [$p<0.001$, t-test comparison between the Cn-7 and Cn-9 Conjugates].

Summary of the Results:

Both Conjugates Cn-7 and Cn-9 manifested significant uptake and gene silencing when incubated with cells in vitro. Gene silencing activity exerted by both Conjugates was evident in both presence or absence of plasma proteins in the culture medium, i.e., in both (S+) conditions and (S−) conditions, respectively. Silencing was of larger amplitude in the serum-free conditions, conceivably consistent with the respective lack of competitive binding of the Conjugates to albumin in these conditions. Importantly, in both (S+) conditions and in (S−) conditions, gene silencing was statistically-significant higher in the Conjugate that comprised three E moieties (Cn-9), as compared to the Conjugate that comprised only two E moieties (Cn-7).

Conclusions:

DsiRNAs, comprising either 2 or 3 E moieties of the invention, manifest significant gene silencing in vitro.

Said gene silencing is encountered in either presence or absence of plasma proteins in the culture medium.

A Conjugate that comprises three E moieties is advantageous over a Conjugate that comprises only two E moieties in providing significant gene silencing.

The invention claimed is:

1. A conjugate, having the structure as set forth in Formula (I):

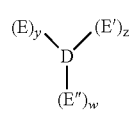

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes, selected from the group consisting of a small-molecule drug, a peptide, a protein, and a native or modified, single-stranded or double-stranded DNA or RNA, siRNA, dsiRNA, and antisense oligonucleotide (ASO);

y, z and w are each an integer, independently selected from 0, 1, 2, 3 or 4, wherein if any of y, z or w or combination thereof is 0, it means that the respective E moiety (or moieties) is (are) null; at least one of y, z or w is different from 0;

E, E', or E" can be the same or different, each having independently a structure as set forth in general Formula (II):

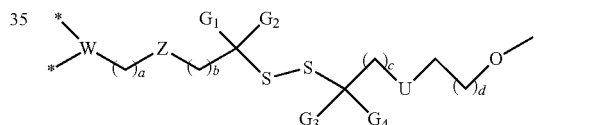

Formula (II)

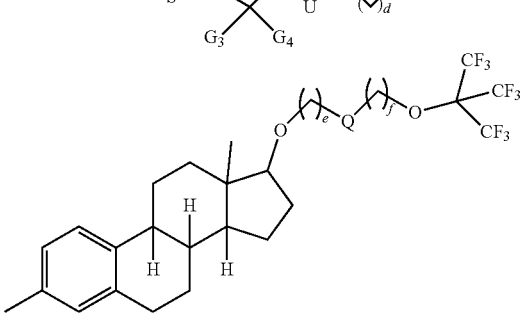

including pharmaceutically acceptable salts, hydrates, solvates and metal chelates of the compound represented by the structure as set forth in Formula (II), and solvates and hydrates of the salts, wherein:

one of U or Q is independently null, and the other one is a selected from the group consisting of —NH—, —N(CH$_3$)—, —N(CH$_2$—CH$_3$)—, —NH—(CH$_2$)$_2$—NH—, and —N(CH$_3$)—(CH$_2$)$_2$—N(CH$_3$)—;

G$_1$, G$_2$, G$_3$ and G$_4$ are each independently selected from the group consisting of hydrogen, methyl or ethyl; G$_1$, G$_2$, G$_3$ and G$_4$ moieties can be the same or different; at least two of G$_1$, G$_2$, G$_3$, and G$_4$ are hydrogen atoms;

Z is selected from the group consisting of null, ether, ester, amine, and amide;

a, b, c, d are integers, each being independently selected from the group consisting of 0, 1, 2, 3, 4, 5, 6 and 7, wherein 0=null; a, b, c, d can be the same or different;

e and f are integers, each being independently selected from the group consisting of 1, 2 and 3; e and f can be the same or different;

if any of each a or b is ≥2, then the respective hydrocarbon chain can be either saturated or non-saturated;

W is selected from a group consisting of null, hydroxyl, di-hydroxyl, natural and modified nucleoside, and the structure set forth in Formula (II'):

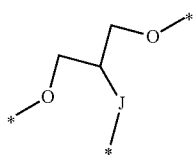

Formula (II')

wherein J is selected from null, —CH$_2$—, a secondary or tertiary amine, and oxygen;

* is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

2. The conjugate according to claim 1, wherein in E, E', or E" moiety, W is a nucleoside, selected from natural or modified adenine, cytosine, thymine and uracil, and the sugar moiety is ribose or 2'-deoxyribose.

3. The conjugate according to claim 2, wherein in E, E', or E" moiety, W is 2'-deoxyuridine.

4. The conjugate according to claim 1, wherein in E, E', or E" moiety, W has the structure set forth in Formula (II'), wherein J is —CH$_2$—.

5. The conjugate according to claim 1, wherein E, E', or E" moiety has the structure as set forth in Formula (III):

one of U or Q is independently null, and the other one is a selected from the group consisting of —NH—, —N(CH$_3$)—, —N(CH$_2$—CH$_3$)—, and —NH —(CH$_2$)$_2$—NH—;

Z is selected from the group consisting of null, ether, ester, amine and amide;

G$_3$ and G$_4$ are each independently selected from the group consisting of hydrogen, methyl and ethyl; G$_3$ and G$_4$ moieties can be the same or different;

a, b, c, d are integers, each being independently selected from the group consisting of 0, 1, 2, 3, 4, 5, 6 and 7, wherein 0=null; a, b, c, d can be the same or different;

e and f are integers, each being independently selected from the group consisting of 1, 2 and 3; e and f can be the same or different;

if any of each a or b is ≥2, then the respective hydrocarbon chain can be either saturated or non-saturated;

W is selected from a group consisting of null, hydroxyl, di-hydroxyl, natural and modified nucleoside, and the structure set forth in Formula (II'):

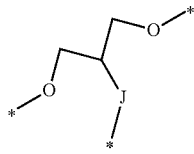

Formula (II')

wherein J is selected from the group consisting of null, —CH$_2$—, a secondary or tertiary amine, and oxygen;

* is selected from the group consisting of null; hydrogen; a linkage point to D; a linkage point to a protecting group for alcohol; a linkage point to a phosphate, sulfate or carboxyl group; and a linkage point to a solid

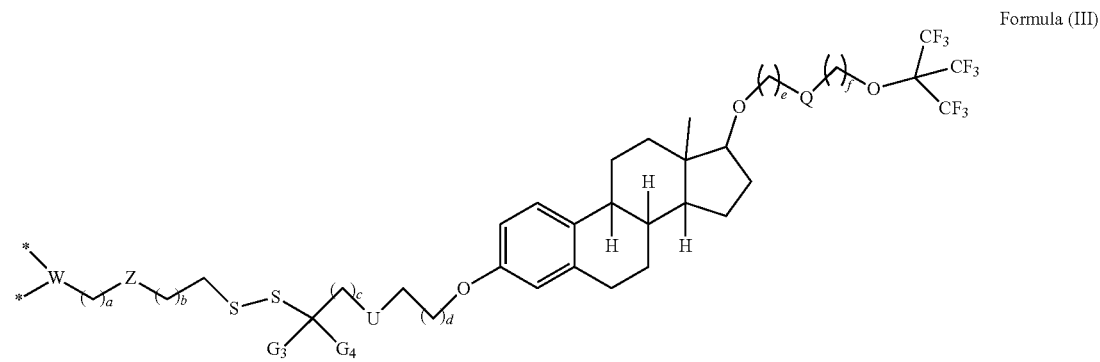

Formula (III)

including pharmaceutically acceptable salts, hydrates, solvates and metal chelates of the compound represented by the structure as set forth in Formula (III), and solvates and hydrates of the salts, wherein:

support; E, E' or E" moiety may be linked to one D moiety via one or two points.

6. The conjugate according to claim 5, wherein E, E', or E" moiety has the structure as set forth in Formula (IVa):

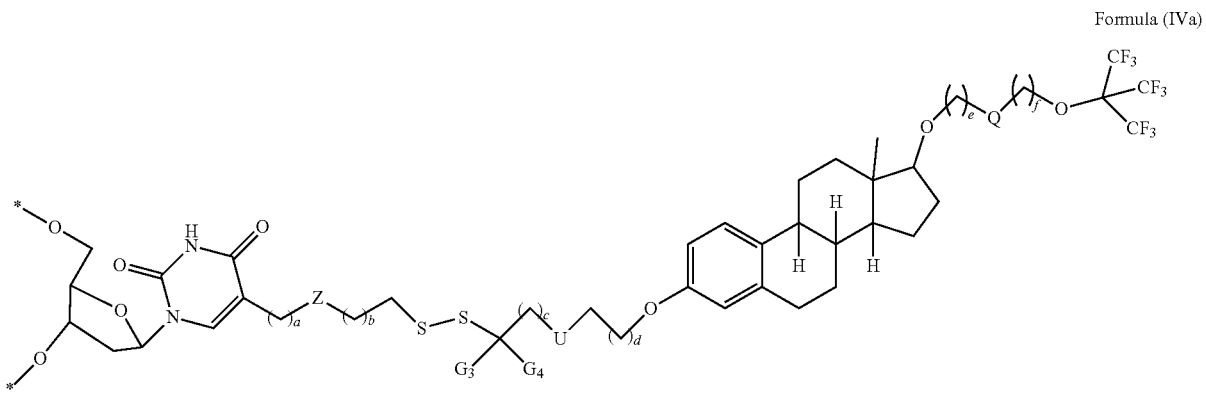

Formula (IVa)

including pharmaceutically acceptable salts, hydrates, solvates and metal chelates of the compound represented by the structure as set forth in Formula (IVa), and solvates and hydrates of the salts; wherein: Z, U, Q, $G_3$, $G_4$, a, b, c, d, e, f and *, each having the same meaning as in Formula (III).

7. The conjugate according to claim 5, wherein E, E', or E" moiety has the structure as set forth in Formula (IVb):

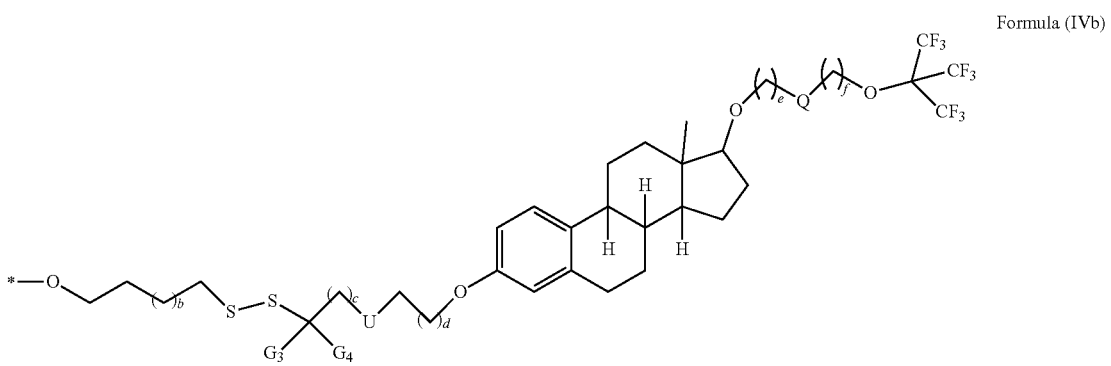

Formula (IVb)

including pharmaceutically acceptable salts, hydrates, solvates and metal chelates of the compound represented by the structure as set forth in Formula (IVb), and solvates and hydrates of the salts; wherein U, Q, $G_3$, $G_4$, b, c, d, e, f and *, each having the same meaning as in Formula (III).

8. The conjugate according to claim 5, wherein E, E', or E" moiety has the structure as set forth in Formula (IVc):

Formula (IVc)

including pharmaceutically acceptable salts, hydrates, solvates and metal chelates of the compound represented by the structure as set forth in Formula (IVc), and solvates and hydrates of the salts; wherein U, Q, $G_3$, $G_4$, b, c, d, e, f, and *, each having the same meaning as in Formula (III); J is selected from the group consisting of null, —$CH_2$—, and oxygen.

9. The conjugate according to claim 6, wherein E, E', or E" moiety has the structure as set forth in Formula (Va'):

Formula (Va')

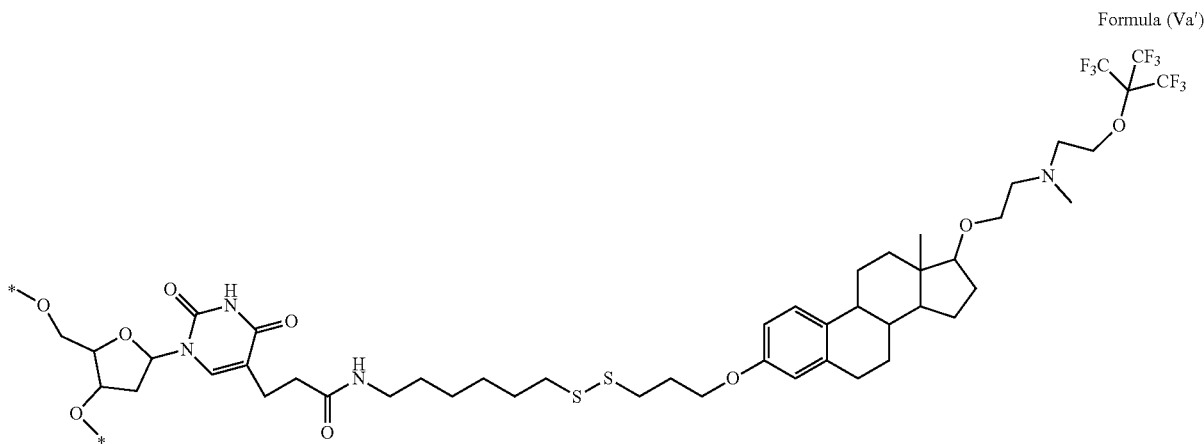

including pharmaceutically acceptable salts, hydrates, solvates and metal chelates of the compound represented by the structure as set forth in Formula (Va'); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

10. The conjugate according to claim 6, wherein E, E', or E" moiety has the structure as set forth in Formula (Va"):

Formula (Va")

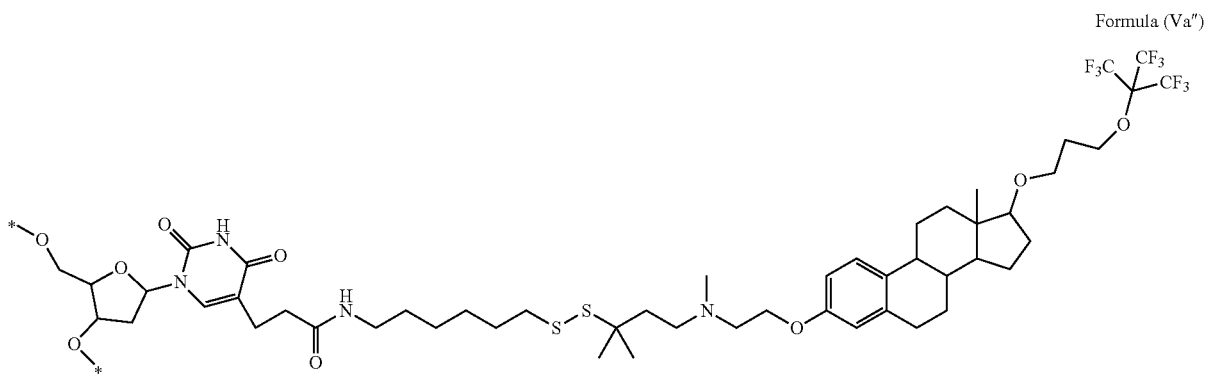

including pharmaceutically acceptable salts, hydrates, solvates and metal chelates of the compound represented by the structure as set forth in Formula (Va"); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

11. The conjugate according to claim 6, having the structure as set forth in Formula (Va'''):

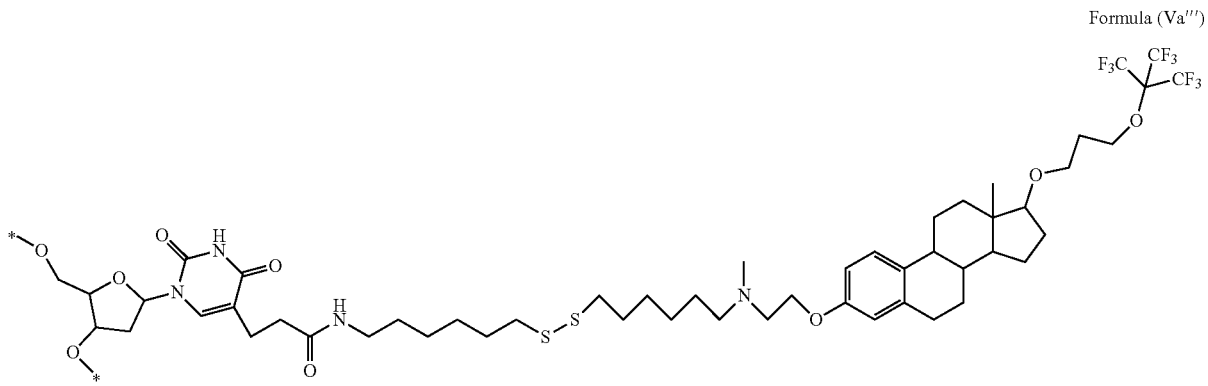

Formula (Va''')

including pharmaceutically acceptable salts, hydrates, solvates and metal chelates of the compound represented by the structure as set forth in Formula (Va'''); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

12. The conjugate according to claim 7, wherein E, E', or E" moiety has the structure as set forth in Formula (Vb'):

structure as set forth in Formula (Vb'); * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

13. The conjugate according to claim 7, wherein E, E', or E" moiety has the structure as set forth in (Vb"):

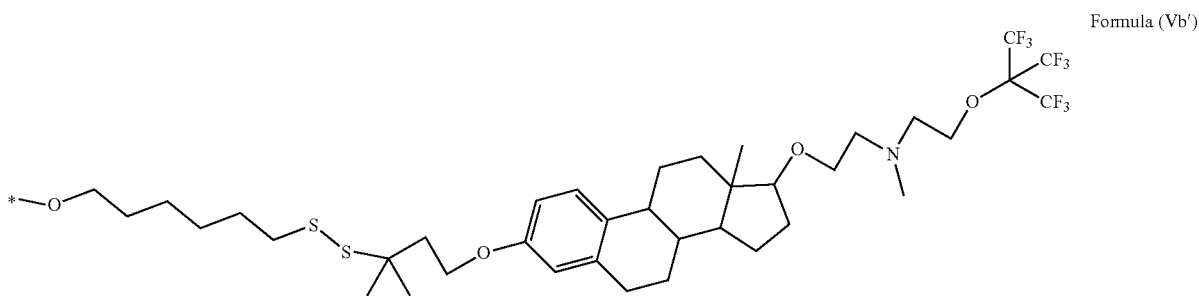

Formula (Vb')

including pharmaceutically acceptable salts, hydrates, solvates and metal chelates of the compound represented by the

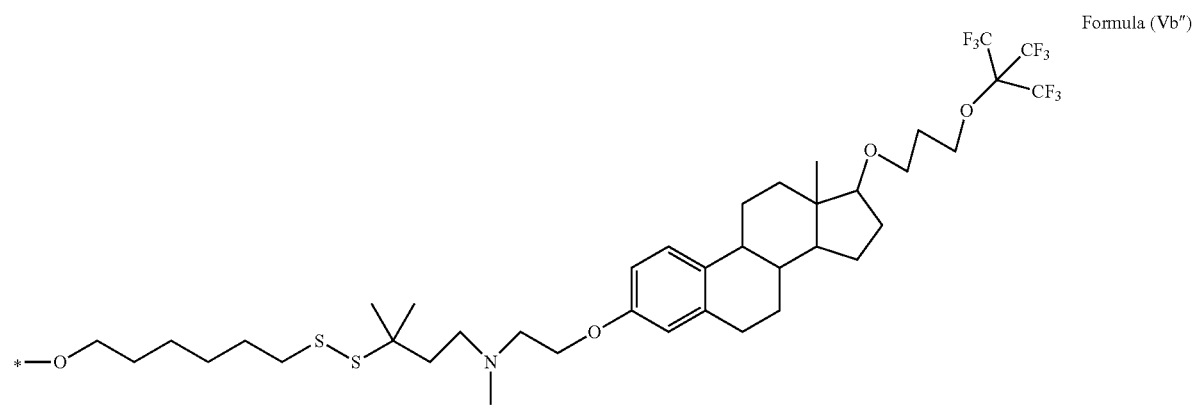

Formula (Vb")

including pharmaceutically acceptable salts, hydrates, solvates and metal chelates of the compound represented by the structure as set forth in Formula (Vb"); * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

14. The conjugate according to claim 7, wherein E, E', or E" moiety has the structure as set forth in Formula (Vb'''):

Formula (Vb''')

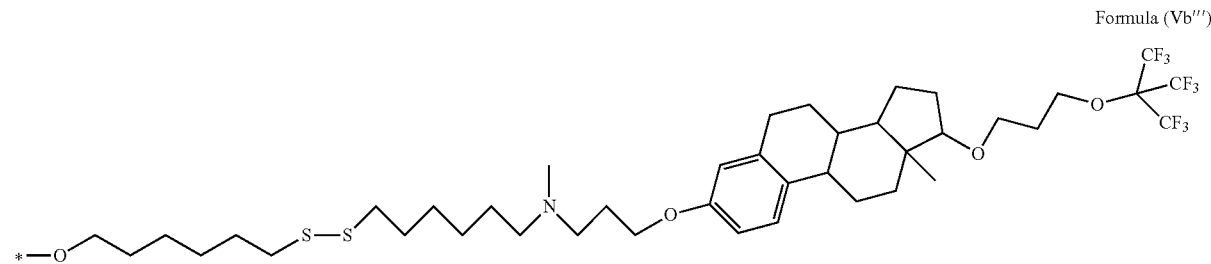

including pharmaceutically acceptable salts, hydrates, solvates and metal chelates of the compound represented by the structure as set forth in Formula (Vb'''); * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

15. The conjugate according to claim 8, wherein E, E', or E" moiety has the structure as set forth in (Vc'):

Formula (Vc')

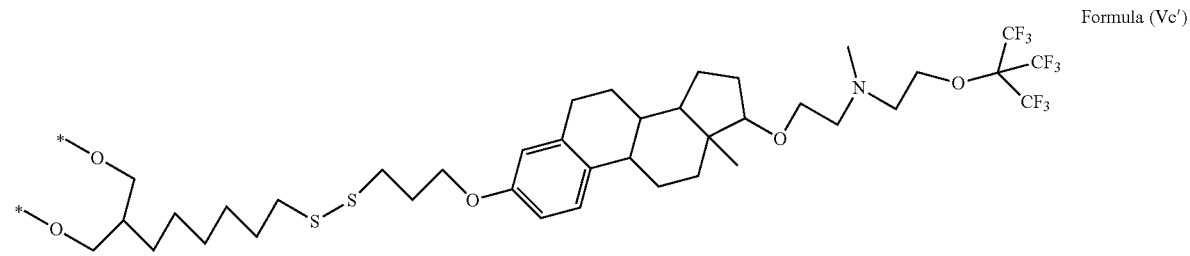

including pharmaceutically acceptable salts, hydrates, solvates and metal chelates of the compound represented by the structure as set forth in Formula (Vc'); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

16. The conjugate according to claim 8, wherein E, E', or E" moiety has the structure as set forth in (Vc"):

Formula (Vc")

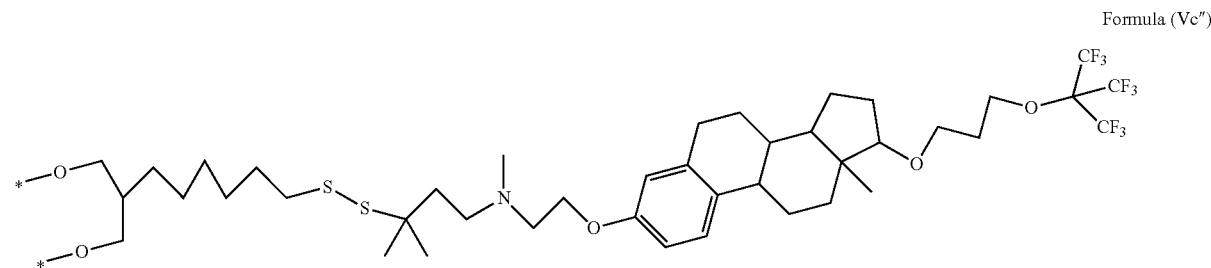

including pharmaceutically acceptable salts, hydrates, solvates and metal chelates of the compound represented by the structure as set forth in Formula (Vc"); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

17. The conjugate according to claim 8, wherein E, E' or E" according to Formula (IVc), having the structure as set forth in Formula (Vc'''):

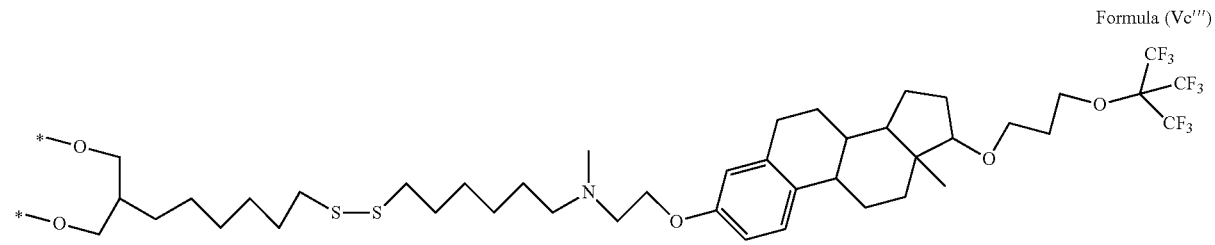

Formula (Vc''')

including pharmaceutically acceptable salts, hydrates, solvates and metal chelates of the compound represented by the structure as set forth in Formula (Vc'''); wherein * is selected from the group consisting of null; hydrogen; a linkage point to D; a linkage point to a protecting group for alcohol; a linkage point to a phosphate, sulfate or carboxyl group; and a linkage point to a solid support; E, E' or E" moiety may be linked to one D moiety via one or two points.

18. A precursor molecule, having the structure as set forth in Formula (IVaP):

Formula (IVaP)

including pharmaceutically acceptable salts, hydrates, solvates and metal chelates of the compound represented by the structure as set forth in Formula (IVaP), and solvates and hydrates of the salts, wherein: Z, U, Q, $G_3$, $G_4$, a, b, c, d, e, f, each having the same meaning as in claim 6.

19. A precursor molecule, having the structure, as set forth in Formula (IVbP):

Formula (IVbP)

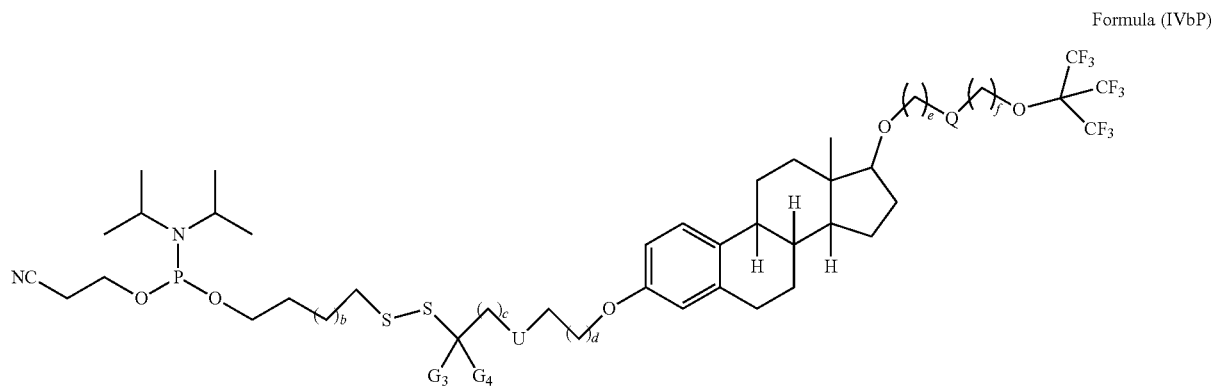

including pharmaceutically acceptable salts, hydrates, solvates and metal chelates of the compound represented by the structure as set forth in Formula (IVbP), and solvates and hydrates of the salts, wherein U, Q, $G_3$, $G_4$, b, c, d, e, f, each having the same meaning as in claim 7.

20. A precursor molecule, having the structure, as set forth in Formula (IVcP):

Formula (IVcP)

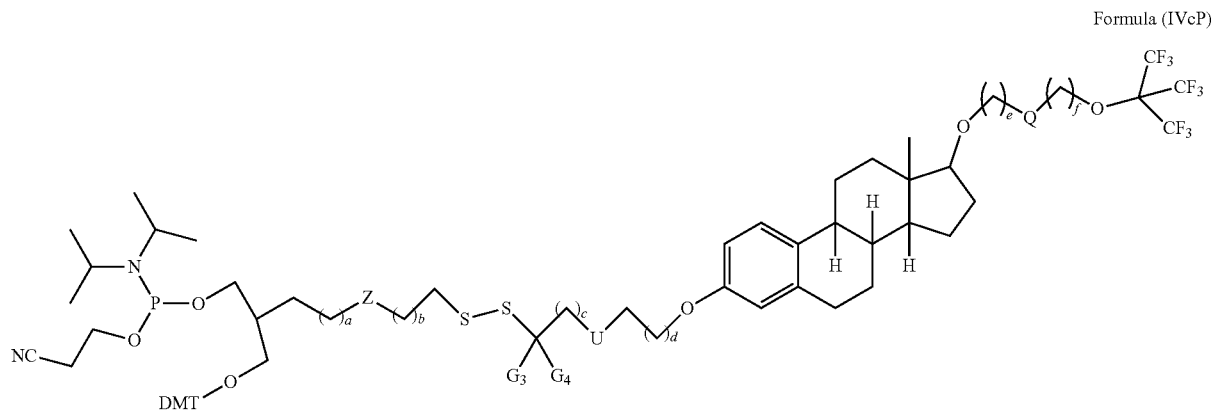

including pharmaceutically acceptable salts, hydrates, solvates and metal chelates of the compound represented by the structure as set forth in Formula (IVcP), and solvates and hydrates of the salts, wherein: Z, U, Q, $G_3$, $G_4$, a, b, c, d, e, f, each having the same meaning as in claim 5.

21. The precursor molecule according to claim 20, having the following structure, as set forth in Formula (PP-1):

Formula (PP-1)

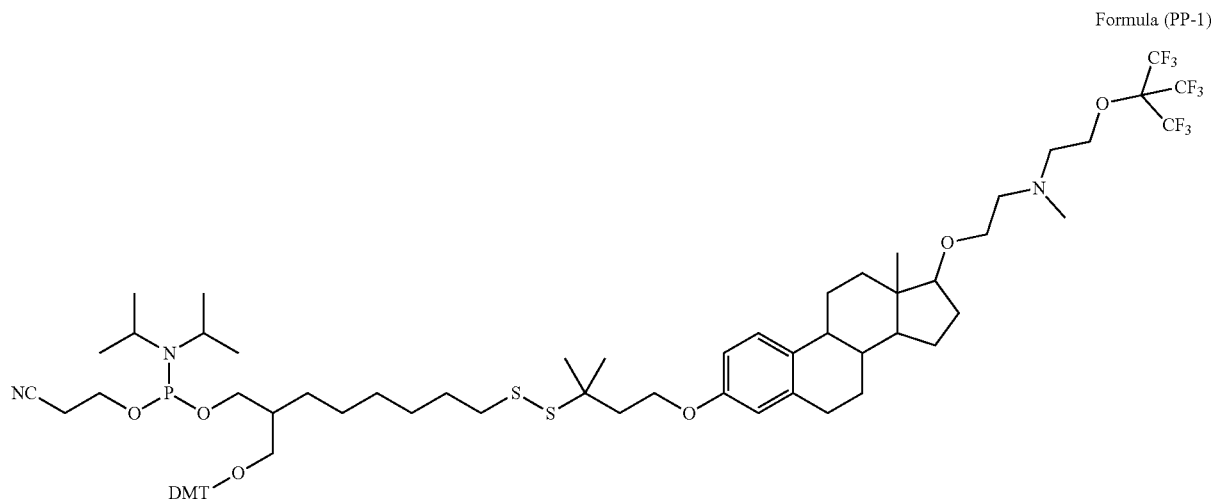

including pharmaceutically acceptable salts, hydrates, solvates and metal chelates of the compound represented by the structure as set forth in Formula (PP-1), and solvates and hydrates of the salts.

22. The precursor molecule according to claim 20, having the following structure, as set forth in Formula (PP-2):

Formula (PP-2)

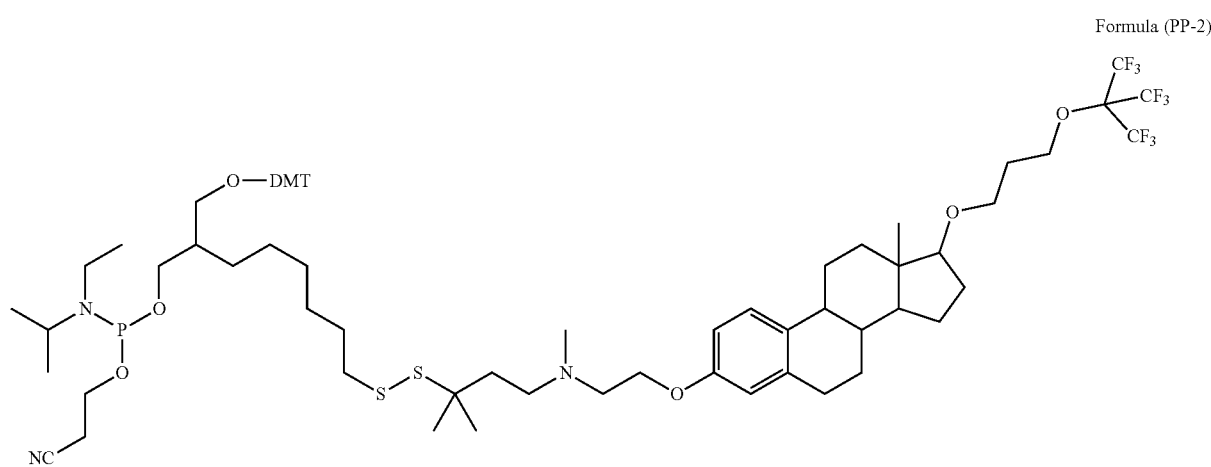

including pharmaceutically acceptable salts, hydrates, solvates and metal chelates of the compound represented by the structure as set forth in Formula (PP-2), and solvates and hydrates of the salts.

23. The precursor molecule according to claim 20, having the following structure, as set forth in Formula (PP-3):

Formula (PP-3)

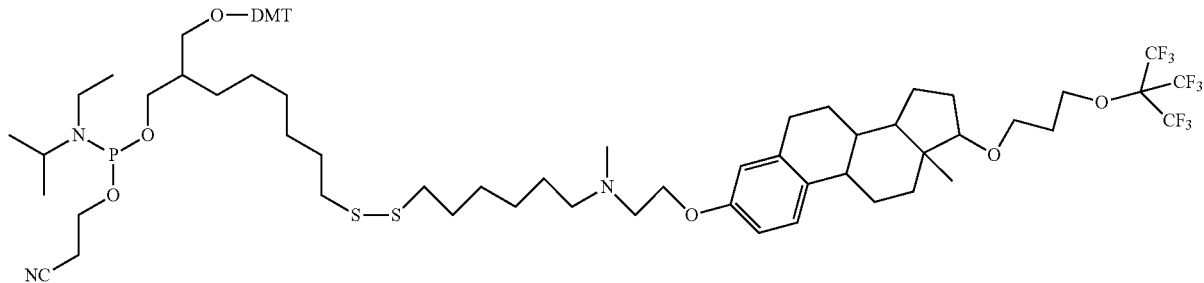

including pharmaceutically acceptable salts, hydrates, solvates and metal chelates of the compound represented by the structure as set forth in Formula (PP-3), and solvates and hydrates of the salts.

24. The conjugate according to claim 1, comprising E, E' or E" moiety according to any of Formulae (II), (III), (IVa), (IVb), (IVc), (Va'), (Va"), (Va'''), (Vb'), (Vb"), (Vb'''), (Vc'), (Vc") or (Vc'''), linked to a drug.

25. The conjugate according to claim 24, wherein the drug is a macromolecule drug.

26. The conjugate according to claim 25, wherein the macromolecule drug is an oligonucleotide drug (OD), comprising natural or modified oligonucleotide chains, and selected from siRNA, dsiRNA, mRNA, microRNA, and antisense oligonucleotide (ASO).

27. A pharmaceutical composition, comprising the conjugate according to claim 24, and a pharmaceutically-acceptable salt or carrier.

28. The conjugate according to claim 26, wherein the OD is linked to either one, two, three, or more than three of E, E', or E" moieties.

29. The conjugate according to claim 26, wherein the OD is a Dicer substrate, being an RNA duplex comprising strands of 24 and 27 nucleotides in length; or an RNA duplex comprising strands of 25 and 27 nucleotides in length.

30. The conjugate according to claim 29, wherein a phosphate, sulfate or a carboxyl group is attached to the linkage or linkages between the duplex RNA and the E, E' or E" moiety.

31. The conjugate according to claim 26, wherein the OD is an siRNA or dsiRNA comprising a duplex between sense and antisense strands and having the structure as set forth in Formula (Cn-1):

Formula (Cn-1)

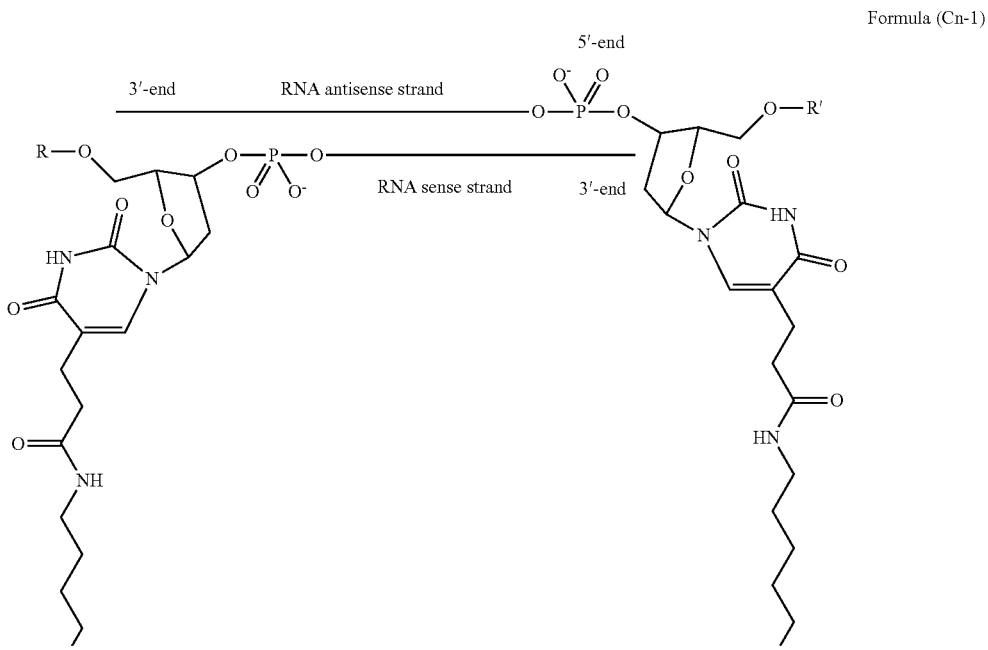

-continued

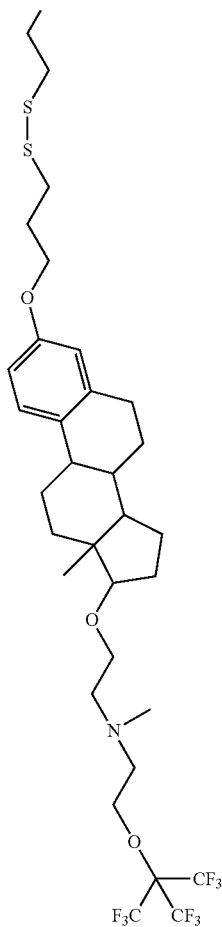

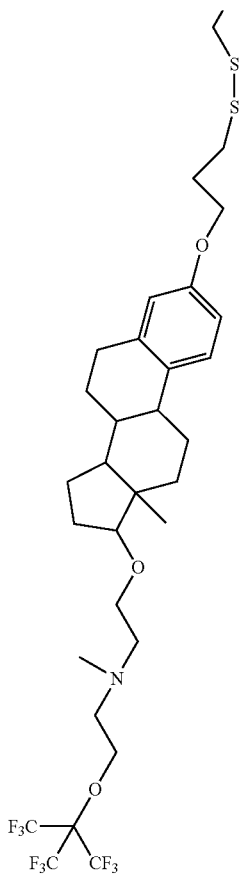

including pharmaceutically acceptable salts, hydrates, solvates and metal chelates of the compound represented by the structure as set forth in Formula (Cn-1), and solvates and hydrates of the salts, wherein R and R' are each selected independently from the group consisting of hydrogen, phosphate, sulfate or carboxyl group.

32. The conjugate according to claim 26, wherein the OD is an siRNA or dsiRNA comprising a duplex between sense and antisense strands and having the structure as set forth in Formula (Cn-2):

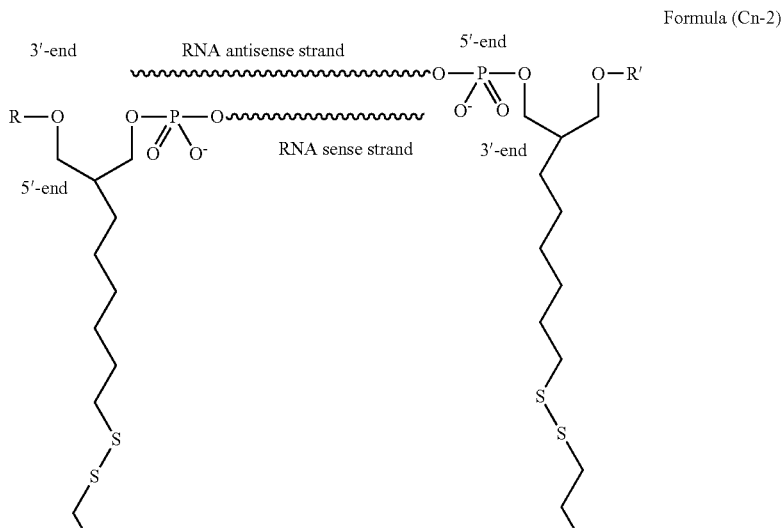

Formula (Cn-2)

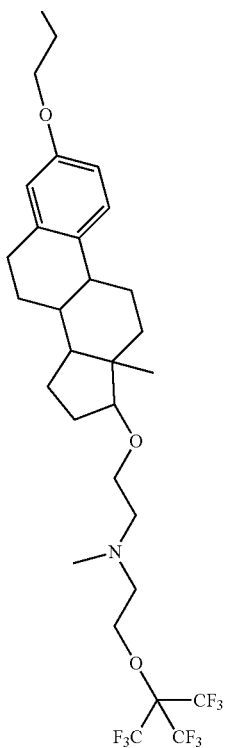
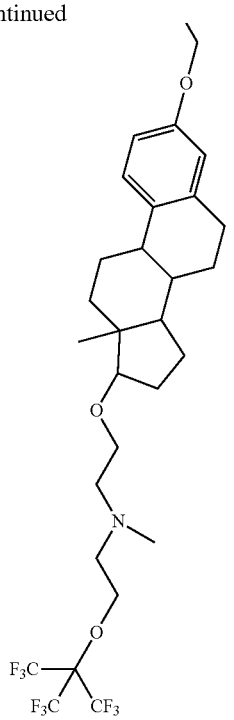

including pharmaceutically acceptable salts, hydrates, solvates and metal chelates of the compound represented by the structure as set forth in Formula (Cn-2), and solvates and hydrates of the salts, wherein R and R' are each selected independently from the group consisting of hydrogen, phosphate, sulfate or carboxyl group.

33. The conjugate, according to claim 26, wherein the OD is an siRNA or dsiRNA comprising a duplex between sense and antisense strands and having the structure as set forth in Formula (Cn-3):

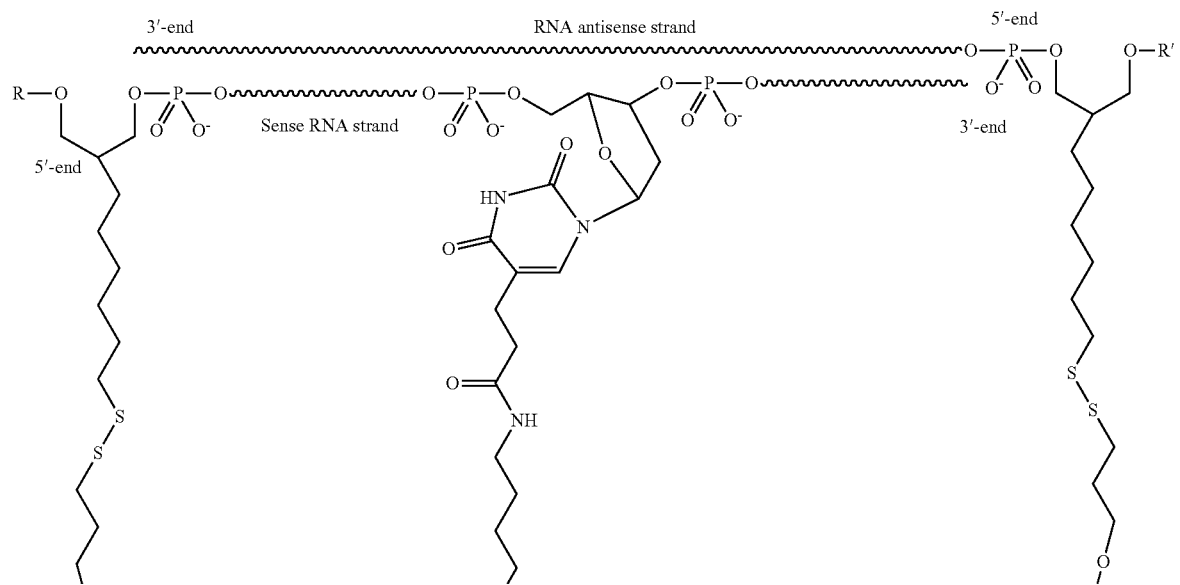

Formula (Cn-3)

-continued

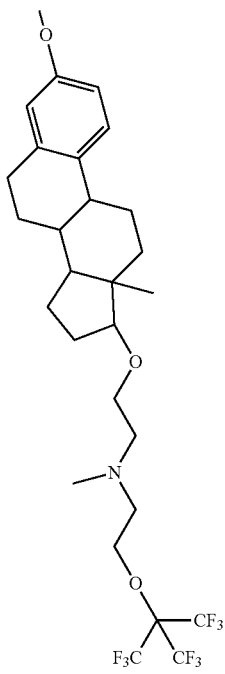
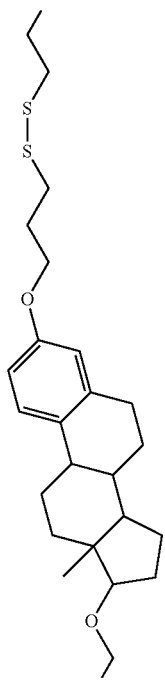
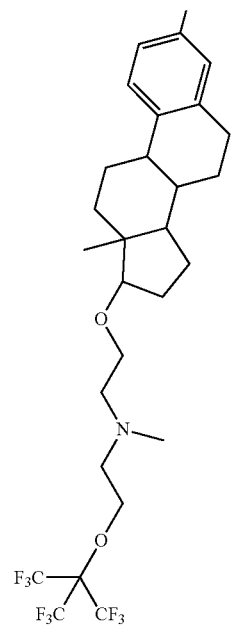

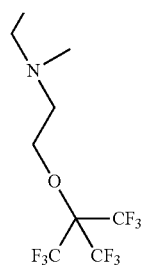

including pharmaceutically acceptable salts, hydrates, solvates and metal chelates of the compound represented by the structure as set forth in Formula (Cn-3), and solvates and hydrates of the salts, wherein R and R' are each selected independently from the group consisting of hydrogen, phosphate, sulfate or carboxyl group.

34. The conjugate, according to claim 26, wherein the OD is an siRNA or dsiRNA comprising a duplex between sense and antisense strands and having the structure as set forth in Formula (Cn-4):

Formula (Cn-4)

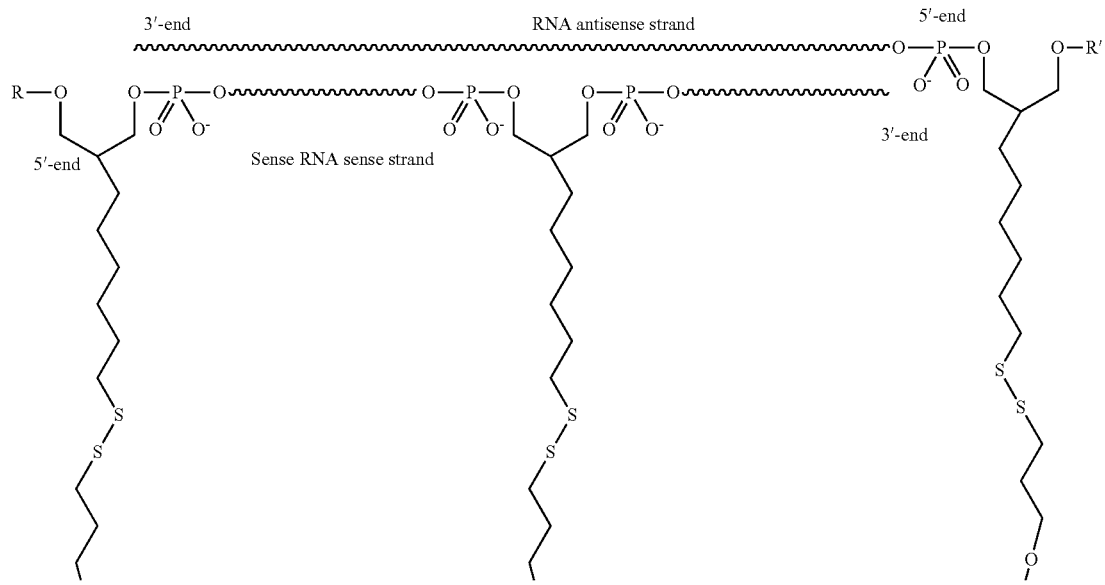

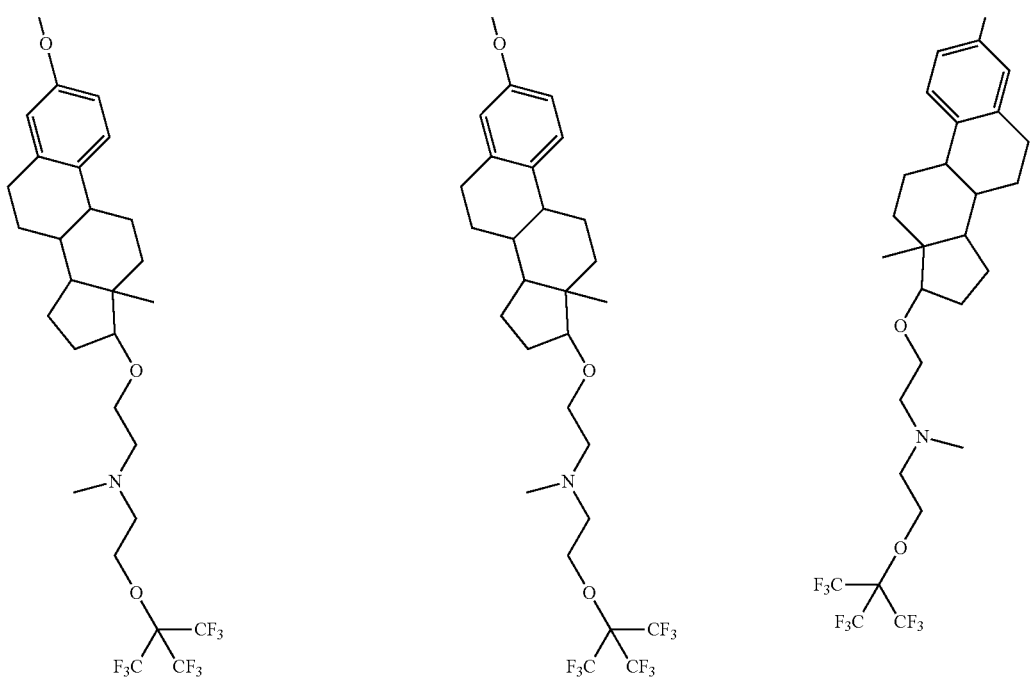

including pharmaceutically acceptable salts, hydrates, solvates and metal chelates of the compound represented by the structure as set forth in Formula (Cn-4), and solvates and hydrates of the salts, wherein R and R' are each selected independently from the group consisting of hydrogen, phosphate, sulfate or carboxyl group.

35. The conjugate, according to claim 26, having the structure as set forth in Formula (Cn-5):

Formula (CN-5)

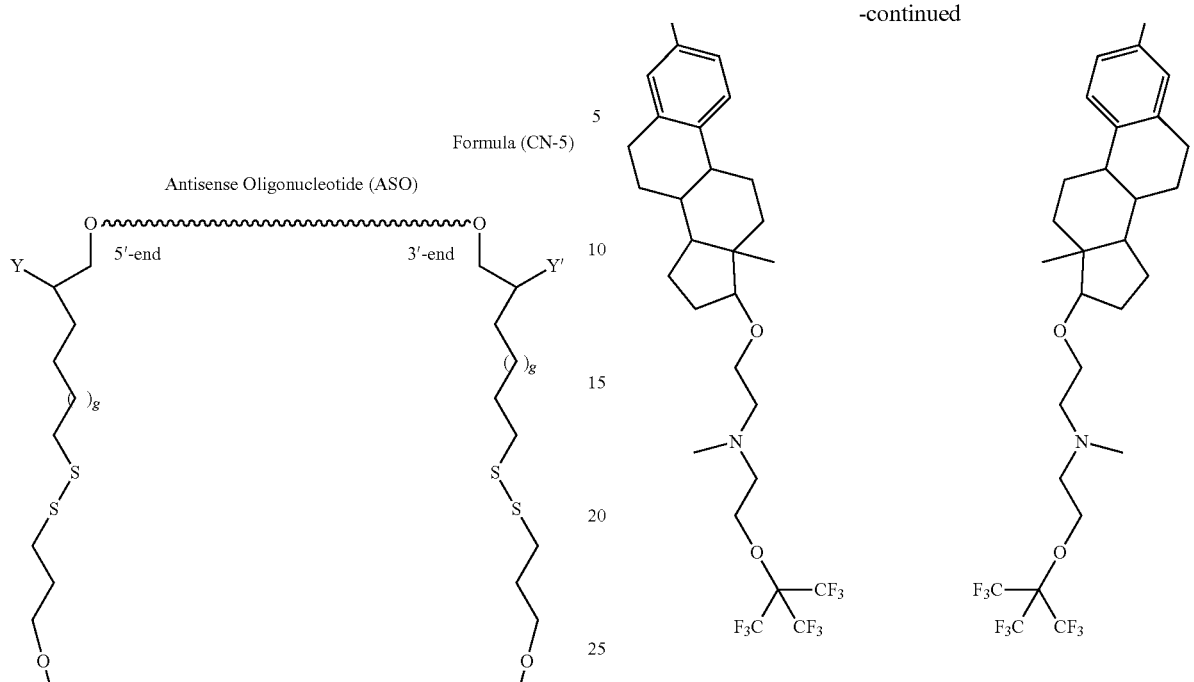

including pharmaceutically acceptable salts, hydrates, solvates and metal chelates of the compound represented by the structure as set forth in Formula (Cn-5), and solvates and hydrates of the salts; wherein Y and Y' are each selected independently from the group consisting of hydrogen, —$CH_2$—Z; —$CH_2$—Z'; —$CH_2$—O—Z; and —$CH_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

36. The conjugate according to claim 26, wherein the OD is an siRNA or dsiRNA comprising a duplex between sense and antisense strands and having the structure as set forth in Formula (Cn-6):

Formula (Cn-6)

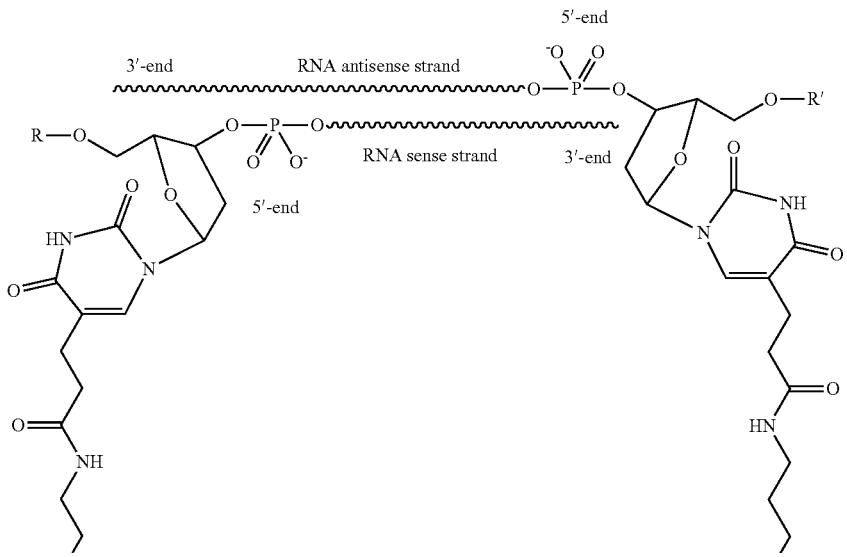

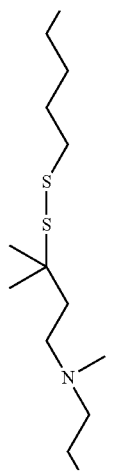
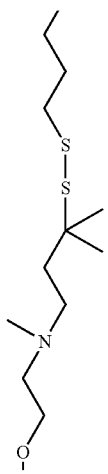
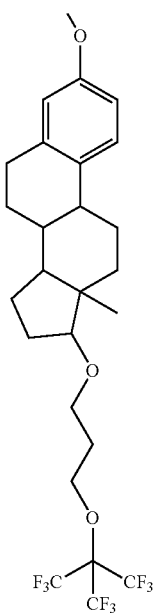
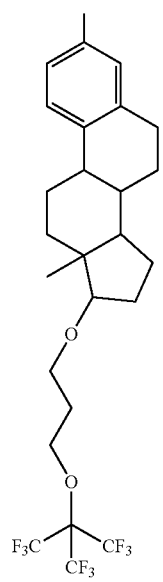

including pharmaceutically acceptable salts, hydrates, solvates and metal chelates of the compound represented by the structure as set forth in Formula (Cn-6), and solvates and hydrates of the salts, wherein R and R' are each selected independently from the group consisting of hydrogen, phosphate, sulfate and carboxyl group.

37. The conjugate according to claim 26, wherein the OD is an siRNA or dsiRNA comprising a duplex between sense and antisense strands and having the structure as set forth in Formula (Cn-7):

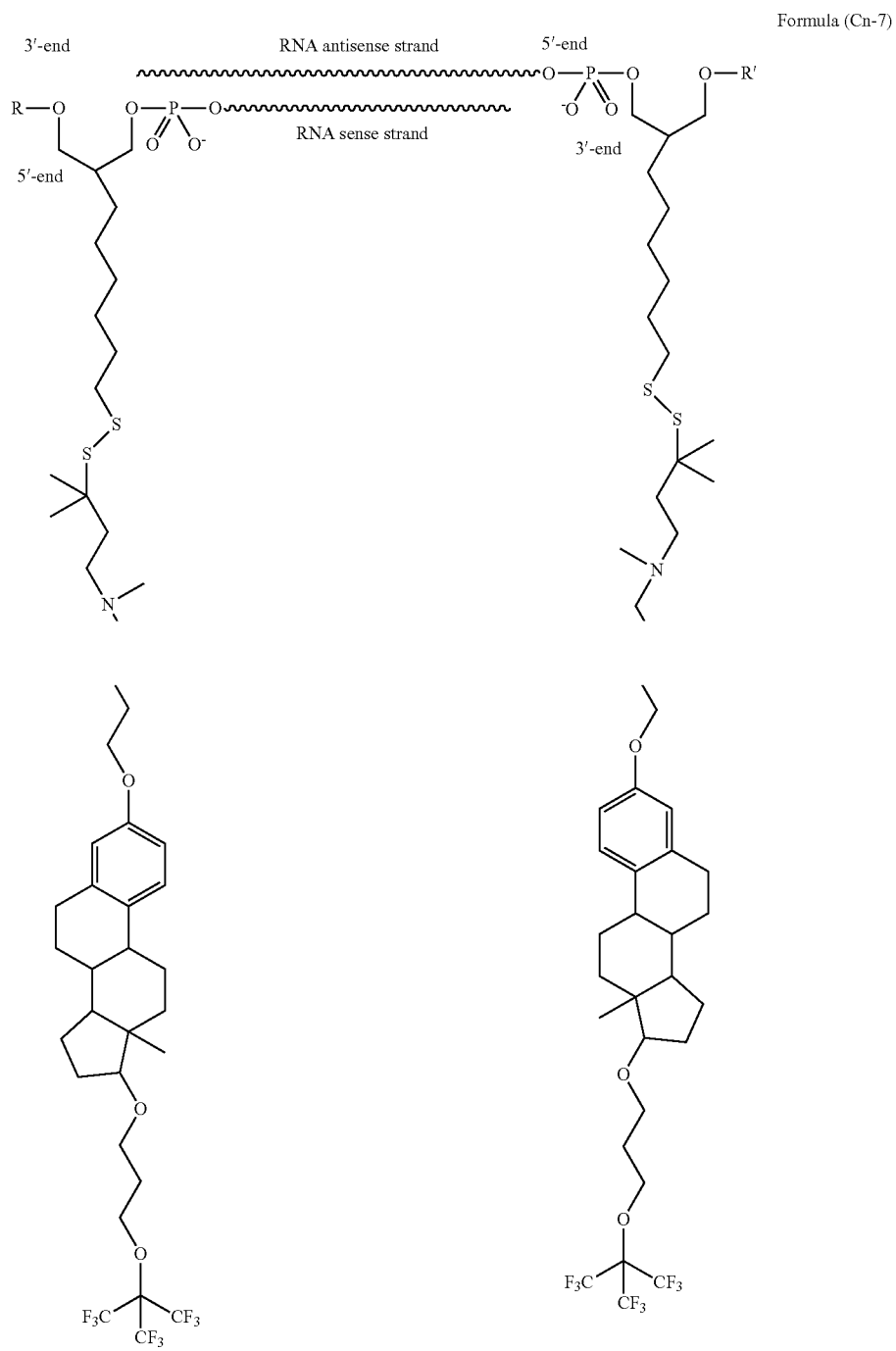

Formula (Cn-7)

including pharmaceutically acceptable salts, hydrates, solvates and metal chelates of the compound represented by the structure as set forth in Formula (Cn-7), and solvates and hydrates of the salts, wherein R and R' are each selected independently from the group consisting of hydrogen, phosphate, sulfate and carboxyl group.

38. The conjugate according to claim 26, wherein the OD is an siRNA or dsiRNA comprising a duplex between sense and antisense strands and having the structure as set forth in Formula (Cn-8):

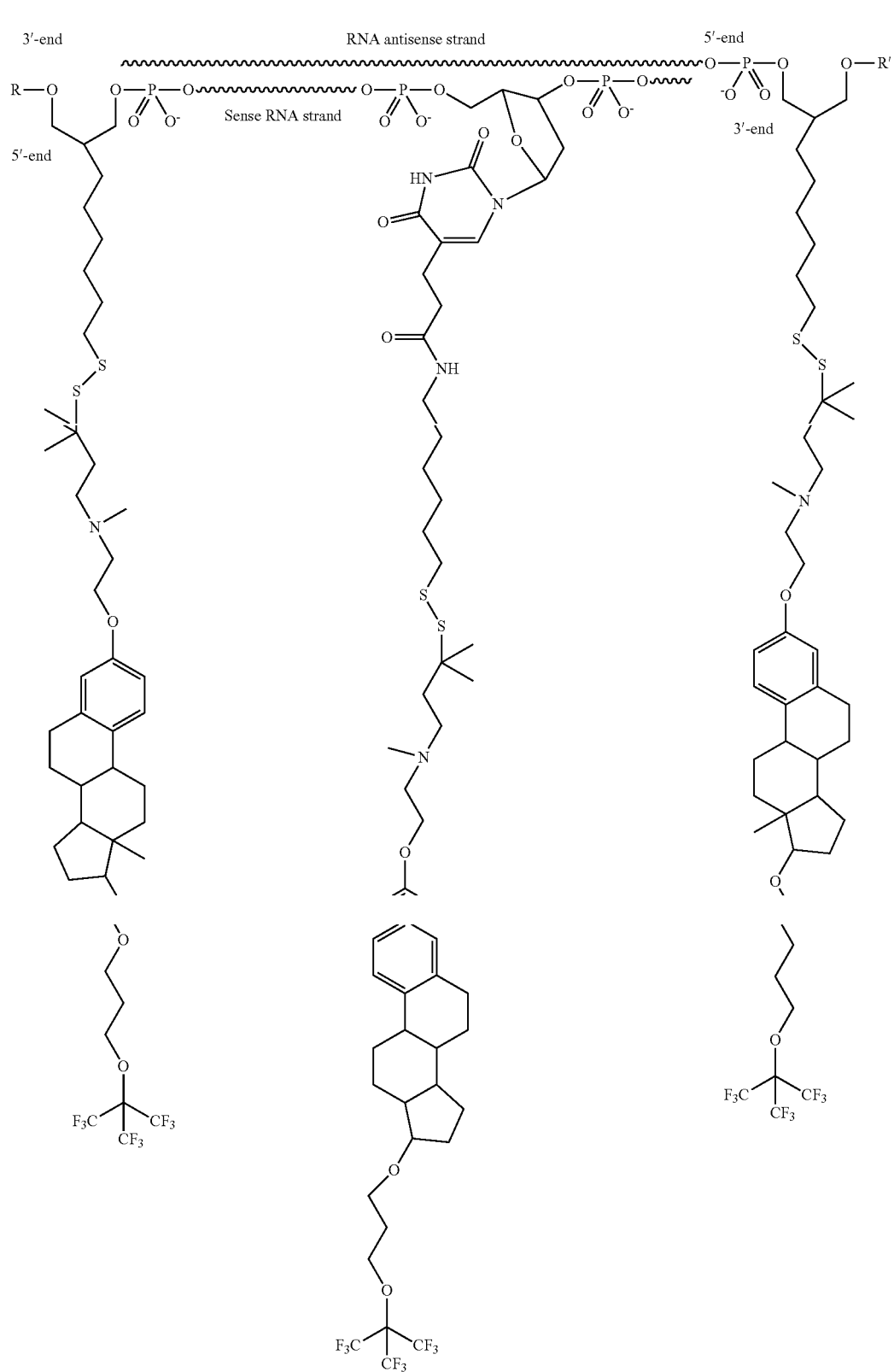
Formula (Cn-8)
including pharmaceutically acceptable salts, hydrates, solvates and metal chelates of the compound represented by the structure as set forth in Formula (Cn-8), and solvates and hydrates of the salts, wherein R and R' are each selected independently from the group consisting of hydrogen, phosphate, sulfate and carboxyl group.

39. The conjugate according to claim 26, wherein the OD is an siRNA or dsiRNA comprising a duplex between sense and antisense strands and having the structure as set forth in Formula (Cn-9):

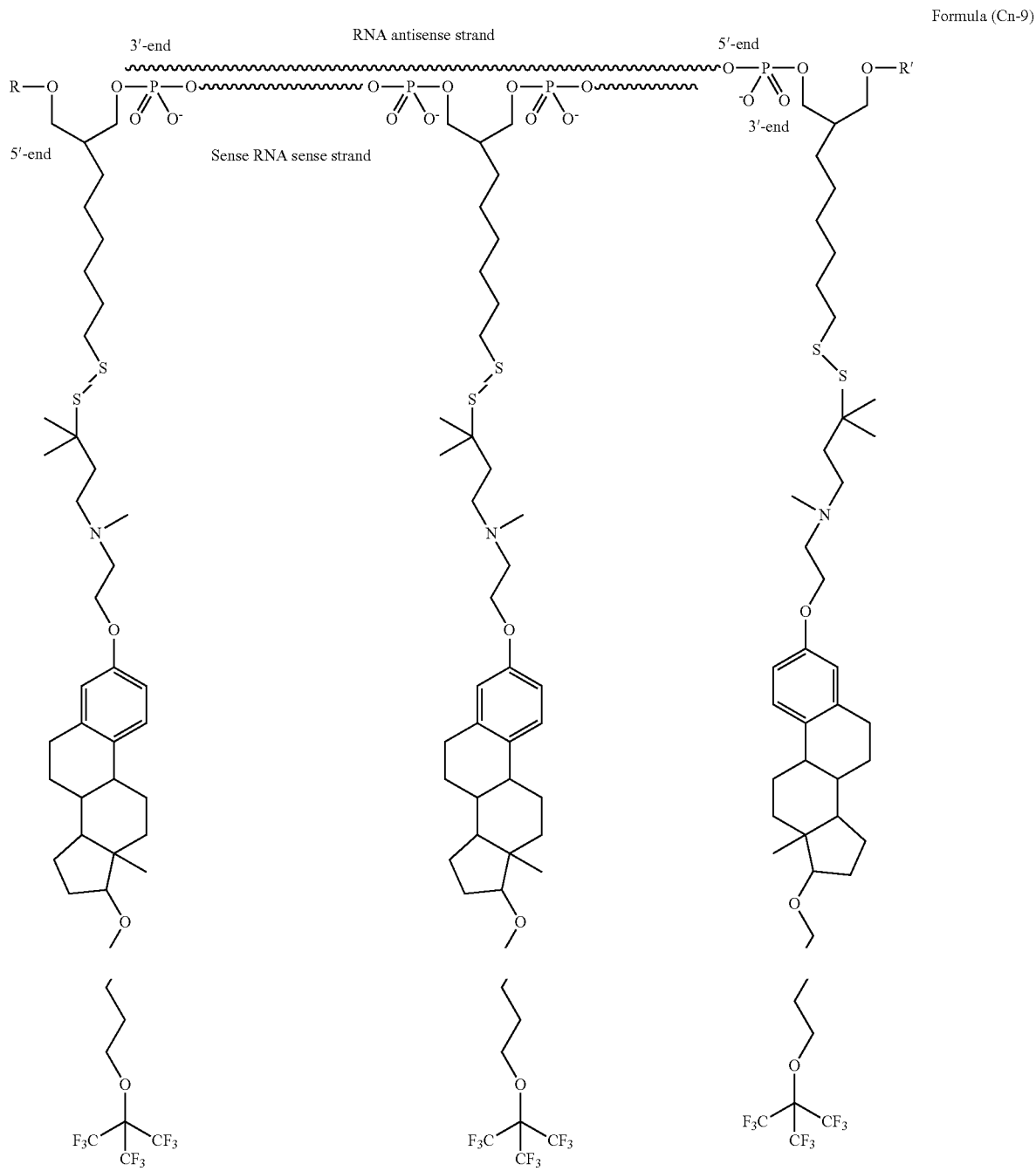

Formula (Cn-9)

including pharmaceutically acceptable salts, hydrates, solvates and metal chelates of the compound represented by the structure as set forth in Formula (Cn-9), and solvates and hydrates of the salts, wherein R and R' are each selected independently from the group consisting of hydrogen, phosphate, sulfate and carboxyl group.

40. The conjugate, according to claim 26, having the structure as set forth in Formula (Cn-10):

Formula (Cn-10)

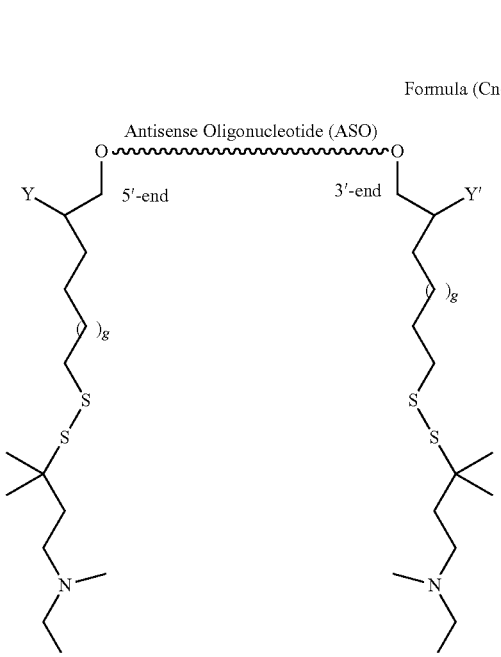

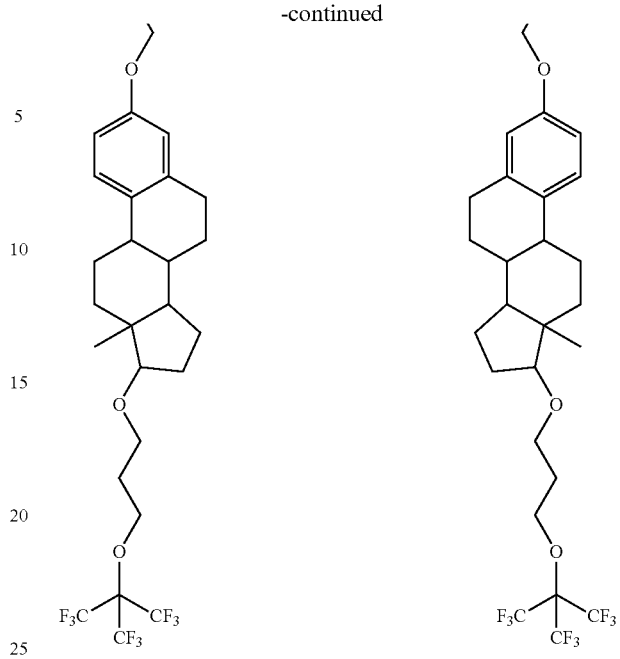

including pharmaceutically acceptable salts, hydrates, solvates and metal chelates of the compound represented by the structure as set forth in Formula (Cn-10), and solvates and hydrates of the salts; wherein Y and Y' are each selected independently from the group consisting of hydrogen, —CH$_2$—Z; —CH$_2$—Z'; —CH$_2$—O—Z; and —CH$_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

41. The conjugate according to claim 26, wherein the OD is an siRNA or dsiRNA comprising a duplex between sense and antisense strands and having the structure as set forth in Formula (Cn-11):

Formula (Cn-11)

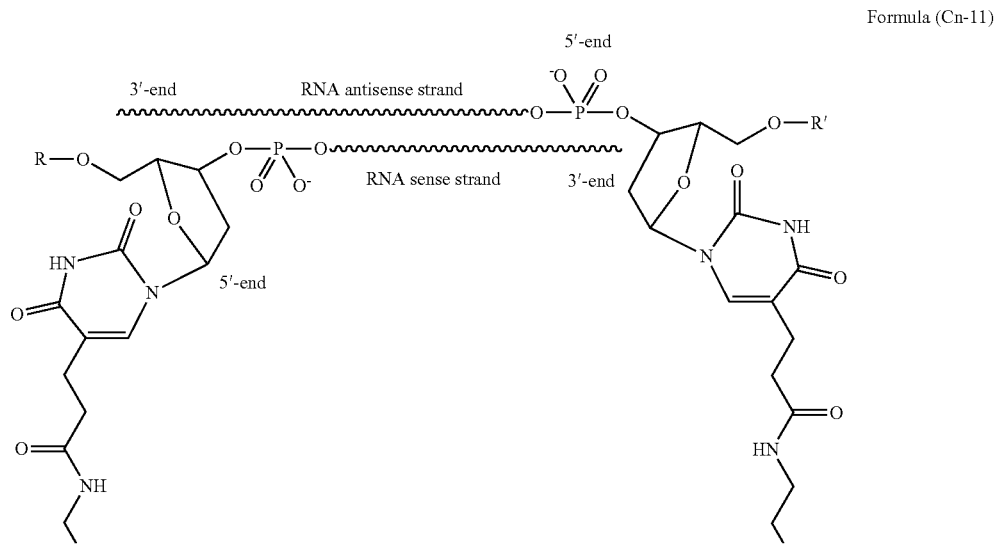

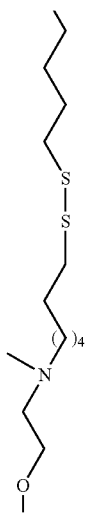

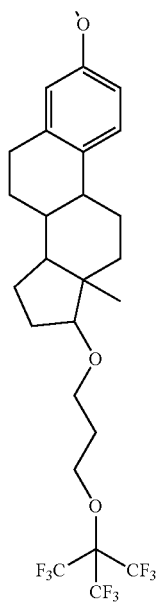

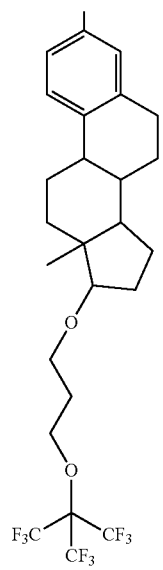

including pharmaceutically acceptable salts, hydrates, solvates and metal chelates of the compound represented by the structure as set forth in Formula (Cn-11), and solvates and hydrates of the salts, wherein R and R' are each selected independently from the group consisting of hydrogen, phosphate, sulfate and carboxyl group.

42. The conjugate according to claim 26, wherein the OD is an siRNA or dsiRNA comprising a duplex between sense and antisense strands and having the structure as set forth in Formula (Cn-12):

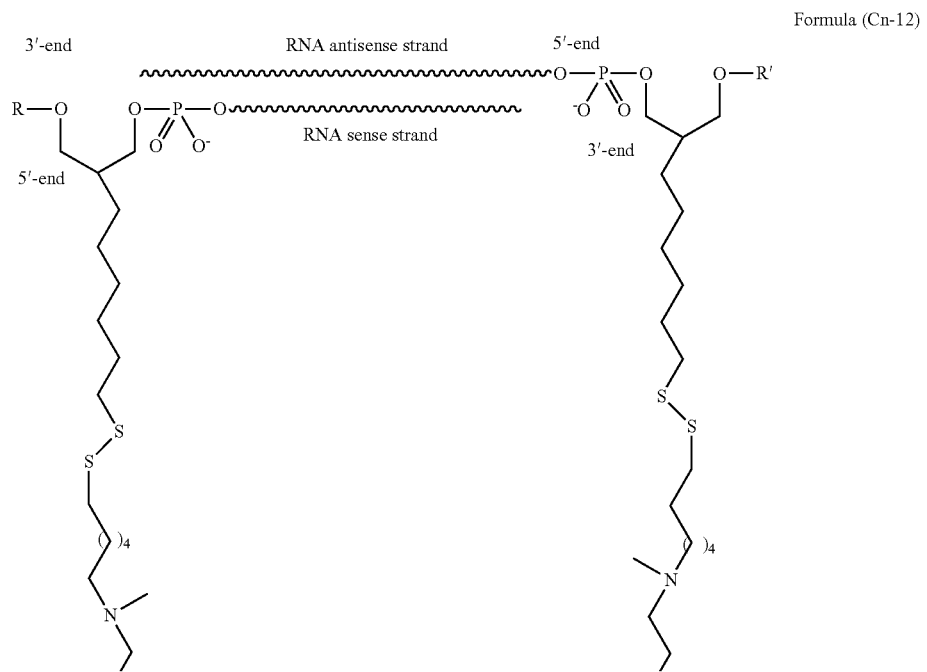

Formula (Cn-12)

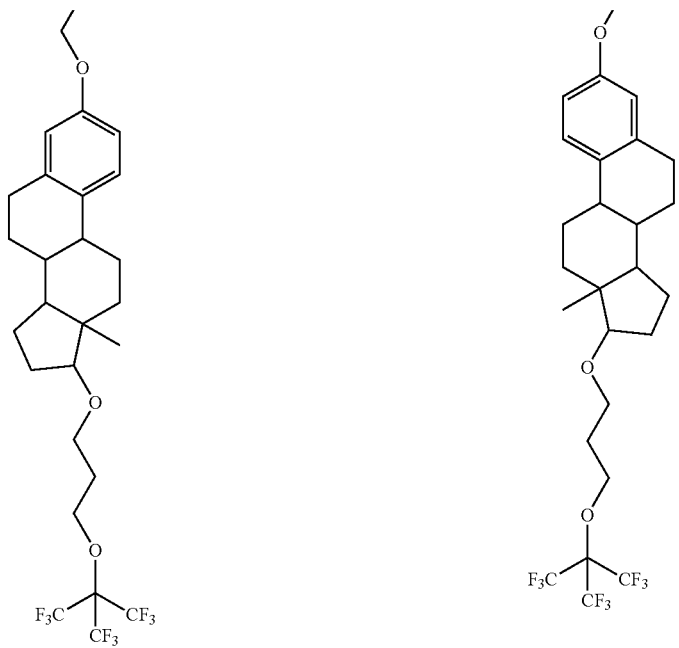

including pharmaceutically acceptable salts, hydrates, solvates and metal chelates of the compound represented by the structure as set forth in Formula (Cn-12), and solvates and hydrates of the salts, wherein R and R' are each selected independently from the group consisting of hydrogen, phosphate, sulfate and carboxyl group.

43. The conjugate according to claim 26, wherein the OD is an siRNA or dsiRNA comprising a duplex between sense and antisense strands and having the structure as set forth in Formula (Cn-13):

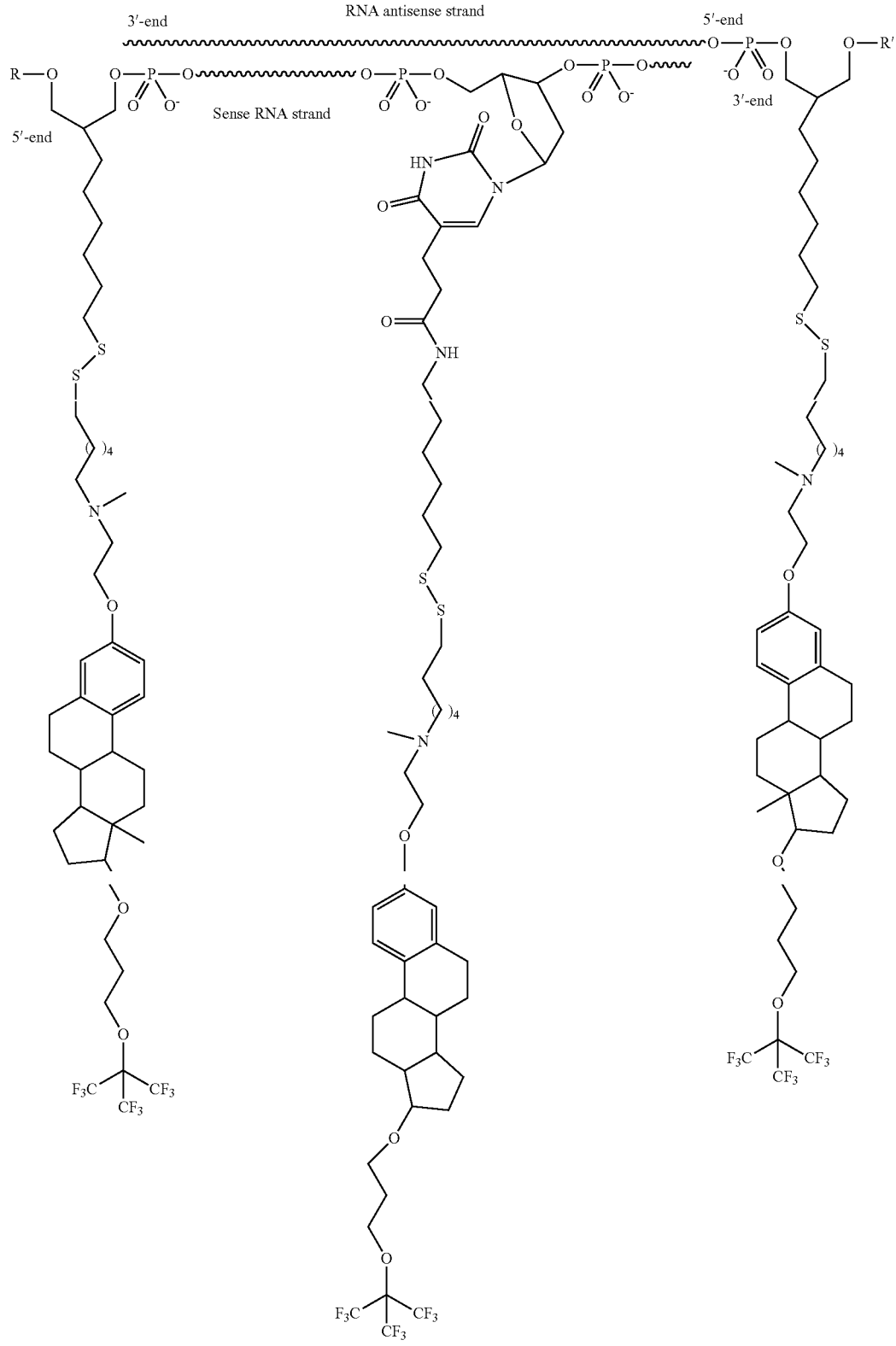
Formula (Cn-13)
including pharmaceutically acceptable salts, hydrates, solvates and metal chelates of the compound represented by the structure as set forth in Formula (Cn-13), and solvates and hydrates of the salts, wherein R and R' are each selected independently from the group consisting of hydrogen, phosphate, sulfate and carboxyl group.

44. The conjugate according to claim 26, wherein the OD is an siRNA or dsiRNA comprising a duplex between sense and antisense strands and having the structure as set forth in Formula (Cn-14):
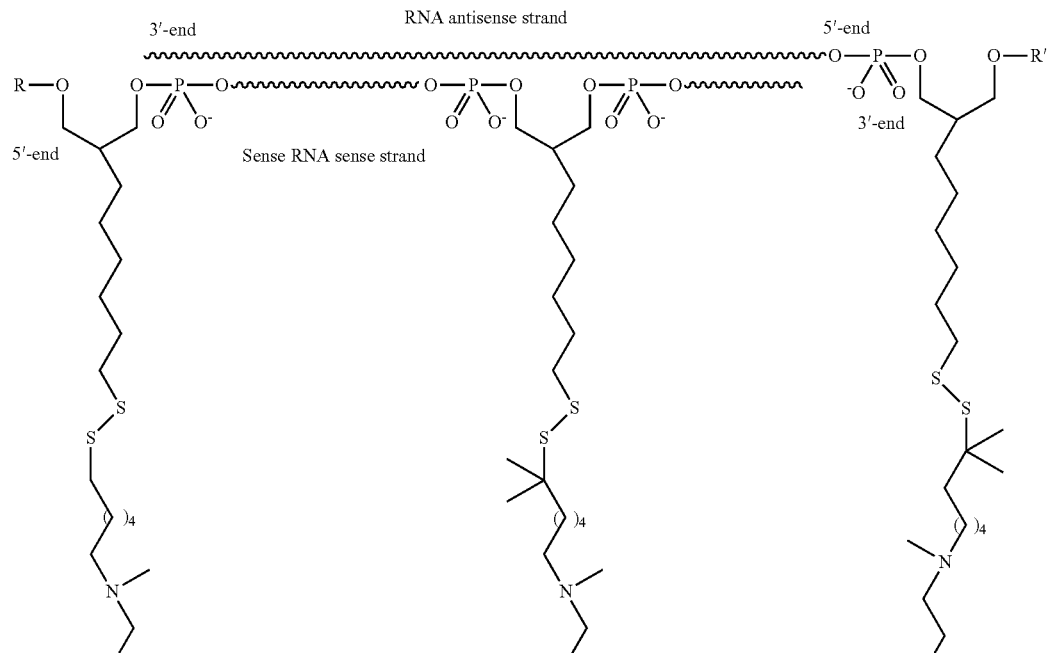
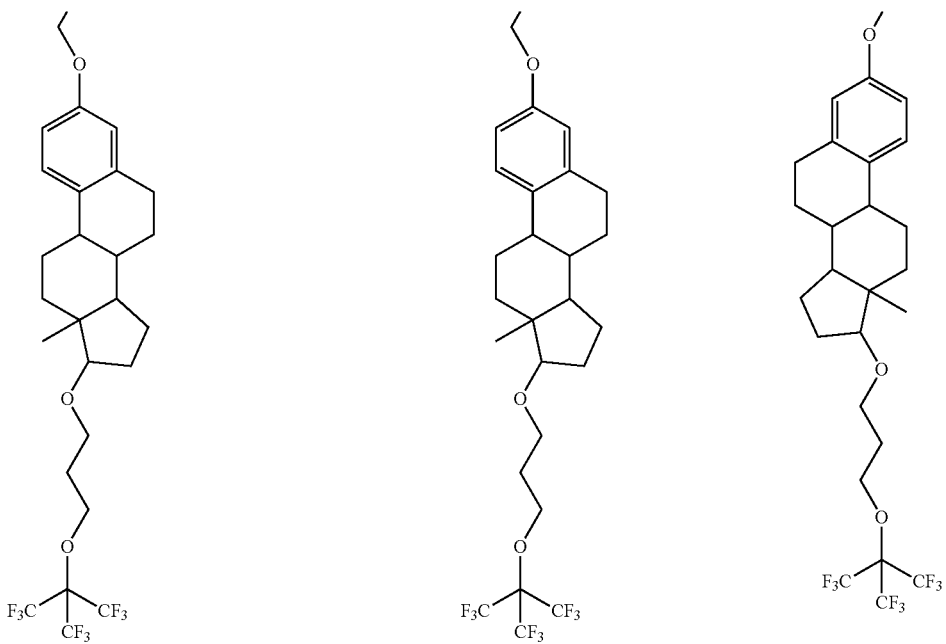
Formula (Cn-14)

including pharmaceutically acceptable salts, hydrates, solvates and metal chelates of the compound represented by the structure as set forth in Formula (Cn-14), and solvates and hydrates of the salts, wherein R and R' are each selected independently from the group consisting of hydrogen, phosphate, sulfate and carboxyl group.

45. The conjugate, according to claim 26, having the structure as set forth in Formula (Cn-15):

Formula (Cn-15)

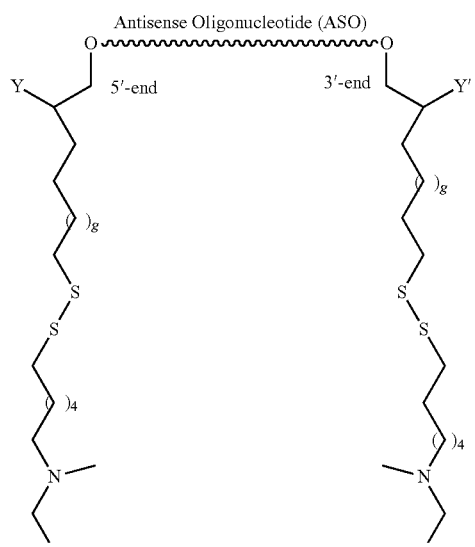

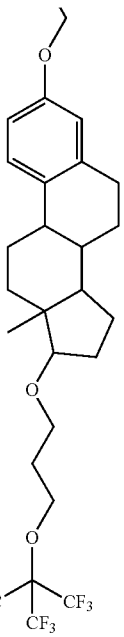

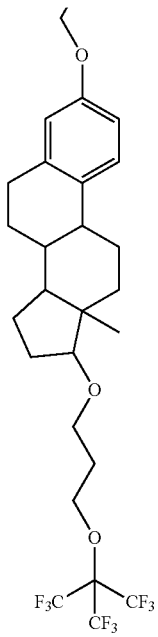

including pharmaceutically acceptable salts, hydrates, solvates and metal chelates of the compound represented by the structure as set forth in Formula (Cn-15), and solvates and hydrates of the salts; wherein Y and Y' are each selected independently from the group consisting of hydrogen, —CH$_2$—Z; —CH$_2$—Z'; —CH$_2$—O—Z; and —CH$_2$—O—Z'; wherein Z and Z' are each selected independently from the group consisting of hydrogen, phosphate, sulfate, carboxyl, 1',2'-Dideoxyribose, nucleotide, or combinations thereof; g is an integer, selected from the group consisting of 0, 1, 2, 3, 4, 5 and 6.

46. A method for delivery of a drug into biological cells, wherein said cells are in culture, or in a living animal or a human subject; the method comprising contacting the cells with a conjugate according to claim 24.

47. A method for delivery of a drug across a phospholipid membrane, comprising conjugation of the drug with E, E' or E" moiety according to any of Formulae (II), (III), (IVa), (IVb), (IVc), (Va'), (Va"), (Va'''), (Vb'), (Vb"), (Vb'''), (Vc'), (Vc") or (Vc'''), and contacting the conjugate with said phospholipid membrane.

48. A method for treatment of a medical disorder, said method comprising administration to a patient in need, therapeutically effective amounts of a pharmaceutical composition according to claim 27.

* * * * *

SEQUENCE LISTING

```
<160> NUMBER OF SEQ ID NOS: 2

<210> SEQ ID NO 1
<211> LENGTH: 27
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: c is attached to a chemical moiety

<400> SEQUENCE: 1
cgguggugca gaugaacuuc aggguca                                              27

<210> SEQ ID NO 2
<211> LENGTH: 25
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: a is attached to a chemical moiety

<400> SEQUENCE: 2
acccugaagu ucaucugcac caccg                                                25
```